US012295976B2

(12) United States Patent
Larson et al.

(10) Patent No.: US 12,295,976 B2
(45) Date of Patent: May 13, 2025

(54) PERSONALIZED CANCER VACCINES

(71) Applicant: EpicentRx, Inc., La Jolla, CA (US)

(72) Inventors: Christopher Larson, San Diego, CA (US); Bryan T. Oronsky, Los Altos Hills, CA (US); Tony R. Reid, San Diego, CA (US)

(73) Assignee: EPICENTRX, INC., La Jolla, CA (US)

( * ) Notice: Subject to any disclaimer, the term of this patent is extended or adjusted under 35 U.S.C. 154(b) by 1169 days.

(21) Appl. No.: 17/042,822

(22) PCT Filed: Mar. 28, 2019

(86) PCT No.: PCT/US2019/024684

§ 371 (c)(1),
(2) Date: Sep. 28, 2020

(87) PCT Pub. No.: WO2019/191494

PCT Pub. Date: Oct. 3, 2019

(65) Prior Publication Data

US 2021/0015878 A1 Jan. 21, 2021

Related U.S. Application Data

(60) Provisional application No. 62/649,206, filed on Mar. 28, 2018.

(51) Int. Cl.

*A61K 35/761* (2015.01)
*A61K 38/16* (2006.01)
*C12N 15/10* (2006.01)
*C12N 15/861* (2006.01)

(52) U.S. Cl.

CPC ............ *A61K 35/761* (2013.01); *A61K 38/16* (2013.01); *C12N 15/102* (2013.01); *C12N 15/861* (2013.01)

(58) Field of Classification Search

CPC .............. A61K 35/761; A61K 39/4611; A61K 39/464401; A61K 2239/55; A61K 2039/525; A61K 2039/585; A61K 38/16; C12N 15/861; C12N 2710/10332; C12N 2710/10343; A61P 35/00; C12Q 1/6806; C12Q 1/6886

See application file for complete search history.

(56) References Cited

U.S. PATENT DOCUMENTS

| | | | |
|---|---|---|---|
| 8,216,819 | B2 | 7/2012 | Hermiston et al. |
| 8,859,287 | B2 | 10/2014 | Rodriguez et al. |
| 9,073,980 | B2 | 7/2015 | Redi et al. |
| 9,115,337 | B2 | 8/2015 | Harden et al. |
| 9,410,129 | B2 | 8/2016 | Ranki et al. |
| 10,016,470 | B2 | 7/2018 | Bonastre et al. |
| 10,047,347 | B2 | 8/2018 | Oberg |
| 2010/0233125 | A1 | 9/2010 | Tagawa et al. |
| 2012/0276045 | A1 | 11/2012 | Ogbourne et al. |
| 2016/0017294 | A1 | 1/2016 | Reid et al. |
| 2017/0152324 | A1 | 6/2017 | Baty et al. |
| 2018/0153946 | A1 | 6/2018 | Alemany et al. |
| 2018/0169271 | A1 | 6/2018 | Cantwell et al. |

FOREIGN PATENT DOCUMENTS

| | | | |
|---|---|---|---|
| EP | 3071697 | B1 | 10/2019 |
| WO | WO-1997006826 | A1 | 2/1997 |
| WO | WO-1998027216 | A1 | 6/1998 |
| WO | WO-2001041741 | A1 | 6/2001 |
| WO | WO-2008080003 | A2 | 7/2008 |
| WO | WO-2010086838 | A2 | 8/2010 |
| WO | WO-2010101921 | A2 | 9/2010 |
| WO | WO-2010128182 | A1 | 11/2010 |
| WO | WO-2010148496 | A1 | 12/2010 |
| WO | WO-2012156933 | A1 | 11/2012 |
| WO | WO-2016049201 | A1 | 3/2016 |
| WO | WO-2017205810 | A1 | 11/2017 |

OTHER PUBLICATIONS

Alemany, (2014). "Oncolytic Adenoviruses in Cancer Treatment," Biomedicines, 2(1):36-49.
Altschul et al., (1994). "Issues in searching molecular sequence databases," Nature Genetics, 6:119-129.
Altschul et al., (1997). "Gapped BLAST and PSI-BLAST: a new generation of protein database search programs," Nucleic Acids Res., 25:3389-3402.
Altschul, (1993). "A protein alignment scoring system sensitive at all evolutionary distances," J. Mol. Evol., 36:290-300.
Berk et al., (1979). "Pre-early adenovirus 5 gene product regulates synthesis of early viral messenger RNAs, " Cell, 17:935-944.
Capasso et al., (2016)."Oncolytic adenoviruses coated with MHC-1 tumor epitopes increase the antitumor immunity and efficacy against melanoma," Oncoimmunology, 5(4):e1105429, 11 pages.
Cheever et al., (2009). "The Prioritization of Cancer Antigens: A National Cancer Institute Pilot Project for the Acceleration of Translational Research," Clin. Cancer Res., 15(17):5323-5337.
Cibulskis et al., (2013). "Sensitive detection of somatic point mutations in impure and heterogeneous cancer samples," Nat. Biotechnol., 31(3):213-9.

(Continued)

*Primary Examiner* — Bao Q Li
(74) *Attorney, Agent, or Firm* — Morrison & Foerster LLP

(57) ABSTRACT

The invention provides for a recombinant adenoviral vector comprising a recombinant oncolytic adenovirus which has: (1) a modified transcription regulatory sequence wherein the adenoviral vector is transcriptionally active in cancer cells and/or hyperproliferative cells and transcriptionally attenuated in normal cells, and (2) a transgene encoding one or more cancer antigens that are specific to a subject. The invention further provides a method of producing said recombinant adenoviral vector. The recombinant oncolytic adenoviral vector described above is used in methods of stimulating a heightened immune response against a cancer antigen in a subject or a method of treating cancer in a subject.

19 Claims, 8 Drawing Sheets

Specification includes a Sequence Listing.

(56) References Cited

OTHER PUBLICATIONS

Feng et al., (1997). "Stable in vivo gene transduction via a novel adenoviral/retroviral chimeric vector," Nature Bio Technology, 15:866-870.
Hedjran et al., (2011). "Deletion analysis of Ad5 E1a transcriptional control region: Impact on tumor-selective expression of E1a and E1b," Cancer Gene Therapy, 18:717-723.
Henikoff et al., (1992). "Amino acid substitution matrices from protein blocks," PNAS USA, 89:10915-10919.
Hoof et al., (2009). "NetMHCpan, a method for MHC class I binding prediction beyond humans," Immunogenetics, 61(1):1-13, 24 pages.
Hsu et al., (2008). "Conditionally replicating E1B-deleted adenovirus driven by the squamous cell carcinoma antigen 2 promoter for uterine cervical cancer therapy," Cancer Gene Therapy, 15(8):526-534.
International Search Report and Written Opinion for PCT/US2019/024684 mailed on Jul. 10, 2019, 13 pages.
Jones et al., (1979). "Isolation of adenovirus type 5 host range deletion mutants defective for transformation of rat embryo cells," Cell, 17:683-689.
Karlin et al., (1990). "Methods for assessing the statistical significance of molecular sequence features by using general scoring schemes," PNAS USA, 87:2264-2268.
Kirn, (2000). "Replication-selective oncolytic adenoviruses: virotherapy aimed at genetic targets in cancer," Oncogene, 19(56):6660-6669.
Kirn, (2001). "Oncolytic virotherapy for cancer with the adenovirus dl1520 (Onyx-015): results of phase I and II trials," Expert Opinion on Biological Therapy, 1(3):525-538.
Kumar et al., (2008). "Virus combinations and chemotherapy for the treatment of human cancers," Current Opinion in Molecular Therapeutics, 10(4):371-379.
Lee et al., (2004). "Targeting Prostate Cancer with Conditionally Replicative Adenovirus Using PSMA Enhancer," Molecular Therapy, 10(6):1051-1058.
Leppard et al., (1997). "E4 Gene Function in Adenovirus, Adenovirus Vector and Adeno-Associated Virus Infections," J. Gen. Virol., 78:2131-8.
Lu et al., (2016). "Cancer immunotherapy targeting neoantigens," Semin. Immunol., 28(1): 22-27.
Montell et al., (1984). "Complete transformation by adenovirus 2 requires both E1A proteins," Cell, 36:951-961.
Nielsen et al., (2016). "NetMHCpan-3.0; improved prediction of binding to MHC class molecules integrating information from multiple receptor and peptide length datasets," Genome Medicine, 8(1):33, 9 pages.
Sjoblom et al., (2014). "The consensus coding sequences of human breast and colorectal cancers," Science, 314:268-74.
Velders et al., (2001). "Defined Flanking Spacers and Enhanced Proteolysis Is Essential for Eradication of Established Tumors by an Epitope String DNA Vaccine," J. Immunol., 166:5366-5373.
Wu et al., (1987). "A Tata box implicated in E1A transcriptional activation of a simple adenovirus 2 promoter," Nature, 326(6112):512-5.
Extended European Search Report received for European Patent Application No. 19774809.8 mailed on Jan. 25, 2022, 12 pages.
Larson et al., (2018). "A practical guide to the handling and administration of personalized transcriptionally attenuated oncolytic adenoviruses (PTAVs)," Oncoimmunology, 7(9):e1478648, 6 pages.
Li et al., (2008). "Oncolytic viroteraphy as a personalized cancer vaccine," International Journal of Cancer, 123(3):493-499.

FIGURE 2A

| | Gene label I Name I RefSeq ID | Mutant peptide sequence (top) / wild type sequence (bottom) |
|---|---|---|
| 1 | CTNNA2 I catenin alpha-2 I NP_004380.2 | DPCSSVKRSTMVRAARA (SEQ ID NO: 10) |
| | | DPCSSVKRGTMVRAARA (SEQ ID NO: 21) |
| 2 | MYO3B I myosin-IIIb isoform 2 I NP_620482.3 | LELCNGGSLTELVKGLL (SEQ ID NO: 22) |
| | | LELCNGGSVTELVKGLL (SEQ ID NO: 23) |
| 3 | SLC8A3 I sodium/calcium exchanger 3 isoform C precursor I NP_892114.1 | STIVGSAAVNMFIIIGI (SEQ ID NO: 24) |
| | | STIVGSAAFNMFIIIGI (SEQ ID NO: 25) |
| 4 | SLC6A19 I sodium-dependent neutral amino acid transporter B(0)AT1 I NP_001003841.1 | IFWQVTWRMVSPLLMLI (SEQ ID NO: 26) |
| | | IFWQVTWRVVSPLLMLI (SEQ ID NO: 27) |
| 5 | ADARB2 I double-stranded RNA-specific editase B2 I NP_061172.1 | CHAEVVARQAFLHFLYT (SEQ ID NO: 28) |
| | | CHAEVVARRAFLHFLYT (SEQ ID NO: 29) |
| 6 | TCP11 I T-complex protein 11 homolog I NP_001087197.1 | LNKQPSLLSHTTKWLTQ (SEQ ID NO: 30) |
| | | LNKQPSLLNHTTKWLTQ (SEQ ID NO: 31) |
| 7 | LRTM2 I leucine-rich repeat and transmembrane domain-containing protein 2 precursor I NP_001034118.1 | LGLTTVPPNVPAATRTL (SEQ ID NO: 32) |
| | | LGLTTVPPDVPAATRTL (SEQ ID NO: 33) |
| 8 | NR5A1 I nuclear receptor subfamily 5 group A member 2 I NP_995582.1 | EAVRADRMKGGRNKFGP (SEQ ID NO: 34) |
| | | EAVRADRMRGGRNKFGP (SEQ ID NO: 35) |
| 9 | PRLHR I prolactin-releasing peptide receptor I NP_004239.1 | CLLVLVIAWVRRLHNVT (SEQ ID NO: 36) |
| | | CLLVLVIARVRRLHNVT (SEQ ID NO: 37) |
| 10 | LRP1 I prolow-density lipoprotein receptor-related protein 1 preproprotein I NP_002323.2 | KEDDCEHGKDETHCNKF (SEQ ID NO: 38) |
| | | KEDDCEHGEDETHCNKF (SEQ ID NO: 39) |
| 11 | A2M I alpha-2-macroglobulin isoform a precursor I NP_000005.2 | SQSLPASHTHLRVTAAP (SEQ ID NO: 40) |
| | | SQSLPASHAHLRVTAAP (SEQ ID NO: 41) |
| 12 | C16orf58 I RUS1 family protein C16orf58 I NP_073581.2 | ELQQLVEGQQESYLLCW (SEQ ID NO: 42) |
| | | ELQQLVEGHQESYLLCW (SEQ ID NO: 43) |
| 1 | BAZ1B I tyrosine-protein kinase | KRSSRRQSPELQKCEEI (SEQ ID NO: 44) |

FIGURE 2A Cont.

| | | |
|---|---|---|
| 3 | BAZ1B I NP_115784.1 | KRSSRRQSLELQKCEEI (SEQ ID NO: 45) |

FIGURE 2B

| | Gene label I Name I RefSeq ID | Mutant peptide sequence (top) / wild type sequence (bottom) |
|---|---|---|
| 14 | PPAP2C I phospholipid phosphatase 2 I NP_003703.1 | RVSDYKHHRSDVLVGLL (SEQ ID NO: 46) |
| | | RVSDYKHHWSDVLVGLL (SEQ ID NO: 47) |
| 15 | TP53 I cellular tumor antigen p53 I NP_000537.3 | GSYGFRLGSLHSGTAKS (SEQ ID NO: 48) |
| | | GSYGFRLGFLHSGTAKS (SEQ ID NO: 49) |
| 16 | CHPF2 I chondroitin sulfate glucuronyltransferase I NP_061888.1 | RAEEFIGADEQARYCHG (SEQ ID NO: 50) |
| | | RAEEFIGAGEQARYCHG (SEQ ID NO: 51) |
| 17 | WDR33 I pre-mRNA 3' end processing protein WDR33 I NP_060853.3 | YVKYWQSNINNVKMFQA (SEQ ID NO: 52) |
| | | YVKYWQSNMNNVKMFQA (SEQ ID NO: 53) |
| 18 | SNRPA (frameshift) I U1 small nuclear ribonucleoprotein A I NP_004587.1 | IKKDELKKVPVRHLLPVWPDPGYPGITEPEDEGPGLCHLQGGQQRHQRPALHAGFPFL (SEQ ID NO: 54) |
| | | IKKDELKKSLYAIFSQFGQILDILVSRSLKMRGQAFVIFKEVSSATNALRSMQGFPFY (SEQ ID NO: 55) |
| 19 | GTPB I GTP-binding protein 1 I NP_004277.2 | QASWEFEAKILVLHHPT (SEQ ID NO: 56) |
| | | QASWEFEAEILVLHHPT (SEQ ID NO: 57) |
| 20 | DDX I probable ATP-dependent RNA helicase DDX46 I NP_001287789.1 | ERVEKWREAQRKKAMEN (SEQ ID NO: 58) |
| | | ERVEKWREEQRKKAMEN (SEQ ID NO: 59) |
| 21 | PRKA I cAMP-dependent protein kinase catalytic subunit beta I NP_891993.1 | ILDKQKVVNLKQIEHTL (SEQ ID NO: 60) |
| | | ILDKQKVVKLKQIEHTL (SEQ ID NO: 61) |
| 22 | KDM I lysine-specific demethylase 5B I NP_001300971.1 | VAVPSISQALRIWLCPH (SEQ ID NO: 62) |
| | | VAVPSISQGLRIWLCPH (SEQ ID NO: 63) |
| 23 | JMJ I jmjC domain-containing protein 8 NP_001005920.2 | PEFHPNKTMLAWLRDTY (SEQ ID NO: 64) |
| | | PEFHPNKTTLAWLRDTY (SEQ ID NO: 65) |

FIGURE 2B Cont.

| | | | |
|---|---|---|---|
| 24 | CTDS | CTD small phosphatase-like protein isoform 1 | NP_001008393.1 | PVADLLDR**C**GVFRARLF | (SEQ ID NO: 66) |
| | | PVADLLDRWGVFRARLF | (SEQ ID NO: 67) |
| 25 | TMEM9B/1 | transmembrane protein 9B isoform a precursor | NP_065695.1 | CLRCECKY**D**ERSSVTIK | (SEQ ID NO: 68) |
| | | CLRCECKYEERSSVTIK | (SEQ ID NO: 69) |

FIGURE 2C

| | Gene label \| Name \| RefSeq ID | Mutant peptide sequence (top) / wild type sequence (bottom) | |
|---|---|---|---|
| 26 | TMEM9B/2 \| transmembrane protein 9B isoform b \| NP_001273024.1 | CLRCECKY**D**ERSSVTIK | (SEQ ID NO: 70) |
| | | CLRCECKYEERSSVTIK | (SEQ ID NO: 71) |
| 27 | DOCK1 \| dedicator of cytokinesis protein 1 NP_001277152.1 | RPKSQVMN**I**IGSERRFS | (SEQ ID NO: 72) |
| | | RPKSQVMNVIGSERRFS | (SEQ ID NO: 73) |
| 28 | RB1 \| retinoblastoma-associated protein \| NP_000312.2 | TFKRVLIK**Q**EEYDSIIV | (SEQ ID NO: 74) |
| | | TFKRVLIKEEEYDSIIV | (SEQ ID NO: 75) |
| 29 | KDM4A \| lysine-specific demethylase 4A \| NP_055478.2 | TDGQVYGA**T**FVASHPIQ | (SEQ ID NO: 76) |
| | | TDGQVYGAKFVASHPIQ | (SEQ ID NO: 77) |
| 30 | NEDD4L \| E3 ubiquitin-protein ligase NEDD4-like \| NP_001138439.1 | FLRLKMAY**V**PKNGGQDE | (SEQ ID NO: 78) |
| | | FLRLKMAYMPKNGGQDE | (SEQ ID NO: 79) |
| 31 | TAOK3 \| serine/threonine-protein kinase TAO3 \| NP_001333416.1 | QTRKLAIL**G**EQYEQSIN | (SEQ ID NO: 80) |
| | | QTRKLAILAEQYEQSIN | (SEQ ID NO: 81) |
| 32 | TCERG1 \| transcription elongation regulator 1 \| NP_006697.2 | DEPVKAKK**W**KRDDNKDI | (SEQ ID NO: 82) |
| | | DEPVKAKKRKRDDNKDI | (SEQ ID NO: 83) |
| 33 | RNF19B \| E3 ubiquitin-protein ligase RNF19B \| NP_699172.2 | MARQQRAQ**P**LRVRTKHT | (SEQ ID NO: 84) |
| | | MARQQRAQTLRVRTKHT | (SEQ ID NO: 85) |
| 34 | HMHA1 \| rho GTPase-activating protein 45 \| NP_036424.2 | HMPLLSIY**L**LALEQDLE | (SEQ ID NO: 86) |
| | | HMPLLSIYSLALEQDLE | (SEQ ID NO: 87) |

FIGURE 2C Cont.

| | | |
|---|---|---|
| 35 | SEMA5A \| semaphorin-5A precursor \| NP_003957.2 | PGMEIANCCRNGGWTPW (SEQ ID NO: 88) |
| | | PGMEIANCSRNGGWTPW (SEQ ID NO: 89) |
| 36 | APC (frameshift) \| adenomatous polyposis coli protein \| NP_001120983.2 | AVQRVQVLQMLILYYILPRKVLQMDFLVHPA (SEQ ID NO: 90) |
| | | AVQRVQVLPDADTLLHFATESTPDGFSCSSS (SEQ ID NO: 91) |
| 37 | ZNF732 \| zinc finger protein 732 \| NP_001131080.1 | RIHAEEKPYTCEECGKI (SEQ ID NO: 92) |
| | | RIHAEEKPFTCEECGKI (SEQ ID NO: 93) |
| 38 | CNTN1 \| contactin-1 isoform 1 precursor \| NP_001834.2 | AFNNKGDGLTA (SEQ ID NO: 94) |
| | | AFNNKGDGPYS (SEQ ID NO: 95) |

Date: 4/24 6/28 8/23 10/25

A B C D

SEQUENCE LISTING

```
<160> NUMBER OF SEQ ID NOS: 116

<210> SEQ ID NO 1
<211> LENGTH: 35938
<212> TYPE: DNA
<213> ORGANISM: Unknown
<220> FEATURE:
<223> OTHER INFORMATION: Oncolytic serotype 5 adenovirus (Ad5)

<400> SEQUENCE: 1

catcatcaat aatatacctt attttggatt gaagccaata tgataatgag gggtggagt      60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180
```

```
gtgtgcgccg gtgtacacag gaagtgacaa ttttcgcgcg gttttaggcg gatgttgtag    240
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagctgacg tgtagtgtat ttatacccgg    480
tgagttcctc aagaggccac tcttgagtgc cagcgagtag agttttctcc tccgagccgc    540
tccgacaccg ggactgaaaa tgagacatat tatctgccac ggaggtgtta ttaccgaaga    600
aatggccgcc agtcttttgg accagctgat cgaagaggta ctggctgata atcttccacc    660
tcctagccat tttgaaccac ctacccttca cgaactgtat gatttagacg tgacggcccc    720
cgaagatccc aacgaggagg cggtttcgca gatttttccc gactctgtaa tgttggcggt    780
gcaggaaggg attgacttac tcacttttcc gccggcgccc ggttctccgg agccgcctca    840
cctttcccgg cagcccgagc agccggagca gagagccttg ggtccggttt ctatgccaaa    900
ccttgtaccg gaggtgatcg atcttacctg ccacgaggct ggctttccac ccagtgacga    960
cgaggatgaa gagggtgagg agtttgtgtt agattatgtg gagcaccccg ggcacggttg   1020
caggtcttgt cattatcacc ggaggaatac gggggaccca gatattatgt gttcgctttg   1080
ctatatgagg acctgtggca tgtttgtcta cagtaagtga aaattatggg cagtgggtga   1140
tagagtggtg ggtttggtgt ggtaattttt tttttaattt ttacagtttt gtggtttaaa   1200
gaattttgta ttgtgatttt tttaaaaggt cctgtgtctg aacctgagcc tgagcccgag   1260
ccagaaccgg agcctgcaag acctacccgc cgtcctaaaa tggcgcctgc tatcctgaga   1320
cgcccgacat cacctgtgtc tagagaatgc aatagtagta cggatagctg tgactccggt   1380
ccttctaaca cacctcctga gatacacccg gtggtcccgc tgtgccccat taaaccagtt   1440
gccgtgagag ttggtgggcg tcgccaggct gtggaatgta tcgaggactt gcttaacgag   1500
cctgggcaac ctttggactt gagctgtaaa cgccccaggc cataaggtgt aaacctgtga   1560
ttgcgtgtgt ggttaacgcc tttgtttgct gaatgagttg atgtaagttt aataaagggt   1620
gagataatgt ttaacttgca tggcgtgtta aatggggcgg ggcttaaagg gtatataatg   1680
cgccgtgggc taatcttggt tacatctgac ctcatggagg cttgggagtg tttggaagat   1740
ttttctgctg tgcgtaactt gctggaacag agctctaaca gtacctcttg gttttggagg   1800
tttctgtggg gctcatccca ggcaaagtta gtctgcagaa ttaaggagga ttacaagtgg   1860
gaatttgaag agcttttgaa atcctgtggt gagctgtttg attctttgaa tctgggtcac   1920
caggcgcttt tccaagagaa ggtcatcaag actttggatt tttccacacc ggggcgcgct   1980
gcggctgctg ttgctttttt gagttttata aaggataaat ggagcgaaga aacccatctg   2040
agcggggggt acctgctgga ttttctggcc atgcatctgt ggagagcggt tgtgagacac   2100
aagaatcgcc tgctactgtt gtcttccgtc cgcccggcga taataccgac ggaggagcag   2160
cagcagcagc aggaggaagc caggcggcgg cggcaggagc agagcccatg gaacccgaga   2220
gccggcctgg accctcggga atgaatgttg tacaggtggc tgaactgtat ccagaactga   2280
gacgcatttt gacaattaca gaggatgggc aggggctaaa gggggtaaag agggagcggg   2340
gggcttgtga ggctacagag gaggctagga atctagcttt tagcttaatg accagacacc   2400
gtcctgagtg tattactttt caacagatca aggataattg cgctaatgag cttgatctgc   2460
tggcgcagaa gtattccata gagcagctga ccacttactg gctgcagcca ggggatgatt   2520
ttgaggaggc tattagggta tatgcaaagg tggcacttag gccagattgc aagtacaaga   2580
```

```
tcagcaaact tgtaaatatc aggaattgtt gctacatttc tgggaacggg gccgaggtgg   2640
agatagatac ggaggatagg gtggccttta gatgtagcat gataaatatg tggccggggg   2700
tgcttggcat ggacggggtg gttattatga atgtaaggtt tactggcccc aattttagcg   2760
gtacggtttt cctggccaat accaacctta tcctacacgg tgtaagcttc tatgggttta   2820
acaatacctg tgtggaagcc tggaccgatg taagggttcg ggctgtgcc ttttactgct   2880
gctggaaggg ggtggtgtgt cgccccaaaa gcagggcttc aattaagaaa tgcctctttg   2940
aaaggtgtac cttgggtatc ctgtctgagg gtaactccag ggtgcgccac aatgtggcct   3000
ccgactgtgg ttgcttcatg ctagtgaaaa gcgtggctgt gattaagcat aacatggtat   3060
gtggcaactg cgaggacagg gcctctcaga tgctgacctg ctcggacggc aactgtcacc   3120
tgctgaagac cattcacgta gccagccact ctcgcaaggc ctggccagtg tttgagcata   3180
acatactgac ccgctgttcc ttgcatttgg gtaacaggag gggggtgttc ctaccttacc   3240
aatgcaattt gagtcacact aagatattgc ttgagcccga gagcatgtcc aaggtgaacc   3300
tgaacggggt gtttgacatg accatgaaga tctggaaggt gctgaggtac gatgagaccc   3360
gcaccaggtg cagaccctgc gagtgtggcg gtaaacatat taggaaccag cctgtgatgc   3420
tggatgtgac cgaggagctg aggcccgatc acttggtgct ggcctgcacc cgcgctgagt   3480
ttggctctag cgatgaagat acagattgag gtactgaaat gtgtgggcgt ggcttaaggg   3540
tgggaaagaa tatataaggt gggggtctta tgtagttttg tatctgtttt gcagcagccg   3600
ccgccgccat gagcaccaac tcgtttgatg gaagcattgt gagctcatat ttgacaacgc   3660
gcatgccccc atgggccggg gtgcgtcaga atgtgatggg ctccagcatt gatggtcgcc   3720
ccgtcctgcc cgcaaactct actaccttga cctacgagac cgtgtctgga acgccgttgg   3780
agactgcagc ctccgccgcc gcttcagccg ctgcagccac cgcccgcggg attgtgactg   3840
actttgcttt cctgagcccg cttgcaagca gtgcagcttc ccgttcatcc gcccgcgatg   3900
acaagttgac ggctcttttg gcacaattgg attctttgac ccgggaactt aatgtcgttt   3960
ctcagcagct gttggatctg cgccagcagg tttctgccct gaaggcttcc tcccctccca   4020
atgcggttta aaacataaat aaaaaaccag actctgtttg gatttggatc aagcaagtgt   4080
cttgctgtct ttatttaggg gttttgcgcg cgcggtaggc ccgggaccag cggtctcggt   4140
cgttgagggt cctgtgtatt ttttccagga cgtggtaaag gtgactctgg atgttcagat   4200
acatgggcat aagcccgtct ctggggtgga ggtagcacca ctgcagagct tcatgctgcg   4260
gggtggtgtt gtagatgatc cagtcgtagc aggagcgctg ggcgtggtgc ctaaaaatgt   4320
ctttcagtag caagctgatt gccaggggca ggcccttggt gtaagtgttt acaaagcggt   4380
taagctggga tgggtgcata cgtggggata tgagatgcat cttggactgt atttttaggt   4440
tggctatgtt cccagccata tccctccggg gattcatgtt gtgcagaacc accagcacag   4500
tgtatccggt gcacttggga aatttgtcat gtagcttaga aggaaatgcg tggaagaact   4560
tggagacgcc cttgtgacct ccaagatttt ccatgcattc gtccataatg atggcaatgg   4620
gcccacgggc ggcggcctgg gcgaagatat ttctgggatc actaacgtca tagttgtgtt   4680
ccaggatgag atcgtcatag gccattttta caaagcgcgg gcggagggtg ccagactgcg   4740
gtataatggt tccatccggc ccaggggcgt agttaccctc acagatttgc atttcccacg   4800
ctttgagttc agatgggggg atcatgtcta cctgcggggc gatgaagaaa acggtttccg   4860
gggtagggga gatcagctgg gaagaaagca ggttcctgag cagctgcgac ttaccgcagc   4920
```

-continued

```
cggtgggccc gtaaatcaca cctattaccg ggtgcaactg gtagttaaga gagctgcagc   4980
tgccgtcatc cctgagcagg ggggccactt cgttaagcat gtccctgact cgcatgtttt   5040
ccctgaccaa atccgccaga aggcgctcgc cgcccagcga tagcagttct tgcaaggaag   5100
caaagttttt caacggtttg agaccgtccg ccgtaggcat gcttttgagc gtttgaccaa   5160
gcagttccag gcggtcccac agctcggtca cctgctctac ggcatctcga tccagcatat   5220
ctcctcgttt cgcgggttgg ggcggctttc gctgtacggc agtagtcggt gctcgtccag   5280
acgggccagg gtcatgtctt tccacgggcg cagggtcctc gtcagcgtag tctgggtcac   5340
ggtgaagggg tgcgctccgg gctgcgcgct ggccagggtg cgcttgaggc tggtcctgct   5400
ggtgctgaag cgctgccggt cttcgccctg cgcgtcggcc aggtagcatt tgaccatggt   5460
gtcatagtcc agcccctccg cggcgtggcc cttggcgcgc agcttgccct tggaggaggc   5520
gccgcacgag gggcagtgca gacttttgag ggcgtagagc ttgggcgcga gaaataccga   5580
ttccggggag taggcatccg cgccgcaggc cccgcagacg gtctcgcatt ccacgagcca   5640
ggtgagctct ggccgttcgg ggtcaaaaac caggtttccc ccatgctttt tgatgcgttt   5700
cttacctctg gtttccatga gccggtgtcc acgctcggtg acgaaaaggc tgtccgtgtc   5760
cccgtataca gacttgagag gcctgtcctc gagcggtgtt ccgcggtcct cctcgtatag   5820
aaactcggac cactctgaga caaaggctcg cgtccaggcc agcacgaagg aggctaagtg   5880
ggaggggtag cggtcgttgt ccactagggg gtccactcgc tccagggtgt gaagacacat   5940
gtcgccctct tcggcatcaa ggaaggtgat tggtttgtag gtgtaggcca cgtgaccggg   6000
tgttcctgaa ggggggctat aaaagggggt gggggcgcgt tcgtcctcac tctcttccgc   6060
atcgctgtct gcgagggcca gctgttgggg tgagtactcc ctctgaaaag cgggcatgac   6120
ttctgcgcta agattgtcag tttccaaaaa cgaggaggat ttgatattca cctggcccgc   6180
ggtgatgcct ttgagggtgg ccgcatccat ctggtcagaa aagacaatct ttttgttgtc   6240
aagcttggtg gcaaacgacc cgtagagggc gttggacagc aacttggcga tggagcgcag   6300
ggtttggttt ttgtcgcgat cggcgcgctc cttggccgcg atgtttagct gcacgtattc   6360
gcgcgcaacg caccgccatt cgggaaagac ggtggtgcgc tcgtcgggca ccaggtgcac   6420
gcgccaaccg cggttgtgca gggtgacaag gtcaacgctg gtggctacct ctccgcgtag   6480
gcgctcgttg gtccagcaga ggcggccgcc cttgcgcgag cagaatggcg gtagggggtc   6540
tagctgcgtc tcgtccgggg ggtctgcgtc cacggtaaag accccgggca gcaggcgcgc   6600
gtcgaagtag tctatcttgc atccttgcaa gtctagcgcc tgctgccatg cgcgggcggc   6660
aagcgcgcgc tcgtatgggt tgagtggggg accccatggc atggggtggg tgagcgcgga   6720
ggcgtacatg ccgcaaatgt cgtaaacgta gaggggctct ctgagtattc caagatatgt   6780
agggtagcat cttccaccgc ggatgctggc gcgcacgtaa tcgtatagtt cgtgcgaggg   6840
agcgaggagg tcgggaccga ggttgctacg ggcgggctgc tctgctcgga agactatctg   6900
cctgaagatg gcatgtgagt tggatgatat ggttggacgc tggaagacgt tgaagctggc   6960
gtctgtgaga cctaccgcgt cacgcacgaa ggaggcgtag gagtcgcgca gcttgttgac   7020
cagctcggcg gtgacctgca cgtctagggc gcagtagtcc agggtttcct tgatgatgtc   7080
atacttatcc tgtccctttt ttttccacag ctcgcggttg aggacaaact cttcgcggtc   7140
tttccagtac tcttggatcg gaaacccgtc ggcctccgaa cggtaagagc ctagcatgta   7200
gaactggttg acggcctggt aggcgcagca tccctttttct acgggtagcg cgtatgcctg   7260
cgcggccttc cggagcgagg tgtgggtgag cgcaaaggtg tccctgacca tgactttgag   7320
```

-continued

```
gtactggtat ttgaagtcag tgtcgtcgca tccgccctgc tcccagagca aaaagtccgt   7380
gcgctttttg gaacgcggat ttggcagggc gaaggtgaca tcgttgaaga gtatctttcc   7440
cgcgcgaggc ataaagttgc gtgtgatgcg gaagggtccc ggcacctcgg aacggttgtt   7500
aattacctgg gcggcgagca cgatctcgtc aaagccgttg atgttgtggc ccacaatgta   7560
aagttccaag aagcgcggga tgcccttgat ggaaggcaat tttttaagtt cctcgtaggt   7620
gagctcttca ggggagctga gcccgtgctc tgaaagggcc cagtctgcaa gatgagggtt   7680
ggaagcgacg aatgagctcc acaggtcacg ggccattagc atttgcaggt ggtcgcgaaa   7740
ggtcctaaac tggcgaccta tggccatttt ttctggggtg atgcagtaga aggtaagcgg   7800
gtcttgttcc cagcggtccc atccaaggtt cgcggctagg tctcgcgcgg cagtcactag   7860
aggctcatct ccgccgaact tcatgaccag catgaagggc acgagctgct tcccaaaggc   7920
ccccatccaa gtataggtct ctacatcgta ggtgacaaag agacgctcgg tgcgaggatg   7980
cgagccgatc gggaagaact ggatctcccg ccaccaattg gaggagtggc tattgatgtg   8040
gtgaaagtag aagtccctgc gacgggccga acactcgtgc tggcttttgt aaaaacgtgc   8100
gcagtactgg cagcggtgca cgggctgtac atcctgcacg aggttgacct gacgaccgcg   8160
cacaaggaag cagagtggga atttgagccc ctcgcctggc gggtttggct ggtggtcttc   8220
tacttcggct gcttgtcctt gaccgtctgg ctgctcgagg ggagttacgg tggatcggac   8280
caccacgccg cgcgagccca aagtccagat gtccgcgcgc ggcggtcgga gcttgatgac   8340
aacatcgcgc agatgggagc tgtccatggt ctggagctcc cgcggcgtca ggtcaggcgg   8400
gagctcctgc aggtttacct cgcatagacg ggtcagggcg cgggctagat ccaggtgata   8460
cctaatttcc aggggctggt tggtggcggc gtcgatggct tgcaagaggc cgcatccccg   8520
cggcgcgact acggtaccgc gcggcgggcg gtgggccgcg ggggtgtcct tggatgatgc   8580
atctaaaagc ggtgacgcgg gcgagccccc ggaggtaggg ggggctccgg acccgccggg   8640
agagggggca ggggcacgtc ggcgccgcgc gcgggcagga gctggtgctg cgcgcgtagg   8700
ttgctggcga acgcgacgac gcggcggttg atctcctgaa tctggcgcct ctgcgtgaag   8760
acgacgggcc cggtgagctt gagcctgaaa gagagttcga cagaatcaat ttcggtgtcg   8820
ttgacggcgg cctggcgcaa aatctcctgc acgtctcctg agttgtcttg ataggcgatc   8880
tcggccatga actgctcgat ctcttcctcc tggagatctc cgcgtccggc tcgctccacg   8940
gtggcggcga ggtcgttgga aatgcgggcc atgagctgcg agaaggcgtt gaggcctccc   9000
tcgttccaga cgcggctgta gaccacgccc ccttcggcat cgcgggcgcg catgaccacc   9060
tgcgcgagat tgagctccac gtgccgggcg aagacggcgt agtttcgcag gcgctgaaag   9120
aggtagttga gggtggtggc ggtgtgttct gccacgaaga agtacataac ccagcgtcgc   9180
aacgtggatt cgttgatatc ccccaaggcc tcaaggcgct ccatggcctc gtagaagtcc   9240
acggcgaagt tgaaaaactg ggagttgcgc gccgacacgg ttaactcctc ctccagaaga   9300
cggatgagct cggcgacagt gtcgcgcacc tcgcgctcaa aggctacagg ggcctcttct   9360
tcttcttcaa tctcctcttc cataagggcc tccccttctt cttcttctgg cggcggtggg   9420
ggagggggga cacggcggcg acgacggcgc accgggaggc ggtcgacaaa gcgctcgatc   9480
atctccccgc ggcgacggcg catggtctcg gtgacggcgc ggccgttctc gcgggggcgc   9540
agttggaaga cgccgcccgt catgtcccgg ttatgggttg gcggggggct gccatgcggc   9600
agggatacgg cgctaacgat gcatctcaac aattgttgtg taggtactcc gccgccgagg   9660
```

-continued gacctgagcg agtccgcatc gaccggatcg gaaaacctct cgagaaaggc gtctaaccag 9720
tcacagtcgc aaggtaggct gagcaccgtg gcgggcggca gcgggcggcg gtcggggttg 9780
tttctggcgg aggtgctgct gatgatgtaa ttaaagtagg cggtcttgag acggcggatg 9840
gtcgacagaa gcaccatgtc cttgggtccg gcctgctgaa tgcgcaggcg gtcggccatg 9900
ccccaggctt cgttttgaca tcggcgcagg tctttgtagt agtcttgcat gagcctttct 9960
accggcactt cttcttctcc ttcctcttgt cctgcatctc ttgcatctat cgctgcggcg 10020
gcggcggagt ttggccgtag gtggcgccct cttcctccca tgcgtgtgac cccgaagccc 10080
ctcatcggct gaagcagggc taggtcggcg acaacgcgct cggctaatat ggcctgctgc 10140
acctgcgtga gggtagactg gaagtcatcc atgtccacaa agcggtggta tgcgcccgtg 10200
ttgatggtgt aagtgcagtt ggccataacg gaccagttaa cggtctggtg acccggctgc 10260
gagagctcgg tgtacctgag acgcgagtaa gccctcgagt caaatacgta gtcgttgcaa 10320
gtccgcacca ggtactggta tcccaccaaa aagtgcggcg gcggctggcg gtagaggggc 10380
cagcgtaggg tggccggggc tccgggggcg agatcttcca acataaggcg atgatatccg 10440
tagatgtacc tggacatcca ggtgatgccg gcggcggtgg tggaggcgcg cggaaagtcg 10500
cggacgcggt tccagatgtt gcgcagcggc aaaaagtgct ccatggtcgg gacgctctgg 10560
ccggtcaggc gcgcgcaatc gttgacgctc tagaccgtgc aaaaggagag cctgtaagcg 10620
ggcactcttc cgtggtctgg tggataaatt cgcaagggta tcatggcgga cgaccggggt 10680
tcgagccccg tatccggccg tccgccgtga tccatgcggt taccgcccgc gtgtcgaacc 10740
caggtgtgcg acgtcagaca acgggggagt gctccttttg gcttccttcc aggcgcggcg 10800
gctgctgcgc tagctttttt ggccactggc cgcgcgcagc gtaagcggtt aggctggaaa 10860
gcgaaagcat taagtggctc gctccctgta gccggagggt tattttccaa gggttgagtc 10920
gcgggacccc cggttcgagt ctcggaccgg ccggactgcg gcgaacgggg gtttgcctcc 10980
ccgtcatgca agaccccgct tgcaaattcc tccggaaaca gggacgagcc cctttttttgc 11040
ttttcccaga tgcatccggt gctgcggcag atgcgccccc ctcctcagca gcggcaagag 11100
caagagcagc ggcagacatg cagggcaccc tcccctcctc ctaccgcgtc aggaggggcg 11160
acatccgcgg ttgacgcggc agcagatggt gattacgaac cccgcggcg ccgggcccgg 11220
cactacctgg acttggagga gggcgagggc ctggcgcggc taggagcgcc ctctcctgag 11280
cggtacccaa gggtgcagct gaagcgtgat acgcgtgagg cgtacgtgcc gcggcagaac 11340
ctgtttcgcg accgcgaggg agaggagccc gaggagatgc gggatcgaaa gttccacgca 11400
gggcgcgagc tgcggcatgg cctgaatcgc gagcggttgc tgcgcgagga ggactttgag 11460
cccgacgcgc gaaccgggat tagtcccgcg cgcgcacacg tggcggccgc cgacctggta 11520
accgcatacg agcagacggt gaaccaggag attaactttc aaaaaagctt taacaaccac 11580
gtgcgtacgc ttgtggcgcg cgaggaggtg gctataggac tgatgcatct gtgggacttt 11640
gtaagcgcgc tggagcaaaa cccaaatagc aagccgctca tggcgcagct gttccttata 11700
gtgcagcaca gcagggacaa cgaggcattc agggatgcgc tgctaaacat agtagagccc 11760
gagggccgct ggctgctcga tttgataaac atcctgcaga gcatagtggt gcaggagcgc 11820
agcttgagcc tggctgacaa ggtggccgcc atcaactatt ccatgcttag cctgggcaag 11880
ttttacgccc gcaagatata ccatacccct tacgttccca tagacaagga ggtaaagatc 11940
gaggggttct acatgcgcat ggcgctgaag gtgcttacct tgagcgacga cctgggcgtt 12000
tatcgcaacg agcgcatcca caaggccgtg agcgtgagcc ggcggcgcga gctcagcgac 12060

```
cgcgagctga tgcacagcct gcaaagggcc ctggctggca cgggcagcgg cgatagagag  12120
gccgagtcct actttgacgc gggcgctgac ctgcgctggg ccccaagccg acgcgccctg  12180
gaggcagctg gggccggacc tgggctggcg gtggcacccg cgcgcgctgg caacgtcggc  12240
ggcgtggagg aatatgacga ggacgatgag tacgagccag aggacggcga gtactaagcg  12300
gtgatgtttc tgatcagatg atgcaagacg caacggaccc ggcggtgcgg gcggcgctgc  12360
agagccagcc gtccggcctt aactccacgg acgactggcg ccaggtcatg gaccgcatca  12420
tgtcgctgac tgcgcgcaat cctgacgcgt tccggcagca gccgcaggcc aaccggctct  12480
ccgcaattct ggaagcggtg gtcccggcgc gcgcaaaccc cacgcacgag aaggtgctgg  12540
cgatcgtaaa cgcgctggcc gaaaacaggg ccatccggcc cgacgaggcc ggcctggtct  12600
acgacgcgct gcttcagcgc gtggctcgtt acaacagcgg caacgtgcag accaacctgg  12660
accggctggt gggggatgtg cgcgaggccg tggcgcagcg tgagcgcgcg cagcagcagg  12720
gcaacctggg ctccatggtt gcactaaacg ccttcctgag tacacagccc gccaacgtgc  12780
cgcggggaca ggaggactac accaactttg tgagcgcact gcggctaatg gtgactgaga  12840
caccgcaaag tgaggtgtac cagtctgggc cagactattt tttccagacc agtagacaag  12900
gcctgcagac cgtaaacctg agccaggctt tcaaaaactt gcaggggctg tggggggtgc  12960
gggctcccac aggcgaccgc gcgaccgtgt ctagcttgct gacgcccaac tcgcgcctgt  13020
tgctgctgct aatagcgccc ttcacggaca gtggcagcgt gtcccgggac acatacctag  13080
gtcacttgct gacactgtac cgcgaggcca taggtcaggc gcatgtggac gagcatactt  13140
tccaggagat tacaagtgtc agccgcgcgc tggggcagga ggacacgggc agcctggagg  13200
caaccctaaa ctacctgctg accaaccggc ggcagaagat cccctcgttg cacagtttaa  13260
acagcgagga ggagcgcatt ttgcgctacg tgcagcagag cgtgagcctt aacctgatgc  13320
gcgacggggt aacgcccagc gtggcgctgg acatgaccgc gcgcaacatg gaaccgggca  13380
tgtatgcctc aaaccggccg tttatcaacc gcctaatgga ctacttgcat cgcgcggccg  13440
ccgtgaaccc cgagtatttc accaatgcca tcttgaaccc gcactggcta ccgccccctg  13500
gtttctacac cgggggattc gaggtgcccg agggtaacga tggattcctc tgggacgaca  13560
tagacgacag cgtgttttcc ccgcaaccgc agaccctgct agagttgcaa cagcgcgagc  13620
aggcagaggc ggcgctgcga aaggaaagct tccgcaggcc aagcagcttg tccgatctag  13680
gcgctgcggc cccgcggtca gatgctagta gcccatttcc aagcttgata gggtctctta  13740
ccagcactcg caccacccgc ccgcgcctgc tgggcgagga ggagtaccta aacaactcgc  13800
tgctgcagcc gcagcgcgaa aaaaacctgc ctccggcatt tcccaacaac gggatagaga  13860
gcctagtgga caagatgagt agatggaaga cgtacgcgca ggagcacagg gacgtgccag  13920
gcccgcgccc gcccacccgt cgtcaaaggc acgaccgtca gcggggtctg gtgtgggagg  13980
acgatgactc ggcagacgac agcagcgtcc tggatttggg agggagtggc aacccgtttg  14040
cgcaccttcg ccccaggctg gggagaatgt tttaaaaaaa aaaaagcatg atgcaaaata  14100
aaaaactcac caaggccatg gcaccgagcg ttggttttct tgtattcccc ttagtatgcg  14160
gcgcgcggcg atgtatgagg aaggtcctcc tccctcctac gagagtgtgg tgagcgcggc  14220
gccagtggcg gcggcgctgg gttctccctt cgatgctccc ctggacccgc cgtttgtgcc  14280
tccgcggtac ctgcggccta ccggggggag aaacagcatc cgttactctg agttggcacc  14340
cctattcgac accacccgtg tgtacctggt ggacaacaag tcaacggatg tggcatccct  14400
```

```
gaactaccag aacgaccaca gcaactttct gaccacggtc attcaaaaca atgactacag  14460
cccgggggag gcaagcacac agaccatcaa tcttgacgac cggtcgcact ggggcggcga  14520
cctgaaaacc atcctgcata ccaacatgcc aaatgtgaac gagttcatgt ttaccaataa  14580
gtttaaggcg cgggtgatgg tgtcgcgctt gcctactaag gacaatcagg tggagctgaa  14640
atacgagtgg gtggagttca cgctgcccga gggcaactac tccgagacca tgaccataga  14700
ccttatgaac aacgcgatcg tggagcacta cttgaaagtg ggcagacaga acggggttct  14760
ggaaagcgac atcggggtaa agtttgacac ccgcaacttc agactggggt ttgaccccgt  14820
cactggtctt gtcatgcctg gggtatatac aaacgaagcc ttccatccag acatcatttt  14880
gctgccagga tgcggggtgg acttcaccca cagccgcctg agcaacttgt tgggcatccg  14940
caagcggcaa cccttccagg agggctttag gatcacctac gatgatctgg agggtggtaa  15000
cattcccgca ctgttggatg tggacgccta ccaggcgagc ttgaaagatg acaccgaaca  15060
gggcgggggt ggcgcaggcg gcagcaacag cagtggcagc ggcgcggaag agaactccaa  15120
cgcggcagcc gcggcaatgc agccggtgga ggacatgaac gatcatgcca ttcgcggcga  15180
cacctttgcc acacgggctg aggagaagcg cgctgaggcc gaagcagcgg ccgaagctgc  15240
cgcccccgct gcgcaacccg aggtcgagaa gcctcagaag aaaccggtga tcaaacccct  15300
gacagaggac agcaagaaac gcagttacaa cctaataagc aatgacagca ccttcaccca  15360
gtaccgcagc tggtaccttg catacaacta cggcgaccct cagaccggaa tccgctcatg  15420
gaccctgctt tgcactcctg acgtaacctg cggctcggag caggtctact ggtcgttgcc  15480
agacatgatg caagaccccg tgaccttccg ctccacgcgc cagatcagca actttccggt  15540
ggtgggcgcc gagctgttgc ccgtgcactc caagagcttc tacaacgacc aggccgtcta  15600
ctcccaactc atccgccagt ttacctctct gacccacgtg ttcaatcgct ttcccgagaa  15660
ccagattttg gcgcgcccgc cagcccccac catcaccacc gtcagtgaaa acgttcctgc  15720
tctcacagat cacgggacgc taccgctgcg caacagcatc ggaggagtcc agcgagtgac  15780
cattactgac gccagacgcc gcacctgccc ctacgtttac aaggccctgg gcatagtctc  15840
gccgcgcgtc ctatcgagcc gcactttttg agcaagcatg tccatcctta tatcgcccag  15900
caataacaca ggctggggcc tgcgcttccc aagcaagatg tttggcgggg ccaagaagcg  15960
ctccgaccaa cacccagtgc gcgtgcgcgg gcactaccgc gcgccctggg gcgcgcacaa  16020
acgcggccgc actgggcgca ccaccgtcga tgacgccatc gacgcggtgg tggaggaggc  16080
gcgcaactac acgcccacgc cgccaccagt gtccacagtg gacgcggcca ttcagaccgt  16140
ggtgcgcgga gcccggcgct atgctaaaat gaagagacgg cggaggcgcg tagcacgtcg  16200
ccaccgccgc cgacccggca ctgccgccca acgcgcggcg gcggccctgc ttaaccgcgc  16260
acgtcgcacc ggccgacggg cggccatgcg ggccgctcga aggctggccg cgggtattgt  16320
cactgtgccc cccaggtcca ggcgacgagc ggccgccgca gcagccgcgg ccattagtgc  16380
tatgactcag ggtcgcaggg gcaacgtgta ttgggtgcgc gactcggtta gcggcctgcg  16440
cgtgcccgtg cgcacccgcc ccccgcgcaa ctagattgca agaaaaaact acttagactc  16500
gtactgttgt atgtatccag cggcggcggc gcgcaacgaa gctatgtcca agcgcaaaat  16560
caaagaagag atgctccagg tcatcgcgcc ggagatctat ggccccccga agaaggaaga  16620
gcaggattac aagccccgaa agctaaagcg ggtcaaaaag aaaaagaaag atgatgatga  16680
tgaacttgac gacgaggtgg aactgctgca cgctaccgcg cccaggcgac gggtacagtg  16740
gaaaggtcga cgcgtaaaac gtgttttgcg acccggcacc accgtagtct ttacgcccgg  16800
```

```
tgagcgctcc acccgcacct acaagcgcgt gtatgatgag gtgtacggcg acgaggacct  16860
gcttgagcag gccaacgagc gcctcgggga gtttgcctac ggaaagcggc ataaggacat  16920
gctggcgttg ccgctggacg agggcaaccc aacacctagc ctaaagcccg taacactgca  16980
gcaggtgctg cccgcgcttg caccgtccga agaaaagcgc ggcctaaagc gcgagtctgg  17040
tgacttggca cccaccgtgc agctgatggt acccaagcgc cagcgactgg aagatgtctt  17100
ggaaaaaatg accgtggaac ctgggctgga gcccgaggtc cgcgtgcggc caatcaagca  17160
ggtggcgccg ggactgggcg tgcagaccgt ggacgttcag atacccacta ccagtagcac  17220
cagtattgcc accgccacag agggcatgga gacacaaacg tccccggttg cctcagcggt  17280
ggcggatgcc gcggtgcagg cggtcgctgc ggccgcgtcc aagacctcta cggaggtgca  17340
aacggacccg tggatgtttc gcgtttcagc cccccggcgc ccgcgcggtt cgaggaagta  17400
cggcgccgcc agcgcgctac tgcccgaata tgccctacat ccttccattg cgcctacccc  17460
cggctatcgt ggctacacct accgccccag aagacgagca actacccgac gccgaaccac  17520
cactggaacc cgccgccgcc gtcgccgtcg ccagcccgtg ctggccccga tttccgtgcg  17580
cagggtggct cgcgaaggag gcaggaccct ggtgctgcca acagcgcgct accaccccag  17640
catcgtttaa aagccggtct ttgtggttct tgcagatatg gccctcacct gccgcctccg  17700
tttcccggtg ccgggattcc gaggaagaat gcaccgtagg aggggcatgg ccggccacgg  17760
cctgacgggc ggcatgcgtc gtgcgcacca ccggcggcgg cgcgcgtcgc accgtcgcat  17820
gcgcggcggt atcctgcccc tccttattcc actgatcgcc gcggcgattg gcgccgtgcc  17880
cggaattgca tccgtggcct tgcaggcgca gagacactga ttaaaaacaa gttgcatgtg  17940
gaaaaatcaa aataaaaagt ctggactctc acgctcgctt ggtcctgtaa ctattttgta  18000
gaatggaaga catcaacttt gcgtctctgg ccccgcgaca cggctcgcgc ccgttcatgg  18060
gaaactggca agatatcggc accagcaata tgagcggtgg cgccttcagc tggggctcgc  18120
tgtggagcgg cattaaaaat ttcggttcca ccgttaagaa ctatggcagc aaggcctgga  18180
acagcagcac aggccagatg ctgagggata agttgaaaga gcaaaatttc caacaaaagg  18240
tggtagatgg cctggcctct ggcattagcg gggtggtgga cctggccaac caggcagtgc  18300
aaaataagat taacagtaag cttgatcccc gccctcccgt agaggagcct ccaccggccg  18360
tggagacagt gtctccagag gggcgtggcg aaaagcgtcc gcgccccgac agggaagaaa  18420
ctctggtgac gcaaatagac gagcctccct cgtacgagga ggcactaaag caaggcctgc  18480
ccaccacccg tcccatcgcg cccatggcta ccggagtgct gggccagcac acacccgtaa  18540
cgctggacct gcctcccccc gccgacaccc agcagaaacc tgtgctgcca ggcccgaccg  18600
ccgttgttgt aacccgtcct agccgcgcgt ccctgcgccg cgccgccagc ggtccgcgat  18660
cgttgcggcc cgtagccagt ggcaactggc aaagcacact gaacagcatc gtgggtctgg  18720
gggtgcaatc cctgaagcgc cgacgatgct tctgaatagc taacgtgtcg tatgtgtgtc  18780
atgtatgcgt ccatgtcgcc gccagaggag ctgctgagcc gccgcgcgcc cgctttccaa  18840
gatggctacc ccttcgatga tgccgcagtg gtcttacatg cacatctcgg gccaggacgc  18900
ctcggagtac ctgagccccg ggctggtgca gtttgcccgc gccaccgaga cgtacttcag  18960
cctgaataac aagtttagaa accccacggt ggcgcctacg cacgacgtga ccacagaccg  19020
gtcccagcgt ttgacgctgc ggttcatccc tgtggaccgt gaggatactg cgtactcgta  19080
caaggcgcgg ttcaccctag ctgtgggtga taaccgtgtg ctggacatgg cttccacgta  19140
```

-continued

```
ctttgacatc cgcggcgtgc tggacagggg ccctactttt aagccctact ctggcactgc  19200
ctacaacgcc ctggctccca agggtgcccc aaatccttgc gaatgggatg aagctgctac  19260
tgctcttgaa ataaacctag aagaagagga cgatgacaac gaagacgaag tagacgagca  19320
agctgagcag caaaaaactc acgtatttgg gcaggcgcct tattctggta taaatattac  19380
aaaggagggt attcaaatag gtgtcgaagg tcaaacacct aaatatgccg ataaaacatt  19440
tcaacctgaa cctcaaatag gagaatctca gtggtacgaa actgaaatta atcatgcagc  19500
tgggagagtc cttaaaaaga ctaccccaat gaaaccatgt tacggttcat atgcaaaacc  19560
cacaaatgaa aatggagggc aaggcattct tgtaaagcaa caaaatggaa agctagaaag  19620
tcaagtggaa atgcaatttt tctcaactac tgaggcgacc gcaggcaatg gtgataactt  19680
gactcctaaa gtggtattgt acagtgaaga tgtagatata gaaaccccag acactcatat  19740
ttcttacatg cccactatta aggaaggtaa ctcacgagaa ctaatgggcc aacaatctat  19800
gcccaacagg cctaattaca ttgcttttag ggacaatttt attggtctaa tgtattacaa  19860
cagcacgggt aatatgggtg ttctggcggg ccaagcatcg cagttgaatg ctgttgtaga  19920
tttgcaagac agaaacacag agctttcata ccagcttttg cttgattcca ttggtgatag  19980
aaccaggtac ttttctatgt ggaatcaggc tgttgacagc tatgatccag atgttagaat  20040
tattgaaaat catggaactg aagatgaact tccaaattac tgctttccac tgggaggtgt  20100
gattaataca gagactctta ccaaggtaaa acctaaaaca ggtcaggaaa atggatggga  20160
aaaagatgct acagaatttt cagataaaaa tgaaataaga gttggaaata attttgccat  20220
ggaaatcaat ctaaatgcca acctgtggag aaatttcctg tactccaaca tagcgctgta  20280
tttgcccgac aagctaaagt acagtccttc caacgtaaaa atttctgata acccaaacac  20340
ctacgactac atgaacaagc gagtggtggc tcccgggtta gtggactgct acattaacct  20400
tggagcacgc tggtcccttg actatatgga caacgtcaac ccatttaacc accaccgcaa  20460
tgctggcctg cgctaccgct caatgttgct gggcaatggt cgctatgtgc ccttccacat  20520
ccaggtgcct cagaagttct ttgccattaa aaacctcctt ctcctgccgg gctcatacac  20580
ctacgagtgg aacttcagga aggatgttaa catggttctg cagagctccc taggaaatga  20640
cctaagggtt gacggagcca gcattaagtt tgatagcatt tgcctttacg ccaccttctt  20700
ccccatggcc cacaacaccg cctccacgct tgaggccatg cttagaaacg acaccaacga  20760
ccagtccttt aacgactatc tctccgccgc caacatgctc taccctatac ccgccaacgc  20820
taccaacgtg cccatatcca tcccctcccg caactgggcg gctttccgcg gctgggcctt  20880
cacgcgcctt aagactaagg aaaccccatc actgggctcg ggctacgacc cttattacac  20940
ctactctggc tctataccct acctagatgg aaccttttac ctcaaccaca cctttaagaa  21000
ggtggccatt acctttgact cttctgtcag ctggcctggc aatgaccgcc tgcttacccc  21060
caacgagttt gaaattaagc gctcagttga cggggagggt tacaacgttg cccagtgtaa  21120
catgaccaaa gactggttcc tggtacaaat gctagctaac tacaacattg gctaccaggg  21180
cttctatatc ccagagagct acaaggaccg catgtactcc ttctttagaa acttccagcc  21240
catgagccgt caggtggtgg atgatactaa atacaaggac taccaacagg tgggcatcct  21300
acaccaacac aacaactctg gatttgttgg ctaccttgcc cccaccatgc gcgaaggaca  21360
ggcctaccct gctaacttcc cctatccgct tataggcaag accgcagttg acagcattac  21420
ccagaaaaag tttctttgcg atcgcaccct ttggcgcatc ccattctcca gtaactttat  21480
gtccatgggc gcactcacag acctgggcca aaaccttctc tacgccaact ccgcccacgc  21540
```

-continued

```
gctagacatg acttttgagg tggatcccat ggacgagccc acccttcttt atgttttgtt  21600
tgaagtcttt gacgtggtcc gtgtgcaccg gccgcaccgc ggcgtcatcg aaaccgtgta  21660
cctgcgcacg cccttctcgg ccggcaacgc cacaacataa agaagcaagc aacatcaaca  21720
acagctgccg ccatgggctc cagtgagcag gaactgaaag ccattgtcaa agatcttggt  21780
tgtgggccat atttttggg cacctatgac aagcgctttc caggctttgt ttctccacac  21840
aagctcgcct gcgccatagt caatacggcc ggtcgcgaga ctgggggcgt acactggatg  21900
gcctttgcct ggaacccgca ctcaaaaaca tgctacctct ttgagccctt tggcttttct  21960
gaccagcgac tcaagcaggt ttaccagttt gagtacgagt cactcctgcg ccgtagcgcc  22020
attgcttctt cccccgaccg ctgtataacg ctggaaaagt ccacccaaag cgtacagggg  22080
cccaactcgg ccgcctgtgg actattctgc tgcatgtttc tccacgcctt tgccaactgg  22140
ccccaaactc ccatggatca caaccccacc atgaacctta ttaccggggt acccaactcc  22200
atgctcaaca gtccccaggt acagcccacc ctgcgtcgca accaggaaca gctctacagc  22260
ttcctggagc gccactcgcc ctacttccgc agccacagtg cgcagattag gagcgccact  22320
tctttttgtc acttgaaaaa catgtaaaaa taatgtacta gagacacttt caataaaggc  22380
aaatgctttt atttgtacac tctcgggtga ttatttaccc ccacccttgc cgtctgcgcc  22440
gtttaaaaat caaaggggtt ctgccgcgca tcgctatgcg ccactggcag ggacacgttg  22500
cgatactggt gtttagtgct ccacttaaac tcaggcacaa ccatccgcgg cagctcggtg  22560
aagttttcac tccacaggct gcgcaccatc accaacgcgt ttagcaggtc gggcgccgat  22620
atcttgaagt cgcagttggg gcctccgccc tgcgcgcgcg agttgcgata cacagggttg  22680
cagcactgga acactatcag cgccgggtgg tgcacgctgg ccagcacgct cttgtcggag  22740
atcagatccg cgtccaggtc ctccgcgttg ctcagggcga acggagtcaa ctttggtagc  22800
tgccttccca aaaagggcgc gtgcccaggc tttgagttgc actcgcaccg tagtggcatc  22860
aaaaggtgac cgtgcccggt ctgggcgtta ggatacagcg cctgcataaa agccttgatc  22920
tgcttaaaag ccacctgagc ctttgcgcct tcagagaaga acatgccgca agacttgccg  22980
gaaaactgat tggccggaca ggccgcgtcg tgcacgcagc accttgcgtc ggtgttggag  23040
atctgcacca catttcggcc ccaccggttc ttcacgatct tggccttgct agactgctcc  23100
ttcagcgcgc gctgcccgtt ttcgctcgtc acatccattt caatcacgtg ctccttattt  23160
atcataatgc ttccgtgtag acacttaagc tcgccttcga tctcagcgca gcggtgcagc  23220
cacaacgcgc agcccgtggg ctcgtgatgc ttgtaggtca cctctgcaaa cgactgcagg  23280
tacgcctgca ggaatcgccc catcatcgtc acaaaggtct tgttgctggt gaaggtcagc  23340
tgcaacccgc ggtgctcctc gttcagccag gtcttgcata cggccgccag agcttccact  23400
tggtcaggca gtagtttgaa gttcgccttt agatcgttat ccacgtggta cttgtccatc  23460
agcgcgcgcg cagcctccat gcccttctcc cacgcagaca cgatcggcac actcagcggg  23520
ttcatcaccg taatttcact ttccgcttcg ctgggctctt cctcttcctc ttgcgtccgc  23580
ataccacgcg ccactgggtc gtcttcattc agccgccgca ctgtgcgctt acctcctttg  23640
ccatgcttga ttagcaccgg tgggttgctg aaacccacca tttgtagcgc cacatcttct  23700
ctttcttcct cgctgtccac gattacctct ggtgatggcg ggcgctcggg cttgggagaa  23760
gggcgcttct ttttcttctt gggcgcaatg gccaaatccg ccgccgaggt cgatggccgc  23820
gggctgggtg tgcgcggcac cagcgcgtct tgtgatgagt cttcctcgtc ctcggactcg  23880
```

-continued

```
atacgccgcc tcatccgctt ttttgggggc gcccggggag gcggcggcga cggggacggg  23940
gacgacacgt cctccatggt tgggggacgt cgcgccgcac cgcgtccgcg ctcgggggtg  24000
gtttcgcgct gctcctcttc ccgactggcc atttccttct cctataggca gaaaaagatc  24060
atggagtcag tcgagaagaa ggacagccta accgcccccct ctgagttcgc caccaccgcc  24120
tccaccgatg ccgccaacgc gcctaccacc ttccccgtcg aggcaccccc gcttgaggag  24180
gaggaagtga ttatcgagca ggacccaggt tttgtaagcg aagacgacga ggaccgctca  24240
gtaccaacag aggataaaaa gcaagaccag gacaacgcag aggcaaacga ggaacaagtc  24300
gggcgggggg acgaaaggca tggcgactac ctagatgtgg gagacgacgt gctgttgaag  24360
catctgcagc gccagtgcgc cattatctgc gacgcgttgc aagagcgcag cgatgtgccc  24420
ctcgccatag cggatgtcag ccttgcctac gaacgccacc tattctcacc gcgcgtaccc  24480
cccaaacgcc aagaaaacgg cacatgcgag cccaacccgc gcctcaactt ctaccccgta  24540
tttgccgtgc cagaggtgct tgccacctat cacatctttt tccaaaactg caagataccc  24600
ctatcctgcc gtgccaaccg cagccgagcg gacaagcagc tggccttgcg gcagggcgct  24660
gtcatacctg atatcgcctc gctcaacgaa gtgccaaaaa tctttgaggg tcttggacgc  24720
gacgagaagc gcgcggcaaa cgctctgcaa caggaaaaca gcgaaaatga aagtcactct  24780
ggagtgttgg tggaactcga gggtgacaac gcgcgcctag ccgtactaaa acgcagcatc  24840
gaggtcaccc actttgccta cccggcactt aacctacccc ccaaggtcat gagcacagtc  24900
atgagtgagc tgatcgtgcg ccgtgcgcag cccctggaga gggatgcaaa tttgcaagaa  24960
caaacagagg agggcctacc cgcagttggc gacgagcagc tagcgcgctg gcttcaaacg  25020
cgcgagcctg ccgacttgga ggagcgacgc aaactaatga tggccgcagt gctcgttacc  25080
gtggagcttg agtgcatgca gcggttcttt gctgacccgg agatgcagcg caagctagag  25140
gaaacattgc actacacctt tcgacagggc tacgtacgcc aggcctgcaa gatctccaac  25200
gtggagctct gcaacctggt ctcctacctt ggaattttgc acgaaaaccg ccttgggcaa  25260
aacgtgcttc attccacgct caagggcgag gcgcgccgcg actacgtccg cgactgcgtt  25320
tacttatttc tatgctacac ctggcagacg gccatgggcg tttggcagca gtgcttggag  25380
gagtgcaacc tcaaggagct gcagaaactg ctaaagcaaa acttgaagga cctatggacg  25440
gccttcaacg agcgctccgt ggccgcgcac ctggcggaca tcattttccc cgaacgcctg  25500
cttaaaaccc tgcaacaggg tctgccagac ttcaccagtc aaagcatgtt gcagaacttt  25560
aggaacttta tcctagagcg ctcaggaatc ttgcccgcca cctgctgtgc acttcctagc  25620
gactttgtgc ccattaagta ccgcgaatgc cctccgccgc tttggggcca ctgctacctt  25680
ctgcagctag ccaactacct tgcctaccac tctgacataa tggaagacgt gagcggtgac  25740
ggtctactgg agtgtcactg tcgctgcaac ctatgcaccc cgcaccgctc cctggtttgc  25800
aattcgcagc tgcttaacga aagtcaaatt atcggtacct ttgagctgca gggtccctcg  25860
cctgacgaaa agtccgcggc tccggggttg aaactcactc cggggctgtg gacgtcggct  25920
taccttcgca aatttgtacc tgaggactac cacgcccacg agattaggtt ctacgaagac  25980
caatcccgcc cgccaaatgc ggagcttacc gcctgcgtca ttacccaggg ccacattctt  26040
ggccaattgc aagccatcaa caaagcccgc caagagtttc tgctacgaaa gggacggggg  26100
gtttacttgg acccccagtc cggcgaggag ctcaacccaa tccccccgcc gccgcagccc  26160
tatcagcagc agccgcgggc ccttgcttcc caggatggca cccaaaaaga agctgcagct  26220
gccgccgcca cccacggacg aggaggaata ctgggacagt caggcagagg aggttttgga  26280
```

cgaggaggag gaggacatga tggaagactg ggagagccta gacgaggaag cttccgaggt 26340
cgaagaggtg tcagacgaaa caccgtcacc ctcggtcgca ttcccctcgc cggcgcccca 26400
gaaatcggca accggttcca gcatggctac aacctccgct cctcaggcgc cgccggcact 26460
gcccgttcgc cgacccaacc gtagatggga caccactgga accagggccg gtaagtccaa 26520
gcagccgccg ccgttagccc aagagcaaca acagcgccaa ggctaccgct catggcgcgg 26580
gcacaagaac gccatagttg cttgcttgca agactgtggg ggcaacatct ccttcgcccg 26640
ccgctttctt ctctaccatc acggcgtggc cttcccccgt aacatcctgc attactaccg 26700
tcatctctac agcccatact gcaccggcgg cagcggcagc ggcagcaaca gcagcggcca 26760
cacagaagca aaggcgaccg gatagcaaga ctctgacaaa gcccaagaaa tccacagcgg 26820
cggcagcagc aggaggagga gcgctgcgtc tggcgcccaa cgaacccgta tcgacccgcg 26880
agcttagaaa caggattttt cccactctgt atgctatatt tcaacagagc aggggccaag 26940
aacaagagct gaaaataaaa aacaggtctc tgcgatccct cacccgcagc tgcctgtatc 27000
acaaaagcga agatcagctt cggcgcacgc tggaagacgc ggaggctctc ttcagtaaat 27060
actgcgcgct gactcttaag gactagtttc gcgccctttc tcaaatttaa gcgcgaaaac 27120
tacgtcatct ccagcggcca cacccggcgc cagcacctgt cgtcagcgcc attatgagca 27180
aggaaattcc cacgccctac atgtggagtt accagccaca aatgggactt gcggctggag 27240
ctgcccaaga ctactcaacc cgaataaact acatgagcgc gggaccccac atgatatccc 27300
gggtcaacgg aatccgcgcc caccgaaacc gaattctctt ggaacaggcg gctattacca 27360
ccacacctcg taataacctt aatccccgta gttggcccgc tgccctggtg taccaggaaa 27420
gtcccgctcc caccactgtg gtacttccca gagacgccca ggccgaagtt cagatgacta 27480
actcaggggc gcagcttgcg ggcggctttc gtcacagggt gcggtcgccc gggcagggta 27540
taactcacct gacaatcaga gggcgaggta ttcagctcaa cgacgagtcg gtgagctcct 27600
cgcttggtct ccgtccggac gggacatttc agatcggcgg cgccggccgt ccttcattca 27660
cgcctcgtca ggcaatccta actctgcaga cctcgtcctc tgagccgcgc tctggaggca 27720
ttggaactct gcaatttatt gaggagtttg tgccatcggt ctactttaac cccttctcgg 27780
gacctcccgg ccactatccg gatcaattta ttcctaactt tgacgcggta aaggactcgg 27840
cggacggcta cgactgaatg ttaagtggag aggcagagca actgcgcctg aaacacctgg 27900
tccactgtcg ccgccacaag tgctttgccc gcgactccgg tgagttttgc tactttgaat 27960
tgcccgagga tcatatcgag ggcccggcgc acggcgtccg gcttaccgcc cagggagagc 28020
ttgcccgtag cctgattcgg gagtttaccc agcgccccct gctagttgag cgggacaggg 28080
gaccctgtgt tctcactgtg atttgcaact gtcctaacct tggattacat caagatcttt 28140
gttgccatct ctgtgctgag tataataaat acagaaatta aaatatactg gggctcctat 28200
cgccatcctg taaacgccac cgtcttcacc cgcccaagca aaccaaggcg aaccttacct 28260
ggtactttta acatctctcc ctctgtgatt tacaacagtt tcaacccaga cggagtgagt 28320
ctacgagaga acctctccga gctcagctac tccatcagaa aaaacaccac cctccttacc 28380
tgccgggaac gtacgagtgc gtcaccggcc gctgcaccac acctaccgcc tgaccgtaaa 28440
ccagactttt tccggacaga cctcaataac tctgtttacc agaacaggag gtgagcttag 28500
aaaaccctta gggtattagg ccaaaggcgc agctactgtg ggtttatga acaattcaag 28560
caactctacg ggctattcta attcaggttt ctctagaatc ggggttgggg ttattctctg 28620

-continued

```
tcttgtgatt ctctttattc ttatactaac gcttctctgc ctaaggctcg ccgcctgctg  28680
tgtgcacatt tgcatttatt gtcagctttt taaacgctgg ggtcgccacc caagatgatt  28740
aggtacataa tcctaggttt actcaccctt gcgtcagccc acggtaccac ccaaaaggtg  28800
gattttaagg agccagcctg taatgttaca ttcgcagctg aagctaatga gtgcaccact  28860
cttataaaat gcaccacaga acatgaaaag ctgcttattc gccacaaaaa caaaattggc  28920
aagtatgctg tttatgctat ttggcagcca ggtgacacta cagagtataa tgttacagtt  28980
ttccagggta aaagtcataa aacttttatg tatacttttc cattttatga aatgtgcgac  29040
attaccatgt acatgagcaa acagtataag ttgtggcccc cacaaaattg tgtggaaaac  29100
actggcactt tctgctgcac tgctatgcta attacagtgc tcgctttggt ctgtacccta  29160
ctctatatta aatacaaaag cagacgcagc tttattgagg aaaagaaaat gccttaattt  29220
actaagttac aaagctaatg tcaccactaa ctgctttact cgctgcttgc aaaacaaatt  29280
caaaaagtta gcattataat tagaatagga tttaaacccc ccggtcattt cctgctcaat  29340
accattcccc tgaacaattg actctatgtg ggatatgctc cagcgctaca accttgaagt  29400
caggcttcct ggatgtcagc atctgacttt ggccagcacc tgtcccgcgg atttgttcca  29460
gtccaactac agcgacccac cctaacagag atgaccaaca caaccaacgc ggccgccgct  29520
accggactta catctaccac aaatacaccc caagtttctg cctttgtcaa taactgggat  29580
aacttgggca tgtggtggtt ctccatagcg cttatgtttg tatgccttat tattatgtgg  29640
ctcatctgct gcctaaagcg caaacgcgcc cgaccaccca tctatagtcc catcattgtg  29700
ctacacccaa acaatgatgg aatccataga ttggacggac tgaaacacat gttcttttct  29760
cttacagtat gattaaatga gacatgattc ctcgagtttt tatattactg acccttgttg  29820
cgcttttttg tgcgtgctcc acattggctg cggtttctca catcgaagta gactgcattc  29880
cagccttcac agtctatttg ctttacggat ttgtcaccct cacgctcatc tgcagcctca  29940
tcactgtggt catcgccttt atccagtgca ttgactgggt ctgtgtgcgc tttgcatatc  30000
tcagacacca tccccagtac agggacagga ctatagctga gcttcttaga attctttaat  30060
tatgaaattt actgtgactt ttctgctgat tatttgcacc ctatctgcgt tttgttcccc  30120
gacctccaag cctcaaagac atatatcatg cagattcact cgtatatgga atattccaag  30180
ttgctacaat gaaaaaagcg atctttccga agcctggtta tatgcaatca tctctgttat  30240
ggtgttctgc agtaccatct tagccctagc tatatatccc taccttgaca ttggctggaa  30300
acgaatagat gccatgaacc acccaacttt ccccgcgccc gctatgcttc cactgcaaca  30360
agttgttgcc ggcggctttg tcccagccaa tcagcctcgc ccccacttctc ccacccccac  30420
tgaaatcagc tactttaatc taacaggagg agatgactga caccctagat ctagaaatgg  30480
acggaattat tacagagcag cgcctgctag aaagacgcag ggcagcggcc gagcaacagc  30540
gcatgaatca agagctccaa gacatggtta acttgcacca gtgcaaaagg ggtatctttt  30600
gtctggtaaa gcaggccaaa gtcacctacg acagtaatac caccggacac cgccttagct  30660
acaagttgcc aaccaagcgt cagaaattgg tggtcatggt gggagaaaag cccattacca  30720
taactcagca ctcggtagaa accgaaggct gcattcactc accttgtcaa ggacctgagg  30780
atctctgcac ccttattaag accctgtgcg gtctcaaaga tcttattccc tttaactaat  30840
aaaaaaaaat aataaagcat cacttactta aaatcagtta gcaaatttct gtccagttta  30900
ttcagcagca cctccttgcc ctcctcccag ctctggtatt gcagcttcct cctggctgca  30960
aactttctcc acaatctaaa tggaatgtca gtttcctcct gttcctgtcc atccgcaccc  31020
```

-continued

```
actatcttca tgttgttgca gatgaagcgc gcaagaccgt ctgaagatac cttcaacccc  31080
gtgtatccat atgacacgga aaccggtcct ccaactgtgc cttttcttac tcctcccttt  31140
gtatccccca atgggtttca agagagtccc cctggggtac tctctttgcg cctatccgaa  31200
cctctagtta cctccaatgg catgcttgcg ctcaaaatgg gcaacggcct ctctctggac  31260
gaggccggca accttacctc ccaaaatgta accactgtga gcccacctct caaaaaaacc  31320
aagtcaaaca taaacctgga aatatctgca cccctcacag ttacctcaga agccctaact  31380
gtggctgccg ccgcacctct aatggtcgcg ggcaacacac tcaccatgca atcacaggcc  31440
ccgctaaccg tgcacgactc caaacttagc attgccaccc aaggacccct cacagtgtca  31500
gaaggaaagc tagccctgca aacatcaggc cccctcacca ccaccgatag cagtaccctt  31560
actatcactg cctcaccccc tctaactact gccactggta gcttgggcat tgacttgaaa  31620
gagcccattt atacacaaaa tggaaaacta ggactaaagt acggggctcc tttgcatgta  31680
acagacgacc taaacacttt gaccgtagca actggtccag gtgtgactat taataatact  31740
tccttgcaaa ctaaagttac tggagccttg ggttttgatt cacaaggcaa tatgcaactt  31800
aatgtagcag gaggactaag gattgattct caaaacagac gccttatact tgatgttagt  31860
tatccgtttg atgctcaaaa ccaactaaat ctaagactag gacagggccc tctttttata  31920
aactcagccc acaacttgga tattaactac aacaaaggcc tttacttgtt tacagcttca  31980
aacaattcca aaaagcttga ggttaaccta agcactgcca aggggttgat gtttgacgct  32040
acagccatag ccattaatgc aggagatggg cttgaatttg gttcacctaa tgcaccaaac  32100
acaaatcccc tcaaaacaaa aattggccat ggcctagaat ttgattcaaa caaggctatg  32160
gttcctaaac taggaactgg ccttagtttt gacagcacag gtgccattac agtaggaaac  32220
aaaaataatg ataagctaac tttgtggacc acaccagctc catctcctaa ctgtagacta  32280
aatgcagaga aagatgctaa actcactttg gtcttaacaa aatgtggcag tcaaatactt  32340
gctacagttt cagttttggc tgttaaaggc agtttggctc caatatctgg aacagttcaa  32400
agtgctcatc ttattataag atttgacgaa aatggagtgc tactaaacaa ttccttcctg  32460
gacccagaat attggaactt tagaaatgga gatcttactg aaggcacagc ctatacaaac  32520
gctgttggat ttatgcctaa cctatcagct tatccaaaat ctcacggtaa aactgccaaa  32580
agtaacattg tcagtcaagt ttacttaaac ggagacaaaa ctaaacctgt aacactaacc  32640
attacactaa acggtacaca ggaaacagga gacacaactc caagtgcata ctctatgtca  32700
ttttcatggg actggtctgg ccacaactac attaatgaaa tatttgccac atcctcttac  32760
actttttcat acattgccca agaataaaga atcgtttgtg ttatgtttca acgtgtttat  32820
ttttcaattg cagaaaattt caagtcattt ttcattcagt agtatagccc caccaccaca  32880
tagcttatac agatcaccgt accttaatca aactcacaga accctagtat tcaacctgcc  32940
acctccctcc caacacacag agtacacagt cctttctccc cggctggcct taaaaagcat  33000
catatcatgg gtaacagaca tattcttagg tgttatattc cacacggttt cctgtcgagc  33060
caaacgctca tcagtgatat taataaactc cccgggcagc tcacttaagt tcatgtcgct  33120
gtccagctgc tgagccacag gctgctgtcc aacttgcggt tgcttaacgg gcggcgaagg  33180
agaagtccac gcctacatgg gggtagagtc ataatcgtgc atcaggatag ggcggtggtg  33240
ctgcagcagc gcgcgaataa actgctgccg ccgccgctcc gtcctgcagg aatacaacat  33300
ggcagtggtc tcctcagcga tgattcgcac cgcccgcagc ataaggcgcc ttgtcctccg  33360
```

-continued

```
ggcacagcag cgcaccctga tctcacttaa atcagcacag taactgcagc acagcaccac  33420
aatattgttc aaaatcccac agtgcaaggc gctgtatcca aagctcatgg cggggaccac  33480
agaacccacg tggccatcat accacaagcg caggtagatt aagtggcgac ccctcataaa  33540
cacgctggac ataaacatta cctcttttgg catgttgtaa ttcaccacct cccggtacca  33600
tataaacctc tgattaaaca tggcgccatc caccaccatc ctaaaccagc tggccaaaac  33660
ctgcccgccg gctatacact gcagggaacc gggactggaa caatgacagt ggagagccca  33720
ggactcgtaa ccatggatca tcatgctcgt catgatatca atgttggcac aacacaggca  33780
cacgtgcata cacttcctca ggattacaag ctcctcccgc gttagaacca tatcccaggg  33840
aacaacccat tcctgaatca gcgtaaatcc cacactgcag ggaagacctc gcacgtaact  33900
cacgttgtgc attgtcaaag tgttacattc gggcagcagc ggatgatcct ccagtatggt  33960
agcgcgggtt tctgtctcaa aaggaggtag acgatcccta ctgtacggag tgcgccgaga  34020
caaccgagat cgtgttggtc gtagtgtcat gccaaatgga acgccggacg tagtcatatt  34080
tcctgaagca aaaccaggtg cgggcgtgac aaacagatct gcgtctccgg tctcgccgct  34140
tagatcgctc tgtgtagtag ttgtagtata tccactctct caaagcatcc aggcgccccc  34200
tggcttcggg ttctatgtaa actccttcat gcgccgctgc cctgataaca tccaccaccg  34260
cagaataagc cacacccagc caacctacac attcgttctg cgagtcacac acgggaggag  34320
cgggaagagc tggaagaacc atgttttttt ttttattcca aaagattatc caaaacctca  34380
aaatgaagat ctattaagtg aacgcgctcc cctccggtgg cgtggtcaaa ctctacagcc  34440
aaagaacaga taatggcatt tgtaagatgt tgcacaatgg cttccaaaag gcaaacggcc  34500
ctcacgtcca agtggacgta aaggctaaac ccttcagggt gaatctcctc tataaacatt  34560
ccagcacctt caaccatgcc caaataattc tcatctcgcc accttctcaa tatatctcta  34620
agcaaatccc gaatattaag tccggccatt gtaaaaatct gctccagagc gccctccacc  34680
ttcagcctca agcagcgaat catgattgca aaaattcagg ttcctcacag acctgtataa  34740
gattcaaaag cggaacatta acaaaaatac cgcgatcccg taggtccctt cgcagggcca  34800
gctgaacata atcgtgcagg tctgcacgga ccagcgcggc cacttccccg ccaggaacca  34860
tgacaaaaga acccacactg attatgacac gcatactcgg agctatgcta accagcgtag  34920
ccccgatgta agcttgttgc atgggcggcg atataaaatg caaggtgctg ctcaaaaaat  34980
caggcaaagc ctcgcgcaaa aaagaaagca catcgtagtc atgctcatgc agataaaggc  35040
aggtaagctc cggaaccacc acagaaaaag acaccatttt tctctcaaac atgtctgcgg  35100
gtttctgcat aaacacaaaa taaaataaca aaaaaacatt taaacattag aagcctgtct  35160
tacaacagga aaaacaaccc ttataagcat aagacggact acggccatgc cggcgtgacc  35220
gtaaaaaaac tggtcaccgt gattaaaaag caccaccgac agctcctcgg tcatgtccgg  35280
agtcataatg taagactcgg taaacacatc aggttgattc acatcggtca gtgctaaaaa  35340
gcgaccgaaa tagcccgggg gaatacatac ccgcaggcgt agagacaaca ttacagcccc  35400
cataggaggt ataacaaaat taataggaga gaaaaacaca taaacacctg aaaaaccctc  35460
ctgcctaggc aaaatagcac cctcccgctc cagaacaaca tacagcgctt ccacagcggc  35520
agccataaca gtcagcctta ccagtaaaaa agaaaaccta ttaaaaaaac accactcgac  35580
acggcaccag ctcaatcagt cacagtgtaa aaaagggcca agtgcagagc gagtatatat  35640
aggactaaaa aatgacgtaa cggttaaagt ccacaaaaaa cacccagaaa accgcacgcg  35700
aacctacgcc cagaaacgaa agccaaaaaa cccacaactt cctcaaatcg tcacttccgt  35760
```

```
tttcccacgt tacgtaactt cccattttaa gaaaactaca attcccaaca catacaagtt    35820

actccgccct aaaacctacg tcacccgccc cgttcccacg ccccgcgcca cgtcacaaac    35880

tccaccccct cattatcata ttggcttcaa tccaaaataa ggtatattat tgatgatg     35938
```

```
<210> SEQ ID NO 2
<211> LENGTH: 10
<212> TYPE: DNA
<213> ORGANISM: Artificial Sequence
<220> FEATURE:
<223> OTHER INFORMATION: Recombinant oncolytic serotype 5 adenovirus
      (Ad5)

<400> SEQUENCE: 2

ggtgttttgg                                                          10

<210> SEQ ID NO 3
<211> LENGTH: 10
<212> TYPE: DNA
<213> ORGANISM: Artificial Sequence
<220> FEATURE:
<223> OTHER INFORMATION: Recombinant oncolytic serotype 5 adenovirus
      (Ad5)

<400> SEQUENCE: 3

gactgtgcgc                                                          10

<210> SEQ ID NO 4
<211> LENGTH: 8
<212> TYPE: DNA
<213> ORGANISM: Unknown
<220> FEATURE:
<223> OTHER INFORMATION: Oncolytic serotype 5 adenovirus (Ad5)

<400> SEQUENCE: 4

ctgacctc                                                             8

<210> SEQ ID NO 5
<211> LENGTH: 8
<212> TYPE: DNA
<213> ORGANISM: Unknown
<220> FEATURE:
<223> OTHER INFORMATION: Oncolytic serotype 5 adenovirus (Ad5)

<400> SEQUENCE: 5

tcaccagg                                                             8

<210> SEQ ID NO 6
<211> LENGTH: 3
<212> TYPE: PRT
<213> ORGANISM: Artificial Sequence
<220> FEATURE:
<223> OTHER INFORMATION: protein linker

<400> SEQUENCE: 6

Ala Ala Tyr
1

<210> SEQ ID NO 7
<211> LENGTH: 46
<212> TYPE: DNA
<213> ORGANISM: Artificial Sequence
<220> FEATURE:
<223> OTHER INFORMATION: Recombinant oncolytic serotype 5 adenovirus
      (Ad5)
```

```
<400> SEQUENCE: 7

atcttggtta catctgacct cgtcgagtca ccaggcgctt ttccaa                    46


<210> SEQ ID NO 8
<211> LENGTH: 8
<212> TYPE: DNA
<213> ORGANISM: Artificial Sequence
<220> FEATURE:
<223> OTHER INFORMATION: Recombinant oncolytic serotype 5 adenovirus
      (Ad5)

<400> SEQUENCE: 8

cagtatga                                                               8


<210> SEQ ID NO 9
<211> LENGTH: 10
<212> TYPE: DNA
<213> ORGANISM: Artificial Sequence
<220> FEATURE:
<223> OTHER INFORMATION: Recombinant oncolytic serotype 5 adenovirus
      (Ad5)

<400> SEQUENCE: 9

taataaaaaa                                                            10


<210> SEQ ID NO 10
<211> LENGTH: 17
<212> TYPE: PRT
<213> ORGANISM: Artificial Sequence
<220> FEATURE:
<223> OTHER INFORMATION: mutant catenin alpha-2

<400> SEQUENCE: 10

Asp Pro Cys Ser Ser Val Lys Arg Ser Thr Met Val Arg Ala Ala Arg
1               5                   10                  15

Ala


<210> SEQ ID NO 11
<211> LENGTH: 8
<212> TYPE: DNA
<213> ORGANISM: Unknown
<220> FEATURE:
<223> OTHER INFORMATION: Oncolytic serotype 5 adenovirus (Ad5)

<400> SEQUENCE: 11

tgccttaa                                                               8


<210> SEQ ID NO 12
<211> LENGTH: 11
<212> TYPE: DNA
<213> ORGANISM: Unknown
<220> FEATURE:
<223> OTHER INFORMATION: Oncolytic serotype 5 adenovirus (Ad5)

<400> SEQUENCE: 12

taaaaaaaaa t                                                          11


<210> SEQ ID NO 13
<211> LENGTH: 553
<212> TYPE: DNA
<213> ORGANISM: Unknown
<220> FEATURE:
<223> OTHER INFORMATION: internal ribosome entry site (IRES)

<400> SEQUENCE: 13
```

-continued

```
taacgttact ggccgaagcc gcttggaata aggccggtgt gcgtttgtct atatgttatt      60

ttccaccata ttgccgtctt ttggcaatgt gagggcccgg aaacctggcc ctgtcttctt     120

gacgagcatt cctaggggtc tttcccctct cgccaaagga atgcaaggtc tgttgaatgt     180

cgtgaaggaa gcagttcctc tggaagcttc ttgaagacaa acaacgtctg tagcgaccct     240

ttgcaggcag cggaaccccc cacctggcga caggtgcctc tgcggccaaa agccacgtgt     300

ataagataca cctgcaaagg cggcacaacc ccagtgccac gttgtgagtt ggatagttgt     360

ggaaagagtc aaatggctct cctcaagcgt attcaacaag gggctgaagg atgcccagaa     420

ggtaccccat tgtatgggat ctgatctggg gcctcggtgc acatgcttta catgtgttta     480

gtcgaggtta aaaaacgtct aggccccccg aaccacgggg acgtggtttt cctttgaaaa     540

acacgatgat aat                                                        553
```

<210> SEQ ID NO 14
<211> LENGTH: 390
<212> TYPE: PRT
<213> ORGANISM: Artificial Sequence
<220> FEATURE:
<223> OTHER INFORMATION: TGF beta trap fusion protein

<400> SEQUENCE: 14

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Pro
145                 150                 155                 160

Lys Ser Cys Asp Lys Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Lys Phe Asn Trp Tyr Val Asp Gly
    210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
```

```
            260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Ser Arg Asp Glu Leu Thr Lys Asn
    290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Tyr Ser Lys
            340                 345                 350

Leu Thr Val Asp Lys Ser Arg Trp Gln Gln Gly Asn Val Phe Ser Cys
        355                 360                 365

Ser Val Met His Glu Ala Leu His Asn His Tyr Thr Gln Lys Ser Leu
    370                 375                 380

Ser Leu Ser Pro Gly Lys
385                 390


<210> SEQ ID NO 15
<211> LENGTH: 402
<212> TYPE: PRT
<213> ORGANISM: Artificial Sequence
<220> FEATURE:
<223> OTHER INFORMATION: TGF beta trap fusion protein

<400> SEQUENCE: 15

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Lys
145                 150                 155                 160

Pro Ser Asn Thr Lys Val Asp Lys Arg Val Glu Pro Lys Ser Cys Asp
                165                 170                 175

Lys Thr His Thr Cys Pro Pro Cys Pro Ala Pro Glu Leu Leu Gly Gly
            180                 185                 190

Pro Ser Val Phe Leu Phe Pro Pro Lys Pro Lys Asp Thr Leu Met Ile
        195                 200                 205

Ser Arg Thr Pro Glu Val Thr Cys Val Val Val Asp Val Ser His Glu
    210                 215                 220

Asp Pro Glu Val Lys Phe Asn Trp Tyr Val Asp Gly Val Glu Val His
```

225 230 235 240

Asn Ala Lys Thr Lys Pro Arg Glu Glu Gln Tyr Asn Ser Thr Tyr Arg
245 250 255

Val Val Ser Val Leu Thr Val Leu His Gln Asp Trp Leu Asn Gly Lys
260 265 270

Glu Tyr Lys Cys Lys Val Ser Asn Lys Ala Leu Pro Ala Pro Ile Glu
275 280 285

Lys Thr Ile Ser Lys Ala Lys Gly Gln Pro Arg Glu Pro Gln Val Tyr
290 295 300

Thr Leu Pro Pro Ser Arg Asp Glu Leu Thr Lys Asn Gln Val Ser Leu
305 310 315 320

Thr Cys Leu Val Lys Gly Phe Tyr Pro Ser Asp Ile Ala Val Glu Trp
325 330 335

Glu Ser Asn Gly Gln Pro Glu Asn Asn Tyr Lys Thr Thr Pro Pro Val
340 345 350

Leu Asp Ser Asp Gly Ser Phe Phe Leu Tyr Ser Lys Leu Thr Val Asp
355 360 365

Lys Ser Arg Trp Gln Gln Gly Asn Val Phe Ser Cys Ser Val Met His
370 375 380

Glu Ala Leu His Asn His Tyr Thr Gln Lys Ser Leu Ser Leu Ser Pro
385 390 395 400

Gly Lys

<210> SEQ ID NO 16
<211> LENGTH: 97
<212> TYPE: DNA
<213> ORGANISM: Unknown
<220> FEATURE:
<223> OTHER INFORMATION: Oncolytic serotype 5 adenovirus (Ad5)

<400> SEQUENCE: 16
gttacatctg acctcgtcga catgactgaa tataaacttg tggtagttgg agctgatggc 60
gtaggcaaga gtgccctcga gtcaccaggc gcttttc 97

<210> SEQ ID NO 17
<211> LENGTH: 9
<212> TYPE: DNA
<213> ORGANISM: Unknown
<220> FEATURE:
<223> OTHER INFORMATION: Oncolytic serotype 5 adenovirus (Ad5)

<400> SEQUENCE: 17 ctaggactg 9

<210> SEQ ID NO 18
<211> LENGTH: 4
<212> TYPE: PRT
<213> ORGANISM: Unknown
<220> FEATURE:
<223> OTHER INFORMATION: furin cleavage site
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be Lys or Arg

<400> SEQUENCE: 18

Arg Xaa Xaa Arg

1

<210> SEQ ID NO 19
<211> LENGTH: 4
<212> TYPE: PRT
<213> ORGANISM: Unknown
<220> FEATURE:
<223> OTHER INFORMATION: furin cleavage site

<400> SEQUENCE: 19

Arg Ala Lys Arg
1

<210> SEQ ID NO 20
<211> LENGTH: 18
<212> TYPE: PRT
<213> ORGANISM: Artificial Sequence
<220> FEATURE:
<223> OTHER INFORMATION: exemplary cancer antigen derived from KRAS G12D

<400> SEQUENCE: 20

Met Thr Glu Tyr Lys Leu Val Val Val Gly Ala Asp Gly Val Gly Lys
1               5                   10                  15

Ser Ala

<210> SEQ ID NO 21
<211> LENGTH: 17
<212> TYPE: PRT
<213> ORGANISM: Homo sapiens

<400> SEQUENCE: 21

Asp Pro Cys Ser Ser Val Lys Arg Gly Thr Met Val Arg Ala Ala Arg
1               5                   10                  15

Ala

<210> SEQ ID NO 22
<211> LENGTH: 17
<212> TYPE: PRT
<213> ORGANISM: Artificial Sequence
<220> FEATURE:
<223> OTHER INFORMATION: mutant myosin-IIIb isoform 2

<400> SEQUENCE: 22

Leu Glu Leu Cys Asn Gly Gly Ser Leu Thr Glu Leu Val Lys Gly Leu
1               5                   10                  15

Leu

<210> SEQ ID NO 23
<211> LENGTH: 17
<212> TYPE: PRT
<213> ORGANISM: Homo sapiens

<400> SEQUENCE: 23

Leu Glu Leu Cys Asn Gly Gly Ser Val Thr Glu Leu Val Lys Gly Leu
1               5                   10                  15

Leu

<210> SEQ ID NO 24
<211> LENGTH: 17
<212> TYPE: PRT
<213> ORGANISM: Artificial Sequence
<220> FEATURE:
<223> OTHER INFORMATION: mutant sodium/calcium exchanger 3 isoform C
      precursor

```
<400> SEQUENCE: 24

Ser Thr Ile Val Gly Ser Ala Ala Val Asn Met Phe Ile Ile Ile Gly
1               5                   10                  15

Ile


<210> SEQ ID NO 25
<211> LENGTH: 17
<212> TYPE: PRT
<213> ORGANISM: Homo sapiens

<400> SEQUENCE: 25

Ser Thr Ile Val Gly Ser Ala Ala Phe Asn Met Phe Ile Ile Ile Gly
1               5                   10                  15

Ile


<210> SEQ ID NO 26
<211> LENGTH: 17
<212> TYPE: PRT
<213> ORGANISM: Artificial Sequence
<220> FEATURE:
<223> OTHER INFORMATION: mutant sodium-dependent neutral amino acid
      transporter B(0)AT1

<400> SEQUENCE: 26

Ile Phe Trp Gln Val Thr Trp Arg Met Val Ser Pro Leu Leu Met Leu
1               5                   10                  15

Ile


<210> SEQ ID NO 27
<211> LENGTH: 17
<212> TYPE: PRT
<213> ORGANISM: Homo sapiens

<400> SEQUENCE: 27

Ile Phe Trp Gln Val Thr Trp Arg Val Val Ser Pro Leu Leu Met Leu
1               5                   10                  15

Ile


<210> SEQ ID NO 28
<211> LENGTH: 17
<212> TYPE: PRT
<213> ORGANISM: Artificial Sequence
<220> FEATURE:
<223> OTHER INFORMATION: mutant double-stranded RNA-specific editase B2

<400> SEQUENCE: 28

Cys His Ala Glu Val Val Ala Arg Gln Ala Phe Leu His Phe Leu Tyr
1               5                   10                  15

Thr


<210> SEQ ID NO 29
<211> LENGTH: 17
<212> TYPE: PRT
<213> ORGANISM: Homo sapiens

<400> SEQUENCE: 29

Cys His Ala Glu Val Val Ala Arg Arg Ala Phe Leu His Phe Leu Tyr
1               5                   10                  15

Thr
```

-continued

<210> SEQ ID NO 30
<211> LENGTH: 17
<212> TYPE: PRT
<213> ORGANISM: Artificial Sequence
<220> FEATURE:
<223> OTHER INFORMATION: mutant T-complex protein 11 homolog

<400> SEQUENCE: 30

Leu Asn Lys Gln Pro Ser Leu Leu Ser His Thr Thr Lys Trp Leu Thr
1 5 10 15

Gln

<210> SEQ ID NO 31
<211> LENGTH: 17
<212> TYPE: PRT
<213> ORGANISM: Homo sapiens

<400> SEQUENCE: 31

Leu Asn Lys Gln Pro Ser Leu Leu Asn His Thr Thr Lys Trp Leu Thr
1 5 10 15

Gln

<210> SEQ ID NO 32
<211> LENGTH: 17
<212> TYPE: PRT
<213> ORGANISM: Artificial Sequence
<220> FEATURE:
<223> OTHER INFORMATION: mutant leucine-rich repeat and transmembrane
domain-containing protein 2 precursor

<400> SEQUENCE: 32

Leu Gly Leu Thr Thr Val Pro Pro Asn Val Pro Ala Ala Thr Arg Thr
1 5 10 15

Leu

<210> SEQ ID NO 33
<211> LENGTH: 17
<212> TYPE: PRT
<213> ORGANISM: Homo sapiens

<400> SEQUENCE: 33

Leu Gly Leu Thr Thr Val Pro Pro Asp Val Pro Ala Ala Thr Arg Thr
1 5 10 15

Leu

<210> SEQ ID NO 34
<211> LENGTH: 17
<212> TYPE: PRT
<213> ORGANISM: Artificial Sequence
<220> FEATURE:
<223> OTHER INFORMATION: mutant nuclear receptor subfamily 5 group A
member 2

<400> SEQUENCE: 34

Glu Ala Val Arg Ala Asp Arg Met Lys Gly Gly Arg Asn Lys Phe Gly
1 5 10 15

Pro

<210> SEQ ID NO 35
<211> LENGTH: 17
<212> TYPE: PRT
<213> ORGANISM: Homo sapiens

<400> SEQUENCE: 35

Glu Ala Val Arg Ala Asp Arg Met Arg Gly Gly Arg Asn Lys Phe Gly
1 5 10 15

Pro

<210> SEQ ID NO 36
<211> LENGTH: 17
<212> TYPE: PRT
<213> ORGANISM: Artificial Sequence
<220> FEATURE:
<223> OTHER INFORMATION: mutant prolactin-releasing peptide receptor

<400> SEQUENCE: 36

Cys Leu Leu Val Leu Val Ile Ala Trp Val Arg Arg Leu His Asn Val
1 5 10 15

Thr

<210> SEQ ID NO 37
<211> LENGTH: 17
<212> TYPE: PRT
<213> ORGANISM: Homo sapiens

<400> SEQUENCE: 37

Cys Leu Leu Val Leu Val Ile Ala Arg Val Arg Arg Leu His Asn Val
1 5 10 15

Thr

<210> SEQ ID NO 38
<211> LENGTH: 17
<212> TYPE: PRT
<213> ORGANISM: Artificial Sequence
<220> FEATURE:
<223> OTHER INFORMATION: mutant prolow-density lipoprotein receptor-
related protein 1 preproprotein

<400> SEQUENCE: 38

Lys Glu Asp Asp Cys Glu His Gly Lys Asp Glu Thr His Cys Asn Lys
1 5 10 15

Phe

<210> SEQ ID NO 39
<211> LENGTH: 17
<212> TYPE: PRT
<213> ORGANISM: Homo sapiens

<400> SEQUENCE: 39

Lys Glu Asp Asp Cys Glu His Gly Glu Asp Glu Thr His Cys Asn Lys
1 5 10 15

Phe

<210> SEQ ID NO 40
<211> LENGTH: 17
<212> TYPE: PRT
<213> ORGANISM: Artificial Sequence
<220> FEATURE:
<223> OTHER INFORMATION: mutant alpha-2-macroglobulin isoform a
precursor

<400> SEQUENCE: 40

Ser Gln Ser Leu Pro Ala Ser His Thr His Leu Arg Val Thr Ala Ala
1 5 10 15

Pro

<210> SEQ ID NO 41
<211> LENGTH: 17
<212> TYPE: PRT
<213> ORGANISM: Homo sapiens

<400> SEQUENCE: 41

```
Ser Gln Ser Leu Pro Ala Ser His Ala His Leu Arg Val Thr Ala Ala
1               5                   10                  15

Pro
```

<210> SEQ ID NO 42
<211> LENGTH: 17
<212> TYPE: PRT
<213> ORGANISM: Artificial Sequence
<220> FEATURE:
<223> OTHER INFORMATION: mutant RUS1 family protein C16orf58

<400> SEQUENCE: 42

```
Glu Leu Gln Gln Leu Val Glu Gly Gln Gln Glu Ser Tyr Leu Leu Cys
1               5                   10                  15

Trp
```

<210> SEQ ID NO 43
<211> LENGTH: 17
<212> TYPE: PRT
<213> ORGANISM: Homo sapiens

<400> SEQUENCE: 43

```
Glu Leu Gln Gln Leu Val Glu Gly His Gln Glu Ser Tyr Leu Leu Cys
1               5                   10                  15

Trp
```

<210> SEQ ID NO 44
<211> LENGTH: 17
<212> TYPE: PRT
<213> ORGANISM: Artificial Sequence
<220> FEATURE:
<223> OTHER INFORMATION: mutant tyrosine-protein kinase BAZ1B

<400> SEQUENCE: 44

```
Lys Arg Ser Ser Arg Arg Gln Ser Pro Glu Leu Gln Lys Cys Glu Glu
1               5                   10                  15

Ile
```

<210> SEQ ID NO 45
<211> LENGTH: 17
<212> TYPE: PRT
<213> ORGANISM: Homo sapiens

<400> SEQUENCE: 45

```
Lys Arg Ser Ser Arg Arg Gln Ser Leu Glu Leu Gln Lys Cys Glu Glu
1               5                   10                  15

Ile
```

<210> SEQ ID NO 46
<211> LENGTH: 17
<212> TYPE: PRT
<213> ORGANISM: Artificial Sequence
<220> FEATURE:
<223> OTHER INFORMATION: mutant phospholipid phosphatase 2

<400> SEQUENCE: 46

-continued

Arg Val Ser Asp Tyr Lys His His Arg Ser Asp Val Leu Val Gly Leu
1 5 10 15

Leu

<210> SEQ ID NO 47
<211> LENGTH: 17
<212> TYPE: PRT
<213> ORGANISM: Homo sapiens

<400> SEQUENCE: 47

Arg Val Ser Asp Tyr Lys His His Trp Ser Asp Val Leu Val Gly Leu
1 5 10 15

Leu

<210> SEQ ID NO 48
<211> LENGTH: 17
<212> TYPE: PRT
<213> ORGANISM: Artificial Sequence
<220> FEATURE:
<223> OTHER INFORMATION: mutant cellular tumor antigen p53

<400> SEQUENCE: 48

Gly Ser Tyr Gly Phe Arg Leu Gly Ser Leu His Ser Gly Thr Ala Lys
1 5 10 15

Ser

<210> SEQ ID NO 49
<211> LENGTH: 17
<212> TYPE: PRT
<213> ORGANISM: Homo sapiens

<400> SEQUENCE: 49

Gly Ser Tyr Gly Phe Arg Leu Gly Phe Leu His Ser Gly Thr Ala Lys
1 5 10 15

Ser

<210> SEQ ID NO 50
<211> LENGTH: 17
<212> TYPE: PRT
<213> ORGANISM: Artificial Sequence
<220> FEATURE:
<223> OTHER INFORMATION: mutant chondroitin sulfate
glucuronyltransferase

<400> SEQUENCE: 50

Arg Ala Glu Glu Phe Ile Gly Ala Asp Glu Gln Ala Arg Tyr Cys His
1 5 10 15

Gly

<210> SEQ ID NO 51
<211> LENGTH: 17
<212> TYPE: PRT
<213> ORGANISM: Homo sapiens

<400> SEQUENCE: 51

Arg Ala Glu Glu Phe Ile Gly Ala Gly Glu Gln Ala Arg Tyr Cys His
1 5 10 15

Gly

<210> SEQ ID NO 52
<211> LENGTH: 17
<212> TYPE: PRT

<213> ORGANISM: Artificial Sequence
<220> FEATURE:
<223> OTHER INFORMATION: mutant pre-mRNA 3' end processing protein WDR33

<400> SEQUENCE: 52

```
Tyr Val Lys Tyr Trp Gln Ser Asn Ile Asn Asn Val Lys Met Phe Gln
1               5                   10                  15

Ala
```

<210> SEQ ID NO 53
<211> LENGTH: 17
<212> TYPE: PRT
<213> ORGANISM: Homo sapiens

<400> SEQUENCE: 53

```
Tyr Val Lys Tyr Trp Gln Ser Asn Met Asn Asn Val Lys Met Phe Gln
1               5                   10                  15

Ala
```

<210> SEQ ID NO 54
<211> LENGTH: 58
<212> TYPE: PRT
<213> ORGANISM: Artificial Sequence
<220> FEATURE:
<223> OTHER INFORMATION: mutant U1 small nuclear ribonucleoprotein A

<400> SEQUENCE: 54

```
Ile Lys Lys Asp Glu Leu Lys Lys Val Pro Val Arg His Leu Leu Pro
1               5                   10                  15

Val Trp Pro Asp Pro Gly Tyr Pro Gly Ile Thr Glu Pro Glu Asp Glu
            20                  25                  30

Gly Pro Gly Leu Cys His Leu Gln Gly Gly Gln Gln Arg His Gln Arg
        35                  40                  45

Pro Ala Leu His Ala Gly Phe Pro Phe Leu
    50                  55
```

<210> SEQ ID NO 55
<211> LENGTH: 58
<212> TYPE: PRT
<213> ORGANISM: Homo sapiens

<400> SEQUENCE: 55

```
Ile Lys Lys Asp Glu Leu Lys Lys Ser Leu Tyr Ala Ile Phe Ser Gln
1               5                   10                  15

Phe Gly Gln Ile Leu Asp Ile Leu Val Ser Arg Ser Leu Lys Met Arg
            20                  25                  30

Gly Gln Ala Phe Val Ile Phe Lys Glu Val Ser Ser Ala Thr Asn Ala
        35                  40                  45

Leu Arg Ser Met Gln Gly Phe Pro Phe Tyr
    50                  55
```

<210> SEQ ID NO 56
<211> LENGTH: 17
<212> TYPE: PRT
<213> ORGANISM: Artificial Sequence
<220> FEATURE:
<223> OTHER INFORMATION: mutant GTP-binding protein 1

<400> SEQUENCE: 56

```
Gln Ala Ser Trp Glu Phe Glu Ala Lys Ile Leu Val Leu His His Pro
1               5                   10                  15
```

Thr

<210> SEQ ID NO 57
<211> LENGTH: 17
<212> TYPE: PRT
<213> ORGANISM: Homo sapiens

<400> SEQUENCE: 57

Gln Ala Ser Trp Glu Phe Glu Ala Glu Ile Leu Val Leu His His Pro
1 5 10 15

Thr

<210> SEQ ID NO 58
<211> LENGTH: 17
<212> TYPE: PRT
<213> ORGANISM: Artificial Sequence
<220> FEATURE:
<223> OTHER INFORMATION: mutant probable ATP-dependent RNA helicase DDX46

<400> SEQUENCE: 58

Glu Arg Val Glu Lys Trp Arg Glu Ala Gln Arg Lys Lys Ala Met Glu
1 5 10 15

Asn

<210> SEQ ID NO 59
<211> LENGTH: 17
<212> TYPE: PRT
<213> ORGANISM: Homo sapiens

<400> SEQUENCE: 59

Glu Arg Val Glu Lys Trp Arg Glu Glu Gln Arg Lys Lys Ala Met Glu
1 5 10 15

Asn

<210> SEQ ID NO 60
<211> LENGTH: 17
<212> TYPE: PRT
<213> ORGANISM: Artificial Sequence
<220> FEATURE:
<223> OTHER INFORMATION: mutant cAMP-dependent protein kinase catalytic subunit beta

<400> SEQUENCE: 60

Ile Leu Asp Lys Gln Lys Val Val Asn Leu Lys Gln Ile Glu His Thr
1 5 10 15

Leu

<210> SEQ ID NO 61
<211> LENGTH: 17
<212> TYPE: PRT
<213> ORGANISM: Homo sapiens

<400> SEQUENCE: 61

Ile Leu Asp Lys Gln Lys Val Val Lys Leu Lys Gln Ile Glu His Thr
1 5 10 15

Leu

<210> SEQ ID NO 62
<211> LENGTH: 17
<212> TYPE: PRT
<213> ORGANISM: Artificial Sequence
<220> FEATURE:

<223> OTHER INFORMATION: mutant lysine-specific demethylase 5B

<400> SEQUENCE: 62

Val Ala Val Pro Ser Ile Ser Gln Ala Leu Arg Ile Trp Leu Cys Pro
1               5                   10                  15

His

<210> SEQ ID NO 63
<211> LENGTH: 17
<212> TYPE: PRT
<213> ORGANISM: Homo sapiens

<400> SEQUENCE: 63

Val Ala Val Pro Ser Ile Ser Gln Gly Leu Arg Ile Trp Leu Cys Pro
1               5                   10                  15

His

<210> SEQ ID NO 64
<211> LENGTH: 17
<212> TYPE: PRT
<213> ORGANISM: Artificial Sequence
<220> FEATURE:
<223> OTHER INFORMATION: mutant jmjC domain-containing protein 8

<400> SEQUENCE: 64

Pro Glu Phe His Pro Asn Lys Thr Met Leu Ala Trp Leu Arg Asp Thr
1               5                   10                  15

Tyr

<210> SEQ ID NO 65
<211> LENGTH: 17
<212> TYPE: PRT
<213> ORGANISM: Homo sapiens

<400> SEQUENCE: 65

Pro Glu Phe His Pro Asn Lys Thr Thr Leu Ala Trp Leu Arg Asp Thr
1               5                   10                  15

Tyr

<210> SEQ ID NO 66
<211> LENGTH: 17
<212> TYPE: PRT
<213> ORGANISM: Artificial Sequence
<220> FEATURE:
<223> OTHER INFORMATION: mutant CTD small phosphatase-like protein
      isoform 1

<400> SEQUENCE: 66

Pro Val Ala Asp Leu Leu Asp Arg Cys Gly Val Phe Arg Ala Arg Leu
1               5                   10                  15

Phe

<210> SEQ ID NO 67
<211> LENGTH: 17
<212> TYPE: PRT
<213> ORGANISM: Homo sapiens

<400> SEQUENCE: 67

Pro Val Ala Asp Leu Leu Asp Arg Trp Gly Val Phe Arg Ala Arg Leu
1               5                   10                  15

Phe

```
<210> SEQ ID NO 68
<211> LENGTH: 17
<212> TYPE: PRT
<213> ORGANISM: Artificial Sequence
<220> FEATURE:
<223> OTHER INFORMATION: mutant transmembrane protein 9B isoform a
      precursor

<400> SEQUENCE: 68

Cys Leu Arg Cys Glu Cys Lys Tyr Asp Glu Arg Ser Ser Val Thr Ile
1               5                   10                  15

Lys


<210> SEQ ID NO 69
<211> LENGTH: 17
<212> TYPE: PRT
<213> ORGANISM: Homo sapiens

<400> SEQUENCE: 69

Cys Leu Arg Cys Glu Cys Lys Tyr Glu Glu Arg Ser Ser Val Thr Ile
1               5                   10                  15

Lys


<210> SEQ ID NO 70
<211> LENGTH: 17
<212> TYPE: PRT
<213> ORGANISM: Artificial Sequence
<220> FEATURE:
<223> OTHER INFORMATION: mutant transmembrane protein 9B isoform b

<400> SEQUENCE: 70

Cys Leu Arg Cys Glu Cys Lys Tyr Asp Glu Arg Ser Ser Val Thr Ile
1               5                   10                  15

Lys


<210> SEQ ID NO 71
<211> LENGTH: 17
<212> TYPE: PRT
<213> ORGANISM: Homo sapiens

<400> SEQUENCE: 71

Cys Leu Arg Cys Glu Cys Lys Tyr Glu Glu Arg Ser Ser Val Thr Ile
1               5                   10                  15

Lys


<210> SEQ ID NO 72
<211> LENGTH: 17
<212> TYPE: PRT
<213> ORGANISM: Artificial Sequence
<220> FEATURE:
<223> OTHER INFORMATION: mutant dedicator of cytokinesis protein 1

<400> SEQUENCE: 72

Arg Pro Lys Ser Gln Val Met Asn Ile Ile Gly Ser Glu Arg Arg Phe
1               5                   10                  15

Ser


<210> SEQ ID NO 73
<211> LENGTH: 17
<212> TYPE: PRT
<213> ORGANISM: Homo sapiens

<400> SEQUENCE: 73
```

-continued

Arg Pro Lys Ser Gln Val Met Asn Val Ile Gly Ser Glu Arg Arg Phe
1               5                   10                  15

Ser

<210> SEQ ID NO 74
<211> LENGTH: 17
<212> TYPE: PRT
<213> ORGANISM: Artificial Sequence
<220> FEATURE:
<223> OTHER INFORMATION: mutant retinoblastoma-associated protein

<400> SEQUENCE: 74

Thr Phe Lys Arg Val Leu Ile Lys Gln Glu Glu Tyr Asp Ser Ile Ile
1               5                   10                  15

Val

<210> SEQ ID NO 75
<211> LENGTH: 17
<212> TYPE: PRT
<213> ORGANISM: Homo sapiens

<400> SEQUENCE: 75

Thr Phe Lys Arg Val Leu Ile Lys Glu Glu Glu Tyr Asp Ser Ile Ile
1               5                   10                  15

Val

<210> SEQ ID NO 76
<211> LENGTH: 17
<212> TYPE: PRT
<213> ORGANISM: Artificial Sequence
<220> FEATURE:
<223> OTHER INFORMATION: mutant lysine-specific demethylase 4A

<400> SEQUENCE: 76

Thr Asp Gly Gln Val Tyr Gly Ala Thr Phe Val Ala Ser His Pro Ile
1               5                   10                  15

Gln

<210> SEQ ID NO 77
<211> LENGTH: 17
<212> TYPE: PRT
<213> ORGANISM: Homo sapiens

<400> SEQUENCE: 77

Thr Asp Gly Gln Val Tyr Gly Ala Lys Phe Val Ala Ser His Pro Ile
1               5                   10                  15

Gln

<210> SEQ ID NO 78
<211> LENGTH: 17
<212> TYPE: PRT
<213> ORGANISM: Artificial Sequence
<220> FEATURE:
<223> OTHER INFORMATION: mutant E3 ubiquitin-protein ligase NEDD4-like

<400> SEQUENCE: 78

Phe Leu Arg Leu Lys Met Ala Tyr Val Pro Lys Asn Gly Gly Gln Asp
1               5                   10                  15

Glu

<210> SEQ ID NO 79

```
<211> LENGTH: 17
<212> TYPE: PRT
<213> ORGANISM: Homo sapiens

<400> SEQUENCE: 79

Phe Leu Arg Leu Lys Met Ala Tyr Met Pro Lys Asn Gly Gly Gln Asp
1               5                   10                  15

Glu


<210> SEQ ID NO 80
<211> LENGTH: 17
<212> TYPE: PRT
<213> ORGANISM: Artificial Sequence
<220> FEATURE:
<223> OTHER INFORMATION: mutant serine/threonine-protein kinase TAO3

<400> SEQUENCE: 80

Gln Thr Arg Lys Leu Ala Ile Leu Gly Glu Gln Tyr Glu Gln Ser Ile
1               5                   10                  15

Asn


<210> SEQ ID NO 81
<211> LENGTH: 17
<212> TYPE: PRT
<213> ORGANISM: Homo sapiens

<400> SEQUENCE: 81

Gln Thr Arg Lys Leu Ala Ile Leu Ala Glu Gln Tyr Glu Gln Ser Ile
1               5                   10                  15

Asn


<210> SEQ ID NO 82
<211> LENGTH: 17
<212> TYPE: PRT
<213> ORGANISM: Artificial Sequence
<220> FEATURE:
<223> OTHER INFORMATION: mutant transcription elongation regulator 1

<400> SEQUENCE: 82

Asp Glu Pro Val Lys Ala Lys Lys Trp Lys Arg Asp Asp Asn Lys Asp
1               5                   10                  15

Ile


<210> SEQ ID NO 83
<211> LENGTH: 17
<212> TYPE: PRT
<213> ORGANISM: Homo sapiens

<400> SEQUENCE: 83

Asp Glu Pro Val Lys Ala Lys Lys Arg Lys Arg Asp Asp Asn Lys Asp
1               5                   10                  15

Ile


<210> SEQ ID NO 84
<211> LENGTH: 17
<212> TYPE: PRT
<213> ORGANISM: Artificial Sequence
<220> FEATURE:
<223> OTHER INFORMATION: mutant E3 ubiquitin-protein ligase RNF19B

<400> SEQUENCE: 84

Met Ala Arg Gln Gln Arg Ala Gln Pro Leu Arg Val Arg Thr Lys His
1               5                   10                  15
```

Thr

<210> SEQ ID NO 85
<211> LENGTH: 17
<212> TYPE: PRT
<213> ORGANISM: Homo sapiens

<400> SEQUENCE: 85

Met Ala Arg Gln Gln Arg Ala Gln Thr Leu Arg Val Arg Thr Lys His
1 5 10 15

Thr

<210> SEQ ID NO 86
<211> LENGTH: 17
<212> TYPE: PRT
<213> ORGANISM: Artificial Sequence
<220> FEATURE:
<223> OTHER INFORMATION: mutant rho GTPase-activating protein 45

<400> SEQUENCE: 86

His Met Pro Leu Leu Ser Ile Tyr Leu Leu Ala Leu Glu Gln Asp Leu
1 5 10 15

Glu

<210> SEQ ID NO 87
<211> LENGTH: 17
<212> TYPE: PRT
<213> ORGANISM: Homo sapiens

<400> SEQUENCE: 87

His Met Pro Leu Leu Ser Ile Tyr Ser Leu Ala Leu Glu Gln Asp Leu
1 5 10 15

Glu

<210> SEQ ID NO 88
<211> LENGTH: 17
<212> TYPE: PRT
<213> ORGANISM: Artificial Sequence
<220> FEATURE:
<223> OTHER INFORMATION: mutant semaphorin-5A precursor

<400> SEQUENCE: 88

Pro Gly Met Glu Ile Ala Asn Cys Cys Arg Asn Gly Gly Trp Thr Pro
1 5 10 15

Trp

<210> SEQ ID NO 89
<211> LENGTH: 17
<212> TYPE: PRT
<213> ORGANISM: Homo sapiens

<400> SEQUENCE: 89

Pro Gly Met Glu Ile Ala Asn Cys Ser Arg Asn Gly Gly Trp Thr Pro
1 5 10 15

Trp

<210> SEQ ID NO 90
<211> LENGTH: 31
<212> TYPE: PRT
<213> ORGANISM: Artificial Sequence
<220> FEATURE:
<223> OTHER INFORMATION: mutant adenomatous polyposis coli protein

<400> SEQUENCE: 90

Ala Val Gln Arg Val Gln Val Leu Gln Met Leu Ile Leu Tyr Tyr Ile
1               5                   10                  15

Leu Pro Arg Lys Val Leu Gln Met Asp Phe Leu Val His Pro Ala
            20                  25                  30

<210> SEQ ID NO 91
<211> LENGTH: 31
<212> TYPE: PRT
<213> ORGANISM: Homo sapiens

<400> SEQUENCE: 91

Ala Val Gln Arg Val Gln Val Leu Pro Asp Ala Asp Thr Leu Leu His
1               5                   10                  15

Phe Ala Thr Glu Ser Thr Pro Asp Gly Phe Ser Cys Ser Ser Ser
            20                  25                  30

<210> SEQ ID NO 92
<211> LENGTH: 17
<212> TYPE: PRT
<213> ORGANISM: Artificial Sequence
<220> FEATURE:
<223> OTHER INFORMATION: mutant zinc finger protein 732

<400> SEQUENCE: 92

Arg Ile His Ala Glu Glu Lys Pro Tyr Thr Cys Glu Glu Cys Gly Lys
1               5                   10                  15

Ile

<210> SEQ ID NO 93
<211> LENGTH: 17
<212> TYPE: PRT
<213> ORGANISM: Homo sapiens

<400> SEQUENCE: 93

Arg Ile His Ala Glu Glu Lys Pro Phe Thr Cys Glu Glu Cys Gly Lys
1               5                   10                  15

Ile

<210> SEQ ID NO 94
<211> LENGTH: 11
<212> TYPE: PRT
<213> ORGANISM: Artificial Sequence
<220> FEATURE:
<223> OTHER INFORMATION: mutant contactin-1 isoform 1 precursor

<400> SEQUENCE: 94

Ala Phe Asn Asn Lys Gly Asp Gly Leu Thr Ala
1               5                   10

<210> SEQ ID NO 95
<211> LENGTH: 11
<212> TYPE: PRT
<213> ORGANISM: Homo sapiens

<400> SEQUENCE: 95

Ala Phe Asn Asn Lys Gly Asp Gly Pro Tyr Ser
1               5                   10

<210> SEQ ID NO 96
<211> LENGTH: 2601
<212> TYPE: DNA

<213> ORGANISM: Artificial Sequence
<220> FEATURE:
<223> OTHER INFORMATION: patient-specific cancer antigen concatemer

<400> SEQUENCE: 96

```
atggacccgt gcagtagtgt gaagagaagt acgatggtga gagcggcgag agcggctgct     60
tatctagagc tatgcaacgg aggaagtcta acagagctag taaagggact actagccgct    120
tatagtacga tagtggggag tgcggcggtg aacatgttca taataatagg gatagcagct    180
tatatctttt ggcaagtcac ctggcgaatg gtctcacccc ttcttatgct tatcgcggct    240
tattgccacg cggaggtggt ggcgaggcag gcgttcctgc acttcctgta cacggctgcc    300
tatctgaaca agcagccgag cctgctgagc cacacgacga agtggctgac gcaggccgcc    360
tatttaggtt taactactgt tcctcctaat gttcctgctg ctactcgcac tttagcagcc    420
tatgaggcag tacgggcaga ccggatgaag ggaggacgga acaagttcgg accggcggcc    480
tattgtttat tagtcttagt cattgcctgg gtccgccgct tacataatgt caccgctgca    540
tataaggagg acgactgcga gcacgggaag gacgagacgc actgcaacaa gttcgccgca    600
tattcacaat cacttcccgc ctcacatacc catcttcgag tcaccgccgc ccccgcagca    660
tatgaattgc aacaattggt tgaaggtcaa caagaatctt atttgttgtg ttgggcggca    720
tataaacgat catcacgacg acaatcaccc gaacttcaaa aatgtgaaga aatcgctgcg    780
tatcgtgttt ctgattataa acatcatcgt tctgatgttt tggttggttt gttggccgcg    840
tatggttcct atggttttcg cttaggttcc ttacattccg gtactgctaa atccgcagcg    900
tatagagcgg aggagttcat aggggcggac gagcaggcga gatactgcca cggggcggcg    960
tattatgtca aatattggca atcaaatatc aataatgtca aaatgtttca agccgctgct   1020
tacatcaaaa aagatgaact taaaaaagtc cccgtccgac atcttcttcc cgtctggccc   1080
gatcccggct atcccggcat caccgaaccc gaagatgaag gccccggcct ttgtcatctt   1140
caaggcggcc aacaacgaca tcaacgaccc gcccttcatg ccggctttcc ctttcttgcc   1200
gcttaccaag cctcatggga atttgaagcc aaaatccttg tccttcatca tcccaccgca   1260
gcttacgagc gggtagagaa gtggcgggag gcacagcgga agaaggcaat ggagaacgcg   1320
gcttacatac tggacaagca gaaggtggtg aacctgaagc agatagagca cacgctggct   1380
gcctacgtag cagtaccatc gatctcgcag gcactccgga tctggctctg cccacacgcc   1440
gcctacccag agttccaccc aaacaagaca atgctcgcat ggctccggga cacatacgca   1500
gcctaccccg tcgccgattt attagatcgc tgtggcgtct ttcgcgcccg cttatttgcg   1560
gcctactgtt tgcgttgtga atgtaaatat gatgaacgtt cttctgttac tattaaagct   1620
gcatacagac caaagagtca ggtaatgaac ataataggaa gtgagagaag attcagtgcc   1680
gcatacacat tcaagcgggt actcatcaag caggaggagt acgactcgat catcgtagca   1740
gcatacactg atggtcaagt ttatggtgct acttttgttg cttcccatcc tattcaagcg   1800
gcatactttc ttcgacttaa aatggcctat gtccccaaaa atggcggcca agatgaagct   1860
gcgtaccaga cacggaagct cgcaatcctc ggagagcagt acgagcagtc gatcaacgcc   1920
gcgtacgacg agccggtgaa ggcgaagaag tggaagaggg acgacaacaa ggacatagca   1980
gcgtacatgg cccgacaaca acgagcccaa ccccttcgag tccgaaccaa acataccgcg   2040
gcgtaccaca tgccactcct ctcgatctac ctcctcgcac tcgagcagga cctcgaggct   2100
gcttatccgg ggatggagat agcgaactgc tgcagaaacg gggggtggac gccgtgggcc   2160
gcttatgcgg tgcagagggt gcaggtgctg cagatgctga tactgtacta catactgccg   2220
```

-continued

```
aggaaggtgc tgcagatgga cttcctggtg cacccggcgg cagcttatag gatacacgcg   2280

gaggagaagc cgtacacgtg cgaggagtgc gggaagatag cggcttatgc gttcaacaac   2340

aagggggacg ggctgacggc ggctgcctat atgcagatct tcgtaaagac actcacagga   2400

aagacaatca cactcgaggt agagccatcg gacacaatcg agaacgtaaa ggcaaagatc   2460

caggacaagg agggaatccc accagaccag cagcggctca tcttcgcagg aaagcagctc   2520

gaggacggac ggacactctc ggactacaac atccagaagg agtcgacact ccacctcgta   2580

ctccggctcc ggggaggata g                                              2601
```

<210> SEQ ID NO 97
<211> LENGTH: 35770
<212> TYPE: DNA
<213> ORGANISM: Unknown
<220> FEATURE:
<223> OTHER INFORMATION: Oncolytic serotype 5 adenovirus (Ad5)

<400> SEQUENCE: 97

```
catcatcaat aatatacctt attttggatt gaagccaata tgataatgag ggggtggagt     60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgttttggg cgtaaccgag taagatttgg ccattttcgc gggaaaactg    240

aataagagga agtgaaatct gaataatttt gtgttactca tagcgcgtaa tatttgtcta    300

gggccgcggg gactttgacc gtttacgtgg agactcgccc aggtgttttt ctcaggtgtt    360

ttccgcgttc cgggtcaaag ttggcgtttt attattatag tcagctgacg tgtagtgtat    420

ttatacccgg tgagttcctc aagaggccac tcttgagtgc cagcgagtag agttttctcc    480

tccgagccgc tccgacaccg ggactgaaaa tgagacatat tatctgccac ggaggtgtta    540

ttaccgaaga aatggccgcc agtcttttgg accagctgat cgaagaggta ctggctgata    600

atcttccacc tcctagccat tttgaaccac ctacccttca cgaactgtat gatttagacg    660

tgacggcccc cgaagatccc aacgaggagg cggtttcgca gatttttccc gactctgtaa    720

tgttggcggt gcaggaaggg attgacttac tcacttttcc gccggcgccc ggttctccgg    780

agccgcctca cctttcccgg cagcccgagc agccggagca gagagccttg ggtccggttt    840

ctatgccaaa ccttgtaccg gaggtgatcg atcttacctg ccacgaggct ggctttccac    900

ccagtgacga cgaggatgaa gagggtgagg agtttgtgtt agattatgtg gagcaccccg    960

ggcacggttg caggtcttgt cattatcacc ggaggaatac gggggaccca gatattatgt   1020

gttcgctttg ctatatgagg acctgtggca tgtttgtcta cagtaagtga aaattatggg   1080

cagtgggtga tagagtggtg ggtttggtgt ggtaattttt tttttaattt ttacagtttt   1140

gtggtttaaa gaattttgta ttgtgatttt tttaaaaggt cctgtgtctg aacctgagcc   1200

tgagcccgag ccagaaccgg agcctgcaag acctacccgc cgtcctaaaa tggcgcctgc   1260

tatcctgaga cgcccgacat cacctgtgtc tagagaatgc aatagtagta cggatagctg   1320

tgactccggt ccttctaaca cacctcctga gatacacccg gtggtcccgc tgtgccccat   1380

taaaccagtt gccgtgagag ttggtgggcg tcgccaggct gtggaatgta tcgaggactt   1440

gcttaacgag cctgggcaac ctttggactt gagctgtaaa cgccccaggc cataaggtgt   1500

aaacctgtga ttgcgtgtgt ggttaacgcc tttgtttgct gaatgagttg atgtaagttt   1560

aataaagggt gagataatgt ttaacttgca tggcgtgtta aatggggcgg ggcttaaagg   1620
```

-continued

```
gtatataatg cgccgtgggc taatcttggt tacatctgac ctcgtcgaca tggacccgtg   1680
cagtagtgtg aagagaagta cgatggtgag agcggcgaga gcggctgctt atctagagct   1740
atgcaacgga ggaagtctaa cagagctagt aaagggacta ctagccgctt atagtacgat   1800
agtggggagt gcggcggtga acatgttcat aataataggg atagcagctt atatcttttg   1860
gcaagtcacc tggcgaatgg tctcacccct tcttatgctt atcgcggctt attgccacgc   1920
ggaggtggtg gcgaggcagg cgttcctgca cttcctgtac acggctgcct atctgaacaa   1980
gcagccgagc ctgctgagcc acacgacgaa gtggctgacg caggccgcct atttaggttt   2040
aactactgtt cctcctaatg ttcctgctgc tactcgcact ttagcagcct atgaggcagt   2100
acgggcagac cggatgaagg gaggacggaa caagttcgga ccggcggcct attgtttatt   2160
agtcttagtc attgcctggg tccgccgctt acataatgtc accgctgcat ataaggagga   2220
cgactgcgag cacgggaagg acgagacgca ctgcaacaag ttcgccgcat attcacaatc   2280
acttcccgcc tcacataccc atcttcgagt caccgccgcc cccgcagcat atgaattgca   2340
acaattggtt gaaggtcaac aagaatctta tttgttgtgt tgggcggcat ataaacgatc   2400
atcacgacga caatcacccg aacttcaaaa atgtgaagaa atcgctgcgt atcgtgtttc   2460
tgattataaa catcatcgtt ctgatgtttt ggttggtttg ttggccgcgt atggttccta   2520
tggttttcgc ttaggttcct tacattccgg tactgctaaa tccgcagcgt atagagcgga   2580
ggagttcata ggggcggacg agcaggcgag atactgccac ggggcggcgt attatgtcaa   2640
atattggcaa tcaaatatca ataatgtcaa aatgtttcaa gccgctgctt acatcaaaaa   2700
agatgaactt aaaaaagtcc ccgtccgaca tcttcttccc gtctggcccg atcccggcta   2760
tcccggcatc accgaacccg aagatgaagg ccccggcctt tgtcatcttc aaggcggcca   2820
acaacgacat caacgacccg cccttcatgc cggctttccc tttcttgccg cttaccaagc   2880
ctcatgggaa tttgaagcca aaatccttgt ccttcatcat cccaccgcag cttacgagcg   2940
ggtagagaag tggcgggagg cacagcggaa gaaggcaatg gagaacgcgg cttacatact   3000
ggacaagcag aaggtggtga acctgaagca gatagagcac acgctggctg cctacgtagc   3060
agtaccatcg atctcgcagg cactccggat ctggctctgc ccacacgccg cctacccaga   3120
gttccaccca aacaagacaa tgctcgcatg gctccgggac acatacgcag cctaccccgt   3180
cgccgattta ttagatcgct gtggcgtctt tcgcgcccgc ttatttgcgg cctactgttt   3240
gcgttgtgaa tgtaaatatg atgaacgttc ttctgttact attaaagctg catacagacc   3300
aaagagtcag gtaatgaaca taataggaag tgagagaaga ttcagtgccg catacacatt   3360
caagcgggta ctcatcaagc aggaggagta cgactcgatc atcgtagcag catacactga   3420
tggtcaagtt tatggtgcta cttttgttgc ttcccatcct attcaagcgg catactttct   3480
tcgacttaaa atggcctatg tccccaaaaa tggcggccaa gatgaagctg cgtaccagac   3540
acggaagctc gcaatcctcg gagagcagta cgagcagtcg atcaacgccg cgtacgacga   3600
gccggtgaag gcgaagaagt ggaagaggga cgacaacaag gacatagcag cgtacatggc   3660
ccgacaacaa cgagcccaac cccttcgagt ccgaaccaaa cataccgcgg cgtaccacat   3720
gccactcctc tcgatctacc tcctcgcact cgagcaggac ctcgaggctg cttatccggg   3780
gatggagata gcgaactgct gcagaaacgg ggggtggacg ccgtgggccg cttatgcggt   3840
gcagagggtg caggtgctgc agatgctgat actgtactac atactgccga ggaaggtgct   3900
gcagatggac ttcctggtgc acccggcggc agcttatagg atacacgcgg aggagaagcc   3960
gtacacgtgc gaggagtgcg ggaagatagc ggcttatgcg ttcaacaaca agggggacgg   4020
```

-continued

```
gctgacggcg gctgcctata tgcagatctt cgtaaagaca ctcacaggaa agacaatcac   4080
actcgaggta gagccatcgg acacaatcga gaacgtaaag gcaaagatcc aggacaagga   4140
gggaatccca ccagaccagc agcggctcat cttcgcagga aagcagctcg aggacggacg   4200
gacactctcg gactacaaca tccagaagga gtcgacactc cacctcgtac tccggctccg   4260
gggaggatag taactcgagt caccaggcgc ttttccaaga gaaggtcatc aagactttgg   4320
atttttccac accggggcgc gctgcggctg ctgttgcttt tttgagtttt ataaaggata   4380
aatggagcga agaaacccat ctgagcgggg ggtacctgct ggattttctg gccatgcatc   4440
tgtggagagc ggttgtgaga cacaagaatc gcctgctact gttgtcttcc gtccgcccgg   4500
cgataatacc gacggaggag cagcagcagc agcaggagga agccaggcgg cggcggcagg   4560
agcagagccc atggaacccg agagccggcc tggaccctcg ggaatgaatg ttgtacaggt   4620
ggctgaactg tatccagaac tgagacgcat tttgacaatt acagaggatg ggcaggggct   4680
aaagggggta aagagggagc ggggggcttg tgaggctaca gaggaggcta ggaatctagc   4740
ttttagctta atgaccagac accgtcctga gtgtattact tttcaacaga tcaaggataa   4800
ttgcgctaat gagcttgatc tgctggcgca gaagtattcc atagagcagc tgaccactta   4860
ctggctgcag ccaggggatg attttgagga ggctattagg gtatatgcaa aggtggcact   4920
taggccagat tgcaagtaca agatcagcaa acttgtaaat atcaggaatt gttgctacat   4980
ttctgggaac ggggccgagg tggagataga tacggaggat agggtggcct ttagatgtag   5040
catgataaat atgtggccgg gggtgcttgg catggacggg gtggttatta tgaatgtaag   5100
gtttactggc cccaatttta gcggtacggt tttcctggcc aataccaacc ttatcctaca   5160
cggtgtaagc ttctatgggt ttaacaatac ctgtgtggaa gcctggaccg atgtaagggt   5220
tcggggctgt gccttttact gctgctggaa gggggtggtg tgtcgcccca aaagcagggc   5280
ttcaattaag aaatgcctct ttgaaaggtg taccttgggt atcctgtctg agggtaactc   5340
cagggtgcgc cacaatgtgg cctccgactg tggttgcttc atgctagtga aaagcgtggc   5400
tgtgattaag cataacatgg tatgtggcaa ctgcgaggac agggcctctc agatgctgac   5460
ctgctcggac ggcaactgtc acctgctgaa gaccattcac gtagccagcc actctcgcaa   5520
ggcctggcca gtgtttgagc ataacatact gacccgctgt tccttgcatt tgggtaacag   5580
gaggggggtg ttcctacctt accaatgcaa tttgagtcac actaagatat tgcttgagcc   5640
cgagagcatg tccaaggtga acctgaacgg ggtgtttgac atgaccatga agatctggaa   5700
ggtgctgagg tacgatgaga cccgcaccag gtgcagaccc tgcgagtgtg gcggtaaaca   5760
tattaggaac cagcctgtga tgctggatgt gaccgaggag ctgaggcccg atcacttggt   5820
gctggcctgc acccgcgctg agtttggctc tagcgatgaa gatacagatt gaggtactga   5880
aatgtgtggg cgtggcttaa gggtgggaaa gaatatataa ggtgggggtc ttatgtagtt   5940
ttgtatctgt tttgcagcag ccgccgccgc catgagcacc aactcgtttg atggaagcat   6000
tgtgagctca tatttgacaa cgcgcatgcc cccatgggcc ggggtgcgtc agaatgtgat   6060
gggctccagc attgatggtc gccccgtcct gcccgcaaac tctactacct tgacctacga   6120
gaccgtgtct ggaacgccgt tggagactgc agcctccgcc gccgcttcag ccgctgcagc   6180
caccgcccgc gggattgtga ctgactttgc tttcctgagc ccgcttgcaa gcagtgcagc   6240
ttcccgttca tccgcccgcg atgacaagtt gacggctctt ttggcacaat tggattcttt   6300
gacccgggaa cttaatgtcg tttctcagca gctgttggat ctgcgccagc aggtttctgc   6360
```

-continued

```
cctgaaggct tcctcccctc ccaatgcggt ttaaaacata aataaaaaac cagactctgt   6420
ttggatttgg atcaagcaag tgtcttgctg tctttattta ggggttttgc gcgcgcggta   6480
ggcccgggac cagcggtctc ggtcgttgag ggtcctgtgt atttttttcca ggacgtggta   6540
aaggtgactc tggatgttca gatacatggg cataagcccg tctctggggt ggaggtagca   6600
ccactgcaga gcttcatgct gcggggtggt gttgtagatg atccagtcgt agcaggagcg   6660
ctgggcgtgg tgcctaaaaa tgtctttcag tagcaagctg attgccaggg gcaggccctt   6720
ggtgtaagtg tttacaaagc ggttaagctg ggatgggtgc atacgtgggg atatgagatg   6780
catcttggac tgtattttta ggttggctat gttcccagcc atatccctcc ggggattcat   6840
gttgtgcaga accaccagca cagtgtatcc ggtgcacttg ggaaatttgt catgtagctt   6900
agaaggaaat gcgtggaaga acttggagac gcccttgtga cctccaagat tttccatgca   6960
ttcgtccata atgatggcaa tgggcccacg ggcggcggcc tgggcgaaga tatttctggg   7020
atcactaacg tcatagttgt gttccaggat gagatcgtca taggccattt ttacaaagcg   7080
cgggcggagg gtgccagact gcggtataat ggttccatcc ggcccagggg cgtagttacc   7140
ctcacagatt tgcatttccc acgctttgag ttcagatggg gggatcatgt ctacctgcgg   7200
ggcgatgaag aaaacggttt ccggggtagg ggagatcagc tgggaagaaa gcaggttcct   7260
gagcagctgc gacttaccgc agccggtggg cccgtaaatc acacctatta ccgggtgcaa   7320
ctggtagtta agagagctgc agctgccgtc atccctgagc aggggggcca cttcgttaag   7380
catgtccctg actcgcatgt tttccctgac caaatccgcc agaaggcgct cgccgcccag   7440
cgatagcagt tcttgcaagg aagcaaagtt tttcaacggt ttgagaccgt ccgccgtagg   7500
catgcttttg agcgtttgac caagcagttc caggcggtcc cacagctcgg tcacctgctc   7560
tacggcatct cgatccagca tatctcctcg tttcgcgggt tggggcggct ttcgctgtac   7620
ggcagtagtc ggtgctcgtc cagacgggcc agggtcatgt ctttccacgg gcgcagggtc   7680
ctcgtcagcg tagtctgggt cacggtgaag ggtgcgctc cgggctgcgc gctggccagg   7740
gtgcgcttga ggctggtcct gctggtgctg aagcgctgcc ggtcttcgcc ctgcgcgtcg   7800
gccaggtagc atttgaccat ggtgtcatag tccagcccct ccgcggcgtg gcccttggcg   7860
cgcagcttgc ccttggagga ggcgccgcac gaggggcagt gcagactttt gagggcgtag   7920
agcttgggcg cgagaaatac cgattccggg gagtaggcat ccgcgccgca ggccccgcag   7980
acggtctcgc attccacgag ccaggtgagc tctggccgtt cggggtcaaa aaccaggttt   8040
cccccatgct tttgatgcg tttcttacct ctggtttcca tgagccggtg tccacgctcg   8100
gtgacgaaaa ggctgtccgt gtccccgtat acagacttga gaggcctgtc ctcgagcggt   8160
gttccgcggt cctcctcgta tagaaactcg gaccactctg agacaaaggc tcgcgtccag   8220
gccagcacga aggaggctaa gtgggagggg tagcggtcgt tgtccactag gggtccact   8280
cgctccaggg tgtgaagaca catgtcgccc tcttcggcat caaggaaggt gattggtttg   8340
taggtgtagg ccacgtgacc gggtgttcct gaagggggc tataaaaggg ggtgggggcg   8400
cgttcgtcct cactctcttc cgcatcgctg tctgcgaggg ccagctgttg gggtgagtac   8460
tccctctgaa aagcgggcat gacttctgcg ctaagattgt cagtttccaa aaacgaggag   8520
gatttgatat tcacctggcc cgcggtgatg cctttgaggg tggccgcatc catctggtca   8580
gaaaagacaa tctttttgtt gtcaagcttg gtggcaaacg acccgtagag ggcgttggac   8640
agcaacttgg cgatggagcg cagggtttgg tttttgtcgc gatcggcgcg ctccttggcc   8700
gcgatgttta gctgcacgta ttcgcgcgca acgcaccgcc attcgggaaa gacggtggtg   8760
```

-continued

```
cgctcgtcgg gcaccaggtg cacgcgccaa ccgcggttgt gcagggtgac aaggtcaacg   8820
ctggtggcta cctctccgcg taggcgctcg ttggtccagc agaggcggcc gcccttgcgc   8880
gagcagaatg gcggtagggg gtctagctgc gtctcgtccg gggggtctgc gtccacggta   8940
aagaccccgg gcagcaggcg cgcgtcgaag tagtctatct tgcatccttg caagtctagc   9000
gcctgctgcc atgcgcgggc ggcaagcgcg cgctcgtatg ggttgagtgg gggaccccat   9060
ggcatggggt gggtgagcgc ggaggcgtac atgccgcaaa tgtcgtaaac gtagaggggc   9120
tctctgagta ttccaagata tgtagggtag catcttccac cgcggatgct ggcgcgcacg   9180
taatcgtata gttcgtgcga gggagcgagg aggtcgggac cgaggttgct acgggcgggc   9240
tgctctgctc ggaagactat ctgcctgaag atggcatgtg agttggatga tatggttgga   9300
cgctggaaga cgttgaagct ggcgtctgtg agacctaccg cgtcacgcac gaaggaggcg   9360
taggagtcgc gcagcttgtt gaccagctcg gcggtgacct gcacgtctag ggcgcagtag   9420
tccagggttt ccttgatgat gtcatactta tcctgtccct tttttttcca cagctcgcgg   9480
ttgaggacaa actcttcgcg gtctttccag tactcttgga tcggaaaccc gtcggcctcc   9540
gaacggtaag agcctagcat gtagaactgg ttgacggcct ggtaggcgca gcatcccttt   9600
tctacgggta gcgcgtatgc ctgcgcggcc ttccggagcg aggtgtgggt gagcgcaaag   9660
gtgtccctga ccatgacttt gaggtactgg tatttgaagt cagtgtcgtc gcatccgccc   9720
tgctcccaga gcaaaaagtc cgtgcgcttt ttggaacgcg gatttggcag ggcgaaggtg   9780
acatcgttga agagtatctt tcccgcgcga ggcataaagt tgcgtgtgat gcggaagggt   9840
cccggcacct cggaacggtt gttaattacc tgggcggcga gcacgatctc gtcaaagccg   9900
ttgatgttgt ggcccacaat gtaaagttcc aagaagcgcg ggatgccctt gatggaaggc   9960
aatttttttaa gttcctcgta ggtgagctct tcaggggagc tgagcccgtg ctctgaaagg  10020
gcccagtctg caagatgagg gttggaagcg acgaatgagc tccacaggtc acgggccatt  10080
agcatttgca ggtggtcgcg aaaggtccta aactggcgac ctatggccat tttttctggg  10140
gtgatgcagt agaaggtaag cgggtcttgt tcccagcggt cccatccaag gttcgcggct  10200
aggtctcgcg cggcagtcac tagaggctca tctccgccga acttcatgac cagcatgaag  10260
ggcacgagct gcttcccaaa ggcccccatc caagtatagg tctctacatc gtaggtgaca  10320
aagagacgct cggtgcgagg atgcgagccg atcgggaaga actggatctc ccgccaccaa  10380
ttggaggagt ggctattgat gtggtgaaag tagaagtccc tgcgacgggc cgaacactcg  10440
tgctggcttt tgtaaaaacg tgcgcagtac tggcagcggt gcacgggctg tacatcctgc  10500
acgaggttga cctgacgacc gcgcacaagg aagcagagtg ggaatttgag cccctcgcct  10560
ggcgggtttg gctggtggtc ttctacttcg gctgcttgtc cttgaccgtc tggctgctcg  10620
aggggagtta cggtggatcg gaccaccacg ccgcgcgagc ccaaagtcca gatgtccgcg  10680
cgcggcggtc ggagcttgat gacaacatcg cgcagatggg agctgtccat ggtctggagc  10740
tcccgcggcg tcaggtcagg cgggagctcc tgcaggttta cctcgcatag acgggtcagg  10800
gcgcgggcta gatccaggtg atacctaatt tccaggggct ggttggtggc ggcgtcgatg  10860
gcttgcaaga ggccgcatcc ccgcggcgcg actacggtac cgcgcggcgg gcggtgggcc  10920
gcgggggtgt ccttggatga tgcatctaaa agcggtgacg cgggcgagcc cccggaggta  10980
gggggggctc cggacccgcc gggagagggg gcaggggcac gtcggcgccg cgcgcgggca  11040
ggagctggtg ctgcgcgcgt aggttgctgg cgaacgcgac gacgcggcgg ttgatctcct  11100
```

-continued gaatctggcg cctctgcgtg aagacgacgg gcccggtgag cttgagcctg aaagagagtt 11160
cgacagaatc aatttcggtg tcgttgacgg cggcctggcg caaaatctcc tgcacgtctc 11220
ctgagttgtc ttgataggcg atctcggcca tgaactgctc gatctcttcc tcctggagat 11280
ctccgcgtcc ggctcgctcc acggtggcgg cgaggtcgtt ggaaatgcgg gccatgagct 11340
gcgagaaggc gttgaggcct ccctcgttcc agacgcggct gtagaccacg ccccccttcgg 11400
catcgcgggc gcgcatgacc acctgcgcga gattgagctc cacgtgccgg gcgaagacgg 11460
cgtagtttcg caggcgctga aagaggtagt tgagggtggt ggcggtgtgt tctgccacga 11520
agaagtacat aacccagcgt cgcaacgtgg attcgttgat atcccccaag gcctcaaggc 11580
gctccatggc ctcgtagaag tccacggcga agttgaaaaa ctgggagttg cgcgccgaca 11640
cggttaactc ctcctccaga agacggatga gctcggcgac agtgtcgcgc acctcgcgct 11700
caaaggctac aggggcctct tcttcttctt caatctcctc ttccataagg gcctcccctt 11760
cttcttcttc tggcggcggt gggggagggg ggacacggcg gcgacgacgg cgcaccggga 11820
ggcggtcgac aaagcgctcg atcatctccc cgcggcgacg gcgcatggtc tcggtgacgg 11880
cgcggccgtt ctcgcggggg cgcagttgga agacgccgcc cgtcatgtcc cggttatggg 11940
ttggcggggg gctgccatgc ggcagggata cggcgctaac gatgcatctc aacaattgtt 12000
gtgtaggtac tccgccgccg agggacctga gcgagtccgc atcgaccgga tcggaaaacc 12060
tctcgagaaa ggcgtctaac cagtcacagt cgcaaggtag gctgagcacc gtggcgggcg 12120
gcagcgggcg gcggtcgggg ttgtttctgg cggaggtgct gctgatgatg taattaaagt 12180
aggcggtctt gagacggcgg atggtcgaca gaagcaccat gtccttgggt ccggcctgct 12240
gaatgcgcag gcggtcggcc atgccccagg cttcgttttg acatcggcgc aggtctttgt 12300
agtagtcttg catgagcctt tctaccggca cttcttcttc tccttcctct tgtcctgcat 12360
ctcttgcatc tatcgctgcg gcggcggcgg agtttggccg taggtggcgc cctcttcctc 12420
ccatgcgtgt gaccccgaag cccctcatcg gctgaagcag ggctaggtcg gcgacaacgc 12480
gctcggctaa tatggcctgc tgcacctgcg tgagggtaga ctggaagtca tccatgtcca 12540
caaagcggtg gtatgcgccc gtgttgatgg tgtaagtgca gttggccata acggaccagt 12600
taacggtctg gtgacccggc tgcgagagct cggtgtacct gagacgcgag taagccctcg 12660
agtcaaatac gtagtcgttg caagtccgca ccaggtactg gtatcccacc aaaaagtgcg 12720
gcggcggctg gcggtagagg ggccagcgta gggtggccgg ggctccgggg gcgagatctt 12780
ccaacataag gcgatgatat ccgtagatgt acctggacat ccaggtgatg ccggcggcgg 12840
tggtggaggc gcgcggaaag tcgcggacgc ggttccagat gttgcgcagc ggcaaaaagt 12900
gctccatggt cgggacgctc tggccggtca ggcgcgcgca atcgttgacg ctctaccgtg 12960
caaaaggaga gcctgtaagc gggcactctt ccgtggtctg gtggataaat tcgcaagggt 13020
atcatggcgg acgaccgggg ttcgagcccc gtatccggcc gtccgccgtg atccatgcgg 13080
ttaccgcccg cgtgtcgaac ccaggtgtgc gacgtcagac aacgggggag tgctcctttt 13140
ggcttccttc caggcgcggc ggctgctgcg ctagcttttt tggccactgg ccgcgcgcag 13200
cgtaagcggt taggctggaa agcgaaagca ttaagtggct cgctccctgt agccggaggg 13260
ttattttcca agggttgagt cgcgggaccc ccggttcgag tctcggaccg gccggactgc 13320
ggcgaacggg ggtttgcctc cccgtcatgc aagaccccgc ttgcaaattc ctccggaaac 13380
agggacgagc ccctttttg cttttcccag atgcatccgg tgctgcggca gatgcgcccc 13440
cctcctcagc agcggcaaga gcaagagcag cggcagacat gcagggcacc ctcccctcct 13500

-continued

```
cctaccgcgt caggaggggc gacatccgcg gttgacgcgg cagcagatgg tgattacgaa  13560
cccccgcggc gccgggcccg gcactacctg gacttggagg agggcgaggg cctggcgcgg  13620
ctaggagcgc cctctcctga gcggtaccca agggtgcagc tgaagcgtga tacgcgtgag  13680
gcgtacgtgc cgcggcagaa cctgtttcgc gaccgcgagg gagaggagcc cgaggagatg  13740
cgggatcgaa agttccacgc agggcgcgag ctgcggcatg gcctgaatcg cgagcggttg  13800
ctgcgcgagg aggactttga gcccgacgcg cgaaccggga ttagtcccgc gcgcgcacac  13860
gtggcggccg ccgacctggt aaccgcatac gagcagacgg tgaaccagga gattaacttt  13920
caaaaaagct ttaacaacca cgtgcgtacg cttgtggcgc gcgaggaggt ggctatagga  13980
ctgatgcatc tgtgggactt tgtaagcgcg ctggagcaaa acccaaatag caagccgctc  14040
atggcgcagc tgttccttat agtgcagcac agcagggaca acgaggcatt cagggatgcg  14100
ctgctaaaca tagtagagcc cgagggccgc tggctgctcg atttgataaa catcctgcag  14160
agcatagtgg tgcaggagcg cagcttgagc ctggctgaca aggtggccgc catcaactat  14220
tccatgctta gcctgggcaa gttttacgcc cgcaagatat accatacccc ttacgttccc  14280
atagacaagg aggtaaagat cgaggggttc tacatgcgca tggcgctgaa ggtgcttacc  14340
ttgagcgacg acctgggcgt ttatcgcaac gagcgcatcc acaaggccgt gagcgtgagc  14400
cggcggcgcg agctcagcga ccgcgagctg atgcacagcc tgcaaagggc cctggctggc  14460
acgggcagcg gcgatagaga ggccgagtcc tactttgacg cgggcgctga cctgcgctgg  14520
gccccaagcc gacgcgccct ggaggcagct ggggccggac ctgggctggc ggtggcaccc  14580
gcgcgcgctg gcaacgtcgg cggcgtggag gaatatgacg aggacgatga gtacgagcca  14640
gaggacggcg agtactaagc ggtgatgttt ctgatcagat gatgcaagac gcaacggacc  14700
cggcggtgcg ggcggcgctg cagagccagc cgtccggcct taactccacg gacgactggc  14760
gccaggtcat ggaccgcatc atgtcgctga ctgcgcgcaa tcctgacgcg ttccggcagc  14820
agccgcaggc caaccggctc tccgcaattc tggaagcggt ggtcccggcg cgcgcaaacc  14880
ccacgcacga gaaggtgctg gcgatcgtaa acgcgctggc cgaaaacagg gccatccggc  14940
ccgacgaggc cggcctggtc tacgacgcgc tgcttcagcg cgtggctcgt tacaacagcg  15000
gcaacgtgca gaccaacctg gaccggctgg tgggggatgt gcgcgaggcc gtggcgcagc  15060
gtgagcgcgc gcagcagcag ggcaacctgg gctccatggt tgcactaaac gccttcctga  15120
gtacacagcc cgccaacgtg ccgcggggac aggaggacta caccaacttt gtgagcgcac  15180
tgcggctaat ggtgactgag acaccgcaaa gtgaggtgta ccagtctggg ccagactatt  15240
ttttccagac cagtagacaa ggcctgcaga ccgtaaacct gagccaggct ttcaaaaact  15300
tgcaggggct gtggggggtg cgggctccca caggcgaccg cgcgaccgtg tctagcttgc  15360
tgacgcccaa ctcgcgcctg ttgctgctgc taatagcgcc cttcacggac agtggcagcg  15420
tgtcccggga cacataccta ggtcacttgc tgacactgta ccgcgaggcc ataggtcagg  15480
cgcatgtgga cgagcatact ttccaggaga ttacaagtgt cagccgcgcg ctggggcagg  15540
aggacacggg cagcctggag gcaaccctaa actacctgct gaccaaccgg cggcagaaga  15600
tcccctcgtt gcacagttta aacagcgagg aggagcgcat tttgcgctac gtgcagcaga  15660
gcgtgagcct taacctgatg cgcgacgggg taacgcccag cgtggcgctg gacatgaccg  15720
cgcgcaacat ggaaccgggc atgtatgcct caaaccggcc gtttatcaac cgcctaatgg  15780
actacttgca tcgcgcggcc gccgtgaacc ccgagtattt caccaatgcc atcttgaacc  15840
```

-continued

```
cgcactggct accgcccccct ggtttctaca ccgggggatt cgaggtgccc gagggtaacg  15900
atggattcct ctgggacgac atagacgaca gcgtgttttc cccgcaaccg cagaccctgc  15960
tagagttgca acagcgcgag caggcagagg cggcgctgcg aaaggaaagc ttccgcaggc  16020
caagcagctt gtccgatcta ggcgctgcgg ccccgcggtc agatgctagt agcccatttc  16080
caagcttgat agggtctctt accagcactc gcaccacccg cccgcgcctg ctgggcgagg  16140
aggagtacct aaacaactcg ctgctgcagc cgcagcgcga aaaaaacctg cctccggcat  16200
ttcccaacaa cgggatagag agcctagtgg acaagatgag tagatggaag acgtacgcgc  16260
aggagcacag ggacgtgcca ggcccgcgcc cgcccacccg tcgtcaaagg cacgaccgtc  16320
agcggggtct ggtgtgggag gacgatgact cggcagacga cagcagcgtc ctggatttgg  16380
gagggagtgg caacccgttt gcgcaccttc gccccaggct ggggagaatg ttttaaaaaa  16440
aaaaaagcat gatgcaaaat aaaaaactca ccaaggccat ggcaccgagc gttggttttc  16500
ttgtattccc cttagtatgc ggcgcgcggc gatgtatgag gaaggtcctc ctccctccta  16560
cgagagtgtg gtgagcgcgg cgccagtggc ggcggcgctg ggttctccct tcgatgctcc  16620
cctggacccg ccgtttgtgc ctccgcggta cctgcggcct accgggggga gaaacagcat  16680
ccgttactct gagttggcac ccctattcga caccacccgt gtgtacctgg tggacaacaa  16740
gtcaacggat gtggcatccc tgaactacca gaacgaccac agcaactttc tgaccacggt  16800
cattcaaaac aatgactaca gcccggggga ggcaagcaca cagaccatca atcttgacga  16860
ccggtcgcac tggggcggcg acctgaaaac catcctgcat accaacatgc caaatgtgaa  16920
cgagttcatg tttaccaata agtttaaggc gcgggtgatg gtgtcgcgct tgcctactaa  16980
ggacaatcag gtggagctga aatacgagtg ggtggagttc acgctgcccg agggcaacta  17040
ctccgagacc atgaccatag accttatgaa caacgcgatc gtggagcact acttgaaagt  17100
gggcagacag aacggggttc tggaaagcga catcggggta aagtttgaca cccgcaactt  17160
cagactgggg tttgaccccg tcactggtct tgtcatgcct ggggtatata caaacgaagc  17220
cttccatcca gacatcattt tgctgccagg atgcggggtg gacttcaccc acagccgcct  17280
gagcaacttg ttgggcatcc gcaagcggca acccttccag gagggcttta ggatcaccta  17340
cgatgatctg gagggtggta acattcccgc actgttggat gtggacgcct accaggcgag  17400
cttgaaagat gacaccgaac agggcggggg tggcgcaggc ggcagcaaca gcagtggcag  17460
cggcgcggaa gagaactcca acgcggcagc cgcggcaatg cagccggtgg aggacatgaa  17520
cgatcatgcc attcgcggcg acacctttgc cacacgggct gaggagaagc gcgctgaggc  17580
cgaagcagcg gccgaagctg ccgcccccgc tgcgcaaccc gaggtcgaga agcctcagaa  17640
gaaaccggtg atcaaacccc tgacagagga cagcaagaaa cgcagttaca acctaataag  17700
caatgacagc accttcaccc agtaccgcag ctggtacctt gcatacaact acggcgaccc  17760
tcagaccgga atccgctcat ggaccctgct ttgcactcct gacgtaacct gcggctcgga  17820
gcaggtctac tggtcgttgc cagacatgat gcaagacccc gtgaccttcc gctccacgcg  17880
ccagatcagc aactttccgg tggtgggcgc cgagctgttg cccgtgcact ccaagagctt  17940
ctacaacgac caggccgtct actcccaact catccgccag tttacctctc tgacccacgt  18000
gttcaatcgc tttcccgaga accagatttt ggcgcgcccg ccagccccca ccatcaccac  18060
cgtcagtgaa aacgttcctg ctctcacaga tcacgggacg ctaccgctgc gcaacagcat  18120
cggaggagtc cagcgagtga ccattactga cgccagacgc cgcacctgcc cctacgttta  18180
caaggccctg ggcatagtct cgccgcgcgt cctatcgagc cgcacttttt gagcaagcat  18240
```

-continued

```
gtccatcctt atatcgccca gcaataacac aggctggggc ctgcgcttcc caagcaagat  18300
gtttggcggg gccaagaagc gctccgacca acacccagtg cgcgtgcgcg ggcactaccg  18360
cgcgccctgg ggcgcgcaca aacgcggccg cactgggcgc accaccgtcg atgacgccat  18420
cgacgcggtg gtggaggagg cgcgcaacta cacgcccacg ccgccaccag tgtccacagt  18480
ggacgcggcc attcagaccg tggtgcgcgg agcccggcgc tatgctaaaa tgaagagacg  18540
gcggaggcgc gtagcacgtc gccaccgccg ccgacccggc actgccgccc aacgcgcggc  18600
ggcggccctg cttaaccgcg cacgtcgcac cggccgacgg gcggccatgc gggccgctcg  18660
aaggctggcc gcgggtattg tcactgtgcc ccccaggtcc aggcgacgag cggccgccgc  18720
agcagccgcg gccattagtg ctatgactca gggtcgcagg ggcaacgtgt attgggtgcg  18780
cgactcggtt agcggcctgc gcgtgcccgt gcgcacccgc cccccgcgca actagattgc  18840
aagaaaaaac tacttagact cgtactgttg tatgtatcca gcggcggcgg cgcgcaacga  18900
agctatgtcc aagcgcaaaa tcaaagaaga gatgctccag gtcatcgcgc cggagatcta  18960
tggcccccg aagaaggaag agcaggatta caagccccga aagctaaagc gggtcaaaaa  19020
gaaaaagaaa gatgatgatg atgaacttga cgacgaggtg gaactgctgc acgctaccgc  19080
gcccaggcga cgggtacagt ggaaaggtcg acgcgtaaaa cgtgttttgc gacccggcac  19140
caccgtagtc tttacgcccg gtgagcgctc cacccgcacc tacaagcgcg tgtatgatga  19200
ggtgtacggc gacgaggacc tgcttgagca ggccaacgag cgcctcgggg agtttgccta  19260
cggaaagcgg cataaggaca tgctggcgtt gccgctggac gagggcaacc caacacctag  19320
cctaaagccc gtaacactgc agcaggtgct gcccgcgctt gcaccgtccg aagaaaagcg  19380
cggcctaaag cgcgagtctg gtgacttggc acccaccgtg cagctgatgg tacccaagcg  19440
ccagcgactg gaagatgtct tggaaaaaat gaccgtggaa cctgggctgg agcccgaggt  19500
ccgcgtgcgg ccaatcaagc aggtggcgcc gggactgggc gtgcagaccg tggacgttca  19560
gatacccact accagtagca ccagtattgc caccgccaca gagggcatgg agacacaaac  19620
gtccccggtt gcctcagcgg tggcggatgc cgcggtgcag gcggtcgctg cggccgcgtc  19680
caagacctct acggaggtgc aaacggaccc gtggatgttt cgcgtttcag ccccccggcg  19740
cccgcgcggt tcgaggaagt acggcgccgc cagcgcgcta ctgcccgaat atgccctaca  19800
tccttccatt gcgcctaccc ccggctatcg tggctacacc taccgcccca gaagacgagc  19860
aactacccga cgccgaacca ccactggaac ccgccgccgc cgtcgccgtc gccagcccgt  19920
gctggccccg atttccgtgc gcagggtggc tcgcgaagga ggcaggaccc tggtgctgcc  19980
aacagcgcgc taccacccca gcatcgttta aaagccggtc tttgtggttc ttgcagatat  20040
ggccctcacc tgccgcctcc gtttcccggt gccgggattc cgaggaagaa tgcaccgtag  20100
gaggggcatg gccggccacg gcctgacggg cggcatgcgt cgtgcgcacc accggcggcg  20160
gcgcgcgtcg caccgtcgca tgcgcggcgg tatcctgccc ctccttattc cactgatcgc  20220
cgcggcgatt ggcgccgtgc ccggaattgc atccgtggcc ttgcaggcgc agagacactg  20280
attaaaaaca agttgcatgt ggaaaaatca aaataaaaag tctggactct cacgctcgct  20340
tggtcctgta actattttgt agaatggaag acatcaactt tgcgtctctg gccccgcgac  20400
acggctcgcg cccgttcatg ggaaactggc aagatatcgg caccagcaat atgagcggtg  20460
gcgccttcag ctggggctcg ctgtggagcg gcattaaaaa tttcggttcc accgttaaga  20520
actatggcag caaggcctgg aacagcagca caggccagat gctgagggat aagttgaaag  20580
```

-continued

```
agcaaaattt ccaacaaaag gtggtagatg gcctggcctc tggcattagc ggggtggtgg  20640
acctggccaa ccaggcagtg caaaataaga ttaacagtaa gcttgatccc cgccctcccg  20700
tagaggagcc tccaccggcc gtggagacag tgtctccaga ggggcgtggc gaaaagcgtc  20760
cgcgccccga cagggaagaa actctggtga cgcaaataga cgagcctccc tcgtacgagg  20820
aggcactaaa gcaaggcctg cccaccaccc gtcccatcgc gcccatggct accggagtgc  20880
tgggccagca cacacccgta acgctggacc tgcctccccc cgccgacacc cagcagaaac  20940
ctgtgctgcc aggcccgacc gccgttgttg taacccgtcc tagccgcgcg tccctgcgcc  21000
gcgccgccag cggtccgcga tcgttgcggc ccgtagccag tggcaactgg caaagcacac  21060
tgaacagcat cgtgggtctg gggggtgcaat ccctgaagcg ccgacgatgc ttctgaatag  21120
ctaacgtgtc gtatgtgtgt catgtatgcg tccatgtcgc cgccagagga gctgctgagc  21180
cgccgcgcgc ccgctttcca agatggctac cccttcgatg atgccgcagt ggtcttacat  21240
gcacatctcg ggccaggacg cctcggagta cctgagcccc gggctggtgc agtttgcccg  21300
cgccaccgag acgtacttca gcctgaataa caagtttaga aaccccacgg tggcgcctac  21360
gcacgacgtg accacagacc ggtcccagcg tttgacgctg cggttcatcc ctgtggaccg  21420
tgaggatact gcgtactcgt acaaggcgcg gttcaccta gctgtgggtg ataaccgtgt  21480
gctggacatg gcttccacgt actttgacat ccgcggcgtg ctggacaggg gccctacttt  21540
taagccctac tctggcactg cctacaacgc cctggctccc aagggtgccc caaatccttg  21600
cgaatgggat gaagctgcta ctgctcttga aataaaccta gaagaagagg acgatgacaa  21660
cgaagacgaa gtagacgagc aagctgagca gcaaaaaact cacgtatttg ggcaggcgcc  21720
ttattctggt ataaatatta caaaggaggg tattcaaata ggtgtcgaag gtcaaacacc  21780
taaatatgcc gataaaacat ttcaacctga acctcaaata ggagaatctc agtggtacga  21840
aactgaaatt aatcatgcag ctgggagagt ccttaaaaag actaccccaa tgaaaccatg  21900
ttacggttca tatgcaaaac ccacaaatga aaatggaggg caaggcattc ttgtaaagca  21960
acaaaatgga aagctagaaa gtcaagtgga aatgcaattt ttctcaacta ctgaggcgac  22020
cgcaggcaat ggtgataact tgactcctaa agtggtattg tacagtgaag atgtagatat  22080
agaaacccca gacactcata tttcttacat gcccactatt aaggaaggta actcacgaga  22140
actaatgggc caacaatcta tgcccaacag gcctaattac attgctttta gggacaattt  22200
tattggtcta atgtattaca acagcacggg taatatgggt gttctggcgg gccaagcatc  22260
gcagttgaat gctgttgtag atttgcaaga cagaaacaca gagctttcat accagctttt  22320
gcttgattcc attggtgata gaaccaggta cttttctatg tggaatcagg ctgttgacag  22380
ctatgatcca gatgttagaa ttattgaaaa tcatggaact gaagatgaac ttccaaatta  22440
ctgctttcca ctgggaggtg tgattaatac agagactctt accaaggtaa aacctaaaac  22500
aggtcaggaa aatggatggg aaaaagatgc tacagaattt tcagataaaa atgaaataag  22560
agttggaaat aattttgcca tggaaatcaa tctaaatgcc aacctgtgga gaaatttcct  22620
gtactccaac atagcgctgt atttgcccga caagctaaag tacagtcctt ccaacgtaaa  22680
aatttctgat aacccaaaca cctacgacta catgaacaag cgagtggtgg ctcccgggtt  22740
agtggactgc tacattaacc ttggagcacg ctggtccctt gactatatgg acaacgtcaa  22800
cccatttaac caccaccgca atgctggcct gcgctaccgc tcaatgttgc tgggcaatgg  22860
tcgctatgtg cccttccaca tccaggtgcc tcagaagttc tttgccatta aaaacctcct  22920
tctcctgccg ggctcataca cctacgagtg gaacttcagg aaggatgtta acatggttct  22980
```

gcagagctcc ctaggaaatg acctaagggt tgacggagcc agcattaagt ttgatagcat 23040
ttgcctttac gccaccttct tccccatggc ccacaacacc gcctccacgc ttgaggccat 23100
gcttagaaac gacaccaacg accagtcctt taacgactat ctctccgccg ccaacatgct 23160
ctaccctata cccgccaacg ctaccaacgt gcccatatcc atcccctccc gcaactgggc 23220
ggctttccgc ggctgggcct tcacgcgcct taagactaag gaaaccccat cactgggctc 23280
gggctacgac ccttattaca cctactctgg ctctataccc tacctagatg gaacctttta 23340
cctcaaccac acctttaaga aggtggccat tacctttgac tcttctgtca gctggcctgg 23400
caatgaccgc ctgcttaccc ccaacgagtt tgaaattaag cgctcagttg acggggaggg 23460
ttacaacgtt gcccagtgta acatgaccaa agactggttc ctggtacaaa tgctagctaa 23520
ctacaacatt ggctaccagg gcttctatat cccagagagc tacaaggacc gcatgtactc 23580
cttctttaga aacttccagc ccatgagccg tcaggtggtg gatgatacta aatacaagga 23640
ctaccaacag gtgggcatcc tacaccaaca caacaactct ggatttgttg gctaccttgc 23700
ccccaccatg cgcgaaggac aggcctaccc tgctaacttc ccctatccgc ttataggcaa 23760
gaccgcagtt gacagcatta cccagaaaaa gtttctttgc gatcgcaccc tttggcgcat 23820
cccattctcc agtaacttta tgtccatggg cgcactcaca gacctgggcc aaaaccttct 23880
ctacgccaac tccgcccacg cgctagacat gacttttgag gtggatccca tggacgagcc 23940
cacccttctt tatgttttgt ttgaagtctt tgacgtggtc cgtgtgcacc ggccgcaccg 24000
cggcgtcatc gaaaccgtgt acctgcgcac gcccttctcg gccggcaacg ccacaacata 24060
aagaagcaag caacatcaac aacagctgcc gccatgggct ccagtgagca ggaactgaaa 24120
gccattgtca aagatcttgg ttgtgggcca tatttttttgg gcacctatga caagcgcttt 24180
ccaggctttg tttctccaca caagctcgcc tgcgccatag tcaatacggc cggtcgcgag 24240
actgggggcg tacactggat ggcctttgcc tggaacccgc actcaaaaac atgctacctc 24300
tttgagccct ttggcttttc tgaccagcga ctcaagcagg tttaccagtt tgagtacgag 24360
tcactcctgc gccgtagcgc cattgcttct tcccccgacc gctgtataac gctggaaaag 24420
tccacccaaa gcgtacaggg gcccaactcg gccgcctgtg gactattctg ctgcatgttt 24480
ctccacgcct ttgccaactg gccccaaact cccatggatc acaaccccac catgaacctt 24540
attaccgggg tacccaactc catgctcaac agtccccagg tacagcccac cctgcgtcgc 24600
aaccaggaac agctctacag cttcctggag cgccactcgc cctacttccg cagccacagt 24660
gcgcagatta ggagcgccac ttctttttgt cacttgaaaa acatgtaaaa ataatgtact 24720
agagacactt tcaataaagg caaatgcttt tatttgtaca ctctcgggtg attatttacc 24780
cccacccttg ccgtctgcgc cgtttaaaaa tcaaaggggt tctgccgcgc atcgctatgc 24840
gccactggca gggacacgtt gcgatactgg tgtttagtgc tccacttaaa ctcaggcaca 24900
accatccgcg gcagctcggt gaagttttca ctccacaggc tgcgcaccat caccaacgcg 24960
tttagcaggt cgggcgccga tatcttgaag tcgcagttgg ggcctccgcc ctgcgcgcgc 25020
gagttgcgat acacagggtt gcagcactgg aacactatca gcgccgggtg gtgcacgctg 25080
gccagcacgc tcttgtcgga gatcagatcc gcgtccaggt cctccgcgtt gctcagggcg 25140
aacggagtca actttggtag ctgccttccc aaaaagggcg cgtgcccagg ctttgagttg 25200
cactcgcacc gtagtggcat caaaaggtga ccgtgcccgg tctgggcgtt aggatacagc 25260
gcctgcataa aagccttgat ctgcttaaaa gccacctgag cctttgcgcc ttcagagaag 25320

-continued aacatgccgc aagacttgcc ggaaaactga ttggccggac aggccgcgtc gtgcacgcag 25380
caccttgcgt cggtgttgga gatctgcacc acatttcggc cccaccggtt cttcacgatc 25440
ttggccttgc tagactgctc cttcagcgcg cgctgcccgt tttcgctcgt cacatccatt 25500
tcaatcacgt gctccttatt tatcataatg cttccgtgta gacacttaag ctcgccttcg 25560
atctcagcgc agcggtgcag ccacaacgcg cagcccgtgg gctcgtgatg cttgtaggtc 25620
acctctgcaa acgactgcag gtacgcctgc aggaatcgcc ccatcatcgt cacaaaggtc 25680
ttgttgctgg tgaaggtcag ctgcaacccg cggtgctcct cgttcagcca ggtcttgcat 25740
acggccgcca gagcttccac ttggtcaggc agtagtttga agttcgcctt tagatcgtta 25800
tccacgtggt acttgtccat cagcgcgcgc gcagcctcca tgcccttctc ccacgcagac 25860
acgatcggca cactcagcgg gttcatcacc gtaatttcac tttccgcttc gctgggctct 25920
tcctcttcct cttgcgtccg cataccacgc gccactgggt cgtcttcatt cagccgccgc 25980
actgtgcgct tacctccttt gccatgcttg attagcaccg gtgggttgct gaaacccacc 26040
atttgtagcg ccacatcttc tctttcttcc tcgctgtcca cgattacctc tggtgatggc 26100
gggcgctcgg gcttgggaga agggcgcttc tttttcttct tgggcgcaat ggccaaatcc 26160
gccgccgagg tcgatggccg cgggctgggt gtgcgcggca ccagcgcgtc ttgtgatgag 26220
tcttcctcgt cctcggactc gatacgccgc ctcatccgct tttttggggg cgcccgggga 26280
ggcggcggcg acggggacgg ggacgacacg tcctccatgg ttgggggacg tcgcgccgca 26340
ccgcgtccgc gctcgggggt ggtttcgcgc tgctcctctt cccgactggc catttccttc 26400
tcctataggc agaaaaagat catggagtca gtcgagaaga aggacagcct aaccgccccc 26460
tctgagttcg ccaccaccgc ctccaccgat gccgccaacg cgcctaccac cttccccgtc 26520
gaggcacccc cgcttgagga ggaggaagtg attatcgagc aggacccagg ttttgtaagc 26580
gaagacgacg aggaccgctc agtaccaaca gaggataaaa agcaagacca ggacaacgca 26640
gaggcaaacg aggaacaagt cgggcggggg gacgaaaggc atggcgacta cctagatgtg 26700
ggagacgacg tgctgttgaa gcatctgcag cgccagtgcg ccattatctg cgacgcgttg 26760
caagagcgca gcgatgtgcc cctcgccata gcggatgtca gccttgccta cgaacgccac 26820
ctattctcac cgcgcgtacc ccccaaacgc caagaaaacg gcacatgcga gcccaacccg 26880
cgcctcaact tctaccccgt atttgccgtg ccagaggtgc ttgccaccta tcacatcttt 26940
ttccaaaact gcaagatacc cctatcctgc cgtgccaacc gcagccgagc ggacaagcag 27000
ctggccttgc ggcagggcgc tgtcatacct gatatcgcct cgctcaacga agtgccaaaa 27060
atctttgagg gtcttggacg cgacgagaag cgcgcggcaa acgctctgca acaggaaaac 27120
agcgaaaatg aaagtcactc tggagtgttg gtggaactcg agggtgacaa cgcgcgccta 27180
gccgtactaa aacgcagcat cgaggtcacc cactttgcct acccggcact taacctaccc 27240
cccaaggtca tgagcacagt catgagtgag ctgatcgtgc gccgtgcgca gcccctggag 27300
agggatgcaa atttgcaaga acaaacagag gagggcctac ccgcagttgg cgacgagcag 27360
ctagcgcgct ggcttcaaac gcgcgagcct gccgacttgg aggagcgacg caaactaatg 27420
atggccgcag tgctcgttac cgtggagctt gagtgcatgc agcggttctt tgctgacccg 27480
gagatgcagc gcaagctaga ggaaacattg cactacacct ttcgacaggg ctacgtacgc 27540
caggcctgca agatctccaa cgtggagctc tgcaacctgg tctcctacct tggaattttg 27600
cacgaaaacc gccttgggca aaacgtgctt cattccacgc tcaagggcga ggcgcgccgc 27660
gactacgtcc gcgactgcgt ttacttattt ctatgctaca cctggcagac ggccatgggc 27720

```
gtttggcagc agtgcttgga ggagtgcaac ctcaaggagc tgcagaaact gctaaagcaa  27780
aacttgaagg acctatggac ggccttcaac gagcgctccg tggccgcgca cctggcggac  27840
atcattttcc ccgaacgcct gcttaaaacc ctgcaacagg gtctgccaga cttcaccagt  27900
caaagcatgt tgcagaactt taggaacttt atcctagagc gctcaggaat cttgcccgcc  27960
acctgctgtg cacttcctag cgactttgtg cccattaagt accgcgaatg ccctccgccg  28020
ctttggggcc actgctacct tctgcagcta gccaactacc ttgcctacca ctctgacata  28080
atggaagacg tgagcggtga cggtctactg gagtgtcact gtcgctgcaa cctatgcacc  28140
ccgcaccgct ccctggtttg caattcgcag ctgcttaacg aaagtcaaat tatcggtacc  28200
tttgagctgc agggtccctc gcctgacgaa aagtccgcgg ctccggggtt gaaactcact  28260
ccggggctgt ggacgtcggc ttaccttcgc aaatttgtac ctgaggacta ccacgcccac  28320
gagattaggt tctacgaaga ccaatcccgc ccgccaaatg cggagcttac cgcctgcgtc  28380
attacccagg gccacattct tggccaattg caagccatca acaaagcccg ccaagagttt  28440
ctgctacgaa agggacgggg ggtttacttg gacccccagt ccggcgagga gctcaaccca  28500
atccccccgc cgccgcagcc ctatcagcag cagccgcggg cccttgcttc ccaggatggc  28560
acccaaaaag aagctgcagc tgccgccgcc acccacggac gaggaggaat actgggacag  28620
tcaggcagag gaggttttgg acgaggagga ggaggacatg atggaagact gggagagcct  28680
agacgaggaa gcttccgagg tcgaagaggt gtcagacgaa acaccgtcac cctcggtcgc  28740
attcccctcg ccggcgcccc agaaatcggc aaccggttcc agcatggcta caacctccgc  28800
tcctcaggcg ccgccggcac tgcccgttcg ccgacccaac cgtagatggg acaccactgg  28860
aaccagggcc ggtaagtcca agcagccgcc gccgttagcc caagagcaac aacagcgcca  28920
aggctaccgc tcatggcgcg ggcacaagaa cgccatagtt gcttgcttgc aagactgtgg  28980
gggcaacatc tccttcgccc gccgctttct tctctaccat cacggcgtgg ccttcccccg  29040
taacatcctg cattactacc gtcatctcta cagcccatac tgcaccggcg gcagcggcag  29100
cggcagcaac agcagcggcc acacagaagc aaaggcgacc ggatagcaag actctgacaa  29160
agcccaagaa atccacagcg gcggcagcag caggaggagg agcgctgcgt ctggcgccca  29220
acgaacccgt atcgacccgc gagcttagaa acaggatttt tcccactctg tatgctatat  29280
ttcaacagag caggggccaa gaacaagagc tgaaaataaa aaacaggtct ctgcgatccc  29340
tcacccgcag ctgcctgtat cacaaaagcg aagatcagct tcggcgcacg ctggaagacg  29400
cggaggctct cttcagtaaa tactgcgcgc tgactcttaa ggactagttt cgcgcccttt  29460
ctcaaattta agcgcgaaaa ctacgtcatc tccagcggcc acacccggcg ccagcacctg  29520
tcgtcagcgc cattatgagc aaggaaattc ccacgcccta catgtggagt taccagccac  29580
aaatgggact tgcggctgga gctgcccaag actactcaac ccgaataaac tacatgagcg  29640
cgggacccca catgatatcc cgggtcaacg gaatccgcgc ccaccgaaac cgaattctct  29700
tggaacaggc ggctattacc accacacctc gtaataacct taatccccgt agttggcccg  29760
ctgccctggt gtaccaggaa agtcccgctc ccaccactgt ggtacttccc agagacgccc  29820
aggccgaagt tcagatgact aactcagggg cgcagcttgc gggcggcttt cgtcacaggg  29880
tgcggtcgcc cgggcagggt ataactcacc tgacaatcag agggcgaggt attcagctca  29940
acgacgagtc ggtgagctcc tcgcttggtc tccgtccgga cgggacattt cagatcggcg  30000
gcgccggccg tccttcattc acgcctcgtc aggcaatcct aactctgcag acctcgtcct  30060
```

ctgagccgcg ctctggaggc attggaactc tgcaatttat tgaggagttt gtgccatcgg 30120
tctactttaa ccccttctcg ggacctcccg gccactatcc ggatcaattt attcctaact 30180
ttgacgcggt aaaggactcg gcggacggct acgactgaat gttaagtgga gaggcagagc 30240
aactgcgcct gaaacacctg gtccactgtc gccgccacaa gtgctttgcc cgcgactccg 30300
gtgagttttg ctactttgaa ttgcccgagg atcatatcga gggcccggcg cacggcgtcc 30360
ggcttaccgc ccagggagag cttgcccgta gcctgattcg ggagtttacc cagcgccccc 30420
tgctagttga gcgggacagg ggaccctgtg ttctcactgt gatttgcaac tgtcctaacc 30480
ttggattaca tcaagatctt tgttgccatc tctgtgctga gtataataaa tacagaaatt 30540
aaaatatact ggggctccta tcgccatcct gtaaacgcca ccgtcttcac ccgcccaagc 30600
aaaccaaggc gaaccttacc tggtactttt aacatctctc cctctgtgat ttacaacagt 30660
ttcaacccag acggagtgag tctacgagag aacctctccg agctcagcta ctccatcaga 30720
aaaaacacca ccctccttac ctgccgggaa cgtacgagtg cgtcaccggc cgctgcacca 30780
cacctaccgc ctgaccgtaa accagacttt ttccggacag acctcaataa ctctgtttac 30840
cagaacagga ggtgagctta gaaaaccctt agggtattag gccaaaggcg cagctactgt 30900
ggggtttatg aacaattcaa gcaactctac gggctattct aattcaggtt tctctagggt 30960
tggggttatt ctctgtcttg tgattctctt tattcttata ctaacgcttc tctgcctaag 31020
gctcgccgcc tgctgtgtgc acatttgcat ttattgtcag ctttttaaac gctggggtcg 31080
ccacccaaga tgattaggta cataatccta ggtttactca cccttgcgtc agcccacggt 31140
accacccaaa aggtggattt taaggagcca gcctgtaatg ttacattcgc agctgaagct 31200
aatgagtgca ccactcttat aaaatgcacc acagaacatg aaaagctgct tattcgccac 31260
aaaaacaaaa ttggcaagta tgctgtttat gctatttggc agccaggtga cactacagag 31320
tataatgtta cagttttcca gggtaaaagt cataaaactt ttatgtatac ttttccattt 31380
tatgaaatgt gcgacattac catgtacatg agcaaacagt ataagttgtg gccccccacaa 31440 aattgtgtgg aaaacactgg cactttctgc tgcactgcta tgctaattac agtgctcgct 31500
ttggtctgta ccctactcta tattaaatac aaaagcagac gcagctttat tgaggaaaag 31560
aaaatgcctt aatttactaa gttacaaagc taatgtcacc actaactgct ttactcgctg 31620
cttgcaaaac aaattcaaaa agttagcatt ataattagaa taggatttaa accccccggt 31680
catttcctgc tcaataccat tcccctgaac aattgactct atgtgggata tgctccagcg 31740
ctacaacctt gaagtcaggc ttcctggatg tcagcatctg actttggcca gcacctgtcc 31800
cgcggatttg ttccagtcca actacagcga cccaccctaa cagagatgac caacacaacc 31860
aacgcggccg ccgctaccgg acttacatct accacaaata caccccaagt ttctgccttt 31920
gtcaataact gggataactt gggcatgtgg tggttctcca tagcgcttat gtttgtatgc 31980
cttattatta tgtggctcat ctgctgccta aagcgcaaac gcgcccgacc acccatctat 32040
agtcccatca ttgtgctaca cccaaacaat gatggaatcc atagattgga cggactgaaa 32100
cacatgttct tttctcttac agtatgataa taaaaaaaaa taataaagca tcacttactt 32160
aaaatcagtt agcaaatttc tgtccagttt attcagcagc acctccttgc cctcctccca 32220
gctctggtat tgcagcttcc tcctggctgc aaactttctc cacaatctaa atggaatgtc 32280
agtttcctcc tgttcctgtc catccgcacc cactatcttc atgttgttgc agatgaagcg 32340
cgcaagaccg tctgaagata ccttcaaccc cgtgtatcca tatgacacgg aaaccggtcc 32400
tccaactgtg cctttttctta ctcctccctt tgtatccccc aatgggtttc aagagagtcc 32460

-continued

```
ccctggggta ctctctttgc gcctatccga acctctagtt acctccaatg gcatgcttgc  32520
gctcaaaatg ggcaacggcc tctctctgga cgaggccggc aaccttacct cccaaaatgt  32580
aaccactgtg agcccacctc tcaaaaaaac caagtcaaac ataaacctgg aaatatctgc  32640
acccctcaca gttacctcag aagccctaac tgtggctgcc gccgcacctc taatggtcgc  32700
gggcaacaca ctcaccatgc aatcacaggc cccgctaacc gtgcacgact ccaaacttag  32760
cattgccacc caaggacccc tcacagtgtc agaaggaaag ctagccctgc aaacatcagg  32820
ccccctcacc accaccgata gcagtaccct tactatcact gcctcacccc ctctaactac  32880
tgccactggt agcttgggca ttgacttgaa agagcccatt tatacacaaa atggaaaact  32940
aggactaaag tacggggctc ctttgcatgt aacagacgac ctaaacactt tgaccgtagc  33000
aactggtcca ggtgtgacta ttaataatac ttccttgcaa actaaagtta ctggagcctt  33060
gggttttgat tcacaaggca atatgcaact taatgtagca ggaggactaa ggattgattc  33120
tcaaaacaga cgccttatac ttgatgttag tttatccgttt gatgctcaaa accaactaaa  33180
tctaagacta ggacagggcc ctctttttat aaactcagcc cacaacttgg atattaacta  33240
caacaaaggc ctttacttgt ttacagcttc aaacaattcc aaaaagcttg aggttaacct  33300
aagcactgcc aaggggttga tgtttgacgc tacagccata gccattaatg caggagatgg  33360
gcttgaattt ggttcaccta atgcaccaaa cacaaatccc ctcaaaacaa aaattggcca  33420
tggcctagaa tttgattcaa acaaggctat ggttcctaaa ctaggaactg gccttagttt  33480
tgacagcaca ggtgccatta cagtaggaaa caaaaataat gataagctaa ctttgtggac  33540
cacaccagct ccatctccta actgtagact aaatgcagag aaagatgcta aactcacttt  33600
ggtcttaaca aaatgtggca gtcaaatact tgctacagtt tcagttttgg ctgttaaagg  33660
cagtttggct ccaatatctg gaacagttca aagtgctcat cttattataa gatttgacga  33720
aaatggagtg ctactaaaca attccttcct ggacccagaa tattggaact ttagaaatgg  33780
agatcttact gaaggcacag cctatacaaa cgctgttgga tttatgccta acctatcagc  33840
ttatccaaaa tctcacggta aaactgccaa aagtaacatt gtcagtcaag tttacttaaa  33900
cggagacaaa actaaacctg taacactaac cattacacta aacggtacac aggaaacagg  33960
agacacaact ccaagtgcat actctatgtc attttcatgg gactggtctg gccacaacta  34020
cattaatgaa atatttgcca catcctctta cactttttca tacattgccc aagaataaag  34080
aatcgtttgt gttatgtttc aacgtgttta tttttcaatt gcagaaaatt tcaagtcatt  34140
tttcattcag tagtatagcc ccaccaccac atagcttata cagatcaccg taccttaatc  34200
aaactcacag aaccctagta ttcaacctgc cacctccctc ccaacacaca gagtacacag  34260
tcctttctcc ccggctggcc ttaaaaagca tcatatcatg ggtaacagac atattcttag  34320
gtgttatatt ccacacggtt tcctgtcgag ccaaacgctc atcagtgata ttaataaact  34380
ccccgggcag ctcacttaag ttcatgtcgc tgtccagctg ctgagccaca ggctgctgtc  34440
caacttgcgg ttgcttaacg ggcggcgaag gagaagtcca cgcctacatg ggggtagagt  34500
cataatcgtg catcaggata gggcggtggt gctgcagcag cgcgcgaata aactgctgcc  34560
gccgccgctc cgtcctgcag gaatacaaca tggcagtggt ctcctcagcg atgattcgca  34620
ccgcccgcag cataaggcgc cttgtcctcc gggcacagca gcgcaccctg atctcactta  34680
aatcagcaca gtaactgcag cacagcacca caatattgtt caaaatccca cagtgcaagg  34740
cgctgtatcc aaagctcatg gcggggacca cagaacccac gtggccatca taccacaagc  34800
```

-continued

```
gcaggtagat taagtggcga cccctcataa acacgctgga cataaacatt acctcttttg  34860

gcatgttgta attcaccacc tcccggtacc atataaacct ctgattaaac atggcgccat  34920

ccaccaccat cctaaaccag ctggccaaaa cctgcccgcc ggctatacac tgcagggaac  34980

cgggactgga acaatgacag tggagagccc aggactcgta accatggatc atcatgctcg  35040

tcatgatatc aatgttggca caacacaggc acacgtgcat acacttcctc aggattacaa  35100

gctcctcccg cgttagaacc atatcccagg gaacaaccca ttcctgaatc agcgtaaatc  35160

ccacactgca gggaagacct cgcacgtaac tcacgttgtg cattgtcaaa gtgttacatt  35220

cgggcagcag cggatgatcc tccagtatgg tagcgcgggt ttctgtctca aaaggaggta  35280

gacgatccct actgtacgga gtgcgccgag acaaccgaga tcgtgttggt cgtagtgtca  35340

tgccaaatgg aacgccggac gtagtcatat ttccagtaaa aaagaaaacc tattaaaaaa  35400

acaccactcg acacggcacc agctcaatca gtcacagtgt aaaaaagggc caagtgcaga  35460

gcgagtatat ataggactaa aaaatgacgt aacggttaaa gtccacaaaa aacacccaga  35520

aaaccgcacg cgaacctacg cccagaaacg aaagccaaaa aacccacaac ttcctcaaat  35580

cgtcacttcc gttttcccac gttacgtaac ttcccatttt aagaaaacta caattcccaa  35640

cacatacaag ttactccgcc ctaaaaccta cgtcacccgc cccgttccca cgccccgcgc  35700

cacgtcacaa actccacccc ctcattatca tattggcttc aatccaaaat aaggtatatt  35760

attgatgatg                                                         35770
```

<210> SEQ ID NO 98
<211> LENGTH: 51
<212> TYPE: DNA
<213> ORGANISM: Artificial Sequence
<220> FEATURE:
<223> OTHER INFORMATION: APC mutation

<400> SEQUENCE: 98

```
gaaaagattg gaactaggtc agctcaagat cctgtgagcg aagttccagc a              51
```

<210> SEQ ID NO 99
<211> LENGTH: 33
<212> TYPE: DNA
<213> ORGANISM: Artificial Sequence
<220> FEATURE:
<223> OTHER INFORMATION: APC mutation

<400> SEQUENCE: 99

```
accctgcaaa tagcagaaat aaaagattgg aac                                  33
```

<210> SEQ ID NO 100
<211> LENGTH: 505
<212> TYPE: DNA
<213> ORGANISM: Unknown
<220> FEATURE:
<223> OTHER INFORMATION: Oncolytic serotype 5 adenovirus (Ad5)

<400> SEQUENCE: 100

```
atgttctttt ctcttacagt atgattaaat gagacatgtg gctgcaatcc ctgctgctct     60

tgggcactgt tgcctgctcc atctctgcac ccgcccgctc gccctccccc tccacgcaac    120

cctgggaaca tgttaatgcc atccaagaag cccggcgcct cctgaacctg tcccgggaca    180

ctgctgctga aatgaatgaa accgttgaag ttatctctga aatgtttgac ctccaagaac    240

cgacctgcct acaaacccgc ctggaactct acaaacaagg cctgcggggc tccctcacca    300

aactcaaagg ccccttgacc atgatggcct cccactacaa acaacactgc cctccaaccc    360
```

cggaaacttc ctgcgcaacc caaattatca cctttgaatc cttcaaagaa aacctgaaag 420
actttctgct tgttatcccc tttgactgct gggaacctgt tcaagaatga cggtctcaaa 480
gatcttattc cctttaacta ataaa 505

<210> SEQ ID NO 101
<211> LENGTH: 8
<212> TYPE: DNA
<213> ORGANISM: Unknown
<220> FEATURE:
<223> OTHER INFORMATION: Oncolytic serotype 5 adenovirus (Ad5)

<400> SEQUENCE: 101 agtgcccg 8

<210> SEQ ID NO 102
<211> LENGTH: 8
<212> TYPE: DNA
<213> ORGANISM: Unknown
<220> FEATURE:
<223> OTHER INFORMATION: Oncolytic serotype 5 adenovirus (Ad5)

<400> SEQUENCE: 102 tattcccg 8

<210> SEQ ID NO 103
<211> LENGTH: 10
<212> TYPE: DNA
<213> ORGANISM: Unknown
<220> FEATURE:
<223> OTHER INFORMATION: Oncolytic serotype 5 adenovirus (Ad5)

<400> SEQUENCE: 103
ttccgtggcg 10

<210> SEQ ID NO 104
<211> LENGTH: 621
<212> TYPE: DNA
<213> ORGANISM: Homo sapiens

<400> SEQUENCE: 104
atgaattttc aacagaggct gcaaagcctg tggactttag ccagaccctt ctgccctcct 60
ttgctggcga cagcctctca aatgcagatg gttgtgctcc cttgcctggg ttttaccctg 120
cttctctgga gccaggtatc aggggcccag ggccaagaat tccactttgg gccctgccaa 180
gtgaaggggg ttgttcccca gaaactgtgg gaagccttct gggctgtgaa agacactatg 240
caagctcagg ataacatcac gagtgcccgg ctgctgcagc aggaggttct gcagaacgtc 300
tcggatgctg agagctgtta ccttgtccac accctgctgg agttctactt gaaaactgtt 360
ttcaaaaact accacaatag aacagttgaa gtcaggactc tgaagtcatt ctctactctg 420
gccaacaact ttgttctcat cgtgtcacaa ctgcaaccca gtcaagaaaa tgagatgttt 480
tccatcagag acagtgcaca caggcggttt ctgctattcc ggagagcatt caaacagttg 540
gacgtagaag cagctctgac caaagccctt ggggaagtgg acattcttct gacctggatg 600
cagaaattct acaagctctg a 621

<210> SEQ ID NO 105
<211> LENGTH: 660
<212> TYPE: DNA
<213> ORGANISM: Mus musculus

<400> SEQUENCE: 105
atgctgactg agcctgccca actttttgtg cacaagaaga accagccacc ttcacacagc 60
agcctccggc ttcactttag gaccctagca ggagcactgg ccctttcttc aacacagatg 120
agttggggac tacagattct cccctgcctg agcctaatcc ttcttctttg gaaccaagtg 180
ccagggcttg agggtcaaga gttccgattt gggtcttgcc aagtgacagg ggtggttctc 240
ccagaactgt gggaggcctt ctggactgtg aagaacactg tgcaaactca ggatgacatc 300
acaagcatcc ggctgttgaa gccgcaggtt ctgcggaatg tctcgggtgc tgagagctgt 360
taccttgccc acagcctgct gaagttctac ttgaacactg ttttcaagaa ctaccacagc 420
aaaatagcca aattcaaggt cttgaggtca ttctccactc tggccaacaa cttcatagtc 480
atcatgtcac aactacagcc cagtaaggac aattccatgc ttcccattag tgagagtgca 540
caccagcggt tttgctgtt ccgcagagca ttcaaacagt tggatacaga agtcgctttg 600
gtgaaagcct ttggggaagt ggacattctc ctgacctgga tgcagaaatt ctaccatctc 660

<210> SEQ ID NO 106
<211> LENGTH: 4
<212> TYPE: PRT
<213> ORGANISM: Artificial Sequence
<220> FEATURE:
<223> OTHER INFORMATION: linker peptide
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be Lys or Arg and cleaves after the
final Arg

<400> SEQUENCE: 106

Arg Xaa Xaa Arg
1

<210> SEQ ID NO 107
<211> LENGTH: 4
<212> TYPE: PRT
<213> ORGANISM: Artificial Sequence
<220> FEATURE:
<223> OTHER INFORMATION: linker peptide

<400> SEQUENCE: 107

Arg Ala Lys Arg
1

<210> SEQ ID NO 108
<211> LENGTH: 2636
<212> TYPE: DNA
<213> ORGANISM: Artificial Sequence
<220> FEATURE:
<223> OTHER INFORMATION: epitope concatemer PSV1

<400> SEQUENCE: 108
atctgacctc gtcgacatgg acccgtgcag tagtgtgaag agaagtacga tggtgagagc 60
ggcgagagcg gctgcttatc tagagctatg caacggagga agtctaacag agctagtaaa 120
gggactacta gccgcttata gtacgatagt ggggagtgcg gcggtgaaca tgttcataat 180
aatagggata gcagcttata tcttttggca agtcacctgg cgaatggtct cacccccttct 240
tatgcttatc gcggcttatt gccacgcgga ggtggtggcg aggcaggcgt tcctgcactt 300

-continued

```
cctgtacacg gctgcctatc tgaacaagca gccgagcctg ctgagccaca cgacgaagtg    360
gctgacgcag gccgcctatt taggtttaac tactgttcct cctaatgttc ctgctgctac    420
tcgcacttta gcagcctatg aggcagtacg ggcagaccgg atgaagggag gacggaacaa    480
gttcggaccg gcggcctatt gtttattagt cttagtcatt gcctgggtcc gccgcttaca    540
taatgtcacc gctgcatata aggaggacga ctgcgagcac gggaaggacg agacgcactg    600
caacaagttc gccgcatatt cacaatcact tcccgcctca catacccatc ttcgagtcac    660
cgccgccccc gcagcatatg aattgcaaca attggttgaa ggtcaacaag aatcttattt    720
gttgtgttgg gcggcatata aacgatcatc acgacgacaa tcacccgaac ttcaaaaatg    780
tgaagaaatc gctgcgtatc gtgtttctga ttataaacat catcgttctg atgttttggt    840
tggtttgttg gccgcgtatg gttcctatgg ttttcgctta ggttccttac attccggtac    900
tgctaaatcc gcagcgtata gagcggagga gttcataggg gcggacgagc aggcgagata    960
ctgccacggg gcggcgtatt atgtcaaata ttggcaatca aatatcaata atgtcaaaat   1020
gtttcaagcc gctgcttaca tcaaaaaaga tgaacttaaa aaagtccccg tccgacatct   1080
tcttcccgtc tggcccgatc ccggctatcc cggcatcacc gaacccgaag atgaaggccc   1140
cggcctttgt catcttcaag gcggccaaca acgacatcaa cgacccgccc ttcatgccgg   1200
ctttcccttt cttgccgctt accaagcctc atgggaattt gaagccaaaa tccttgtcct   1260
tcatcatccc accgcagctt acgagcgggt agagaagtgg cgggaggcac agcggaagaa   1320
ggcaatggag aacgcggctt acatactgga caagcagaag gtggtgaacc tgaagcagat   1380
agagcacacg ctggctgcct acgtagcagt accatcgatc tcgcaggcac tccggatctg   1440
gctctgccca cacgccgcct acccagagtt ccacccaaac aagacaatgc tcgcatggct   1500
ccgggacaca tacgcagcct accccgtcgc cgatttatta gatcgctgtg gcgtctttcg   1560
cgcccgctta tttgcggcct actgtttgcg ttgtgaatgt aaatatgatg aacgttcttc   1620
tgttactatt aaagctgcat acagaccaaa gagtcaggta atgaacataa taggaagtga   1680
gagaagattc agtgccgcat acacattcaa gcgggtactc atcaagcagg aggagtacga   1740
ctcgatcatc gtagcagcat acactgatgg tcaagtttat ggtgctactt ttgttgcttc   1800
ccatcctatt caagcggcat actttcttcg acttaaaatg gcctatgtcc ccaaaaatgg   1860
cggccaagat gaagctgcgt accagacacg gaagctcgca atcctcggag agcagtacga   1920
gcagtcgatc aacgccgcgt acgacgagcc ggtgaaggcg aagaagtgga agagggacga   1980
caacaaggac atagcagcgt acatggcccg acaacaacga gcccaacccc ttcgagtccg   2040
aaccaaacat accgcggcgt accacatgcc actcctctcg atctacctcc tcgcactcga   2100
gcaggacctc gaggctgctt atccggggat ggagatagcg aactgctgca gaaacggggg   2160
gtggacgccg tgggccgctt atgcggtgca gagggtgcag gtgctgcaga tgctgatact   2220
gtactacata ctgccgagga aggtgctgca gatggacttc ctggtgcacc cggcggcagc   2280
ttataggata cacgcggagg agaagccgta cacgtgcgag gagtgcggga agatagcggc   2340
ttatgcgttc aacaacaagg gggacgggct gacggcggct gcctatatgc agatcttcgt   2400
aaagacactc acaggaaaga caatcacact cgaggtagag ccatcggaca caatcgagaa   2460
cgtaaaggca aagatccagg acaaggaggg aatcccacca gaccagcagc ggctcatctt   2520
cgcaggaaag cagctcgagg acggacggac actctcggac tacaacatcc agaaggagtc   2580
gacactccac ctcgtactcc ggctccgggg aggatagtaa ctcgagtcac caggcg       2636
```

<210> SEQ ID NO 109
<211> LENGTH: 329
<212> TYPE: DNA
<213> ORGANISM: Artificial Sequence
<220> FEATURE:
<223> OTHER INFORMATION: epitope concatemer PSV2

<400> SEQUENCE: 109
atctgacctc gtcgacatgg aaaagattgg aactaggtca gctcaagatc ctgtgagcga 60
agttccagca gccgcttaca tgcagatctt cgtgaaaacc cttaccggca agaccatcac 120
ccttgaggtg gagcccagtg acaccatcga aaatgtgaag gccaagatcc aggataagga 180
aggcattccc cccgaccagc agaggctcat ctttgcaggc aagcagctgg aagatggccg 240
tactctttct gactacaaca tccagaagga gtcgaccctg cacctggtcc tgcgtctgag 300
aggtggttag taactcgagt caccaggcg 329

<210> SEQ ID NO 110
<211> LENGTH: 311
<212> TYPE: DNA
<213> ORGANISM: Artificial Sequence
<220> FEATURE:
<223> OTHER INFORMATION: epitope concatemer PSV3

<400> SEQUENCE: 110
atctgacctc gtcgacatga ccctgcaaat agcagaaata aaagattgga acgccgctta 60
catgcagatc ttcgtgaaaa cccttaccgg caagaccatc acccttgagg tggagcccag 120
tgacaccatc gaaaatgtga aggccaagat ccaggataag gaaggcattc cccccgacca 180
gcagaggctc atctttgcag gcaagcagct ggaagatggc cgtactcttt ctgactacaa 240
catccagaag gagtcgaccc tgcacctggt cctgcgtctg agaggtggtt agtaactcga 300
gtcaccaggc g 311

<210> SEQ ID NO 111
<211> LENGTH: 17
<212> TYPE: PRT
<213> ORGANISM: Artificial Sequence
<220> FEATURE:
<223> OTHER INFORMATION: APC point mutation cancer antigen

<400> SEQUENCE: 111

Glu Lys Ile Gly Thr Arg Ser Ala Gln Asp Pro Val Ser Glu Val Pro
1 5 10 15

Ala

<210> SEQ ID NO 112
<211> LENGTH: 11
<212> TYPE: PRT
<213> ORGANISM: Artificial Sequence
<220> FEATURE:
<223> OTHER INFORMATION: APC frameshift mutation cancer antigen

<400> SEQUENCE: 112

Thr Leu Gln Ile Ala Glu Ile Lys Asp Trp Asn
1 5 10

<210> SEQ ID NO 113
<211> LENGTH: 34794
<212> TYPE: DNA
<213> ORGANISM: Human adenovirus 35

<400> SEQUENCE: 113

-continued

```
catcatcaat aatatacctt atagatggaa tggtgccaat atgtaaatga ggtgatttta     60
aaaagtgtgg gccgtgtggt gattggctgt ggggttaacg gttaaaaggg gcggcgcggc    120
cgtgggaaaa tgacgtttta tgggggtgga gttttttttgc aagttgtcgc gggaaatgtt   180
acgcataaaa aggcttcttt tctcacggaa ctacttagtt ttcccacggt atttaacagg    240
aaatgaggta gttttgaccg gatgcaagtg aaaattgctg attttcgcgc gaaaactgaa    300
tgaggaagtg tttttctgaa taatgtggta tttatggcag ggtggagtat ttgttcaggg    360
ccaggtagac tttgacccat tacgtggagg tttcgattac cgtgtttttt acctgaattt    420
ccgcgtaccg tgtcaaagtc ttctgttttt acgtaggtgt cagctgatcg ctagggtatt    480
tatacctcag ggtttgtgtc aagaggccac tcttgagtgc cagcgagaag agttttctcc    540
tctgcgccgg cagtttaata ataaaaaaat gagagatttg cgatttctgc ctcaggaaat    600
aatctctgct gagactggaa atgaaatatt ggagcttgtg gtgcacgccc tgatgggaga    660
cgatccggag ccacctgtgc agctttttga gcctcctacg cttcaggaac tgtatgattt    720
agaggtagag ggatcggagg attctaatga ggaagctgtg aatggctttt ttaccgattc    780
tatgctttta gctgctaatg aaggattaga attagatccg cctttggaca ctttcaatac    840
tccaggggtg attgtggaaa gcggtacagg tgtaagaaaa ttacctgatt tgagttccgt    900
ggactgtgat ttgcactgct atgaagacgg gtttcctccg agtgatgagg aggaccatga    960
aaaggagcag tccatgcaga ctgcagcggg tgagggagtg aaggctgcca atgttggttt   1020
tcagttggat tgcccggagc ttcctggaca tggctgtaag tcttgtgaat ttcacaggaa   1080
aaatactgga gtaaaggaac tgttatgttc gctttgttat atgagaacgc actgccactt   1140
tatttacagt aagtgtgttt aagttaaaat ttaaaggaat atgctgtttt tcacatgtat   1200
attgagtgtg agttttgtgc ttcttattat aggtcctgtg tctgatgctg atgaatcacc   1260
atctcctgat tctactacct cacctcctga tattcaagca cctgttcctg tggacgtgcg   1320
caagcccatt cctgtgaagc ttaagcctgg gaaacgtcca gcagtggaga aacttgagga   1380
cttgttacag ggtggggacg gacctttgga cttgagtaca cggaaacgtc caagacaata   1440
agtgttccat atccgtgttt acttaaggtg acgtcaatat ttgtgtgaga gtgcaatgta   1500
ataaaaatat gttaactgtt cactggtttt tattgctttt tgggcgggga ctcaggtata   1560
taagtagaag cagacctgtg tggttagctc ataggagctg gctttcatcc atggaggttt   1620
gggccatttt ggaagacctt aggaagacta ggcaactgtt agagagcgct tcggacggag   1680
tctccggttt ttggagattc tggttcgcta gtgaattagc tagggtagtt tttaggataa   1740
aacaggacta taaacaagaa tttgaaaagt tgttggtaga ttgcccagga ctttttgaag   1800
ctcttaattt gggccatcag gttcacttta aagaaaaagt tttatcagtt ttagactttt   1860
caaccccagg tagaactgct gctgctgtgg cttttcttac ttttatatta gataaatgga   1920
tcccgcagac tcatttcagc aggggatacg ttttggattt catagccaca gcattgtgga   1980
gaacatggaa ggttcgcaag atgaggacaa tcttaggtta ctggccagtg cagcctttgg   2040
gtgtagcggg aatcctgagg catccaccgg tcatgccagc ggttctggag gaggaacagc   2100
aagaggacaa cccgagagcc ggcctggacc ctccagtgga ggaggcggag tagctgactt   2160
gtctcctgaa ctgcaacggg tgcttactgg atctacgtcc actggacggg ataggggcgt   2220
taagagggag agggcatcca gtggtactga tgctagatct gagttggctt taagtttaat   2280
gagtcgcaga cgtcctgaaa ccatttggtg gcatgaggtt cagaaagagg gaagggatga   2340
agtttctgta ttgcaggaga aatattcact ggaacaggtg aaaacatgtt ggttggagcc   2400
```

agaggatgat tgggcggtgg ccattaaaaa ttatgccaag atagctttga ggcctgataa 2460
acagtataag atcagtagac ggattaatat ccggaatgct tgttacatat ctggaaatgg 2520
ggctgaggtg gtaatagata ctcaagacaa gacagttatt agatgctgca tgatggatat 2580
gtggcctgga gtagtcggta tggaagcagt cacttttgta aatgttaagt ttaggggaga 2640
tggttataat ggaatagtgt ttatggccaa taccaaactt atattgcatg gttgtagctt 2700
ttttggtttc aacaatacct gtgtagatgc ctggggacag gttagtgtac gggggtgtag 2760
tttctatgcg tgttggattg ccacagctgg cagaaccaag agtcaattgt ctctgaagaa 2820
atgcatattc caaagatgta acctgggcat tctgaatgaa ggcgaagcaa gggtccgtca 2880
ctgcgcttct acagatactg gatgttttat tttaattaag ggaaatgcca gcgtaaagca 2940
taacatgatt tgtggtgctt ccgatgagag gccttatcaa atgctcactt gtgctggtgg 3000
gcattgtaat atgctggcta ctgtgcatat tgtttcccat caacgcaaaa aatggcctgt 3060
ttttgatcac aatgtgttga ccaagtgcac catgcatgca ggtgggcgta gaggaatgtt 3120
tatgccttac cagtgtaaca tgaatcatgt gaaagtgttg ttggaaccag atgccttttc 3180
cagaatgagc ctaacaggaa tctttgacat gaacacgcaa atctggaaga tcctgaggta 3240
tgatgatacg agatcgaggg tgcgcgcatg cgaatgcgga ggcaagcatg ccaggttcca 3300
gccggtgtgt gtagatgtga ccgaagatct cagaccggat catttggtta ttgcccgcac 3360
tggagcagag ttcggatcca gtggagaaga aactgactaa ggtgagtatt gggaaaactt 3420
tggggtggga ttttcagatg gacagattga gtaaaaattt gtttttctg tcttgcagct 3480
gacatgagtg gaaatgcttc ttttaagggg ggagtcttca gcccttatct gacagggcgt 3540
ctcccatcct gggcaggagt tcgtcagaat gttatgggat ctactgtgga tggaagaccc 3600
gttcaacccg ccaattcttc aacgctgacc tatgctactt taagttcttc acctttggac 3660
gcagctgcag ccgctgccgc cgcctctgtc gccgctaaca ctgtgcttgg aatgggttac 3720
tatggaagca tcgtggctaa ttccacttcc tctaataacc cttctacact gactcaggac 3780
aagttacttg tccttttggc ccagctggag gctttgaccc aacgtctggg tgaactttct 3840
cagcaggtgg ccgagttgcg agtacaaact gagtctgctg tcggcacggc aaagtctaaa 3900
taaaaaaaat tccagaatca atgaataaat aaacgagctt gttgttgatt taaaatcaag 3960
tgtttttatt tcatttttcg cgcacggtat gccctggacc accgatctcg atcattgaga 4020
actcggtgga tttttccag aatcctatag aggtgggatt gaatgtttag atacatgggc 4080
attaggccgt ctttggggtg gagatagctc cattgaaggg attcatgctc cggggtagtg 4140
ttgtaaatca cccagtcata acaaggtcgc agtgcatggt gttgcacaat atcttttaga 4200
agtaggctga ttgccacaga taagcccttg gtgtaggtgt ttacaaaccg gttgagctgg 4260
gaggggtgca ttcgaggtga aattatgtgc attttggatt ggatttttaa gttggcaata 4320
ttgccgccaa gatcccgtct tgggttcatg ttatgaagga ctaccaagac ggtgtatccg 4380
gtacatttag gaaatttatc gtgcagcttg gatggaaaag cgtggaaaaa tttggagaca 4440
cccttgtgtc ctccgagatt ttccatgcac tcatccatga taatagcaat ggggccgtgg 4500
gcagcggcgc gggcaaacac gttccgtggg tctgacacat catagttatg ttcctgagtt 4560
aaatcatcat aagccatttt aatgaatttg gggcggagcg taccagattg ggtatgaat 4620
gttccttcgg gccccggagc atagttcccc tcacagattt gcatttccca agctttcagt 4680
tctgagggtg gaatcatgtc cacctggggg gctatgaaga acaccgtttc gggggcgggg 4740

-continued

```
gtgattagtt gggatgatag caagtttctg agcaattgag atttgccaca tccggtgggg   4800
ccataaataa ttccgattac aggttgcagg tggtagttta gggaacggca actgccgtct   4860
tctcgaagca agggggccac ctcgttcatc atttccctta catgcatatt ttcccgcacc   4920
aaatccatta ggaggcgctc tcctcctagt gatagaagtt cttgtagtga ggaaaagttt   4980
ttcagcggtt ttagaccgtc agccatgggc attttggaaa gagtttgctg caaaagttct   5040
agtctgttcc acagttcagt gatgtgttct atggcatctc gatccagcag acctcctcgt   5100
ttcgcgggtt tggacggctc ctggagtagg gtatgagacg atgggcgtcc agcgctgcca   5160
gggttcggtc cttccagggt ctcagtgttc gagtcagggt tgtttccgtc acagtgaagg   5220
ggtgtgcgcc tgcttgggcg cttgccaggg tgcgcttcag actcattctg ctggtggaga   5280
acttctgtcg cttggcgccc tgtatgtcgg ccaagtagca gtttaccatg agttcgtagt   5340
tgagcgcctc ggctgcgtgg cctttggcgc ggagcttacc tttggaagtt ttcttgcata   5400
ccgggcagta taggcatttc agcgcataca gcttgggcgc aaggaaaatg gattctgggg   5460
agtatgcatc cgcgccgcag gaggcgcaaa cagtttcaca ttccaccagc caggttaaat   5520
ccggttcatt ggggtcaaaa acaagttttc cgccatattt tttgatgcgt ttcttacctt   5580
tggtctccat aagttcgtgt cctcgttgag tgacaaacag gctgtccgta tctccgtaga   5640
ctgattttac aggcctcttc tccagtggag tgcctcggtc ttcttcgtac aggaactctg   5700
accactctga tacaaaggcg cgcgtccagg ccagcacaaa ggaggctatg tgggaggggt   5760
agcgatcgtt gtcaaccagg gggtccacct tttccaaagt atgcaaacac atgtcaccct   5820
cttcaacatc caggaatgtg attggcttgt aggtgtattt cacgtgacct ggggtccccg   5880
ctggggggt ataaaagggg gcggttcttt gctcttcctc actgtcttcc ggatcgctgt   5940
ccaggaacgt cagctgttgg ggtaggtatt ccctctcgaa ggcgggcatg acctctgcac   6000
tcaggttgtc agtttctaag aacgaggagg atttgatatt gacagtgccg gttgagatgc   6060
ctttcatgag gttttcgtcc atttggtcag aaaacacaat ttttttattg tcaagtttgg   6120
tggcaaatga tccatacagg gcgttggata aaagtttggc aatggatcgc atggtttggt   6180
tcttttcctt gtccgcgcgc tctttggcgg cgatgttgag ttggacatac tcgcgtgcca   6240
ggcacttcca ttcggggaag atagttgtta attcatctgg cacgattctc acttgccacc   6300
ctcgattatg caaggtaatt aaatccacac tggtggccac ctcgcctcga aggggttcat   6360
tggtccaaca gagcctacct cctttcctag aacagaaagg gggaagtggg tctagcataa   6420
gttcatcggg agggtctgca tccatggtaa agattcccgg aagtaaatcc ttatcaaaat   6480
agctgatggg agtggggtca tctaaggcca tttgccattc tcgagctgcc agtgcgcgct   6540
catatgggtt aaggggactg ccccagggca tgggatgggt gagagcagag gcatacatgc   6600
cacagatgtc atagacgtag atgggatcct caaagatgcc tatgtaggtt ggatagcatc   6660
gcccccctct gatacttgct cgcacatagt catatagttc atgtgatggc gctagcagcc   6720
ccggacccaa gttggtgcga ttgggttttt ctgttctgta gacgatctgg cgaaagatgg   6780
cgtgagaatt ggaagagatg gtgggtcttt gaaaaatgtt gaaatgggca tgaggtagac   6840
ctacagagtc tctgacaaag tgggcataag attcttgaag cttggttacc agttcggcgg   6900
tgacaagtac gtctagggcg cagtagtcaa gtgtttcttg aatgatgtca taacctggtt   6960
ggtttttctt ttcccacagt tcgcggttga gaaggtattc ttcgcgatcc ttccagtact   7020
cttctagcgg aaacccgtct ttgtctgcac ggtaagatcc tagcatgtag aactgattaa   7080
ctgccttgta agggcagcag cccttctcta cgggtagaga gtatgcttga gcagcttttc   7140
```

```
gtagcgaagc gtgagtaagg gcaaaggtgt ctctgaccat gactttgaga aattggtatt   7200
tgaagtccat gtcgtcacag gctccctgtt cccagagttg gaagtctacc cgtttcttgt   7260
aggcggggtt gggcaaagcg aaagtaacat cattgaagag aatcttaccg gctctgggca   7320
taaaattgcg agtgatgcgg aaaggctgtg gtacttccgc tcgattgttg atcacctggg   7380
cagctaggac gatttcgtcg aaaccgttga tgttgtgtcc tacgatgtat aattctatga   7440
aacgcggcgt gcctctgacg tgaggtagct tactgagctc atcaaaggtt aggtctgtgg   7500
ggtcagataa ggcgtagtgt tcgagagccc attcgtgcag gtgaggattt gcatgtagga   7560
atgatgacca aagatctacc gccagtgctg tttgtaactg gtcccgatac tgacgaaaat   7620
gccggccaat tgccattttt tctggagtga cacagtagaa ggttctgggg tcttgttgcc   7680
atcgatccca cttgagttta atggctagat cgtgggccat gttgacgaga cgctcttctc   7740
ctgagagttt catgaccagc atgaaaggaa ctagttgttt gccaaaggat cccatccagg   7800
tgtaagtttc cacatcgtag gtcaggaaga gtctttctgt gcgaggatga gagccgatcg   7860
ggaagaactg gatttcctgc caccagttgg aggattggct gttgatgtga tggaagtaga   7920
agtttctgcg gcgcgccgag cattcgtgtt tgtgcttgta cagacggccg cagtagtcgc   7980
agcgttgcac gggttgtatc tcgtgaatga gctgtacctg gcttcccttg acgagaaatt   8040
tcagtgggaa gccgaggcct ggcgattgta tctcgtgctc ttctatattc gctgtatcgg   8100
cctgttcatc ttctgtttcg atggtggtca tgctgacgag cccccgcggg aggcaagtcc   8160
agacctcggc gcgggagggg cggagctgaa ggacgagagc gcgcaggctg gagctgtcca   8220
gagtcctgag acgctgcgga ctcaggttag taggtaggga cagaagatta acttgcatga   8280
tcttttccag ggcgtgcggg aggttcagat ggtacttgat ttccacaggt tcgtttgtag   8340
agacgtcaat ggcttgcagg gttccgtgtc ctttgggcgc cactaccgta cctttgtttt   8400
ttcttttgat cggtggtggc tctcttgctt cttgcatgct cagaagcggt gacggggacg   8460
cgcgccgggc ggcagcggtt gttccggacc cgggggcatg gctggtagtg gcacgtcggc   8520
gccgcgcacg ggcaggttct ggtattgcgc tctgagaaga cttgcgtgcg ccaccacgcg   8580
tcgattgacg tcttgtatct gacgtctctg ggtgaaagct accggccccg tgagcttgaa   8640
cctgaaagag agttcaacag aatcaatttc ggtatcgtta acggcagctt gtctcagtat   8700
ttcttgtacg tcaccagagt tgtcctggta ggcgatctcc gccatgaact gctcgatttc   8760
ttcctcctga agatctccgc gacccgctct ttcgacggtg gccgcgaggt cattggagat   8820
acggcccatg agttgggaga atgcattcat gcccgcctcg ttccagacgc ggctgtaaac   8880
cacggccccc tcggagtctc ttgcgcgcat caccacctga gcgaggttaa gctccacgtg   8940
tctggtgaag accgcatagt tgcataggcg ctgaaaaagg tagttgagtg tggtggcaat   9000
gtgttcggcg acgaagaaat acatgatcca tcgtctcagc ggcatttcgc taacatcgcc   9060
cagagcttcc aagcgctcca tggcctcgta gaagtccacg gcaaaattaa aaaactggga   9120
gtttcgcgcg gacacggtca attcctcctc gagaagacgg atgagttcgg ctatggtggc   9180
ccgtacttcg cgttcgaagg ctcccgggat ctcttcttcc tcttctatct cttcttccac   9240
taacatctct tcttcgtctt caggcggggg cggagggggc acgcggcgac gtcgacggcg   9300
cacgggcaaa cggtcgatga atcgttcaat gacctctccg cggcggcggc gcatggtttc   9360
agtgacggcg cggccgttct cgcgcggtcg cagagtaaaa acaccgccgc gcatctcctt   9420
aaagtggtga ctgggaggtt ctccgtttgg gagggagagg gcgctgatta tacattttat   9480
```

-continued taattggccc gtagggactg cgcgcagaga tctgatcgtg tcaagatcca cgggatctga 9540
aaacctttcg acgaaagcgt ctaaccagtc acagtcacaa ggtaggctga gtacggcttc 9600
ttgtgggcgg gggtggttat gtgttcggtc tgggtcttct gtttcttctt catctcggga 9660
aggtgagacg atgctgctgg tgatgaaatt aaagtaggca gttctaagac ggcggatggt 9720
ggcgaggagc accaggtctt tgggtccggc ttgctggata cgcaggcgat tggccattcc 9780
ccaagcatta tcctgacatc tagcaagatc tttgtagtag tcttgcatga gccgttctac 9840
gggcacttct tcctcacccg ttctgccatg catacgtgtg agtccaaatc cgcgcattgg 9900
ttgtaccagt gccaagtcag ctacgactct ttcggcgagg atggcttgct gtacttgggt 9960
aagggtggct tgaaagtcat caaaatccac aaagcggtgg taagcccctg tattaatggt 10020
gtaagcacag ttggccatga ctgaccagtt aactgtctgg tgaccagggc gcacgagctc 10080
ggtgtattta aggcgcgaat aggcgcgggt gtcaaagatg taatcgttgc aggtgcgcac 10140
cagatactgg taccctataa gaaaatgcgg cggtggttgg cggtagagag gccatcgttc 10200
tgtagctgga gcgccagggg cgaggtcttc caacataagg cggtgatagc cgtagatgta 10260
cctggacatc caggtgattc ctgcggcggt agtagaagcc cgaggaaact cgcgtacgcg 10320
gttccaaatg ttgcgtagcg gcatgaagta gttcattgta ggcacggttt gaccagtgag 10380
gcgcgcgcag tcattgatgc tctatagaca cggagaaaat gaaagcgttc agcgactcga 10440
ctccgtagcc tggaggaacg tgaacgggtt gggtcgcggt gtaccccggt tcgagacttg 10500
tactcgagcc ggccggagcc gcggctaacg tggtattggc actcccgtct cgacccagcc 10560
tacaaaaatc caggatacgg aatcgagtcg ttttgctggt ttccgaatgg cagggaagtg 10620
agtcctattt tttttttttt tttgccgctc agatgcatcc cgtgctgcga cagatgcgcc 10680
cccaacaaca gcccccctcg cagcagcagc agcagcaacc acaaaaggct gtccctgcaa 10740
ctactgcaac tgccgccgtg agcggtgcgg gacagcccgc ctatgatctg gacttggaag 10800
agggcgaagg actggcacgt ctaggtgcgc cttcgcccga gcggcatccg cgagttcaac 10860
tgaaaaaaga ttctcgcgag gcgtatgtgc cccaacagaa cctatttaga gacagaagcg 10920
gcgaggagcc ggaggagatg cgagcttccc gctttaacgc gggtcgtgag ctgcgtcacg 10980
gtttggaccg aagacgagtg ttgcgagacg aggatttcga agttgatgaa gtgacaggga 11040
tcagtcctgc cagggcacac gtggctgcag ccaaccttgt atcggcttac gagcagacag 11100
taaaggaaga gcgtaacttc caaaagtctt ttaataatca tgtgcgaacc ctgattgccc 11160
gcgaagaagt tacccttggt ttgatgcatt tgtgggattt gatggaagct atcattcaga 11220
accctactag caaacctctg accgcccagc tgtttctggt ggtgcaacac agcagagaca 11280
atgaggcttt cagagaggcg ctgctgaaca tcaccgaacc cgaggggaga tggttgtatg 11340
atcttatcaa cattctacag agtatcatag tgcaggagcg gagcctgggc ctggccgaga 11400
aggtagctgc catcaattac tcggttttga gcttgggaaa atattacgct cgcaaaatct 11460
acaagactcc atacgttccc atagacaagg aggtgaagat agatgggttc tacatgcgca 11520
tgacgctcaa ggtcttgacc ctgagcgatg atcttggggt gtatcgcaat gacagaatgc 11580
atcgcgcggt tagcgccagc aggaggcgcg agttaagcga cagggaactg atgcacagtt 11640
tgcaaagagc tctgactgga gctggaaccg agggtgagaa ttacttcgac atgggagctg 11700
acttgcagtg gcagcctagt cgcagggctc tgagcgccgc gacggcagga tgtgagcttc 11760
cttacataga agaggcggat gaaggcgagg aggaagaggg cgagtacttg gaagactgat 11820
ggcacaaccc gtgtttttg ctagatggaa cagcaagcac cggatcccgc aatgcgggcg 11880
gcgctgcaga gccagccgtc cggcattaac tcctcggacg attggaccca ggccatgcaa 11940
cgtatcatgg cgttgacgac tcgcaacccc gaagccttta gacagcaacc ccaggccaac 12000
cgtctatcgg ccatcatgga agctgtagtg ccttcccgat ctaatcccac tcatgagaag 12060
gtcctggcca tcgtgaacgc gttggtggag aacaaagcta ttcgtccaga tgaggccgga 12120
ctggtataca acgctctctt agaacgcgtg gctcgctaca acagtagcaa tgtgcaaacc 12180
aatttggacc gtatgataac agatgtacgc gaagccgtgt ctcagcgcga aaggttccag 12240
cgtgatgcca acctgggttc gctggtggcg ttaaatgctt tcttgagtac tcagcctgct 12300
aatgtgccgc gtggtcaaca ggattatact aactttttaa gtgctttgag actgatggta 12360
tcagaagtac ctcagagcga agtgtatcag tccggtcctg attacttctt tcagactagc 12420
agacagggct tgcagacggt aaatctgagc caagctttta aaaaccttaa aggtttgtgg 12480
ggagtgcatg ccccggtagg agaaagagca accgtgtcta gcttgttaac tccgaactcc 12540
cgcctgttat tactgttggt agctcctttc accgacagcg gtagcatcga ccgtaattcc 12600
tatttgggtt acctactaaa cctgtatcgc gaagccatag ggcaaagtca ggtggacgag 12660
cagacctatc aagaaattac ccaagtcagt cgcgctttgg gacaggaaga cactggcagt 12720
ttggaagcca ctctgaactt cttgcttacc aatcggtctc aaaagatccc tcctcaatat 12780
gctcttactg cggaggagga gaggatcctt agatatgtgc agcagagcgt gggattgttt 12840
ctgatgcaag agggggcaac tccgactgca gcactggaca tgacagcgcg aaatatggag 12900
cccagcatgt atgccagtaa ccgacctttc attaacaaac tgctggacta cttgcacaga 12960
gctgccgcta tgaactctga ttatttcacc aatgccatct taaacccgca ctggctgccc 13020
ccacctggtt tctacacggg cgaatatgac atgcccgacc ctaatgacgg atttctgtgg 13080
gacgacgtgg acagcgatgt tttttcacct ctttctgatc atcgcacgtg gaaaaaggaa 13140
ggcggtgata gaatgcattc ttctgcatcg ctgtccgggg tcatgggtgc taccgcggct 13200
gagcccgagt ctgcaagtcc ttttcctagt ctaccctttt ctctacacag tgtacgtagc 13260
agcgaagtgg gtagaataag tcgcccgagt ttaatgggcg aagaggagta cctaaacgat 13320
tccttgctca gaccggcaag agaaaaaaat ttcccaaaca atggaataga aagtttggtg 13380
gataaaatga gtagatggaa gacttatgct caggatcaca gagacgagcc tgggatcatg 13440
gggactacaa gtagagcgag ccgtagacgc cagcgccatg acagacagag ggtcttgtg 13500
tgggacgatg aggattcggc cgatgatagc agcgtgttgg acttgggtgg gagaggaagg 13560
ggcaacccgt ttgctcattt gcgccctcgc ttgggtggta tgttgtgaaa aaaaataaaa 13620
aagaaaaact caccaaggcc atggcgacga gcgtacgttc gttcttcttt attatctgtg 13680
tctagtataa tgaggcgagt cgtgctaggc ggagcggtgg tgtatccgga gggtcctcct 13740
ccttcgtacg agagcgtgat gcagcagcag caggcgacgg cggtgatgca atccccactg 13800
gaggctccct ttgtgcctcc gcgatacctg gcacctacgg agggcagaaa cagcattcgt 13860
tactcggaac tggcacctca gtacgatacc accaggttgt atctggtgga caacaagtcg 13920
gcggacattg cttctctgaa ctatcagaat gaccacagca acttcttgac cacggtggtg 13980
cagaacaatg actttacccc tacggaagcc agcacccaga ccattaactt tgatgaacga 14040
tcgcggtggg gcggtcagct aaagaccatc atgcatacta acatgccaaa cgtgaacgag 14100
tatatgttta gtaacaagtt caaagcgcgt gtgatggtgt ccagaaaacc tcccgacggt 14160
gctgcagttg ggatacttta tgatcacaag caggatattt tggaatatga gtggttcgag 14220

```
tttactttgc cagaaggcaa cttttcagtt actatgacta ttgatttgat gaacaatgcc  14280
atcatagata attacttgaa agtgggtaga cagaatggag tgcttgaaag tgacattggt  14340
gttaagttcg acaccaggaa cttcaagctg ggatgggatc ccgaaaccaa gttgatcatg  14400
cctggagtgt atacgtatga agccttccat cctgacattg tcttactgcc tggctgcgga  14460
gtggatttta ccgagagtcg tttgagcaac cttcttggta tcagaaaaaa acagccattt  14520
caagagggtt ttaagatttt gtatgaagat ttagaaggtg gtaatattcc ggccctcttg  14580
gatgtagatg cctatgagaa cagtaagaaa gaacaaaaag ccaaaataga agctgctaca  14640
gctgctgcag aagctaaggc aaacatagtt gccagcgact ctacaagggt tgctaacgct  14700
ggagaggtca gaggagacaa ttttgcgcca acacctgttc cgactgcaga atcattattg  14760
gccgatgtgt ctgaaggaac ggacgtgaaa ctcactattc aacctgtaga aaaagatagt  14820
aagaatagaa gctataatgt gttggaagac aaaatcaaca cagcctatcg cagttggtat  14880
ctttcgtaca attatggcga tcccgaaaaa ggagtgcgtt cctggacatt gctcaccacc  14940
tcagatgtca cctgcggagc agagcaggtt tactggtcgc ttccagacat gatgaaggat  15000
cctgtcactt tccgctccac tagacaagtc agtaactacc ctgtggtggg tgcagagctt  15060
atgcccgtct tctcaaagag cttctacaac gaacaagctg tgtactccca gcagctccgc  15120
cagtccacct cgcttacgca cgtcttcaac cgctttcctg agaaccagat tttaatccgt  15180
ccgccggcgc ccaccattac caccgtcagt gaaaacgttc ctgctctcac agatcacggg  15240
accctgccgt tgcgcagcag tatccgggga gtccaacgtg tgaccgttac tgacgccaga  15300
cgccgcacct gtccctacgt gtacaaggca ctgggcatag tcgcaccgcg cgtcctttca  15360
agccgcactt tctaaaaaaa aaaaatgtcc attcttatct cgcccagtaa taacaccggt  15420
tggggtctgc gcgctccaag caagatgtac ggaggcgcac gcaaacgttc tacccaacat  15480
cccgtgcgtg ttcgcggaca ttttcgcgct ccatggggtg ccctcaaggg ccgcactcgc  15540
gttcgaacca ccgtcgatga tgtaatcgat caggtggttg ccgacgcccg taattatact  15600
cctactgcgc ctacatctac tgtggatgca gttattgaca gtgtagtggc tgacgctcgc  15660
aactatgctc gacgtaagag ccggcgaagg cgcattgcca gacgccaccg agctaccact  15720
gccatgcgag ccgcaagagc tctgctacga agagctagac gcgtggggcg aagagccatg  15780
cttagggcgg ccagacgtgc agcttcgggc gccagcgccg gcaggtcccg caggcaagca  15840
gccgctgtcg cagcggcgac tattgccgac atggcccaat cgcgaagagg caatgtatac  15900
tgggtgcgtg acgctgccac cggtcaacgt gtacccgtgc gcacccgtcc ccctcgcact  15960
tagaagatac tgagcagtct ccgatgttgt gtcccagcgg cgaggatgtc caagcgcaaa  16020
tacaaggaag aaatgctgca ggttatcgca cctgaagtct acggccaacc gttgaaggat  16080
gaaaaaaaac cccgcaaaat caagcgggtt aaaaaggaca aaaaagaaga ggaagatggc  16140
gatgatgggc tggcggagtt tgtgcgcgag tttgccccac ggcgacgcgt gcaatggcgt  16200
gggcgcaaag ttcgacatgt gttgagacct ggaacttcgg tggtctttac acccggcgag  16260
cgttcaagcg ctacttttaa gcgttcctat gatgaggtgt acggggatga tgatattctt  16320
gagcaggcgg ctgaccgatt aggcgagttt gcttatggca agcgtagtag aataacttcc  16380
aaggatgaga cagtgtcaat acccttggat catggaaatc ccacccctag tcttaaaccg  16440
gtcactttgc agcaagtgtt acccgtaact ccgcgaacag gtgttaaacg cgaaggtgaa  16500
gatttgtatc ccactatgca actgatggta cccaaacgcc agaagttgga ggacgttttg  16560
gagaaagtaa aagtggatcc agatattcaa cctgaggtta aagtgagacc cattaagcag  16620
```

-continued

```
gtagcgcctg gtctgggggt acaaactgta gacattaaga ttcccactga aagtatggaa  16680
gtgcaaactg aacccgcaaa gcctactgcc acctccactg aagtgcaaac ggatccatgg  16740
atgcccatgc ctattacaac tgacgccgcc ggtcccactc gaagatcccg acgaaagtac  16800
ggtccagcaa gtctgttgat gcccaattat gttgtacacc catctattat tcctactcct  16860
ggttaccgag gcactcgcta ctatcgcagc cgaaacagta cctcccgccg tcgccgcaag  16920
acacctgcaa atcgcagtcg tcgccgtaga cgcacaagca aaccgactcc cggcgccctg  16980
gtgcggcaag tgtaccgcaa tggtagtgcg gaacctttga cactgccgcg tgcgcgttac  17040
catccgagta tcatcactta atcaatgttg ccgctgcctc cttgcagata tggccctcac  17100
ttgtcgcctt cgcgttccca tcactggtta ccgaggaaga aactcgcgcc gtagaagagg  17160
gatgttggga cgcggaatgc gacgctacag gcgacggcgt gctatccgca agcaattgcg  17220
gggtggtttt ttaccagcct taattccaat tatcgctgct gcaattggcg cgataccagg  17280
catagcttcc gtggcggttc aggcctcgca acgacattga cattggaaaa aaaacgtata  17340
aataaaaaaa aatacaatgg actctgacac tcctggtcct gtgactatgt tttcttagag  17400
atggaagaca tcaatttttc atccttggct ccgcgacacg gcacgaagcc gtacatgggc  17460
acctggagcg acatcggcac gagccaactg aacgggggcg ccttcaattg gagcagtatc  17520
tggagcgggc ttaaaaattt tggctcaacc ataaaaacat acgggaacaa agcttggaac  17580
agcagtacag gacaggcgct tagaaataaa cttaaagacc agaacttcca acaaaaagta  17640
gtcgatggga tagcttccgg catcaatgga gtggtagatt tggctaacca ggctgtgcag  17700
aaaaagataa acagtcgttt ggacccgccg ccagcaaccc caggtgaaat gcaagtggag  17760
gaagaaattc ctccgccaga aaaacgaggc gacaagcgtc cgcgtcccga tttggaagag  17820
acgctggtga cgcgcgtaga tgaaccgcct tcttatgagg aagcaacgaa gcttggaatg  17880
cccaccacta gaccgatagc cccaatggcc accggggtga tgaaaccttc tcagttgcat  17940
cgacccgtca ccttggattt gccccctccc cctgctgcta ctgctgtacc cgcttctaag  18000
cctgtcgctg ccccgaaacc agtcgccgta gccaggtcac gtcccggggg cgctcctcgt  18060
ccaaatgcgc actggcaaaa tactctgaac agcatcgtgg gtctaggcgt gcaaagtgta  18120
aaacgccgtc gctgctttta attaaatatg gagtagcgct taacttgcct atctgtgtat  18180
atgtgtcatt acacgccgtc acagcagcag aggaaaaaag gaagaggtcg tgcgtcgacg  18240
ctgagttact ttcaagatgg ccaccccatc gatgctgccc caatgggcat acatgcacat  18300
cgccggacag gatgcttcgg agtacctgag tccgggtctg gtgcagttcg cccgcgccac  18360
agacacctac ttcaatctgg gaaataagtt tagaaatccc accgtagcgc cgacccacga  18420
tgtgaccacc gaccgtagcc agcggctcat gttgcgcttc gtgcccgttg accgggagga  18480
caatacatac tcttacaaag tgcggtacac cctggccgtg ggcgacaaca gagtgctgga  18540
tatggccagc acgttctttg acattagggg cgtgttggac agaggtccca gtttcaaacc  18600
ctattctggt acggcttaca actctctggc tcctaaaggc gctccaaatg catctcaatg  18660
gattgcaaaa ggcgtaccaa ctgcagcagc cgcaggcaat ggtgaagaag aacatgaaac  18720
agaggagaaa actgctactt acacttttgc caatgctcct gtaaaagccg aggctcaaat  18780
tacaaaagag ggcttaccaa taggtttgga gatttcagct gaaaacgaat ctaaacccat  18840
ctatgcagat aaactttatc agccagaacc tcaagtggga gatgaaactt ggactgacct  18900
agacggaaaa accgaagagt atggaggcag ggctctaaag cctactacta acatgaaacc  18960
```

-continued

```
ctgttacggg tcctatgcga agcctactaa tttaaaaggt ggtcaggcaa aaccgaaaaa  19020
ctcggaaccg tcgagtgaaa aaattgaata tgatattgac atggaatttt ttgataactc  19080
atcgcaaaga acaaacttca gtcctaaaat tgtcatgtat gcagaaaatg taggtttgga  19140
aacgccagac actcatgtag tgtacaaacc tggaacagaa gacacaagtt ccgaagctaa  19200
tttgggacaa cagtctatgc ccaacagacc caactacatt ggcttcagag ataactttat  19260
tggactcatg tactataaca gtactggtaa catgggggtg ctggctggtc aagcgtctca  19320
gttaaatgca gtggttgact tgcaggacag aaacacagaa ctttcttacc aactcttgct  19380
tgactctctg ggcgacagaa ccagatactt tagcatgtgg aatcaggctg tggacagtta  19440
tgatcctgat gtacgtgtta ttgaaaatca tggtgtggaa gatgaacttc ccaactattg  19500
ttttccactg gacggcatag gtgttccaac aaccagttac aaatcaatag ttccaaatgg  19560
agaagataat aataattgga aagaacctga agtaaatgga acaagtgaga tcggacaggg  19620
taatttgttt gccatggaaa ttaaccttca agccaatcta tggcgaagtt tcctttattc  19680
caatgtggct ctgtatctcc cagactcgta caaatacacc ccgtccaatg tcactcttcc  19740
agaaaacaaa aacacctacg actacatgaa cgggcgggtg gtgccgccat ctctagtaga  19800
cacctatgtg aacattggtg ccaggtggtc tctggatgcc atggacaatg tcaacccatt  19860
caaccaccac cgtaacgctg gcttgcgtta ccgatctatg cttctgggta acggacgtta  19920
tgtgcctttc cacatacaag tgcctcaaaa attcttcgct gttaaaaacc tgctgcttct  19980
cccaggctcc tacacttatg agtggaactt taggaaggat gtgaacatgg ttctacagag  20040
ttccctcggt aacgacctgc gggtagatgg cgccagcatc agtttcacga gcatcaacct  20100
ctatgctact tttttcccca tggctcacaa caccgcttcc acccttgaag ccatgctgcg  20160
gaatgacacc aatgatcagt cattcaacga ctacctatct gcagctaaca tgctctaccc  20220
cattcctgcc aatgcaacca atattcccat ttccattcct tctcgcaact gggcggcttt  20280
cagaggctgg tcatttacca gactgaaaac caaagaaact ccctctttgg ggtctggatt  20340
tgacccctac tttgtctatt ctggttctat tccctacctg gatggtacct tctacctgaa  20400
ccacactttt aagaaggttt ccatcatgtt tgactcttca gtgagctggc ctggaaatga  20460
caggttacta tctcctaacg aatttgaaat aaagcgcact gtggatggcg aaggctacaa  20520
cgtagcccaa tgcaacatga ccaaagactg gttcttggta cagatgctcg ccaactacaa  20580
catcggctat cagggcttct acattccaga aggatacaaa gatcgcatgt attcattttt  20640
cagaaacttc cagcccatga gcaggcaggt ggttgatgag gtcaattaca aagacttcaa  20700
ggccgtcgcc ataccctacc aacacaacaa ctctggcttt gtgggttaca tggctccgac  20760
catgcgccaa ggtcaaccct atcccgctaa ctatccctat ccactcattg gaacaactgc  20820
cgtaaatagt gttacgcaga aaaagttctt gtgtgacaga accatgtggc gcataccgtt  20880
ctcgagcaac ttcatgtcta tgggggccct tacagacttg ggacagaata tgctctatgc  20940
caactcagct catgctctgg acatgacctt tgaggtggat cccatggatg agcccaccct  21000
gctttatctt ctcttcgaag ttttcgacgt ggtcagagtg catcagccac accgcggcat  21060
catcgaggca gtctacctgc gtacaccgtt ctcggccggt aacgctacca cgtaagaagc  21120
ttcttgcttc ttgcaaatag cagctgcaac catggcctgc ggatcccaaa acggctccag  21180
cgagcaagag ctcagagcca ttgtccaaga cctgggttgc ggaccctatt ttttgggaac  21240
ctacgataag cgcttcccgg ggttcatggc ccccgataag ctcgcctgtg ccattgtaaa  21300
tacggccgga cgtgagacgg ggggagagca ctggttggct ttcggttgga acccacgttc  21360
```

-continued

```
taacacctgc tacctttttg atccttttgg attctcggat gatcgtctca aacagattta  21420
ccagtttgaa tatgagggtc tcctgcgccg cagcgctctt gctaccaagg accgctgtat  21480
tacgctggaa aaatctaccc agaccgtgca gggcccccgt tctgccgcct gcggactttt  21540
ctgctgcatg ttccttcacg cctttgtgca ctggcctgac cgtcccatgg acggaaaccc  21600
caccatgaaa ttgctaactg gagtgccaaa caacatgctt cattctccta aagtccagcc  21660
caccctgtgt gacaatcaaa aagcactcta ccattttctt aatacccatt cgccttattt  21720
tcgctctcat cgtacacaca tcgaaagggc cactgcgttc gaccgtatgg atgttcaata  21780
atgactcatg taaacaacgt gttcaataaa catcacttta tttttttaca tgtatcaagg  21840
ctctggatta cttatttatt tacaagtcga atgggttctg acgagaatca gaatgacccg  21900
caggcagtga tacgttgcgg aactgatact tgggttgcca cttgaattcg ggaatcacca  21960
acttgggaac cggtatatcg ggcaggatgt cactccacag ctttctggtc agctgcaaag  22020
ctccaagcag gtcaggagcc gaaatcttga aatcacaatt aggaccagtg ctctgagcgc  22080
gagagttgcg gtacaccgga ttgcagcact gaaacaccat cagcgacgga tgtctcacgc  22140
ttgccagcac ggtgggatct gcaatcatgc ccacatccag atcttcagca ttggcaatgc  22200
tgaacggggt catcttgcag gtctgcctac ccatggcggg cacccaatta ggcttgtggt  22260
tgcaatcgca gtgcaggggg atcagtatca tcttggcctg atcctgtctg attcctggat  22320
acacggctct catgaaagca tcatattgct tgaaagcctg ctgggcttta ctaccctcgg  22380
tataaaacat cccgcaggac ctgctcgaaa actggttagc tgcacagccg gcatcattca  22440
cacagcagcg ggcgtcattg ttggctattt gcaccacact tctgccccag cggttttggg  22500
tgattttggt tcgctcggga ttctccttta aggctcgttg tccgttctcg ctggccacat  22560
ccatctcgat aatctgctcc ttctgaatca taatattgcc atgcaggcac ttcagcttgc  22620
cctcataatc attgcagcca tgaggccaca acgcacagcc tgtacattcc caattatggt  22680
gggcgatctg agaaaaagaa tgtatcattc cctgcagaaa tcttcccatc atcgtgctca  22740
gtgtcttgtg actagtgaaa gttaactgga tgcctcggtg ctcttcgttt acgtactggt  22800
gacagatgcg cttgtattgt tcgtgttgct caggcattag tttaaaacag gttctaagtt  22860
cgttatccag cctgtacttc tccatcagca gacacatcac ttccatgcct ttctcccaag  22920
cagacaccag gggcaagcta atcggattct taacagtgca ggcagcagct cctttagcca  22980
gagggtcatc tttagcgatc ttctcaatgc ttcttttgcc atccttctca acgatgcgca  23040
cgggcgggta gctgaaaccc actgctacaa gttgcgcctc ttctctttct tcttcgctgt  23100
cttgactgat gtcttgcatg gggatatgtt tggtcttcct tggcttcttt ttgggggggta  23160
tcggaggagg aggactgtcg ctccgttccg gagacaggga ggattgtgac gtttcgctca  23220
ccattaccaa ctgactgtcg gtagaagaac ctgaccccac acggcgacag gtgtttttct  23280
tcgggggcag aggtggaggc gattgcgaag ggctgcggtc cgacctggaa ggcggatgac  23340
tggcagaacc ccttccgcgt tcgggggtgt gctccctgtg gcggtcgctt aactgatttc  23400
cttcgcggct ggccattgtg ttctcctagg cagagaaaca acagacatgg aaactcagcc  23460
attgctgtca acatcgccac gagtgccatc acatctcgtc ctcagcgacg aggaaaagga  23520
gcagagctta agcattccac cgcccagtcc tgccaccacc tctaccctag aagataagga  23580
ggtcgacgca tctcatgaca tgcagaataa aaaagcgaaa gagtctgaga cagacatcga  23640
gcaagacccg ggctatgtga caccggtgga acacgaggaa gagttgaaac gctttctaga  23700
```

-continued

```
gagagaggat gaaaactgcc caaaacagcg agcagataac tatcaccaag atgctggaaa  23760
tagggatcag aacaccgact acctcatagg gcttgacggg gaagacgcgc tccttaaaca  23820
tctagcaaga cagtcgctca tagtcaagga tgcattattg gacagaactg aagtgcccat  23880
cagtgtggaa gagctcagct gcgcctacga gcttaacctt ttttcacctc gtactccccc  23940
caaacgtcag ccaaacggca cctgcgagcc aaatcctcgc ttaaactttt atccagcttt  24000
tgctgtgcca gaagtactgg ctacctatca catctttttt aaaaatcaaa aaattccagt  24060
ctcctgccgc gctaatcgca cccgcgccga tgccctactc aatctgggac ctggttcacg  24120
cttacctgat atagcttcct tggaagaggt tccaaagatc ttcgagggtc tgggcaataa  24180
tgagactcgg gccgcaaatg ctctgcaaaa gggagaaaat ggcatggatg agcatcacag  24240
cgttctggtg gaattggaag gcgataatgc cagactcgca gtactcaagc gaagcgtcga  24300
ggtcacacac ttcgcatatc ccgctgtcaa cctgcccccct aaagtcatga cggcggtcat  24360
ggaccagtta ctcattaagc gcgcaagtcc cctttcagaa gacatgcatg acccagatgc  24420
ctgtgatgag ggtaaaccag tggtcagtga tgagcagcta acccgatggc tgggcaccga  24480
ctctccccgg gatttggaag agcgtcgcaa gcttatgatg gccgtggtgc tggttaccgt  24540
agaactagag tgtctccgac gtttctttac cgattcagaa accttgcgca aactcgaaga  24600
gaatctgcac tacactttta gacacggctt tgtgcggcag gcatgcaaga tatctaacgt  24660
ggaactcacc aacctggttt cctacatggg tattctgcat gagaatcgcc taggacaaag  24720
cgtgctgcac agcaccctta agggggaagc ccgccgtgat tacatccgcg attgtgtcta  24780
tctctacctg tgccacacgt ggcaaaccgg catgggtgta tggcagcaat gtttagaaga  24840
acagaacttg aaagagcttg acaagctctt acagaaatct cttaaggttc tgtggacagg  24900
gttcgacgag cgcaccgtcg cttccgacct ggcagacctc atcttcccag agcgtctcag  24960
ggttactttg cgaaacggat tgcctgactt tatgagccag agcatgctta acaattttcg  25020
ctctttcatc ctggaacgct ccggtatcct gcccgccacc tgctgcgcac tgccctccga  25080
ctttgtgcct ctcacctacc gcgagtgccc cccgccgcta tggagtcact gctacctgtt  25140
ccgtctggcc aactatctct cctaccactc ggatgtgatc gaggatgtga gcggagacgg  25200
cttgctggag tgccactgcc gctgcaatct gtgcacgccc caccggtccc tagcttgcaa  25260
cccccagttg atgagcgaaa cccagataat aggcaccttt gaattgcaag gccccagcag  25320
ccaaggcgat gggtcttctc ctgggcaaag tttaaaactg accccgggac tgtggacctc  25380
cgcctacttg cgcaagtttg ctccggaaga ttaccacccc tatgaaatca agttctatga  25440
ggaccaatca cagcctccaa aggccgaact ttcggcttgc gtcatcaccc agggggcaat  25500
tctggcccaa ttgcaagcca tccaaaaatc ccgccaagaa tttctactga aaaagggtaa  25560
gggggtctac cttgaccccc agaccggcga ggaactcaac acaaggttcc ctcaggatgt  25620
cccaacgacg agaaaacaag aagttgaagg tgcagccgcc gcccccagaa gatatggagg  25680
aagattggga cagtcaggca gaggaggcgg aggaggacag tctggaggac agtctggagg  25740
aagacagttt ggaggaggaa aacgaggagg cagaggaggt ggaagaagta accgccgaca  25800
aacagttatc ctcggctgcg gagacaagca acagcgctac catctccgct ccgagtcgag  25860
gaacccggcg gcgtcccagc agtagatggg acgagaccgg acgcttcccg aacccaacca  25920
gcgcttccaa gaccggtaag aaggatcggc agggatacaa gtcctggcgg gggcataaga  25980
atgccatcat ctcctgcttg catgagtgcg ggggcaacat atccttcacg cggcgctact  26040
tgctattcca ccatggggtg aactttccgc gcaatgtttt gcattactac cgtcacctcc  26100
```

acagcccta ctatagccag caaatcccga cagtctcgac agataaagac agcggcggcg 26160
acctccaaca gaaaaccagc agcggcagtt agaaaataca caacaagtgc agcaacagga 26220
ggattaaaga ttacagccaa cgagccagcg caaacccgag agttaagaaa tcggatcttt 26280
ccaaccctgt atgccatctt ccagcagagt cggggtcaag agcaggaact gaaaataaaa 26340
aaccgatctc tgcgttcgct caccagaagt tgtttgtatc acaagagcga agatcaactt 26400
cagcgcactc tcgaggacgc cgaggctctc ttcaacaagt actgcgcgct gactcttaaa 26460
gagtaggcag cgaccgcgct tattcaaaaa aggcgggaat tacatcatcc tcgacatgag 26520
taaagaaatt cccacgcctt acatgtggag ttatcaaccc caaatgggat tggcagcagg 26580
cgcctcccag gactactcca cccgcatgaa ttggctcagc gccgggcctt ctatgatttc 26640
tcgagttaat gatatacgcg cctaccgaaa ccaaatactt ttggaacagt cagctcttac 26700
caccacgccc cgccaacacc ttaatcccag aaattggccc gccgccctag tgtaccagga 26760
aagtcccgct cccaccactg tattacttcc tcgagacgcc caggccgaag tccaaatgac 26820
taatgcaggt gcgcagttag ctggcggctc caccctatgt cgtcacaggc ctcggcataa 26880
tataaaacgc ctgatgatca gaggccgagg tatccagctc aacgacgagt cggtgagctc 26940
tccgcttggt ctacgaccag acggaatctt tcagattgcc ggctgcggga gatcttcctt 27000
cacccctcgt caggctgttc tgactttgga aagttcgtct tcgcaacccc gctcgggcgg 27060
aatcgggacc gttcaatttg tagaggagtt tactccctct gtctacttca accccttctc 27120
cggatctcct gggcactacc cggacgagtt cataccgaac ttcgacgcga ttagcgagtc 27180
agtggacggc tacgattgat gtctggtgac gcggctgagc tatctcggct gcgacatcta 27240
gaccactgcc gccgctttcg ctgctttgcc cgggaactta ttgagttcat ctacttcgaa 27300
ctccccaagg atcaccctca aggtccggcc cacggagtgc ggattactat cgaaggcaaa 27360
atagactctc gcctgcaacg aattttctcc cagcggcccg tgctgatcga gcgagaccag 27420
ggaaacacca cggtttccat ctactgcatt tgtaatcacc ccggattgca tgaaagcctt 27480
tgctgtctta tgtgtactga gtttaataaa aactgaatta agactctcct acggactgcc 27540
gcttcttcaa cccggatttt acaaccagaa gaacaaaact tttcctgtcg tccaggactc 27600
tgttaacttc acctttccta ctcacaaact agaagctcaa cgactacacc gcttttccag 27660
aagcattttc cctactaata ctactttcaa aaccggaggt gagctccacg gtctccctac 27720
agaaaaccct tgggtggaag cgggccttgt agtactagga attcttgcgg gtgggcttgt 27780
gattattctt tgctacctat acacaccttg cttcactttc ctagtggtgt tgtggtattg 27840
gtttaaaaaa tggggcccat actagtcttg cttgttttac tttcgctttt ggaaccgggt 27900
tctgccaatt acgatccatg tctagacttt gacccagaaa actgcacact tacttttgca 27960
cccgacacaa gccgcatctg tggagttctt attaagtgcg gatgggaatg caggtccgtt 28020
gaaattacac acaataacaa aacctggaac aataccttat ccaccacatg ggagccagga 28080
gttcccgagt ggtacactgt ctctgtccga ggtcctgacg gttccatccg cattagtaac 28140
aacactttca ttttttctga aatgtgcgat ctggccatgt tcatgagcaa acagtattct 28200
ctatggcctc ctagcaagga caacatcgta acgttctcca ttgcttattg cttgtgcgct 28260
tgccttctta ctgctttact gtgcgtatgc atacacctgc ttgtaaccac tcgcatcaaa 28320
aacgccaata acaaagaaaa aatgccttaa cctctttctg tttacagaca tggcttctct 28380
tacatctctc atatttgtca gcattgtcac tgccgctcac ggacaaacag tcgtctctat 28440

-continued

```
cccactagga cataattaca ctctcatagg acccccaatc acttcagagg tcatctggac  28500
caaactggga agcgttgatt actttgatat aatctgtaac aaaacaaaac caataatagt  28560
aacttgcaac atacaaaatc ttacattgat taatgttagc aaagtttaca gcggttacta  28620
ttatggttat gacagataca gtagtcaata tagaaattac ttggttcgtg ttacccagtt  28680
gaaaaccacg aaaatgccaa atatggcaaa gattcgatcc gatgacaatt ctctagaaac  28740
ttttacatct cccaccacac ccgacgaaaa aaacatccca gattcaatga ttgcaattgt  28800
tgcagcggtg gcagtggtga tggcactaat aataatatgc atgcttttat atgcttgtcg  28860
ctacaaaaag tttcatccta aaaaacaaga tctcctacta aggcttaaca tttaatttct  28920
ttttatacag ccatggtttc cactaccaca ttccttatgc ttactagtct cgcaactctg  28980
acttctgctc gctcacacct cactgtaact ataggctcaa actgcacact aaaaggacct  29040
caaggtggtc atgtcttttg gtggagaata tatgacaatg gatggtttac aaaaccatgt  29100
gaccaacctg gtagattttt ctgcaacggc agagacctaa ccattatcaa cgtgacagca  29160
aatgacaaag gcttctatta tggaaccgac tataaaagta gtttagatta taacattatt  29220
gtactgccat ctaccactcc agcaccccgc acaactactt tctctagcag cagtgtcgct  29280
aacaatacaa tttccaatcc aacctttgcc gcgcttttaa aacgcactgt gaataattct  29340
acaacttcac atacaacaat ttccacttca acaatcagca tcatcgctgc agtgacaatt  29400
ggaatatcta ttcttgtttt taccataacc tactacgcct gctgctatag aaaagacaaa  29460
cataaaggtg atccattact tagatttgat atttaatttg ttcttttttt ttatttacag  29520
tatggtgaac accaatcatg gtacctagaa atttcttctt caccatactc atctgtgctt  29580
ttaatgtttg cgctactttc acagcagtag ccacagcaac cccagactgt ataggagcat  29640
ttgcttccta tgcacttttt gcttttgtta cttgcatctg cgtatgtagc atagtctgcc  29700
tggttattaa ttttttccaa cttctagact ggatccttgt gcgaattgcc tacctgcgcc  29760
accatcccga ataccgcaac caaaatatcg cggcacttct tagactcatc taaaaccatg  29820
caggctatac taccaatatt tttgcttcta ttgcttccct acgctgtctc aaccccagct  29880
gcctatagta ctccaccaga acaccttaga aaatgcaaat tccaacaacc gtggtcattt  29940
cttgcttgct atcgagaaaa atcagaaatc cccccaaatt taataatgat tgctggaata  30000
attaatataa tctgttgcac cataatttca tttttgatat acccccctatt tgattttggc  30060
tggaatgctc ccaatgcaca tgatcatcca caagacccag aggaacacat tcccccacaa  30120
aacatgcaac atccaatagc gctaatagat tacgaaagtg aaccacaacc cccactactc  30180
cctgctatta gttacttcaa cctaaccggc ggagatgact gaaacactca ccacctccaa  30240
ttccgccgag gatctgctcg atatggacgg ccgcgtctca gaacaacgac ttgcccaact  30300
acgcatccgc cagcagcagg aacgcgtggc caaagagctc agagatgtca tccaaattca  30360
ccaatgcaaa aaaggcatat tctgtttggt aaaacaagcc aagatatcct acgagatcac  30420
cgctactgac catcgcctct cttacgaact tggcccccaa cgacaaaaat ttacctgcat  30480
ggtgggaatc aaccccatag ttatcaccca acaaagtgga gatactaagg gttgcattca  30540
ctgctcctgc gattccatcg agtgcaccta caccctgctg aagaccctat gcggcctaag  30600
agacctgcta ccaatgaatt aaaaaaaaat gattaataaa aaatcactta cttgaaatca  30660
gcaataaggt ctctgttgaa attttctccc agcagcacct cacttccctc ttcccaactc  30720
tggtattcta aaccccgttc agcggcatac tttctccata ctttaaaggg gatgtcaaat  30780
tttagctcct ctcctgtacc cacaatcttc atgtctttct tcccagatga ccaagagagt  30840
```

```
ccggctcagt gactccttca accctgtcta cccctatgaa gatgaaagca cctcccaaca  30900
cccctttata aacccagggt ttatttcccc aaatggcttc acacaaagcc cagacggagt  30960
tcttacttta aaatgtttaa ccccactaac aaccacaggc ggatctctac agctaaaagt  31020
gggagggggga cttacagtgg atgacactga tggtacctta caagaaaaca tacgtgctac  31080
agcacccatt actaaaaata atcactctgt agaactatcc attggaaatg gattagaaac  31140
tcaaaacaat aaactatgtg ccaaattggg aaatgggtta aaatttaaca acggtgacat  31200
ttgtataaag gatagtatta acaccttatg gactggaata aaccctccac ctaactgtca  31260
aattgtggaa aacactaata caaatgatgg caaacttact ttagtattag taaaaaatgg  31320
agggcttgtt aatggctacg tgtctctagt tggtgtatca gacactgtga accaaatgtt  31380
cacacaaaag acagcaaaca tccaattaag attatatttt gactcttctg gaaatctatt  31440
aactgaggaa tcagacttaa aaattccact taaaaataaa tcttctacag cgaccagtga  31500
aactgtagcc agcagcaaag cctttatgcc aagtactaca gcttatccct tcaacaccac  31560
tactagggat agtgaaaact acattcatgg aatatgttac tacatgacta gttatgatag  31620
aagtctattt cccttgaaca tttctataat gctaaacagc cgtatgattt cttccaatgt  31680
tgcctatgcc atacaatttg aatggaatct aaatgcaagt gaatctccag aaagcaacat  31740
agctacgctg accacatccc ccttttctt ttcttacatt acagaagacg acaactaaaa  31800
taaagtttaa gtgtttttat ttaaaatcac aaaattcgag tagttatttt gcctccacct  31860
tcccatttga cagaatacac caatctctcc ccacgcacag ctttaaacat ttggatacca  31920
ttagagatag acattgtttt agattccaca ttccaaacag tttcagagcg agccaatctg  31980
gggtcagtga tagataaaaa tccatcgcga tagtctttta aagcgctttc acagtccaac  32040
tgctgcggat gcgactccgg agtttggatc acggtcatct ggaagaagaa cgatgggaat  32100
cataatccga aaacggtatc ggacgattgt gtctcatcaa acccacaagc agccgctgtc  32160
tgcgtcgctc cgtgcgactg ctgtttatgg gatcagggtc cacagtttcc tgaagcatga  32220
ttttaatagc ccttaacatc aactttctgg tgcgatgcgc gcagcaacgc attctgattt  32280
cactcaaatc tttgcagtag gtacaacaca ttattacaat attgtttaat aaaccataat  32340
taaaagcgct ccagccaaaa ctcatatctg atataatcgc ccctgcatga ccatcatacc  32400
aaagtttaat ataaattaaa tgacgttccc tcaaaaacac actacccaca tacatgatct  32460
cttttggcat gtgcatatta acaatctgtc tgtaccatgg acaacgttgg ttaatcatgc  32520
aacccaatat aaccttccgg aaccacactg ccaacaccgc tcccccagcc atgcattgaa  32580
gtgaaccctg ctgattacaa tgacaatgaa gaacccaatt ctctcgaccg tgaatcactt  32640
gagaatgaaa aatatctata gtggcacaac atagacataa atgcatgcat cttctcataa  32700
tttttaactc ctcaggattt agaaacatat cccagggaat aggaagctct tgcagaacag  32760
taaagctggc agaacaagga agaccacgaa cacaacttac actatgcata gtcatagtat  32820
cacaatctgg caacagcggg tggtcttcag tcatagaagc tcgggtttca ttttcctcac  32880
aacgtggtaa ctgggctctg gtgtaagggt gatgtctggc gcatgatgtc gagcgtgcgc  32940
gcaaccttgt cataatggag ttgcttcctg acattctcgt attttgtata gcaaaacgcg  33000
gccctggcag aacacactct tcttcgcctt ctatcctgcc gcttagcgtg ttccgtgtga  33060
tagttcaagt acagccacac tcttaagttg gtcaaaagaa tgctggcttc agttgtaatc  33120
aaaactccat cgcatctaat tgttctgagg aaatcatcca cggtagcata tgcaaatccc  33180
```

```
aaccaagcaa tgcaactgga ttgcgtttca agcaggagag gagagggaag agacggaaga  33240
accatgttaa tttttattcc aaacgatctc gcagtacttc aaattgtaga tcgcgcagat  33300
ggcatctctc gcccccactg tgttggtgaa aaagcacagc taaatcaaaa gaaatgcgat  33360
tttcaaggtg ctcaacggtg gcttccaaca aagcctccac gcgcacatcc aagaacaaaa  33420
gaataccaaa agaaggagca ttttctaact cctcaatcat catattacat tcctgcacca  33480
ttcccagata attttcagct ttccagcctt gaattattcg tgtcagttct tgtggtaaat  33540
ccaatccaca cattacaaac aggtcccgga gggcgccctc caccaccatt cttaaacaca  33600
ccctcataat gacaaaatat cttgctcctg tgtcacctgt agcgaattga gaatggcaac  33660
atcaattgac atgcccttgg ctctaagttc ttctttaagt tctagttgta aaaactctct  33720
catattatca ccaaactgct tagccagaag ccccccggga acaagagcag ggacgctac  33780
agtgcagtac aagcgcagac ctccccaatt ggctccagca aaaacaagat tggaataagc  33840
atattgggaa ccaccagtaa tatcatcgaa gttgctggaa atataatcag gcagagtttc  33900
ttgtagaaat tgaataaaag aaaaatttgc caaaaaaaca ttcaaaacct ctgggatgca  33960
aatgcaatag gttaccgcgc tgcgctccaa cattgttagt tttgaattag tctgcaaaaa  34020
taaaaaaaaa acaagcgtca tatcatagta gcctgacgaa caggtggata aatcagtctt  34080
tccatcacaa gacaagccac agggtctcca gctcgaccct cgtaaaacct gtcatcgtga  34140
ttaaacaaca gcaccgaaag ttcctcgcgg tgaccagcat gaataagtct tgatgaagca  34200
tacaatccag acatgttagc atcagttaag gagaaaaaac agccaacata gcctttgggt  34260
ataattatgc ttaatcgtaa gtatagcaaa gccacccctc gcggatacaa agtaaaaggc  34320
acaggagaat aaaaaatata attatttctc tgctgctgtt taggcaacgt cgcccccggt  34380
ccctctaaat acacatacaa agcctcatca gccatggctt accagagaaa gtacagcggg  34440
cacacaaacc acaagctcta aagtcactct ccaacctctc cacaatatat atacacaagc  34500
cctaaactga cgtaatggga ctaaagtgta aaaaatcccg ccaaacccaa cacacacccc  34560
gaaactgcgt caccagggaa aagtacagtt tcacttccgc aatcccaaca agcgtcactt  34620
cctctttctc acggtacgtc acatcccatt aacttacaac gtcattttcc cacggccgcg  34680
ccgccccttt taaccgttaa ccccacagcc aatcaccaca cggcccacac tttttaaaat  34740
cacctcattt acatattggc accattccat ctataaggta tattattgat gatg        34794
```

<210> SEQ ID NO 114
<211> LENGTH: 1146
<212> TYPE: DNA
<213> ORGANISM: Mus musculus

<400> SEQUENCE: 114

```
atgactgcca tggaggagtc acagtcggat atcagcctcg agctccctct gagccaggag    60
acattttcag gcttatggaa actacttcct ccagaagata tcctgccatc acctcactgc   120
atggacgatc tgttgctgcc ccaggatgtt gaggagtttt ttgaaggccc aagtgaagcc   180
ctccgagtgt caggagctcc tgcagcacag gaccctgtca ccgagacccc tgggccagtg   240
gcccctgccc cagccactcc atggcccctg tcatcttttg tcccttctca aaaaacttac   300
cagggcaact atggcttcca cctgggcttc ctgcagtctg ggacagccaa gtctgttatg   360
tgcacgtact ctcctcccct caataagcta ttctgccagc tggcgaagac gtgccctgtg   420
cagttgtggg tcagcgccac acctccagct gggagccgtg tccgcgccat ggccatctac   480
aagaagtcac agcacatgac ggaggtcgtg agacactgcc cccaccatga gcgctgctcc   540
```

gatggtgatg gcctggctcc tccccagcat cttatccggg tggaaggaaa tttgtatccc 600
gagtatctgg aagacaggca gacttttcgc cacagcgtgg tggtacctta tgagccaccc 660
gaggccggct ctgagtatac caccatccac tacaagtaca tgtgtaatag ctcctgcatg 720
gggggcatga accgccgacc tatccttacc atcatcacac tggaagactc cagtgggaac 780
cttctgggac gggacagctt tgaggttcgt gtttgtgcct gccctgggag agaccgccgt 840
acagaagaag aaaatttccg caaaaaggaa gtcctttgcc ctgaactgcc cccagggagc 900
gcaaagagag cgctgcccac ctgcacaagc gcctctcccc cgcaaaagaa aaaaccactt 960
gatggagagt atttcaccct caagatccgc gggcgtaaac gcttcgagat gttccgggag 1020
ctgaatgagg ccttagagtt aaaggatgcc catgctacag aggagtctgg agacagcagg 1080
gctcactcca gcctccagcc tagagccttc caagccttga tcaaggagga aagcccaaac 1140
tgctag 1146

<210> SEQ ID NO 115
<211> LENGTH: 699
<212> TYPE: DNA
<213> ORGANISM: Mus musculus

<400> SEQUENCE: 115
atgacagtgc tggcgccagc ctggagccca aattcctccc tgttgctgct gttgctgctg 60
ctgagtcctt gcctgcgggg gacacctgac tgttacttca gccacagtcc catctcctcc 120
aacttcaaag tgaagtttag agagttgact gaccacctgc ttaaagatta cccagtcact 180
gtggccgtca atcttcagga cgagaagcac tgcaaggcct tgtggagcct cttcctagcc 240
cagcgctgga tagagcaact gaagactgtg gcagggtcta agatgcaaac gcttctggag 300
gacgtcaaca ccgagataca ttttgtcacc tcatgtacct tccagcccct accagaatgt 360
ctgcgattcg tccagaccaa catctcccac ctcctgaagg acacctgcac acagctgctt 420
gctctgaagc cctgtatcgg gaaggcctgc cagaatttct ctcggtgcct ggaggtgcag 480
tgccagccgg actcctccac cctgctgccc ccaaggagtc ccatagccct agaagccacg 540
gagctcccag agcctcggcc caggcagctg ttgctcctcc tgctacttct cctgcctctc 600
acactggtgc tgctggcagc cgcctggggc cttcgctggc aaagggcaag aaggaggggg 660
gagctccacc ctggggtgcc cctcccctcc catccctag 699

<210> SEQ ID NO 116
<211> LENGTH: 570
<212> TYPE: DNA
<213> ORGANISM: Mus musculus

<400> SEQUENCE: 116
atgacagtgc tggcgccagc ctggagccca aattcctccc tgttgctgct gttgctgctg 60
ctgagtcctt gcctgcgggg gacacctgac tgttacttca gccacagtcc catctcctcc 120
aacttcaaag tgaagtttag agagttgact gaccacctgc ttaaagatta cccagtcact 180
gtggccgtca atcttcagga cgagaagcac tgcaaggcct tgtggagcct cttcctagcc 240
cagcgctgga tagagcaact gaagactgtg gcagggtcta agatgcaaac gcttctggag 300
gacgtcaaca ccgagataca ttttgtcacc tcatgtacct tccagcccct accagaatgt 360

-continued

```
ctgcgattcg tccagaccaa catctcccac ctcctgaagg acacctgcac acagctgctt    420

gctctgaagc cctgtatcgg gaaggcctgc cagaatttct ctcggtgcct ggaggtgcag    480

tgccagccgg actcctccac cctgctgccc ccaaggagtc ccatagccct agaagccacg    540

gagctcccag agcctcggcc caggcagtag                                      570
```

PERSONALIZED CANCER VACCINES

CROSS-REFERENCE TO RELATED APPLICATIONS

This application is a national stage application under 35 U.S.C. § 371 of International Application No. PCT/US2019/024684, filed internationally on Mar. 28, 2019, which claims priority to, and the benefits of U.S. Provisional Patent Application Ser. No. 62/649,206, filed Mar. 28, 2018, the disclosures of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 203592001700SEQLIST.TXT, date recorded: Sep. 28, 2020, size: 179 KB).

FIELD OF THE INVENTION

The field of the invention is methods and compositions for treating cancer.

BACKGROUND

Despite extensive knowledge of the underlying molecular mechanisms that cause cancer, most advanced cancers remain incurable with current chemotherapy and radiation protocols. Oncolytic viruses have emerged as a platform technology that has the potential to significantly augment current standard treatment for a variety of malignancies (Kumar, S. et al. (2008) Current Opinion in Molecular Therapeutics 10(4):371-379; Kim, D. (2001) Expert Opinion on Biological Therapy 1 (3):525-538; Kim D. (2000) Oncogene 19(56):6660-6669). These viruses have shown promise as oncolytic agents that not only directly destroy malignant cells via an infection-to-reproduction-to-lysis chain reaction but also indirectly induce anti-tumor immunity. These immune stimulatory properties have been augmented with the insertion of therapeutic transgenes that are copied and expressed each time the virus replicates.

Previously developed oncolytic viruses include the oncolytic serotype 5 adenovirus (Ad5) referred to as TAV-255 that is transcriptionally attenuated in normal cells but transcriptionally active in cancer cells (see, PCT Publication No. WO2010/101921). It is believed that the mechanism by which the TAV-255 vector achieves such tumor selectivity is through targeted deletion of three transcriptional factor (TF) binding sites for the transcription factors Pea3 and E2F, proteins that regulate adenovirus expression of E1a, the earliest gene to be transcribed after virus entry into the host cell, through binding to specific DNA sequences.

Despite the efforts to date, there is a need for improved oncolytic viruses for treating cancers and hyperproliferative disorders in human patients, and improved methods for treating cancers and hyperproliferative disorders in human patients which are explicitly tailored to the individual patient.

SUMMARY OF THE INVENTION

The invention is based, in part, upon the discovery that a recombinant vector, e.g., a recombinant oncolytic adenovirus, can be used to express selectively express a cancer antigen in a cancer cell in a subject and stimulate a heightened immune response against the cancer antigen in the subject and/or treat the cancer in the subject. In addition, a recombinant vector, e.g., a recombinant oncolytic adenovirus, can be used to selectively express in a cancer cell in a subject a cancer antigen that has been identified by sequencing DNA or RNA from a sample from the subject, thereby stimulating a heightened immune response against an antigen that is specific to the cancer of the subject. The features of the recombinant vectors, e.g., recombinant oncolytic adenoviruses, described herein, enable the repeated generation and administration of different recombinant vectors, e.g., recombinant oncolytic adenoviruses that express different subject-specific cancer antigens, thereby to treat refractory cancers.

The present disclosure provides a personalized cancer vaccine. In some embodiments, the personalized cancer vaccine comprises a personalized recombinant virus. In some embodiments, the personalized recombinant virus is an oncolytic adenovirus. In some embodiments, the personalized recombinant adenovirus is capable of stimulating a heightened immune response against one or more cancer antigens in a specific subject in need thereof.

In some embodiments, the personalized recombinant adenovirus comprises a modified transcription regulatory sequence compared to a corresponding wild type adenovirus. In some embodiments, the modified transcription regulatory sequence comprises one or more modifications of one or more transcription factor binding sites. The modified transcription regulatory sequence is transcriptionally active in cancer cells and/or hyperproliferative cells, but is transcriptionally attenuated in normal cells.

In some embodiments, the personalized recombinant adenovirus comprises one or more transgenes. In some embodiments, each of the transgene comprises one or more nucleotide sequences encoding one or more cancer antigen specific to the subject.

In some embodiments, a cancer antigen comprises about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 44, 43, 44, 45, 46, 47, 48, 49, 50 or more amino acids of a protein in a cancer cell of the subject. In some embodiments, the cancer antigen comprises one or more mutations compared to a corresponding wild type sequence of the same species that the subject belongs to. In some embodiments, the mutation is a substation, a deletion, an insertion, a frameshift, or combination thereof. In some embodiments, the cancer antigen polypeptide comprises the mutation, and amino acids flanking the mutation.

In some embodiments, the one or more transgenes are located at one or more insertion sites in the genome of the recombinant oncolytic adenovirus, and are under the regulation of the modified transcription regulatory sequence.

In some embodiments, the adenovirus is a human adenovirus. In some embodiments, the adenovirus is a type 5 adenovirus (Ad5) or a type 2 adenovirus (Ad2). More oncolytic adenovirus are described in Alemany 2014 (Biomedicines. 2014 March; 2(1): 36-49.), and U.S. Pat. Nos. 9,115,337, 10,016,470, 10,047,347, 8,859,287, 9,410,129, and US20180153946, US20100233125, US20180169271, WO/2008/080003A2, WO/2012/156933A1, and WO/2010/128182A1, each of which is incorporated by reference in its entirety. In certain embodiments, the recombinant adenovirus is a type 35 adenovirus (Ad35).

In some embodiments, the nucleotide sequences encoding one or more cancer antigen specific to the subject are identified by sequencing DNA or RNA in a sample obtained from the subject. In some embodiments, the sample is a tumor tissue or a blood sample.

In some embodiments, the modification of the transcription factor binding site is a deletion, a substitution, an addition of one or more nucleotides compared to the corresponding wild type transcription regulatory sequence, or any combination thereof. In some embodiments, the modified transcription regulatory sequence comprises a modified Ela promoter. In some embodiments, the modified Ela promoter comprises one or more modifications on one or more binding sites selected from Pea3 I, E2F I, Pea3 II, E2F II, Pea3 III, Pea3 IV, and Pea3 V. In some embodiments, the modified Ela promoter comprises a modified Pea3 binding site.

In some embodiments, the modified Pea3 binding site comprise: a deletion of nucleotides corresponding to about −300 to about −250 upstream of the initiation site of Ela, a deletion of nucleotides corresponding to −305 to −255 upstream of the initiation site of Ela, and/or a deletion of nucleotides corresponding to 195-244 of the Ad5 genome (SEQ ID NO: 1). In some embodiments, the modified Ela promoter comprises the sequence GGTGTTTTGG (SEQ ID NO: 2). In some embodiments, the modified Ela promoter comprises the sequence CTAGGACTG (SEQ ID NO: 17), AGTGCCCG (SEQ ID NO: 101), or TATTCCCG (SEQ ID NO: 102).

In some embodiments, the recombinant adenovirus comprises one or more Pea3 transcription binding site deletions without one or more E2F transcription binding site deletions in the E1A region.

In some embodiments, the recombinant adenovirus comprises one or more E2F transcription binding site deletions without one or more Pea3 transcription binding site deletions in the E1A region.

In some embodiments, the recombinant adenovirus comprises an Ela promoter lacking a functional TATA box or lacking a functional CAAT box. In some embodiments, the Ela promoter comprises a deletion of the entire TATA box. In some embodiments, the Ela promoter comprises a deletion of the entire CAAT box.

In some embodiments, the recombinant adenovirus comprises a deletion of nucleotides corresponding to −27 to −24 of the E1a promoter, a deletion of nucleotides corresponding to −29 to −26 of the E1a promoter, a deletion of nucleotides corresponding to −33 to −26 of the E1a promoter, a deletion of nucleotides corresponding to −31 to −24 of the E1a promoter, a deletion of nucleotides corresponding to −44 to +52 of the E1a promoter, a deletion of nucleotides corresponding to −44 to +54 of the E1a promoter, a deletion of nucleotides corresponding to −148 to +52 of the E1a promoter, a deletion of nucleotides corresponding to 353-552 of the Ad5 genome (SEQ ID NO: 1), a deletion of nucleotides corresponding to 423 to 431 of the Ad5 genome (SEQ ID NO: 1), a deletion of nucleotides corresponding to 468 to 475 of the Ad5 genome (SEQ ID NO: 1), a deletion of nucleotides corresponding to 472 to 475 of the Ad5 genome (SEQ ID NO: 1), a deletion of nucleotides corresponding to 455 to 552 of the Ad5 genome (SEQ ID NO: 1), a deletion of nucleotides corresponding to 560-1545 of the Ad5 genome (SEQ ID NO: 1), a deletion of nucleotides corresponding to 557-1678 of the Ad5 genome (SEQ ID NO: 1), or the sequence GACTGTGCGC (SEQ ID NO: 3).

In some embodiments, the one or more insertion sites are selected from the group consisting of an E1b-19K insertion site, an E3 insertion site, an E4 insertions site, an IX-E2 insertion site, an L5-E4 insertion site, and combinations thereof.

In some embodiments, the E1b-19K insertion site is located between the start site of E1b-19K and the stop codon of E1b-19K. In some embodiments, the E1b-19K insertion site comprises a deletion of about 200 nucleotides adjacent the start site of E1b-19K. In some embodiments, the E1b-19K insertion site comprises a deletion of 202 or 203 nucleotides adjacent the start site of E1b-19K, or a deletion corresponding to nucleotides 1714-1917 or 1714-1916 of the Ad5 genome (SEQ ID NO: 1).

In some embodiments, the transgene is inserted either between nucleotides corresponding to 1714 and 1917 of the Ad5 genome (SEQ ID NO: 1), or inserted between CTGACCTC (SEQ ID NO: 4) and TCACCAGG (SEQ ID NO: 5).

In some embodiments, the E3 insertion site is located between the stop codon of pVIII and the start site of Fiber. In some embodiments, the E3 insertion site is located between the stop codon of E3-10.5K and the stop codon of E3-14.7K and the start site of Fiber. In some embodiments, the E3 insertion site comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or about 3000 to about 3185 nucleotides. In some embodiments, the E3 insertion site comprises a deletion of from about 500 to about 1551, from about 500 to about 1500, from about 500 to about 1000, from about 1000 to about 1551, from about 1000 to about 1500, or from about 1500 to about 1551 nucleotides adjacent the stop codon of E3-10.5K. In some embodiments, the E3 insertion site comprises a deletion of about 1,050 nucleotides adjacent the stop codon of E3-10.5K. In some embodiments, the E3 insertion site comprises a deletion of 1,063 or 1,064 nucleotides adjacent the stop codon of E3-10.5K. In some embodiments, the E3 insertion site comprises a deletion corresponding to the Ad5 dl309 E3 deletion. In some embodiments, the E3 insertion site comprises a deletion of the RID alpha, RID beta, and 14.7K genes positioned after adenoviral death protein. In some embodiments, the E3 insertion site is a disrupted E3 gp19K gene wherein the fourth codon is mutated to a stop codon. In some embodiments, the E3 insertion site comprises a deletion corresponding to nucleotides 29773-30836 of the Ad5 genome (SEQ ID NO: 1). In some embodiments, the E3 insertion site is located between CAGTATGA (SEQ ID NO: 8) and TAATAAAAAA (SEQ ID NO: 9).

In some embodiments, the IX-E2 insertion site is located between the stop codon of adenovirus IX gene and the stop codon of adenovirus IVa2 gene.

In some embodiments, the L5-E4 insertion site is located between the stop codon of adenovirus fiber gene and the stop codon of ORF6 or ORF6/7 of adenovirus E4 gene.

In some embodiments, the transgene comprises at least two nucleotide sequences encoding one or more cancer antigen in the subject.

In some embodiments, the transgene comprises at least about 1 to about 100 nucleotide sequences encoding about 1 to about 100 cancer antigens in the subject, such as about 5, about 10, about 15, about 20, about 25, about 30, about 35, about 40, about 45, about 50, about 55, about 60, about 65, about 70, about 75, about 80, about 85, about 90, about 95, or about 100 cancer antigens.

In some embodiments, the transgene encodes a concatemer, wherein the concatemer comprises the at least two cancer antigens specific to the subject, wherein the cancer antigens are separated by a peptide linker, an internal ribosome entry site (IRES), a ribosome skipping sequence, or a combination thereof. In some embodiments, the peptide linker promotes proteasomal cleavage between the cancer antigens. In some embodiments, the peptide linker consists of SEQ ID NO: 6. In some embodiments, the IRES is an encephalomyocarditis virus IRES, a foot-and-mouth disease virus IRES, a poliovirus IRES, or a combination thereof. In some embodiments, the concatemer further comprises a C-terminal ubiquitin.

In some embodiments, at least one cancer antigen polypeptide specific to the subject is a polypeptide of catenin alpha-2 (CTNNA2), myosin-IIIb isoform 2 (MYO3B), sodium/calcium exchanger 3 isoform C precursor (SLC8A3), sodium-dependent neutral amino acid transporter B(0)AT1 (SLC6A19), double-stranded RNA-specific editase B2 (ADARB2), T-complex protein 11 homolog (TCP11), leucine-rich repeat and transmembrane domain-containing protein 2 precursor (LRTM2), nuclear receptor subfamily 5 group A member 2 (NR5A1), prolactin-releasing peptide receptor (PRLHR), prolow-density lipoprotein receptor-related protein 1 preproprotein (LRP1), alpha-2-macroglobulin isoform a precursor (A2M), RUS1 family protein C16orf58 (C16orf58), tyrosine-protein kinase BAZ1B (BAZ1B), phospholipid phosphatase 2 (PPAP2C), chondroitin sulfate glucuronyltransferase (CHPF2), pre-mRNA 3' end processing protein WDR33 (WDR33), U1 small nuclear ribonucleoprotein A (SNRPA), GTP-binding protein 1 (GTPB), probable ATP-dependent RNA helicase DDX46 (DDX), cAMP-dependent protein kinase catalytic subunit beta (PRKA), lysine-specific demethylase 5B (KDM), jmjC domain-containing protein 8 (JMJ), CTD small phosphatase-like protein isoform 1 (CTDS), transmembrane protein 9B isoform a precursor (TMEM9B/1), transmembrane protein 9B isoform b (TMEM9B/2), dedicator of cytokinesis protein 1 (DOCK1), retinoblastoma-associated protein (RB1), lysine-specific demethylase 4A (KDM4A), E3 ubiquitin-protein ligase NEDD4-like (NEDD4L), serine/threonine-protein kinase TAO3 (TAOK3), transcription elongation regulator 1 (TCERG1), E3 ubiquitin-protein ligase RNF19B (RNF19B), rho GTPase-activating protein 45 (HMHA1), semaphorin-5A precursor (SEMASA), adenomatous polyposis coli protein (APC), zinc finger protein 732 (ZNF732), contactin-1 isoform 1 precursor (CNTN1), cellular tumor antigen p53 (TP53), KRAS, BRAF, NRAS, PIK3CA, EGFR, IDH1, SETD1B, RPL22, or RNF43.

In some embodiments, a nucleotide sequence encoding the cancer antigen polypeptide comprises at least one modification compared to its corresponding wild type nucleotide sequence. In some embodiments, the modification leads to substitution, deletion, insertion of one or more amino acids, stop codon, or frameshift of each of the cancer antigen compared to the corresponding wild type sequence.

In some embodiments, the cancer antigen polypeptide comprises at least one of the following: a substitution mutation in TP53; a substitution mutation in KRAS; a substitution mutation in BRAF; a substitution mutation in NRAS; a substitution mutation in PIK3CA; a substitution mutation in EGFR; a substitution mutation in IDH1; a frameshift mutation in SETD1B; a frameshift mutation in RPL22; and/or a frameshift mutation in RNF43.

In some embodiments, the cancer antigen polypeptide comprises at least one of the following: a substitution mutation in TP53, selected from R175H, R273C, R248Q, R273H, R248W, R282W, Y220C, G245S, H179R, and V157F; a substitution mutation in KRAS, selected from G12D, G12V, G12C, G13D, G12A, G12R, G12S, G13C, A146T, and Q61H; a substitution mutation in BRAF, selected from V600E and V600M; a substitution mutation in NRAS, selected from Q61R and Q61K; a substitution mutation in PIK3CA, selected from E545K, H1047R, E542K, R88Q, G118D, N345K, C420R, E453K, Q546R, E726K, and H1047L; a substitution mutation in EGFR, selected from A289V, G598V, and L858R, a substitution mutation in IDH1, comprising R132H, a frameshift mutation in SETD1B, comprising H8 frameshift; a frameshift mutation in RPL22, comprising K15 frameshift; and/or a frameshift mutation in RNF43, comprising G659 frameshift.

In some embodiments, the cancer antigen polypeptide comprises at least one of the following: a substitution mutation in CTNNA2; a substitution mutation in MYO3B; a substitution mutation in SLC8A3; a substitution mutation in SLC6A19; a substitution mutation in ADARB2; a substitution mutation in TCP11; a substitution mutation in LRTM2; a substitution mutation in NR5A1; a substitution mutation in PRLHR; a substitution mutation in LRP1; a substitution mutation in A2M; a substitution mutation in C16orf58; a substitution mutation in BAZ1B; a substitution mutation in PPAP2C; a substitution mutation in CHPF2; a substitution mutation in WDR33; a frameshift mutation SNRPA; a substitution mutation in GTPB; a substitution mutation in DDX46; a substitution mutation in PRKA; a substitution mutation in KDM; a substitution mutation in JMJ; a substitution mutation in CTDS; a substitution mutation in TMEM9B/1; a substitution mutation in TMEM9B/2; a substitution mutation in DOCK1; a substitution mutation in RB1; a substitution mutation in KDM4A; a substitution mutation in NEDD4L; a substitution mutation in TAOK3; a substitution mutation in TCERG1; a substitution mutation in RNF19B; a substitution mutation in HMHA1; a substitution mutation in SEMA5A; a substitution mutation in ZNF732; a substitution mutation in CNTN1; a substitution mutation in tumor antigen p53 (TP53); a substitution mutation in APC; and a frameshift mutation in APC.

In some embodiments, the cancer antigen polypeptide comprises any of SEQ ID NOs. 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 98, and 99.

In some embodiments, the recombinant oncolytic adenovirus comprises one or more compensatory deletions to one or more genomic regions.

The present disclosure further provides a method for producing a personalized recombinant oncolytic adenovirus for a subject in need thereof. In some embodiments, the method comprises sequencing DNA or RNA in a sample obtained from the subject to identify one or more mutant nucleotide sequences encoding one or more cancer antigens specific to the subject. In some embodiments, the method further comprises producing one or more transgenes, wherein each of the transgenes comprises one or more mutant nucleotide sequences identified. In some embodiments, the one or more mutant nucleotide sequences are separated by a peptide linker, an internal ribosome entry site (IRES), a ribosome skipping sequence, or a combination thereof. In some embodiments, the method further comprises inserting the one or more transgenes into the genome of a recombinant oncolytic adenovirus to produce the personalized recombinant oncolytic adenovirus. In some embodiments, transcription of the transgenes is active in cancer cells and/or hyperproliferative cells, but is attenuated in normal cells;

In some embodiments, the subject of the present invention is a human. In some embodiments. In some embodiments, the subject is a pediatric human.

In some embodiments, the cancer of the present invention is selected from melanoma, squamous cell carcinoma of the skin, basal cell carcinoma, head and neck cancer, breast cancer, anal cancer, cervical cancer, non-small cell lung cancer, mesothelioma, small cell lung cancer, renal cell carcinoma, prostate cancer, gastroesophageal cancer, colorectal cancer, testicular cancer, bladder cancer, ovarian cancer, hepatocellular carcinoma, cholangiocarcinoma, brain cancer, endometrial cancer, neuroendocrine cancer, merkel cell carcinoma, gastrointestinal stromal tumors, a sarcoma, and pancreatic cancer.

The present disclosure further provides a method of stimulating a heightened immune response against a cancer antigen in a subject in need thereof. In some embodiments, the method comprises administering to the subject an effective amount of a recombinant vector, e.g., a recombinant oncolytic vector, comprising an exogenous nucleotide sequence encoding the cancer antigen to stimulate the heightened immune response against the cancer antigen in the subject, wherein the cancer antigen has been identified by sequencing DNA or RNA from a sample from the subject. Any recombinant adenovirus of the present disclosure can be used.

In another aspect, the invention provides a method of treating a cancer in a subject in need thereof, the method comprising administering to the subject an effective amount of a recombinant vector, e.g., a recombinant oncolytic vector, comprising an exogenous nucleotide sequence encoding at least one cancer antigen to treat the cancer in the subject, wherein the cancer antigen has been identified by sequencing DNA or RNA from a sample from the subject. Any recombinant adenovirus of the present disclosure can be used.

In certain embodiments, in any of the foregoing methods, the subject has previously been administered a prior recombinant vector comprising an exogenous nucleotide sequence encoding at least one cancer antigen. In certain embodiments, the cancer is refractory to the administration of the prior recombinant vector and/or the recombinant vector encodes at least one cancer antigen that was not encoded by the prior recombinant oncolytic vector.

In another aspect, the invention provides a method of treating a cancer in a subject in need thereof, the method comprising: (a) identifying a cancer antigen by sequencing DNA or RNA from a sample from the subject; and (b) administering to the subject an effective amount of a recombinant vector, e.g., a recombinant oncolytic vector, comprising a nucleotide sequence encoding the cancer antigen to treat the cancer in the subject. In certain embodiments, the method further comprises, after step (b): (c) identifying an additional cancer antigen by sequencing DNA or RNA from a sample from the subject; and (d) administering to the subject an effective amount of an additional recombinant vector, e.g., a recombinant oncolytic vector, comprising a nucleotide sequence encoding the additional cancer antigen to treat the cancer in the subject. The cancer may, for example, be refractory to the administration of step (b).

In certain embodiments, in any of the foregoing methods, the sample is a tumor sample (e.g., from a tumor biopsy), or a blood sample.

In certain embodiments, in any of the foregoing methods, the exogenous nucleotide sequence comprises at least about 1 to about 100 nucleotide sequences encoding about 10 to about 100 cancer antigens in the subject, such as about 5, about 10, about 15, about 20, about 25, about 30, about 35, about 40, about 45, about 50, about 55, about 60, about 65, about 70, about 75, about 80, about 85, about 90, about 95, or about 100 cancer antigens.

In certain embodiments, in any of the foregoing methods, the cancer antigen or cancer antigens stimulate the release of an immunostimulatory cytokine, e.g., IFN-γ, from autologous lymphocytes isolated from the subject. In certain embodiments, the cancer antigen or cancer antigens stimulate the release of an immunosuppressive cytokine, e.g., TGF-β, IL-10 or IL-5, from autologous lymphocytes isolated from the subject. In certain embodiments, the cancer antigen or cancer antigens comprise a self-antigen. In certain embodiments, in any of the foregoing methods, the cancer antigen or cancer antigens are selected by a method comprising (i) identifying a candidate cancer antigen by sequencing DNA or RNA from a sample from a subject with cancer; (ii) culturing autologous lymphocytes in the presence of the candidate cancer antigen; and (iii) assaying for the release of an immunosuppressive cytokine, e.g., TGF-β, IL-10 or IL-5, from the autologous lymphocytes.

In certain embodiments, in any of the foregoing methods, the cancer antigen or antigens are derived from 9D7, androgen receptor, a BAGE family protein, β-catenin, BING-4, BRAF, BRCA1/2, a CAGE family protein, calcium-activated chloride channel 2, CD19, CD20, CD30, CDK4, CEA, CML66, CT9, CT10, cyclin-B1, EGFRvIII, Ep-CAM, EphA3, fibronectin, a GAGE family protein, gp100/pme117, Her-2/neu, HPV E6, HPV E7, Ig, immature laminin receptor, a MAGE family protein (e.g., MAGE-A3), MART-1/melan-A, MART2, MC1R, mesothelin, a mucin family protein (e.g., MUC-1), NY-ESO-1/LAGE-1, P. polypeptide, p53, podocalyxin (Podxl), PRAME, a ras family protein (e.g., KRAS), prostate specific antigen, a SAGE family protein, SAP-1, SSX-2, survivin, TAG-72, TCR, telomerase, TGF-βRII, TRP-1, TRP-2, tyrosinase, a XAGE family protein.

In certain embodiments, in any of the foregoing methods, the cancer antigen is derived from KRAS, e.g., KRAS where Gly at position 12 has been substituted with Asp (KRAS G12D). For example, in certain embodiments, the recombinant vector comprises the nucleotide sequence of SEQ ID NO: 16, or a nucleotide sequence encoding the amino acid sequence encoded by SEQ ID NO: 16.

In certain embodiments, in any of the foregoing methods, the nucleotide sequences encoding each cancer antigen are separated by an internal ribosome entry site (IRES), e.g., an encephalomyocarditis virus IRES, a foot-and-mouth disease virus IRES, or a poliovirus IRES, e.g., an IRES comprising SEQ ID NO: 13. In certain embodiments, the nucleotide sequences encoding each cancer antigen are separated by a nucleotide sequence encoding a protein linker, e.g., a protein linker comprising AAY (SEQ ID NO: 6), or protein linker comprising a cleavage site.

In certain embodiments, in any of the foregoing methods, the recombinant vector is a recombinant adenovirus, e.g., a type 5 adenovirus (Ad5) or a type 2 adenovirus (Ad2).

In certain embodiments, the recombinant adenovirus, e.g., recombinant oncolytic adenovirus, comprises an E1a promoter having a deletion of a functional Pea3 binding site. In certain embodiments, the deletion of a functional Pea3 binding site comprises a deletion of nucleotides corresponding to about −300 to about −250 upstream of the initiation site of E1a or a deletion of nucleotides corresponding to −304 to −255 upstream of the initiation site of E1a. In certain embodiments, the deletion comprises a deletion of nucleotides corresponding to 195-244 of the Ad5 genome (SEQ ID NO: 1). In certain embodiments, the deletion of a functional Pea3 binding site results in a recombinant adenovirus comprising the sequence GGTGTTTTGG (SEQ ID NO: 2).

In certain embodiments, the recombinant adenovirus, e.g., recombinant oncolytic adenovirus, comprises an E1a promoter having a deletion of a functional TATA box, e.g., the deletion of an entire TATA box. For example, in certain embodiments, the virus comprises a deletion of nucleotides corresponding to −27 to −24, −31 to −24, −44 to +54, or −146 to +54 of the adenovirus type 5 E1a promoter, which correspond, respectively, to nucleotides 472 to 475, 468 to 475, 455 to 552, and 353 to 552 of the Ad5 genome (SEQ ID NO: 1). In certain embodiments, the virus comprises a polynucleotide deletion that results in a virus comprising the sequence CTAGGACTG (SEQ ID NO: 17), AGTGCCCG (SEQ ID NO: 101), or TATTCCCG (SEQ ID NO: 102), which result from joining the two polynucleotide sequences that would otherwise flank the deleted polynucleotide sequence.

In certain embodiments, the recombinant adenovirus, e.g., recombinant oncolytic adenovirus, comprises an E1a promoter having a deletion of a functional CAAT box, e.g., the deletion of an entire CAAT box. For example, in certain embodiments, the virus comprises a deletion of nucleotides corresponding to −76 to −68 of the adenovirus type 5 E1a promoter, which corresponds to nucleotides 423 to 431 of the Ad5 genome (SEQ ID NO: 1). In certain embodiments, the virus comprises a polynucleotide deletion that results in a virus comprising the sequence TTCCGTGGCG (SEQ ID NO: 103), which results from joining the two polynucleotide sequences that would otherwise flank the deleted polynucleotide sequence. In certain embodiments, the recombinant adenovirus comprises a deletion of nucleotides corresponding to 477 to 484 of the Ad35 genome (SEQ ID NO: 113).

In certain embodiments, the recombinant adenovirus, e.g., recombinant oncolytic adenovirus, comprises a deletion of a functional E1a coding region. In certain embodiments, the deletion of a functional E1a coding region comprises a deletion of nucleotides corresponding to the entire coding region of the E1a gene. In certain embodiments, the deletion of a functional E1a coding region comprises a deletion of nucleotides corresponding to 560-1545 of the Ad5 genome or a deletion of nucleotides corresponding to 557-1678 of the Ad5 genome (SEQ ID NO: 1). In certain embodiments, the deletion of a functional E1a coding region results in a recombinant adenovirus comprising the sequence GACTGTGCGC (SEQ ID NO: 3).

In certain embodiments, the recombinant adenovirus, e.g., recombinant oncolytic adenovirus, comprises a deletion of a functional E1b-19k coding region. In certain embodiments, the deletion of a functional E1b-19k coding region comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent to the start site of E1b-19K. In certain embodiments, the deletion of a functional E1b-19k coding region comprises a deletion of about 200 nucleotides, e.g., 203 nucleotides adjacent to the start site of E1b-19K. In certain embodiments, the deletion of a functional E1b-19k coding region comprises a deletion corresponding to nucleotides 1714-1916 of the Ad5 genome (SEQ ID NO: 1).

In certain embodiments the recombinant adenovirus, e.g., recombinant oncolytic adenovirus, comprises an E3 deletion. In certain embodiments, the E3 deletion comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or from about 3000 to about 3185 nucleotides. In certain embodiments, the E3 deletion site is located between the stop site of pVIII and the start site of Fiber. In certain embodiments, the E3 deletion site is located between the stop site of E3-10.5K and the stop site of E3-14.7K. In certain embodiments, the E3 deletion comprises a deletion of from about 500 to about 1551, from about 500 to about 1500, from about 500 to about 1000, from about 1000 to about 1551, from about 1000 to about 1500, or from about 1500 to about 1551 nucleotides adjacent to the stop site of E3-10.5K. In certain embodiments, the E3 deletion comprises a deletion of about 1050 nucleotides adjacent to the stop site of E3-10.5K, e.g., the E3 deletion comprises a deletion of 1064 nucleotides adjacent to the stop site of E3-10.5K. In certain embodiments, the E3 deletion comprises a deletion corresponding to the Ad5 dl309 E3 deletion. In certain embodiments, the E3 deletion comprises a deletion corresponding to nucleotides 29773-30836 of the Ad5 genome (SEQ ID NO: 1).

In certain embodiments, the exogenous nucleotide sequence encoding the at least one cancer antigen is inserted into the deletion of a functional E1b-19k coding region, the deletion of a functional E1a coding region, or the E3 deletion. For example, in certain embodiments, the recombinant adenovirus comprises an exogenous nucleotide sequence inserted into the deletion of a functional E1b-19k coding region, for example, the exogenous nucleotide sequence is inserted between CTGACCTC (SEQ ID NO: 4) and TCACCAGG (SEQ ID NO: 5), e.g., the recombinant adenovirus comprises, in a 5' to 3' orientation, CTGACCTC (SEQ ID NO: 4), the exogenous nucleotide sequence, and TCACCAGG (SEQ ID NO: 5). In certain embodiments, the recombinant adenovirus comprises an exogenous nucleotide sequence inserted into the E3 deletion, for example, the exogenous nucleotide sequence is inserted between CAGTATGA (SEQ ID NO: 8) and TAATAAAAAA (SEQ ID NO: 9), e.g., the recombinant adenovirus comprises, in a 5' to 3' orientation, CAGTATGA (SEQ ID NO: 8), the exogenous nucleotide sequence, and TAATAAAAAA (SEQ ID NO: 9).

In certain embodiments, the recombinant adenovirus, e.g., recombinant oncolytic adenovirus, may comprise a deletion of at least one E2F binding site, or a functional portion thereof. In certain embodiments, the recombinant adenovirus may comprise a deletion of at least one E2F binding site, or a functional portion thereof, and not comprise a deletion of a Pea3 binding site.

In certain embodiments, in any of the foregoing methods, the recombinant vector, e.g., recombinant oncolytic vector, further comprises an exogenous nucleotide sequence encoding a therapeutic transgene. For example, in certain embodiments, the recombinant vector further comprises an exogenous nucleotide sequence encoding a polypeptide, or a fragment thereof, selected from CD80, CD137L, IL-23, IL-23A/p19, IL-27, IL-27A/p28, IL-27B/EBI3, ICAM-1, a TGF-β trap, TGF-β, CD19, CD20, IL-1, IL-3, IL-4, IL-5, IL-6, IL-8, IL-9, CD154, CD86, BORIS/CTCFL, FGF, IL-24, MAGE, NY-ESO-1, acetylcholine, interferon-gamma, DKK1/Wnt, p53, thymidine kinase, an anti-PD-1 antibody heavy chain or light chain, an anti-PD-L1 antibody heavy chain or light chain, FLT3L, and FLT3.

In certain embodiments, in any of the foregoing methods, the recombinant vector may be a recombinant oncolytic vector. In certain embodiments, in any of the foregoing methods, the recombinant oncolytic vector may selectively express the transgene in a hyperproliferative cell. The hyperproliferative cell may be a cancer cell, e.g., a lung cancer cell, a colon cancer cell, and a pancreatic cancer cell.

In certain embodiments, the recombinant vector, e.g., recombinant oncolytic vector, does not comprise an exogenous promoter sequence and the nucleotide sequence encoding the cancer antigen is not operably linked to an exogenous promoter sequence.

In certain embodiments, in any of the foregoing methods, the cancer is selected from melanoma, squamous cell carcinoma of the skin, basal cell carcinoma, head and neck cancer, breast cancer, anal cancer, cervical cancer, non-small cell lung cancer, mesothelioma, small cell lung cancer, renal cell carcinoma, prostate cancer, gastroesophageal cancer, colorectal cancer, testicular cancer, bladder cancer, ovarian cancer, hepatocellular carcinoma, cholangiocarcinoma, brain cancer, endometrial cancer, neuroendocrine cancer, merkel cell carcinoma, gastrointestinal stromal tumors, a sarcoma, and pancreatic cancer.

In each of the foregoing methods, the recombinant adenovirus can, e.g., be administered in combination with one or more therapies selected from surgery, radiation, chemotherapy, immunotherapy, hormone therapy, phototherapy, and virotherapy. In each of the foregoing methods, the recombinant adenovirus can, e.g., be administered in combination with a TGF-β trap or an expression vector comprising a nucleotide sequence encoding a TGF-β trap.

In another aspect, the invention provides a method of stimulating a heightened immune response against an antigen in a subject. The method comprises administering to the subject an effective amount of a recombinant vector comprising an exogenous nucleotide sequence encoding the antigen. In certain embodiments, the antigen is derived from a pathogenic organism, e.g., HIV, HepC, feline immunodeficiency virus (FIV), lymphocytic choriomeningitis virus (LCMV), Ebola virus and *Mycobacterium tuberculosis.*

In each of the foregoing methods, the effective amount of the recombinant adenovirus can be, e.g., $10^2$-$10^{15}$ plaque forming units (pfus). In each of the foregoing methods, the subject can, e.g., be a human, e.g., a pediatric human, or an animal.

These and other aspects and advantages of the invention are illustrated by the following figures, detailed description and claims.

STATEMENT REGARDING SEQUENCE LISTING

The Sequence Listing associated with this application is provided in text format in lieu of a paper copy, and is hereby incorporated by reference into the specification. The name of the text file containing the Sequence Listing is RDX-036WO_SeqList_ST25.txt. The text file is about 182 KB, was created on Mar. 27, 2019 and is being submitted electronically via EFS-Web.

BRIEF DESCRIPTION OF THE DRAWINGS

FIGS. 2A-2C are tables listing the cancer-associated antigens identified from a patient, as described in Example 2. In each instance, a mutant amino acid sequence (top) and the corresponding wild-type amino acid sequence (bottom) are displayed. The mutated amino acid residues are in boxes.

DETAILED DESCRIPTION

Figure 1:
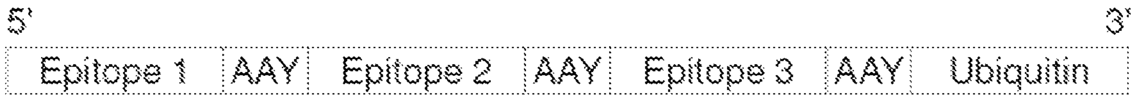
FIG. 1 is a schematic representation of a protein concatemer containing three cancer antigens or epitopes separated by Alanine-Alanine-Tyrosine (AAY; SEQ ID NO: 6) linkers and a C-terminal Ubiquitin that promotes proteasomal targeting and processing for MHC presentation.

It is to be understood that the terminology used herein is for the purpose of describing particular embodiments only and is not intended to be limiting.

Unless defined otherwise, all technical and scientific terms used herein have the same meaning as commonly understood by one of ordinary skill in the art to which the present application belongs. Although any methods and materials similar or equivalent to those described herein can be used in the practice or testing of the present application, representative methods and materials are herein described.

Following long-standing patent law convention, the terms "a", "an", and "the" refer to "one or more" when used in this application, including the claims. Thus, for example, reference to "a foam suppression agent" includes mixtures of one or more foam suppression agent, two or more foam suppression agent.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the present application. As used herein, the term "about" or "approximately" when preceding a numerical value indicates the value plus or minus a range of 10%. For example, "about 100" encompasses 90 and 110.

The term "wild type", abbreviated as "WT", is a term of the art understood by skilled persons and means the typical form of an organism, strain, gene, protein, or characteristic as it occurs in nature as distinguished from mutant or variant forms. For example, a WT protein is the typical form of that protein as it occurs in nature.

The term "mutant protein" is a term of the art understood by skilled persons and refers to a protein that is distinguished from the WT form of the protein on the basis of the presence of amino acid modifications, such as, for example, amino acid frameshift mutations, substitutions, insertions and/or deletions.

Amino acid substitution, interchangeably referred to as amino acid replacement, at a specific position on the protein sequence is denoted herein in the following manner. "one letter code of the WT amino acid residue-amino acid position-one letter code of the amino acid residue that replaces this WT residue". For example, a p53 polypeptide which is a R175H mutant refers to a mutant p53 polypeptide in which the wild type residue at the 175th amino acid position (R or arginine) is replaced with H or histidine.

As used herein, "treatment" is an approach for obtaining beneficial or desired clinical results. For purposes of this invention, beneficial or desired clinical results include, but are not limited to, one or more of the following: improvement in at least one symptom associated with cancer, including lessening severity or alleviation of one or more symptoms associated with cancer, preventing, and/or the delaying the development and/or progression of cancer.

The invention is based, in part, upon the discovery that a recombinant vector, e.g., a recombinant oncolytic adenovirus, can be used to express selectively express a cancer antigen in a cancer cell in a subject and stimulate a heightened immune response against the cancer antigen in the subject and/or treat the cancer in the subject. In addition, a recombinant vector, e.g., a recombinant oncolytic adenovirus, can be used to selectively express in a cancer cell in a subject a cancer antigen that has been identified by sequencing DNA or RNA from a sample from the subject, thereby stimulating a heightened immune response against an antigen that is specific to the cancer of the subject. The features of the recombinant vectors, e.g., recombinant oncolytic adenoviruses, described herein, enable the repeated generation and administration of different recombinant vectors, e.g., recombinant oncolytic adenoviruses that express different subject-specific cancer antigens, thereby to treat refractory cancers.

Accordingly, in one aspect, the present disclosure provides a method of stimulating a heightened immune response against a cancer antigen in a subject in need thereof, the method comprising administering to the subject an effective amount of a recombinant vector, e.g., a recombinant oncolytic vector, comprising an exogenous nucleotide sequence encoding the cancer antigen to stimulate the heightened immune response against the cancer antigen in the subject, wherein the cancer antigen has been identified by sequencing DNA or RNA from a sample from the subject.

In another aspect, the present disclosure provides a method of treating a cancer in a subject in need thereof, the method comprising administering to the subject an effective amount of a recombinant vector e.g., a recombinant oncolytic vector, comprising an exogenous nucleotide sequence encoding at least one cancer antigen to treat the cancer in the subject, wherein the cancer antigen has been identified by sequencing DNA or RNA from a sample from the subject.

In certain embodiments, in any of the foregoing methods, the subject has previously been administered a prior recombinant vector comprising an exogenous nucleotide sequence encoding at least one cancer antigen. In certain embodiments, the cancer is refractory to the administration of the prior recombinant vector and/or the recombinant vector encodes at least one cancer antigen that was not encoded by the prior recombinant vector. It is contemplated that the subject may have previously been administered more than one prior recombinant vector (e.g., 1, 2, 3, 4, 5, 6, 7, 8, 9, 10 or more prior recombinant vectors).

In another aspect, the present disclosure provides a method of treating a cancer in a subject in need thereof, the method comprising: (a) identifying a cancer antigen by sequencing DNA or RNA from a sample from the subject; and (b) administering to the subject an effective amount of a recombinant vector e.g., a recombinant oncolytic vector, comprising a nucleotide sequence encoding the cancer antigen to treat the cancer in the subject. In certain embodiments, the method further comprises, after step (b): (c) identifying an additional cancer antigen by sequencing DNA or RNA from a sample from the subject; and (d) administering to the subject an effective amount of an additional recombinant vector e.g., a recombinant oncolytic vector, comprising a nucleotide sequence encoding the additional cancer antigen to treat the cancer in the subject. The cancer may, for example, be refractory to the administration of step (b) It is contemplated that the subject may be administered more than one additional recombinant vectors (e.g., 1, 2, 3, 4, 5, 6, 7, 8, 9, 10 or more recombinant vectors).

The present disclosure also provides a recombinant vector. In some embodiments, the recombinant vector is an oncolytic vector, e.g., a vector that exhibits tumor-selective gene expression and/or replication. In certain embodiments, a recombinant vector of the invention exhibits selective expression of a transgene (e.g., a cancer antigen) in a hyperproliferative cell, e.g., a cancer cell, relative to a non-hyperproliferative cell. As used herein, the term cancer antigen refers to an antigenic substance produced in a cancer cell. The cancer antigen can be a full length protein, or a fragment thereof, such as about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 44, 43, 44, 45, 46, 47, 48, 49, 50 or more amino acids of a full length protein in a cancer cell. In some embodiments, the cancer antigen comprises one or more mutations compared to a corresponding wild type sequence. In some embodiments, the mutation is a substation, a deletion, an insertion, a frameshift, or combination thereof. In some embodiments, the cancer antigen polypeptide comprises the mutation, and amino acids flanking the mutation.

In certain embodiments, the expression of a transgene in a non-hyperproliferative cell is about 90%, about 80%, about 70%, about 60%, about 50%, about 40%, about 30%, about 20%, about 10%, or about 5% of the expression of the gene in the hyperproliferative cell. In certain embodiments, the vector exhibits no detectable expression of a transgene in a non-hyperproliferative cell. Transgene expression may be determined by any appropriate method known in the art, e.g., Western blot or ELISA. The hyperproliferative cell may be a cancer cell, e.g., a carcinoma, sarcoma, leukemia, lymphoma, prostate cancer, lung cancer, gastrointestinal tract cancer, colorectal cancer, pancreatic cancer, breast cancer, ovarian cancer, cervical cancer, stomach cancer, thyroid cancer, mesothelioma, liver cancer, kidney cancer, skin cancer, head and neck cancer, or brain cancer cell.

I. Recombinant Vectors

Recombinant vectors suitable for use in the invention include, e.g., viruses, bacteria (e.g., *Listeria monocytogenes, Salmonella enterica* or *Serovar typhimurium*), nanoparticles, liposomes, exosomes, or microemulsions.

The term "virus" is used herein to refer any of the obligate intracellular parasites having no protein-synthesizing or energy-generating mechanism. The viral genome may be RNA or DNA. The viruses useful in the practice of the present invention include recombinantly modified enveloped or non-enveloped DNA and RNA viruses, preferably selected from baculoviridiae, parvoviridiae, picornoviridiae, herpesviridiae, poxyiridae, or adenoviridiae. A recombinantly modified virus is referred to herein as a "recombinant virus." A recombinant virus may, e.g., be modified by recombinant DNA techniques to be replication deficient, conditionally replicating, or replication competent, and/or be modified by recombinant DNA techniques to include expression of exogenous transgenes. Chimeric viral vectors which exploit advantageous elements of each of the parent vector properties (See, e.g., Feng et al. (1997) Nature Biotechnology 15:866-870) may also be useful in the practice of the present invention. Although it is generally favored to employ a virus from the species to be treated, in some instances it may be advantageous to use vectors derived from different species that possess favorable pathogenic features. For example, equine herpes virus vectors for human gene therapy are described in PCT Publication No. WO 98/27216. The vectors are described as useful for the treatment of humans as the equine virus is not pathogenic to humans. Similarly, ovine adenoviral vectors may be used in human gene therapy as they are claimed to avoid the antibodies against the human adenoviral vectors. Such vectors are described in PCT Publication No. WO 97/06826.

Exemplary viruses useful in the practice of the invention include adenovirus, adeno-associated virus (AAV), rhabdovirus, measles virus, vaccinia virus, myxoma virus, parvovirus, Newcastle disease virus, Semliki Forest virus, fowlpox virus, lentivirus, herpes virus, vesicular stomatitis virus (VSV), Maraba virus, polio virus, and alpha virus. In certain embodiments, without wishing to be bound by theory, it is believed that a recombinant virus can provide a "danger signal" that can active that innate immune system and increase the efficacy of an immune response against a cancer antigens in a subject.

In certain embodiments, the recombinant virus is selected from an adenovirus and an adeno-associated virus (AAV). Preferably, the recombinant virus is an adenovirus. Adenoviruses are medium-sized (90-100 nm), non-enveloped (naked), icosahedral viruses composed of a nucleocapsid and a double-stranded linear DNA genome. Adenoviruses replicate in the nucleus of mammalian cells using the host's replication machinery. The term "adenovirus" refers to any virus in the genus Adenoviridiae including, but not limited to, human, bovine, ovine, equine, canine, porcine, murine, and simian adenovirus subgenera. In particular, human adenoviruses includes the A-F subgenera as well as the individual serotypes thereof, the individual serotypes and A-F subgenera including but not limited to human adenovirus types 1, 2, 3, 4, 4a, 5, 6, 7, 8, 9, 10, 11 (Ad11a and Ad11p), 12, 13, 14, 15, 16, 17, 18, 19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. Preferred are recombinant adenoviruses derived from human adenovirus types 2 and 5. Unless stated otherwise, all adenovirus type 5 nucleotide numbers are relative to the NCBI reference sequence AC_000008.1, which is depicted herein in SEQ ID NO: 1.

The adenovirus replication cycle has two phases: an early phase, during which 4 transcription units E1, E2, E3, and E4 are expressed, and a late phase which occurs after the onset of viral. DNA synthesis when late transcripts are expressed primarily from the major late promoter (MLP). The late messages encode most of the virus's structural proteins. The gene products of E1, E2 and E4 are responsible for transcriptional activation, cell transformation, viral DNA replication, as well as other viral functions, and are necessary for viral growth.

The E1a gene of Ad5 is processed by mRNA splicing to yield five distinct isoforms; 13S, 12S, 11S, 10S and 9S. The major forms 13S and 12S code for two E1a proteins, 289R and 243R respectively, that regulate transcription of both viral and cellular genes in adenovirus-infected cells and are essential for adenoviral replication. The 289R form includes a critical transactivation domain that activates transcription of the early adenoviral genes: E2, E3, and E4 (Berk, Lee et al. 1979; Jones and Shenk 1979). This domain is spliced out to generate the 243R isoform of E1a and viruses expressing only the 243R form are unable to transactivate expression from the early viral genes (Montell, Courtois et al. 1984). E1a induces expression of cellular genes including c-Fos, c-Jun, and c-Myc and represses the transcription of c-erbB2 and epidermal growth factor receptor. E1a proteins can drive quiescent cells into cell division by interaction with critical cellular cell cycle proteins including pRB, p27, cyclin A, cyclin E, CtBP, and p300/CBP.

The general structure of the mature Adenovirion is conserved among different Adenoviral species. The Adenoviral capsid is composed of three major proteins (II, III, and IV) and five minor proteins, VI, VIII, IX, IIIa, and IVa2. "IVa2 gene" used herein refers to the gene encoding the IVa2 protein, modified versions, and/or fragment thereof. "IX gene" used herein refers to the gene encoding the IX protein, modified versions, and/or fragment thereof.

Primary transcripts from E4 are subject to alternative splicing events and are predicted to encode seven different polypeptides: ORF1, ORF2, ORF3, ORF3/4, ORF4, ORF5, ORF6, and ORF6/7. (Leppard et al., Journal of General Virology (1997) 78:2131-8) "ORF" is used herein to refer to either the polypeptide or the nucleotide sequence encoding the polypeptide, modified versions, and/or fragment thereof.

In addition, the fiber protein (also known as protein IV or SPIKE) forms spikes that protrude from each vertex of the icosahedral capsid. "Fiber gene" used herein refers to the gene encoding the fiber protein, also known as L5 gene, modified versions, and/or fragment thereof.

Recombinant adenoviruses and method of making and using them are described in U.S. application Ser. No. 15/991,745, U.S. application Ser. No. 16/058,886, PCT/US2018/034888, and PCT/US2018/030929, each of which is incorporated by reference in its entirety.

A. Modified E1a Transcriptional Control Region

In certain embodiments, the recombinant adenoviruses comprise one or more modifications to a regulatory sequence or promoter. A modification to a regulatory sequence or promoter comprises a deletion, substitution, or addition of one or more nucleotides compared to the wild-type sequence of the regulatory sequence or promoter.

In one embodiment, the modification of a regulatory sequence or promoter comprises a modification of sequence of a transcription factor binding site to reduce affinity for the transcription factor, for example, by deleting a portion thereof, or by inserting a single point mutation into the binding site. In certain embodiments, the additional modified regulatory sequence enhances expression in neoplastic cells, but attenuates expression in normal cells.

In one embodiment, at least one of these seven binding sites, or a functional binding site, is deleted. As used herein, a "functional binding site" refers to a binding site that is capable of binding to a respective binding partner, e.g., a transcription factor, e.g., a binding site that has at least 100%, at least 90%, at least 80%, at least 70%, at least 60%, at least 50%, or at least 40%, of the binding activity of a corresponding wild-type binding site sequence. As used herein, a "non-functional binding site" refers to a binding site that, e.g., has less than 30%, less than 20%, less than 10%, or 0% of the binding activity of a corresponding wild-type binding site sequence.

In certain embodiments, the recombinant adenoviruses comprise a modified E1a regulatory sequence. In certain embodiments, a disclosed recombinant adenovirus may, e.g., comprise a deletion of a functional E1a coding region. As used herein, a "functional E1a coding region" refers to an E1a coding region that encodes for a functional E1a protein, e.g., an E1a protein that is capable of binding to a respective binding partner (e.g., CREB binding protein (CBP)), e.g., an E1a protein that has at least 100%, at least 90%, at least 80%, at least 70%, at least 60%, at least 50%, or at least 40%, of the binding activity of a corresponding wild-type E1a protein. As used herein, a "non-functional E1a coding region" refers to a coding region that encodes for an E1a protein that, e.g., has less than 30%, less than 20%, less than 10%, or 0% of the binding activity of a corresponding wild-type E1a protein.

In certain embodiments, the deletion of a functional E1a coding region comprises a deletion of nucleotides corresponding to the entire coding region of the E1a gene. In certain embodiments, the deletion of a functional E1a coding region comprises a deletion of nucleotides corresponding to 560-1545 of the Ad5 genome or a deletion of nucleotides corresponding to 557-1678 of the Ad5 genome (SEQ ID NO: 1). In certain embodiments, the deletion of a functional E1a coding region results in a recombinant adenovirus comprising the sequence GACTGTGCGC (SEQ ID NO: 3). In certain embodiments, the recombinant adenovirus includes an E1a insertion site, e.g., the adenovirus has a transgene inserted into the deletion of a functional E1a coding region.

The adenoviral E1b-19k gene functions primarily as an anti-apoptotic gene and is a homolog of the cellular anti-apoptotic gene, BCL-2. Since host cell death prior to maturation of the progeny viral particles would restrict viral replication, E1b-19k is expressed as part of the E1 cassette to prevent premature cell death thereby allowing the infection to proceed and yield mature virions. Accordingly, in certain embodiments, a recombinant adenovirus is provided that includes a deletion of a functional E1b-19k coding region.

A disclosed recombinant adenovirus may, e.g., comprise a deletion of a functional E1b-19k coding region. As used herein, a "functional E1b-19k coding region" refers to an E1b-19k coding region that encodes for a functional E1b-19k protein, e.g., an E1b-19k protein that is capable of binding to a respective binding partner (e.g., BAK), e.g., an E1b-19k protein that has at least 100%, at least 90%, at least 80%, at least 70%, at least 60%, at least 50%, or at least 40%, of the binding activity of a corresponding wild-type E1b-19k protein. As used herein, a "non-functional E1b-19k coding region" refers to a coding region that encodes for an E1b-19k protein that, e.g., has less than 30%, less than 20%, less than 10%, or 0% of the binding activity of a corresponding wild-type E1b-19k protein.

In certain embodiments, the deletion of a functional E1b-19k coding region comprises a deletion located between the start site of E1b-19K (i.e., the nucleotide sequence encoding the start codon of E1b-19k, e.g., corresponding to nucleotides 1714-1716 of SEQ ID NO: 1) and the start site of E1b-55K (i.e., the nucleotide sequence encoding the start codon of E1b-55k, e.g., corresponding to nucleotides 2019-2021 of SEQ ID NO: 1). In certain embodiments, the deletion of a functional E1b-19k coding region comprises a deletion located between the start site of E1b-19K (i.e., the nucleotide sequence encoding the start codon of E1b-19k, e.g., corresponding to nucleotides 1714-1716 of SEQ ID NO: 1) and the stop site of E1b-19K (i.e., the nucleotide sequence encoding the stop codon of E1b-19k, e.g., corresponding to nucleotides 2242-2244 of SEQ ID NO: 1). Throughout the description and claims, an insertion between two sites, for example, an insertion between (i) a start site of a first gene (e.g., E1b-19k) and a start site of a second gene, (e.g., E1b-55K), (ii) a start site of a first gene and a stop site of a second gene, (iii) a stop site of a first gene and start site of a second gene, or (iv) a stop site of first gene and a stop site of a second gene, is understood to mean that all or a portion of the nucleotides constituting a given start site or a stop site surrounding the insertion may be present or absent in the final virus. Similarly, an insertion between two nucleotides is understood to mean that the nucleotides surrounding the insertion may be present or absent in the final virus. The term "transgene" refers to an exogenous gene, or fragment thereof, or exogenous polynucleotide sequence. As used herein "transgene" is understood to encompass a single a exogenous gene, or fragment thereof, or exogenous polynucleotide sequence, or multiple (e.g., 1, 2, 3, 4, 5, 6, 7, 8, 9, 10, 11, 12, 13, 14, or 15) exogenous genes, or fragments thereof, or exogenous polynucleotide sequences The term "therapeutic transgene" refers to a transgene, which when replicated and/or expressed in or by the virus imparts a therapeutic effect in a target cell, body fluid, tissue, organ, physiological system, or subject.

In certain embodiments, the deletion of a functional E1b-19k coding region comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent to the start site of E1b-19K (i.e., the nucleotide sequence encoding the start codon of E1b-19k, e.g., corresponding to nucleotides 1714-1716 of SEQ ID NO: 1). In certain embodiments, the deletion of a functional E1b-19k coding region comprises a deletion of about 200 nucleotides, e.g., 203 nucleotides adjacent to the start site of E1b-19K. In certain embodiments, the deletion of a functional E1b-19k coding region comprises a deletion corresponding to nucleotides 1714-1916 of the Ad5 genome (SEQ ID NO: 1). Throughout the description and claims, a deletion adjacent to a site, for example, a deletion adjacent to a start site of a gene or a deletion adjacent to a stop site of a gene, is understood to mean that the deletion may include a deletion of all, a portion, or none of the nucleotides constituting a given start site or a stop site.

In certain embodiments, the recombinant adenovirus comprises one or more exogenous nucleotide sequences inserted in one or more of an E1b-19K insertion site, an E3 insertion site, an E4 insertion site, an IX-E2 insertion site, an L5-E4 insertion site, and any combinations thereof. In certain embodiments, the recombinant adenovirus selectively expresses the cancer antigen in tumor cells. In certain embodiments, the recombinant adenovirus selectively replicates in cells of a cancer.

In certain embodiments, the nucleotide sequence is inserted between nucleotides corresponding to about 3899 and 3970 of the Ad35 genome (SEQ ID NO: 113). In certain embodiments, the nucleotide sequence is inserted between nucleotides corresponding to 3899 and 3920, nucleotides corresponding to 3920 and 3940, or nucleotides corresponding to 3940 and 3970 of the Ad35 genome (SEQ ID NO: 113). In certain embodiments, the nucleotide sequence is inserted between nucleotides corresponding to about 31799 and 31821 of the Ad35 genome (SEQ ID NO: 113). In certain embodiments, the nucleotide sequence is inserted between nucleotides corresponding to 31799 and 32810, or nucleotides corresponding to 32810 and 31821 of the Ad35 genome (SEQ ID NO: 113).

In certain embodiments, the recombinant adenovirus comprises an E1b-19K insertion site, e.g., the adenovirus has an exogenous nucleotide sequence inserted into the deletion of a functional E1b-19k coding region. For example, in certain embodiments, an exogenous nucleotide sequence is inserted between nucleotides corresponding to 1714 and 1916 of the Ad5 genome (SEQ ID NO: 1). In certain embodiments, an exogenous nucleotide sequence is inserted between CTGACCTC (SEQ ID NO: 4) and TCACCAGG (SEQ ID NO: 5), e.g., the recombinant adenovirus comprises, in a 5' to 3' orientation, CTGACCTC (SEQ ID NO: 4), the exogenous nucleotide sequence, and TCACCAGG (SEQ ID NO: 5). CTGACCTC (SEQ ID NO: 4) and TCACCAGG (SEQ ID NO: 5) define unique boundary sequences for a E1b-19K insertion site within the Ad5 genome (SEQ ID NO: 1).

In certain embodiments the recombinant adenovirus comprises an E3 deletion. In certain embodiments, the E3 deletion comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or from about 3000 to about 3185 nucleotides.

In certain embodiments, the E3 deletion comprises a deletion located between the stop site of pVIII (i.e., the nucleotide sequence encoding the stop codon of pVIII, e.g., corresponding to nucleotides 27855-27857 of SEQ ID NO: 1) and the start site of Fiber (i.e., the nucleotide sequence encoding the start codon of Fiber, e.g., corresponding to nucleotides 31042-31044 of SEQ ID NO: 1). In certain embodiments, the E3 deletion comprises a deletion located between the stop site of E3-10.5K (i.e., the nucleotide sequence encoding the stop codon of E3-10.5K, e.g., corresponding to nucleotides 29770-29772 of SEQ ID NO: 1) and the stop site of E3-14.7K (i.e., the nucleotide sequence encoding the stop codon of E3-14.7K, e.g., corresponding to nucleotides 30837-30839 of SEQ ID NO: 1). In certain embodiments, the E3 deletion comprises a deletion of from about 500 to about 1551, from about 500 to about 1500, from about 500 to about 1000, from about 1000 to about 1551, from about 1000 to about 1500, or from about 1500 to about 1551 nucleotides adjacent to the stop site of E3-10.5K. In certain embodiments, the E3 deletion comprises a deletion of about 1050 nucleotides adjacent to the stop site of E3-10.5K (i.e., the nucleotide sequence encoding the stop codon of E3-10.5K, e.g., corresponding to nucleotides 29770-29772 of SEQ ID NO: 1), e.g., the E3 deletion comprises a deletion of 1064 nucleotides adjacent to the stop site of E3-10.5K. In certain embodiments, the E3 deletion comprises a deletion corresponding to the Ad5 dl309 E3 deletion. In certain embodiments, the E3 deletion comprises a deletion corresponding to nucleotides 29773-30836 of the Ad5 genome (SEQ ID NO: 1).

In certain embodiments, the E3 deletion comprises a deletion located between the stop site of E3-gp19K (i.e., the nucleotide sequence encoding the stop codon of E3-gp19K, e.g., corresponding to nucleotides 29215-29217 of SEQ ID NO: 1) and the stop site of E3-14.7K (i.e., the nucleotide sequence encoding the stop codon of E3-14.7K, e.g., corresponding to nucleotides 30837-30839 of SEQ ID NO: 1). In certain embodiments, the E3 deletion comprises a deletion of from about 500 to about 1824, from about 500 to about 1500, from about 500 to about 1000, from about 1000 to about 1824, from about 1000 to about 1500, or from about 1500 to about 1824 nucleotides adjacent the stop site of E3-gp19K. In certain embodiments, the E3 deletion comprises a deletion of about 1600 nucleotides adjacent the stop site of E3-gp19K. e.g., the E3 insertion site comprises a deletion of 1622 nucleotides adjacent the stop site of E3-19K. In certain embodiments, the E3 deletion comprises a deletion corresponding to nucleotides 29218-30839 of the Ad5 genome (SEQ ID NO: 1).

In certain embodiments, the recombinant adenovirus comprises an E3 insertion site, e.g., the adenovirus has an exogenous nucleotide sequence inserted into the E3 deletion. For example, in certain embodiments, an exogenous nucleotide sequence is inserted between nucleotides corresponding to 29773 and 30836 of the Ad5 genome (SEQ ID NO: 1). In certain embodiments, the exogenous nucleotide sequence is inserted between CAGTATGA (SEQ ID NO: 8) and TAATAAAAAA (SEQ ID NO: 9), e.g., the recombinant adenovirus comprises, in a 5' to 3' orientation, CAGTATGA (SEQ ID NO: 8), the exogenous nucleotide sequence, and TAATAAAAAA (SEQ ID NO: 9). CAGTATGA (SEQ ID NO: 8) and TAATAAAAAA (SEQ ID NO: 9) define unique boundary sequences for an E3 insertion site within the Ad5 genome (SEQ ID NO: 1).

In certain embodiments, the exogenous nucleotide sequence is inserted between nucleotides corresponding to 29218 and 30839 of the Ad5 genome (SEQ ID NO: 1). In certain embodiments, the exogenous nucleotide sequence is inserted between TGCCTTAA (SEQ ID NO: 11) and TAAAAAAAAAT (SEQ ID NO: 12), e.g., the recombinant adenovirus comprises, in a 5' to 3' orientation, TGCCTTAA (SEQ ID NO: 11), the exogenous nucleotide sequence, and TAAAAAAAAAT (SEQ ID NO: 12). TGCCTTAA (SEQ ID NO: 11) and TAAAAAAAAAT (SEQ ID NO: 12) define unique boundary sequences for an E3 insertion site within the Ad5 genome (SEQ ID NO: 1).

In certain embodiments, the recombinant adenovirus comprises an E4 deletion. In certain embodiments, the E4 deletion is located between the start site of E4-ORF6/7 (i.e., the nucleotide sequence encoding the start codon of E4-ORF6/7, e.g., corresponding to nucleotides 34075-34077 of SEQ ID NO: 1) and the right inverted terminal repeat (ITR; e.g., corresponding to nucleotides 35836-35938 of SEQ ID NO: 1). In certain embodiments, the E4 deletion is located between the start site of E4-ORF6/7 and the start site of E4-ORF1 (i.e., the nucleotide sequence encoding the start codon of E4-ORF1, e.g., corresponding to nucleotides 35524-35526 of SEQ ID NO: 1). In certain embodiments, the E4 deletion comprises a deletion of a nucleotide sequence between the start site of E4-ORF6/7 and the start site of E4-ORF1. In certain embodiments, the E4 deletion comprises a deletion of from about 500 to about 2500, from about 500 to about 2000, from about 500 to about 1500, from about 500 to about 1000, from about 1000 to about 2500, from about 1000 to about 2000, from about 1000 to about 1500, from about 1500 to about 2500, from about 1500 to about 2000, or from about 2000 to about 2500 nucleotides. In certain embodiments, the E4 deletion comprises a deletion of from about 250 to about 1500, from about 250 to about 1250, from about 250 to about 1000, from about 250 to about 750, from about 250 to about 500, from 500 to about 1500, from about 500 to about 1250, from about 500 to about 1000, from about 500 to about 750, from 750 to about 1500, from about 750 to about 1250, from about 750 to about 1000, from about 1000 to about 1500, or from about 1000 to about 1250 nucleotides adjacent the start site of E4-ORF6/7. In certain embodiments, the E4 deletion comprises a deletion of about 1450 nucleotides adjacent the start site of E4-ORF6/7, e.g., the E4 deletion comprises a deletion of about 1449 nucleotides adjacent the start site of E4-ORF6/7. In certain embodiments, the E4 deletion comprises a deletion corresponding to nucleotides 34078-35526 of the Ad5 genome (SEQ ID NO: 1).

In certain embodiments, an E4 insertion site comprises any one of the ORF of the E4 gene. For example, a nucleotide sequence can be inserted in E4 ORF1, and/or E4 ORF2. In certain embodiments, portions of or the entire E4 region may be deleted.

In certain embodiments, the insertion site is the IX-E2 insertion site. In certain embodiments, the IX-E2 insertion site is located between the stop codon of adenovirus IX gene and the stop codon of adenovirus IVa2 gene. In certain embodiments, the exogenous nucleotide sequence is inserted between nucleotides corresponding to 4029 and 4093 of the Ad5 genome (SEQ ID NO: 1). In certain embodiments, the exogenous nucleotide sequence is inserted between nucleotides corresponding to 4029 and 4050, nucleotides corresponding to 4051 and 4070, or nucleotides corresponding to 4071 and 4093 of the Ad5 genome (SEQ ID NO: 1). In some embodiments, the IX-E2 insertion site has at least 60%, at least 70%, at least 80%, at least 90%, at least 95%, or at least 99% identity to nucleotides corresponding to 4029 and 4093 of the Ad5 genome (SEQ ID NO: 1).

In certain embodiments, the insertion site is an L5-E4 insertion site. In certain embodiments, the L5-E4 insertion site is located between the stop codon of adenovirus fiber gene and the stop codon of ORF6 or ORF6/7 of the adenovirus E4 gene. In certain embodiments, the exogenous nucleotide sequence is inserted between nucleotides corresponding to 32785 to 32916 of the Ad5 genome (SEQ ID NO: 1). In certain embodiments, the exogenous nucleotide sequence is inserted between nucleotides corresponding to 32785 and 32800, nucleotides corresponding to 32801 and 32820, nucleotides corresponding to 32821 and 32840, nucleotides corresponding to 32841 and 32860, nucleotides corresponding to 32861 and 32880, nucleotides corresponding to 32881 and 32900, or nucleotides corresponding to 32901 and 32916 of the Ad5 genome (SEQ ID NO: 1). In some embodiments, the L5-E4 insertion site has at least 60%, at least 70%, at least 80%, at least 90%, at least 95%, or at least 99% identity to nucleotides corresponding to 32785 to 32916 of the Ad5 genome (SEQ ID NO: 1).

In certain embodiments, the IX-E2 insertion site comprises a deletion of about 5, 10, 15, 20, 25, 30, 35, 40, 45, 50, 55, or 60 nucleotides. In certain embodiments, the L5-E4 insertion site comprises a deletion of about 5, 10, 15, 20, 25, 30, 35, 40, 45, 50, 55, 60, 65, 70, 75, 80, 85, 90, 95, 100, 105, 110, 115, 120, 125, or 130 nucleotides.

The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a gene if it affects the transcription of the gene. Operably linked nucleotide sequences are typically contiguous. However, as enhancers generally function when separated from the promoter by several kilobases and intronic sequences may be of variable lengths, some polynucleotide elements may be operably linked but not directly flanked and may even function in trans from a different allele or chromosome.

In certain embodiments, the virus has one or more modifications to a regulatory sequence or promoter. A modification to a regulatory sequence or promoter comprises a deletion, substitution, or addition of one or more nucleotides compared to the wild-type sequence of the regulatory sequence or promoter.

In certain embodiments, the modification of a regulatory sequence or promoter comprises a modification of the sequence of a transcription factor binding site to reduce affinity for the transcription factor, for example, by deleting a portion thereof, or by inserting a single point mutation into the binding site. In certain embodiments, the modified regulatory sequence enhances expression in neoplastic cells and/or attenuates expression in normal cells.

In certain embodiments, the modified regulatory sequence is operably linked to a sequence encoding a protein. In certain embodiments, at least one of the adenoviral E1a and E1b genes (coding regions) is operably linked to a modified regulatory sequence. In certain embodiments, the E1a gene is operably linked to a modified regulatory sequence.

The E1a regulatory sequence contains five binding sites for the transcription factor Pea3, designated Pea3 I, Pea3 II, Pea3 III, Pea3 IV, and Pea3 V, where Pea3 I is the Pea3 binding site most proximal to the E1a start site, and Pea3 V is most distal. The E1a regulatory sequence also contains binding sites for the transcription factor E2F, hereby designated E2F I and E2F II, where E2F I is the E2F binding site most proximal to the E1a start site, and E2F II is more distal. From the E1a start site, the binding sites are arranged: Pea3 I, E2F I, Pea3 II, E2F II, Pea3 III, Pea3 IV, and Pea3 V.

In certain embodiments, at least one of these seven binding sites, or at least one of seven functional binding sites, is deleted. As used herein, a "functional binding site" refers to a binding site that is capable of binding to a respective binding partner, e.g., a transcription factor, e.g., a binding site that has at least 100%, at least 90%, at least 80%, at least 70%, at least 60%, at least 50%, or at least 40%, of the binding activity of a corresponding wild-type binding site sequence. As used herein, a "non-functional binding site" refers to a binding site that, e.g., has less than 30%, less than 20%, less than 10%, or 0% of the binding activity of a corresponding wild-type binding site sequence.

In certain embodiments, the recombinant adenovirus comprises an E1a promoter having a deletion of a functional Pea3 binding site, e.g., the deletion of an entire Pea3 binding site. As used herein, a "functional Pea3 binding site" refers to a Pea3 binding site that is capable of binding to its respective transcription factor (e.g., Pea3), e.g., a Pea3 binding site that has at least 100%, at least 90%, at least 80%, at least 70%, at least 60%, at least 50%, or at least 40%, of the Pea3 binding activity of a corresponding wild-type Pea3 binding site sequence. As used herein, a "non-functional Pea3 binding site" refers to a Pea3 binding site that, e.g., has less than 30%, less than 20%, less than 10%, or 0% of the Pea3 binding activity of a corresponding wild-type Pea3 binding site sequence. Assays for determining whether a Pea3 binding site binds to Pea3 are known in the art. Exemplary binding assays include electrophoretic mobility shift assays, chromatin immunoprecipitation assays, and DNAse footprinting assays.

In certain embodiments, at least one Pea3 binding site, or a functional Pea3 binding site, is deleted. The deleted Pea3 binding site can be Pea3 I, Pea3 II, Pea3 III, Pea3 IV, and/or Pea3 V. In certain embodiments, the deleted Pea3 binding site is Pea3 II, Pea3 III, Pea3 IV, and/or Pea3 V. In certain embodiments, the deleted Pea3 binding site is Pea3 IV and/or Pea3 V. In another embodiment, the deleted Pea3 binding site is Pea3 II and/or Pea3 III. In certain embodiments, the deleted Pea3 binding site is both Pea3 II and Pea3 III. In certain embodiments, the Pea3 I binding site, or a functional Pea3 I binding site, is retained.

In certain embodiments, at least one E2F binding site, or a functional E2F binding site, is deleted. In certain embodiments, at least one E2F binding site, or a functional E2F binding site, is retained. In certain embodiments, the retained E2F binding site is E2F I and/or E2F II. In certain embodiments, the retained E2F binding site is E2F II. In certain embodiments, the total deletion consists essentially of one or more of Pea3 II, Pea3 III, Pea3 IV, and/or Pea3 V. In certain embodiments, the virus has a deletion of a 50 base pair region located from −304 to −255 upstream of the E1a initiation site, e.g., corresponding to 195-244 of the Ad5 genome (SEQ ID NO: 1), hereafter referred to as the TAV-255 deletion. In certain embodiments, the TAV-255 deletion results in an E1a promoter that comprises the sequence GGTGTTTTGG (SEQ ID NO: 2).

In one embodiment, the recombinant adenovirus has the same or similar E1a modification as in the oncolytic serotype 5 adenovirus (Ad5) called TAV-255 described in PCT Publication No. WO2010101921 and US Publication No. 20160017294A1, each of which is incorporated by reference herein in its entirety. It is believed that the mechanism by which the TAV-255 vector achieves this tumor selectivity is through targeted deletion of three transcriptional factor (TF) binding sites for the transcription factors Pea3 and E2F, proteins that regulate adenovirus expression of E1a, the earliest gene to be transcribed after virus entry into the host cell, through binding to specific DNA sequences. These three Pea3 and E2F deletions attenuate replication in growth-arrested, normal cells but not in malignant ones, indicating that these DNA sequences are only dispensable for transcriptional regulation and growth in cancer cells.

In one embodiment, the recombinant adenovirus comprises one or more Pea3 transcription binding site deletions without one or more E2F transcription binding site deletions in the E1A region. In other embodiment, the recombinant adenovirus comprises one or more E2F transcription binding site deletions without one or more Pea3 transcription binding site deletions in the E1A region.

In certain embodiments, the recombinant adenovirus comprises an E1a promoter lacking a functional TATA box, or lacking a functional CAAT box. In certain embodiments, the recombinant adenovirus comprises a deletion of the entire TATA box. In certain embodiments, the recombinant adenovirus comprises a deletion of the entire CAAT box.

The TATA box is recognized by Transcription Factor IIB (TFIIB) and the TATA binding protein (TBP), which are required for the recruitment of RNA pol II. The central role of the TATA box in transcription is supported by experimental observations of impaired or inactivated transcription following the mutation or removal of a TATA box, e.g., the removal of the TATA box in the promoter of the adenoviral E1a gene (Wu et al. (1987) NATURE 326(6112):512-5).

An additional sequence present in many promoters is a CAAT box. A CAAT box is typically located approximately 60-100 bases upstream of a gene's transcription start site and has the consensus sequence GG(T/C)CAATCT. The CAAT box is recognized by core binding factors (also referred to as nuclear factor Y or NF-Y) and CCAAT/enhancer binding proteins (C/EBPs).

In certain embodiments, a recombinant adenovirus comprises an E1a promoter having a deletion of a functional TATA box, e.g., the deletion of an entire TATA box. As used herein, a "functional TATA box" refers to a TATA box that is capable of binding to a TATA box binding protein (TBP), e.g., a TATA box that has at least 100%, at least 90%, at least 80%, at least 70%, at least 60%, at least 50%, or at least 40%, of the TBP binding activity of a corresponding wild-type TATA box sequence. As used herein, a "non-functional TATA box" refers to a TATA box that, e.g., has less than 30%, less than 20%, less than 10%, or 0% of the TBP binding activity of a corresponding wild-type TATA box sequence. Assays for determining whether a TBP binds to a TATA box are known in the art. Exemplary binding assays include electrophoretic mobility shift assays, chromatin immunoprecipitation assays, and DNAse footprinting assays.

In certain embodiments, the recombinant adenovirus comprises a modified TATA box-based promoter may, e.g., comprise a deletion of the entire E1a promoter TATA box, e.g., comprise a deletion corresponding to nucleotides −27 to −24 of the Ad5 E1a promoter. For example, in certain embodiments, a recombinant adenovirus comprises a deletion of nucleotides corresponding to −27 to −24, −31 to −24, −44 to +54, or −146 to +54 of the adenovirus type 5 E1a promoter, which correspond, respectively, to nucleotides 472 to 475, 468 to 475, 455 to 552, and 353 to 552 of the Ad5 genome (SEQ ID NO: 1). In certain embodiments, the virus comprises a polynucleotide deletion that results in a virus comprising the sequence CTAGGACTG (SEQ ID NO: 17), AGTGCCCG (SEQ ID NO: 101), or TATTCCCG (SEQ ID NO: 102), which result from joining the two polynucleotide sequences that would otherwise flank the deleted polynucleotide sequence. In some embodiments, the virus may comprise a deletion of nucleotides corresponding to −29 to −26, −33 to −26, −44 to +52, or −148 to +52 upstream of the initiation site of E1a. In certain embodiments, the deletion comprises a deletion of nucleotides corresponding to 353-552 of the Ad5 genome (SEQ ID NO: 1), and/or the E1a promoter comprises the sequence CTAGGACTG (SEQ ID NO: 17).

In certain embodiments, a recombinant adenovirus may comprise an E1a promoter having a deletion of a functional CAAT box, e.g., the deletion of an entire CAAT box. As used herein, a "functional CAAT box" refers to a CAAT box that is capable of binding to a C/EBP or NF-Y protein, e.g., a CAAT box that has at least 100%, at least 90%, at least 80%, at least 70%, at least 60%, at least 50%, or at least 40%, of the a C/EBP or NF-Y binding activity of a corresponding wild-type CAAT box sequence. As used herein, a "non-functional CAAT box" refers to a CAAT box that, e.g., has less than 30%, less than 20%, less than 10%, or 0% of the a C/EBP or NF-Y binding activity of a corresponding wild-type CAAT box sequence. Assays for determining whether a C/EBP or NF-Y protein binds to a CAAT box are known in the art. Exemplary binding assays include electrophoretic mobility shift assays, chromatin immunoprecipitation assays, and DNAse footprinting assays. In certain embodiments, the recombinant adenovirus comprises a modified CAAT box-based promoter may, e.g., comprise a deletion of the entire E1a promoter CAAT box, e.g., comprise a deletion corresponding to nucleotides −76 to −68 of the adenovirus type 5 E1a promoter, which corresponds to nucleotides 423 to 431 of SEQ ID NO: 1.

For example, in certain embodiments, a recombinant adenovirus comprises a deletion of nucleotides corresponding to −76 to −68 of the adenovirus type 5 E1a promoter, which corresponds to nucleotides 423 to 431 of the Ad5 genome (SEQ ID NO: 1). In certain embodiments, the virus comprises a polynucleotide deletion that results in a virus comprising the sequence TTCCGTGGCG (SEQ ID NO: 103), which results from joining the two polynucleotide sequences that would otherwise flank the deleted polynucleotide sequence.

B. Insertion Sites

In certain embodiments, the recombinant adenovirus comprises one or more nucleotide sequences comprising a transgene inserted in one of more of an E1b-19K insertion site, an E3 insertion site, an E4 insertion site, an IX-E2 insertion site, an L5-E4 insertion site, and combinations thereof. In certain embodiments, the recombinant adenovirus selectively expresses the transgene in tumor cells. In certain embodiments, the recombinant adenovirus selectively replicates in cells of a cancer.

In certain embodiments, the E1b-19K insertion site is located between the start site of E1b-19K and the start site of E1b-55K. The adenoviral E1b-19k gene functions primarily as an anti-apoptotic gene and is a homolog of the cellular anti-apoptotic gene, BCL-2. Since host cell death prior to maturation of the progeny viral particles would restrict viral replication, E1b-19k is expressed as part of the E1 cassette to prevent premature cell death thereby allowing the infection to proceed and yield mature virions. Accordingly, in certain embodiments, a recombinant virus is provided that includes an E1b-19K insertion site, e.g., the adenovirus has an exogenous nucleotide sequence inserted into an E1b-19K insertion site. In certain embodiments, the insertion site is located between the start site of E1b-19K and the stop codon of E1b-19K.

In certain embodiments, the E1b-19K insertion site comprises a deletion of from about 100 to about 305, about 100 to about 300, about 100 to about 250, about 100 to about 200, about 100 to about 150, about 150 to about 305, about 150 to about 300, about 150 to about 250, or about 150 to about 200 nucleotides adjacent to the start site of E1b-19K. In certain embodiments, the E1b-19K insertion site comprises a deletion of about 200 nucleotides, e.g., 202 nucleotides adjacent to the start site of E1b-19K. In certain embodiments, the E1b-19K insertion site comprises a deletion corresponding to nucleotides 1714-1917 of the Ad5 genome (SEQ ID NO: 1), or, an exogenous nucleotide sequence encoding a transgene is inserted between nucleotides corresponding to 1714 and 1917 of the Ad5 genome (SEQ ID NO: 1). In certain embodiments, an exogenous nucleotide sequence encoding a transgene is inserted between CTGACCTC (SEQ ID NO: 4) and TCACCAGG (SEQ ID NO: 5), e.g., the recombinant adenovirus comprises, in a 5' to 3' orientation, CTGACCTC (SEQ ID NO: 4), an exogenous nucleotide sequence encoding a transgene, and TCACCAGG (SEQ ID NO: 5).

In certain embodiments, the E3 insertion site is located between the stop codon of pVIII and the start site of Fiber. In certain embodiments, the E3 insertion site is located between the stop codon of E3-10.5K and the stop codon of E3-14.7K and the start site of Fiber.

In certain embodiments, the E3 insertion site comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or about 3000 to about 3185 nucleotides. In certain embodiments, the E3 insertion site is located between the stop codon of E3-10.5K and the stop codon of E3-14.7K. In certain embodiments, the E3 insertion site comprises a deletion of from about 500 to about 1551, from about 500 to about 1500, from about 500 to about 1000, from about 1000 to about 1551, from about 1000 to about 1500, or from about 1500 to about 1551 nucleotides adjacent the stop codon of E3-10.5K. In certain embodiments, the E3 insertion site comprises a deletion of about 1050 nucleotides adjacent the stop codon of E3-10.5K, e.g., the E3 insertion site comprises a deletion of 1063 nucleotides adjacent the stop codon of E3-10.5K. In certain embodiments, the E3 insertion site comprises a deletion corresponding to the Ad5 dl309 E3 deletion. In certain embodiments, the E3 insertion site comprises a deletion corresponding to nucleotides 29773-30836 of the Ad5 genome (SEQ ID NO: 1), or the second therapeutic transgene is inserted between nucleotides corresponding to 29773 and 30836 of the Ad5 genome (SEQ ID NO: 1). In certain embodiments, the E3 insertion site comprises a deletion corresponding to nucleotides 29119-30622 of the Ad35 genome (SEQ ID NO: 113).

In certain embodiments, an E4 insertion site comprises any one of the ORF of the E4 gene. For example, a nucleotide sequence can be inserted in E4 ORF1, and/or E4 ORF2. In certain embodiments, portions of or the entire E4 region may be deleted.

In certain embodiments, the insertion site is the IX-E2 insertion site. In certain embodiments, the IX-E2 insertion site is located between the stop codon of adenovirus IX gene and the stop codon of adenovirus IVa2 gene. In certain embodiments, the nucleotide sequence is inserted between nucleotides corresponding to 4029 and 4093 of the Ad5 genome (SEQ ID NO: 1). In certain embodiments, the nucleotide sequence is inserted between nucleotides corresponding to 4029 and 4050, nucleotides corresponding to 4051 and 4070, or nucleotides corresponding to 4071 and 4093 of the Ad5 genome (SEQ ID NO: 1). In some embodiments, the IX-E2 insertion site has at least 60%, at least 70%, at least 80%, at least 90%, at least 95%, or at least 99% identity to nucleotides corresponding to 4029 and 4093 of the Ad5 genome (SEQ ID NO: 1).

In certain embodiments, the insertion site is an L5-E4 insertion site. In certain embodiments, the L5-E4 insertion site is located between the stop codon of adenovirus fiber gene and the stop codon of ORF6 or ORF6/7 of the adenovirus E4 gene. In certain embodiments, the nucleotide sequence is inserted between nucleotides corresponding to 32785 to 32916 of the Ad5 genome (SEQ ID NO: 1). In certain embodiments, the nucleotide sequence is inserted between nucleotides corresponding to 32785 and 32800, nucleotides corresponding to 32801 and 32820, nucleotides corresponding to 32821 and 32840, nucleotides corresponding to 32841 and 32860, nucleotides corresponding to 32861 and 32880, nucleotides corresponding to 32881 and 32900, or nucleotides corresponding to 32901 and 32916 of the Ad5 genome (SEQ ID NO: 1). In some embodiments, the L5-E4 insertion site has at least 60%, at least 70%, at least 80%, at least 90%, at least 95%, or at least 99% identity to nucleotides corresponding to 32785 to 32916 of the Ad5 genome (SEQ ID NO: 1).

In certain embodiments, the IX-E2 insertion site comprises a deletion of about 5, 10, 15, 20, 25, 30, 35, 40, 45, 50, 55, or 60 nucleotides. In certain embodiments, the L5-E4 insertion site comprises a deletion of about 5, 10, 15, 20, 25, 30, 35, 40, 45, 50, 55, 60, 65, 70, 75, 80, 85, 90, 95, 100, 105, 110, 115, 120, 125, or 130 nucleotides.

In certain embodiments, the recombinant adenovirus comprises two or more nucleotide sequences, wherein the nucleotide sequences each comprises a transgene, wherein the nucleotide sequences are optionally separated by a linker. In certain embodiments, the recombinant adenovirus expresses two transgenes, when expressed, produce a single polypeptide chain, which may be cleaved posttranslationally into two polypeptide chains. In certain embodiments, the linker is an internal ribosome entry site (IRES) element and/or a self-cleaving 2A peptide sequence. The IRES may, e.g., be selected from the group consisting of the encephalomyocarditis virus IRES, the foot-and-mouth disease virus IRES, and the poliovirus IRES.

In certain embodiments, the two or more nucleotide sequences are inserted in an E1b-19K insertion site, an E3 insertion site, an E4 insertion site, an IX-E2 insertion site, or an L5-E4 insertion site. In certain embodiments, the two or more nucleotide sequences are inserted in the same insertion site. In certain embodiments, the two or more nucleotide sequences are inserted in different insertion sites.

Nucleic acids encoding viral genes can be incorporated into plasmids and introduced into host cells through conventional transfection or transformation techniques. Specific production and purification conditions will vary depending upon the virus and the production system employed. For adenovirus, the traditional method for the generation of viral particles is co-transfection followed by subsequent in vivo recombination of a shuttle plasmid (usually containing a small subset of the adenoviral genome and optionally containing a potential transgene an expression cassette) and an adenoviral helper plasmid (containing most of the entire adenoviral genome).

In certain embodiments, a recombinant adenovirus of the invention is an oncolytic virus, e.g., a virus that exhibits tumor-selective replication and/or viral mediated lysis. In certain embodiments, a recombinant adenovirus of the invention exhibits selective expression of a patient-specific transgene in a hyperproliferative cell, e.g., a cancer cell, a tumor cell, relative to a nonhyperproliferative cell. In certain embodiments, the expression of a patient transgene in a non-hyperproliferative cell is about 90%, about 80%, about 70%, about 60%, about 50%, about 40%, about 30%, about 20%, about 10%, or about 5% of the expression of the gene in the hyperproliferative cell. In certain embodiments, the virus exhibits no detectable expression of a patient-specific transgene in a non-hyperproliferative cell. Transgene expression may be determined by any appropriate method known in the art, e.g., Western blot or ELISA. The hyperproliferative cell may be a cancer cell, e.g., a carcinoma, sarcoma, leukemia, lymphoma, prostate cancer, lung cancer, gastrointestinal tract cancer, colorectal cancer, pancreatic cancer, breast cancer, ovarian cancer, cervical cancer, stomach cancer, thyroid cancer, mesothelioma, liver cancer, kidney cancer, skin cancer, head and neck cancer, or brain cancer cell.

II. Methods of Viral Production

Methods for producing recombinant viruses of the invention are known in the art. Typically, a disclosed virus is produced in a suitable host cell line using conventional techniques including culturing a transfected or infected host cell under suitable conditions so as to allow the production of infectious viral particles. Nucleic acids encoding viral genes can be incorporated into plasmids and introduced into host cells through conventional transfection or transformation techniques. Exemplary suitable host cells for production of disclosed viruses include human cell lines such as HeLa, Hela-S3, HEK293, 911, A549, HER96, or PER-C6 cells. Specific production and purification conditions will vary depending upon the virus and the production system employed. For adenovirus, the traditional method for the generation of viral particles is co-transfection followed by subsequent in vivo recombination of a shuttle plasmid (usually containing a small subset of the adenoviral genome and optionally containing a potential transgene an expression cassette) and an adenoviral helper plasmid (containing most of the entire adenoviral genome).

Alternative technologies for the generation of adenovirus include utilization of the bacterial artificial chromosome (BAC) system, in vivo bacterial recombination in a recA÷bacterial strain utilizing two plasmids containing complementary adenoviral sequences, and the yeast artificial chromosome (YAC) system.

Following production, infectious viral particles are recovered from the culture and optionally purified. Typical purification steps may include plaque purification, centrifugation, e.g., cesium chloride gradient centrifugation, clarification, enzymatic treatment, e.g., benzonase or protease treatment, chromatographic steps, e.g., ion exchange chromatography or filtration steps.

III. Cancer Antigens

The disclosed recombinant vectors, e.g., recombinant oncolytic viruses, may comprise an exogenous nucleotide sequence that encodes for one or more cancer antigens, e.g., one or more tumor associated antigens or neoantigens.

As used herein, the term "antigen" refers a substance capable of being recognized and bound specifically by an antibody or by a T cell receptor. An antigen may additionally be capable of inducing a humoral immune response and/or cellular immune response leading to the production of B- and/or T-lymphocytes. Antigens can include, for example, peptides, proteins, glycoproteins, polysaccharides, gangliosides and lipids, portions thereof and combinations thereof. As used herein, the term antigen is understood to include a portion of an antigen that is bound specifically by an antibody or by a T cell receptor, also referred to as an "epitope." Furthermore, it is understood that an antigen may be derived from a sequence of substituents that are consequence or non-consecutive, for example, in a protein, it is understood that an antigen may be defined by the primary sequence of amino acids in the protein and/or by the tertiary structure of the protein.

As here herein, a "mutant cancer-associated protein" or "mutant tumor-associated protein" is a version of a protein that comprises at least one mutation as compared to the wild-type form of the protein. In some aspects, the mutant cancer-associated protein is identified as being present in a subject having at least one symptom of cancer or in a subject susceptible to cancer. In some embodiments, a cancer antigen of the present disclosure comprise amino acids of a mutant cancer-associated protein. In some embodiments, the cancer antigen comprises a polypeptide derived from a mutant cancer-associated protein. In some embodiments, the cancer antigen comprises at least one mutation present in the mutant cancer-associated protein.

In some aspects, the cancer antigen ranges in length of about 4 amino acids to about 50 amino acids, or more. For example, the cancer antigen may be about 5 amino acids, 6 amino acids, 7 amino acids, 8 amino acids, 9 amino acids, 10 amino acids, 11 amino acids, 12 amino acids, 13 amino acids, 14 amino acids, 15 amino acids, 16 amino acids, 17 amino acids, 18 amino acids, 19 amino acids, 20 amino acids, 25 amino acids, 30 amino acids, 35 amino acids, 40 amino acids, 45 amino acids, or 50 amino acids, including all sub ranges and values therebetween. In some aspects, the cancer antigen is about 9 amino acids long.

In some aspects, the cancer antigen is capable of inducing an immune response against the cancer cells. In some aspects, the induced immune response delays the development and/or progression of the cancer. In some aspects, the induced immune response kills the cancer cells.

In some aspects, the mutant cancer-associated protein is identified as being present in a subject having at least one symptom of cancer or in a subject susceptible to cancer through sequencing of the whole or part of the genome and/or transcriptome of the subject.

In certain embodiments, whole or part of the genomic DNA or expressed RNA (transcriptome) is isolated from a sample from a subject, and sequenced e.g., using next generation sequencing (NGS). Based on the sequencing results, one or more mutant proteins that are associated with or correlated with cancer are identified. In some aspects, the one or more mutant cancer-associated proteins have amino acid modifications such as point mutation, for example, amino acid insertions, deletions, or substitutions. In some aspects, the one or more mutant cancer-associated proteins have one or more frameshift mutations.

In some aspects, the subject has been diagnosed to have cancer. In other aspects, the subject has not been diagnosed to have cancer. In some aspects, the subject who does not have cancer is determined to be at high risk or susceptible to the development of cancer, such as hereditary cancer. The sample may, for example, be a tumor sample (e.g., from a tumor biopsy), or a blood sample.

Any technique for sequencing nucleic acid known to those skilled in the art may be used in the methods disclosed herein. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of the separated molecules has more recently been demonstrated by sequential or single extension reactions using polymerases or ligases as well as by single or sequential differential hybridizations with libraries of probes. These reactions have been performed on many clonal sequences in parallel including demonstrations in current commercial applications of over 100 million sequences in parallel.

In some aspects, the genome of the subject is sequenced by next-generation sequencing (NGS). As used herein, NGS, refers to oligonucleotide sequencing technologies that have the capacity to sequence oligonucleotides at speeds above those possible with conventional sequencing methods (e.g., Sanger sequencing), due to performing and reading out thousands to millions of sequencing reactions in parallel. Non-limiting examples of next-generation sequencing methods/platforms include Massively Parallel Signature Sequencing (Lynx Therapeutics), 454 pyro-sequencing (454 Life Sciences/Roche Diagnostics), solid-phase, reversible dye-terminator sequencing (Solexa/Illumina), SOLiD technology (Applied Biosystems), Ion semiconductor sequencing (ION Torrent), DNA nanoball sequencing (Complete Genomics), True Single Molecule Sequencing, and technologies available from Pacific Biosciences, Intelligen Biosystems, Oxford Nanopore Technologies, and Helicos Biosciences.

In some aspects, 454 pyro-sequencing, which involves two steps, is used for sequencing in the methods disclosed herein. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

In some aspects, Solexa/Illumina sequencing is used in the methods disclosed herein. SOLEXA sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

In some aspects, SOLiD sequencing technology is used in the methods disclosed herein. In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Further details on sequencing techniques are provided in U.S. Patent Publication No. US 2018/0112278 A1, the contents of which are incorporated herein by reference in its entirety.

Sequencing data, for example, whole exome sequencing (WES) or whole genome sequencing (WGS) data, can be analyzed for mutations, for example, single nucleotide variations (SNV), small insertions/deletions (indels), larger copy-number aberrations (CNAs) and large-genome rearrangements, also called structural variants (SVs). Preferred cancer antigens to be encoded by a disclosed recombinant vector include antigens corresponding to "driver mutations" which push or drive the growth of the tumor cells, providing them with a selective advantage over their non-malignant counterparts. Driver mutations are distinguished from "passenger mutations" that, while present, do not increase the fitness of the tumor cells and, as such, are not responsible for a cancer phenotype. Mutations may be detected in DNA or RNA sequencing data using methods known in the art, e.g., using mutation calling algorithms such as MuTect (Cibulskis et al. (2013) Nat. Biotechnol. 31(3): 213-9).

Cancer antigens to be encoded by a disclosed recombinant vector e.g., a recombinant oncolytic vector, generate peptides which are presented by one or more Major Histocompatibility Complex (MHC) molecules in a subject. Furthermore, preferred cancer antigens to be encoded by a disclosed recombinant vector, e.g., a recombinant oncolytic vector, include immunogenic antigens, e.g., antigens capable stimulating a cytotoxic T-cell (CTL) response Immunogenicity of cancer antigens identified by sequencing DNA or RNA from a sample from a subject may be assayed by methods known in the art, including in silico epitope prediction algorithms such as NetMHCpan (Nielsen et al. (2016) Genome Medicine 8(1): 33, Hoof et al. (2009) Immunogenetics 61(1): 1-13).

Immunogenicity of cancer antigens identified by sequencing DNA or RNA from a sample from a subject may also be assayed by functional or immunologic assays, including peptide-HLA binding assays, or cytokine secretion assays (CSA), e.g., ELISPOT (enzyme-linked immunospot) assays. In cytokine secretion assays, candidate cancer antigens, or peptides derived therefrom, are co-cultured with autologous lymphocytes to determine the response of host lymphocytes upon exposure to the antigen, as measured by the release of cytokines. To control for auto-reactivity, corresponding wild-type antigens can also be tested for their effect on lymphocytes to ensure that responses display specificity for the mutated cancer antigen.

In certain embodiments, co-culturing a cancer antigen with autologous lymphocytes stimulates secretion of an immunostimulatory cytokine, e.g., IFN-γ, from the lymphocytes. In other embodiments, co-culturing a cancer antigen with autologous lymphocytes stimulates secretion of an immunosuppressive cytokine, e.g., TGF-β, IL-10 or IL-5, from the lymphocytes. In certain embodiments, the cancer antigen or cancer antigens are selected by a method comprising (i) identifying a candidate cancer antigen by sequencing DNA or RNA from a sample from a subject with cancer; (ii) culturing autologous lymphocytes in the presence of the candidate cancer antigen; and (iii) assaying for the release of an immunosuppressive cytokine, e.g., TGF-β, IL-10 or IL-5, from the autologous lymphocytes. Surprisingly, it has been discovered that a subject may be treated for cancer using a cancer vaccine that comprises or encodes for an immunosuppressive cancer antigen, e.g., a cancer antigen that stimulates the secretion of an immunosuppressive cytokine, e.g., TGF-β, IL-10 or IL-5, from autologous lymphocytes. Without wishing to be bound by theory, it is believed that a cancer vaccine may best treat a cancer in a subject by eliciting an effective immune response against a cancer antigen that the subject's immune system was unable to respond to effectively without the aid of the cancer vaccine. As an immunosuppressive cancer antigen represents a cancer antigen that the subject's immune system was unable to effectively respond to, it certain instances, an optimal cancer vaccine may comprise or encode for an immunosuppressive cancer antigen.

In certain embodiments, the cancer antigen is a self-antigen.

In certain embodiments, the one or more cancer antigens are derived from 9D7, androgen receptor, a BAGE family protein, β-catenin, BING-4, BRAF, BRCA1/2, a CAGE family protein, calcium-activated chloride channel 2, CD19, CD20, CD30, CDK4, CEA, CML66, CT9, CT10, cyclin-B1, EGFRvIII, Ep-CAM, EphA3, fibronectin, a GAGE family protein, gp100/pme117, Her-2/neu, HPV E6, HPV E7, Ig, immature laminin receptor, a MAGE family protein (e.g., MAGE-A3), MART-1/melan-A, MART2, MC1R, mesothelin, a mucin family protein (e.g., MUC-1), NY-ESO-1/LAGE-1, P. polypeptide, p53, podocalyxin (Podxl), PRAME, a ras family protein (e.g., KRAS), prostate specific antigen, a SAGE family protein, SAP-1, SSX-2, survivin, TAG-72, TCR, telomerase, TGF-βRII, TRP-1, TRP-2, tyrosinase, or a XAGE family protein. Additional exemplary cancer antigens are described in U.S. Patent Publication Nos. US2012/0276045 and US2017/0152324, International (PCT) Publication Nos. WO2001/041741 and WO2010/148496, Cheever et al. (2009) Clin. Cancer Res. 15(17): 5323-5337, Lu et al. (2016) Semin. Immunol. 28(1): 22-27, and Sjöblom et al. (2014) Science 314: 268-24, each of which is incorporated herein by reference in its entirety.

In certain embodiments, the one or more cancer antigens are derived from catenin alpha-2 (CTNNA2), myosin-IIIb isoform 2 (MYO3B), sodium/calcium exchanger 3 isoform C precursor (SLC8A3), sodium-dependent neutral amino acid transporter B(0)AT1 (SLC6A19), double-stranded RNA-specific editase B2 (ADARB2), T-complex protein 11 homolog (TCP11), leucine-rich repeat and transmembrane domain-containing protein 2 precursor (LRTM2), nuclear receptor subfamily 5 group A member 2 (NR5A1), prolactin-releasing peptide receptor (PRLHR), prolow-density lipoprotein receptor-related protein 1 preproprotein (LRP1), alpha-2-macroglobulin isoform a precursor (A2M), RUS1 family protein C16orf58 (C16orf58), tyrosine-protein kinase BAZ1B (BAZ1B), phospholipid phosphatase 2 (PPAP2C), chondroitin sulfate glucuronyltransferase (CHPF2), pre-mRNA 3' end processing protein WDR33 (WDR33), U1 small nuclear ribonucleoprotein A (SNRPA), GTP-binding protein 1 (GTPB), probable ATP-dependent RNA helicase DDX46 (DDX), cAMP-dependent protein kinase catalytic subunit beta (PRKA), lysine-specific demethylase 5B (KDM), jmjC domain-containing protein 8 (JMJ), CTD small phosphatase-like protein isoform 1 (CTDS), transmembrane protein 9B isoform a precursor (TMEM9B/1), transmembrane protein 9B isoform b (TMEM9B/2), dedicator of cytokinesis protein 1 (DOCK1), retinoblastoma-associated protein (RB1), lysine-specific demethylase 4A (KDM4A), E3 ubiquitin-protein ligase NEDD4-like (NEDD4L), serine/threonine-protein kinase TAO3 (TAOK3), transcription elongation regulator 1 (TCERG1), E3 ubiquitin-protein ligase RNF19B (RNF19B), rho GTPase-activating protein 45 (HMHA1), semaphorin-5A precursor (SEMASA), adenomatous polyposis coli protein (APC), zinc finger protein 732 (ZNF732), contactin-1 isoform 1 precursor (CNTN1), cellular tumor antigen p53 (TP53), KRAS, BRAF, NRAS, PIK3CA, EGFR, IDH1, SETD1B, RPL22, or RNF43.

In some embodiments, the one or more cancer antigens are derived from a mutant p53 protein carrying one or more of the amino acid substitutions—R175H, R273C, R248Q, R273H, R248W, R282W, Y220C, G245S, H179R, V157F; a KRAS mutant protein carrying one or more of the following amino acid substitutions—G12D, G12V, G12C, G13D, G12A, G12R, G12S, G13C, A146T, Q61H; a BRAF mutant protein carrying the amino acid substitutions V600E and/or V600M; an NRAS mutant protein carrying the amino acid substitution Q61R and/or Q61K; a PIK3CA mutant protein carrying one or more of the following amino acid substitutions—E545K, H1047R, E542K, R88Q, G118D, N345K, C420R, E453K, Q546R, E726K, H1047L; a mutant EGFR protein carrying one or more of the amino acid substitutions—A289V, G598V, L858R; a mutant IDH1 protein carrying the amino acid substitution, R132H; a mutant SETD1B protein carrying a frameshift mutant at H8 position; a mutant RPL22 protein carrying a frameshift mutation at K15 position; a mutant RNF43 protein carrying a frameshift mutation at G659; or any combination thereof.

In certain embodiments, the cancer antigen is derived from KRAS, e.g., KRAS where Gly at position 12 has been substituted with Asp (KRAS G12D). An exemplary cancer antigen derived from KRAS G12D is MTEYKLVVVGADGVGKSA (SEQ ID NO: 20). In certain embodiments, the recombinant vector comprises a nucleotide sequence encoding SEQ ID NO: 20, or comprises a sequence having 80%, 85%, 86%, 87%, 88%, 89%, 90%, 91%, 92%, 93%, 94%, 95%, 96%, 97%, 98%, or 99% sequence identity to SEQ ID NO: 20, e.g., the recombinant vector comprises the nucleotide sequence of SEQ ID NO: 16.

In some aspects, the one or more cancer antigens are derived from a mutant APC protein. In some aspects, the mutant APC protein contains at least one amino acid modification such as a frameshift mutation. For example, a nucleotide sequence encoding a cancer antigen derived from a mutant APC protein with a frameshift mutation is set forth in SEQ ID NO: 99. In some aspects, the mutant APC protein contains at least one amino acid modification such as point mutation, for example, an amino acid insertion, deletion and/or substitution. For example, a nucleotide sequence encoding a cancer antigen derived from a mutant APC protein with an amino acid substitution is set forth in SEQ ID NO: 98 (see Example 2).

Sequence identity may be determined in various ways that are within the skill in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) Proc. Natl. Acad. Sci. USA 87:2264-2268; Altschul, (1993) J. Mol. Evol. 36, 290-300; Altschul et al., (1997) Nucleic Acids Res. 25:3389-3402, incorporated by reference) are tailored for sequence similarity searching. For a discussion of basic issues in searching sequence databases see Altschul et al., (1994) Nature Genetics 6:119-129, which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. natl. Acad. Sci. USA 89:10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: −G, Cost to open gap [Integer]: default=5 for nucleotides/11 for proteins; −E, Cost to extend gap [Integer]: default=2 for nucleotides/1 for proteins; −q, Penalty for nucleotide mismatch [Integer]: default=−3; −r, reward for nucleotide match [Integer]: default=1; −e, expect value [Real]: default=10; −W, wordsize [Integer]: default=11 for nucleotides/28 for megablast/3 for proteins; −y, Dropoff (X) for blast extensions in bits: default=20 for blastn/7 for others; −X, X dropoff value for gapped alignment (in bits): default=15 for all programs, not applicable to blastn; and −Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In certain embodiments, the nucleotide sequences encoding each cancer antigen are separated by an internal ribosome entry site (IRES). The IRES may, e.g., be selected from the group consisting of the encephalomyocarditis virus IRES (e.g., an IRES comprising SEQ ID NO: 13), the foot-and-mouth disease virus IRES, and the poliovirus IRES.

IV. Construction of Recombinant Vectors

In some aspects, the recombinant vectors disclosed herein comprise an exogenous nucleotide sequence comprising one or more nucleotide sequences, each encoding a cancer antigen. In some aspects, the exogenous nucleotide sequence comprises multiple nucleotide sequences, each encoding a different cancer antigen. An exogenous nucleotide sequence comprising multiple nucleotide sequences may be referred to herein as a concatemer.

For instance, the exogenous nucleotide sequence may comprise a range of about 1 nucleotide sequence encoding about 1 cancer antigen to about 100 nucleotide sequences encoding about 100 cancer antigens. For example, the exogenous nucleotide sequence may comprise about 5 nucleotide sequences encoding 5 cancer antigens, 10 nucleotide sequences encoding 10 cancer antigens, 15 nucleotide sequences encoding 15 cancer antigens, 20 nucleotide sequences encoding 20 cancer antigens, 25 nucleotide sequences encoding 25 cancer antigens, 30 nucleotide sequences encoding 30 cancer antigens, 35 nucleotide sequences encoding 35 cancer antigens, 40 nucleotide sequences encoding 40 cancer antigens, 45 nucleotide sequences encoding 45 cancer antigens, 50 nucleotide sequences encoding 50 cancer antigens, 55 nucleotide sequences encoding 55 cancer antigens, 60 nucleotide sequences encoding 60 cancer antigens, 65 nucleotide sequences encoding 65 cancer antigens, 70 nucleotide sequences encoding 70 cancer antigens, 75 nucleotide sequences encoding 75 cancer antigens, 80 nucleotide sequences encoding 80 cancer antigens, 85 nucleotide sequences encoding 85 cancer antigens, 90 nucleotide sequences encoding 90 cancer antigens, or 95 nucleotide sequences encoding 95 cancer antigens, inclusive of any subranges and values that lie therebetween.

In certain embodiments, the multiple nucleotide sequences each encoding a cancer antigen are separated from each other by one or more nucleotide sequences, each encoding a protein linker. In some aspects, the linker comprises from about 5 to about 50 amino acid residues. For example, the amino acid linker may comprise, e.g., from about 5 to about 15, from about 5 to about 20, from about 5 to about 30, from about 10 to about 15, from about 10 to about 20, from about 10 to about 30, from about 10 to about 40, from about 15 to about 20, from about 15 to about 30, or from about 15 to about 50 amino acid residues, inclusive of any subranges and values that lie therebetween.

In some aspects, the protein linker comprises an amino acid sequence of AAY (SEQ ID NO: 6). See Velders et al. (2001) J. Immunol.166:5366-5373, the contents of which are incorporated herein by reference in its entirety. In some aspects, the protein linker consists of an amino acid sequence of AAY (SEQ ID NO: 6). In some embodiments, the linker comprises a self-cleaving 2A peptide sequence.

In some aspects, the linker comprises a cleavage site, e.g., a proteolytic or a non-proteolytic cleavage site, or a ribosome skipping sequence, e.g., a T2A sequence. In certain embodiments, the multiple nucleotide sequences each encoding a cancer antigen are separated by a proteolytic cleavage site. In certain embodiments, the proteolytic cleavage site is cleaved by a protease present in a specific tissue, organelle or intracellular compartment. In certain embodiments, the linker comprises a proteolytic cleavage site and two cysteine residues that result in a disulfide linkage following proteolytic cleavage. In certain embodiments, the proteolytic cleavage site is cleaved by a protease selected from a matrix metalloproteinase (MMP), furin, PC1, PC2, PC3, cathepsin B, proteinase 3, and caspase 3.

In certain embodiments, the cleavage site is a proteolytic cleavage site that is cleaved by a protease that is present in the endoplasmic reticulum or golgi of a eukaryotic cell. In certain embodiments, the proteolytic cleavage site is a furin cleavage site. Furin is a protease that is ubiquitously expressed and is localized to the Golgi, where it recognizes the consensus sequence $RX_1X_2R$ (SEQ ID NO: 18), wherein $X_1$ is any amino acid, and $X_2$ is Lys or Arg, and cleaves after the final Arg. Furin plays a biological role in cleaving propeptides of proteins that are trafficked through the Golgi. Accordingly, in certain embodiments the proteolytic cleavage site is a furin cleavage site comprising the sequence $RX_1X_2R$ (SEQ ID NO: 18), wherein $X_1$ is any amino acid, and $X_2$ is Lys or Arg, e.g., a furin cleavage site comprising the sequence RAKR (SEQ ID NO: 19).

In certain embodiments, wherein a recombinant vector e.g., a recombinant oncolytic vector, comprises multiple nucleotide sequences, each of which encodes a cancer antigen, for example, wherein the recombinant vector comprises a nucleotide sequence encoding a single polypeptide chain comprising multiple cancer antigens, each separated by a protein linker, the recombinant vector may further comprise anucleotide sequence encoding ubiquitin to enhance proteolysis of the single polypeptide chain (see, Velders et al. (2001) J. Immunol. 166: 5366-5373, the contents of which are incorporated herein by reference in its entirety).

In some aspects, the exogenous nucleotide sequence comprising one or more nucleotide sequences, each encoding a cancer antigen, is inserted into one insertion site selected from the group consisting of E1b-19K insertion site, E3 insertion site, E4 insertion site, IX-E2 insertion site, and L5-E4 insertion site, wherein each of the nucleotide sequences is separated from each other by at least one linker. In some aspects, multiple nucleotide sequences, each encoding a cancer antigen, are inserted in such a manner that they are distributed among 2 or more insertion sites selected from the following insertion sites—E1b-19K insertion site, E3 insertion site, E4 insertion site, IX-E2 insertion site, and L5-E4 insertion site. For instance, if the exogenous nucleotide sequences comprises 2 nucleotide sequences, each encoding a cancer antigen, then the 2 nucleotide sequences may be inserted in the following combinations as shown below:

TABLE 1

| | Elb-19K insertion site | E3 insertion site | E4 insertion site | IX-E2 insertion site | L5-E4 insertion site |
|---|---|---|---|---|---|
| Combination 1 | 2 | 0 | 0 | 0 | 0 |
| Combination 2 | 0 | 2 | 0 | 0 | 0 |
| Combination 3 | 0 | 0 | 2 | 0 | 0 |
| Combination 4 | 0 | 0 | 0 | 2 | 0 |
| Combination 5 | 0 | 0 | 0 | 0 | 2 |
| Combination 6 | 1 | 1 | | | |
| Combination 7 | 1 | | 1 | | |
| Combination 8 | 1 | | | 1 | |
| Combination 9 | 1 | | | | 1 |
| Combination 10 | | 1 | 1 | | |
| Combination 11 | | 1 | | 1 | |
| Combination 12 | | 1 | | | 1 |
| Combination 13 | | | 1 | 1 | |
| Combination 14 | | | 1 | | 1 |
| Combination 15 | | | | 1 | 1 |

As another example, if the exogenous nucleotide sequences comprises 3 nucleotide sequences, each encoding a cancer antigen, then the 3 nucleotide sequences may be inserted in the following combinations as shown below:

TABLE 2

| | Elb-19K insertion site | E3 insertion site | E4 insertion site | IX-E2 insertion site | L5-E4 insertion site |
|---|---|---|---|---|---|
| Combination 1 | 3 | 0 | 0 | 0 | 0 |
| Combination 2 | 0 | 3 | 0 | 0 | 0 |
| Combination 3 | 0 | 0 | 3 | 0 | 0 |
| Combination 4 | 0 | 0 | 0 | 3 | 0 |
| Combination 5 | 0 | 0 | 0 | 0 | 3 |
| Combination 6 | 2 | 1 | | | |
| Combination 7 | 2 | | 1 | | |
| Combination 8 | 2 | | | 1 | |
| Combination 9 | 2 | | | | 1 |
| Combination 10 | 1 | 2 | | | |
| Combination 11 | | 2 | 1 | | |
| Combination 12 | | 2 | | 1 | |
| Combination 13 | | 2 | | | 1 |
| Combination 14 | 1 | | 2 | | |
| Combination 15 | | 1 | 2 | | |
| Combination 16 | | | 2 | 1 | |
| Combination 17 | | | 2 | | 1 |
| Combination 18 | 1 | | | 2 | |
| Combination 19 | | 1 | | 2 | |
| Combination 20 | | | 1 | 2 | |

TABLE 2-continued

| | Elb-19K insertion site | E3 insertion site | E4 insertion site | IX-E2 insertion site | L5-E4 insertion site |
|---|---|---|---|---|---|
| Combination 21 | | | | 2 | 1 |
| Combination 22 | 1 | | | | 2 |
| Combination 23 | | 1 | | | 2 |
| Combination 24 | | | 1 | | 2 |
| Combination 25 | | | | 1 | 2 |
| Combination 26 | 1 | 1 | 1 | | |
| Combination 27 | 1 | 1 | | 1 | |
| Combination 28 | 1 | 1 | | | 1 |
| Combination 29 | 1 | | 1 | 1 | |
| Combination 30 | 1 | | 1 | | 1 |
| Combination 31 | 1 | | | 1 | 1 |
| Combination 32 | | 1 | 1 | 1 | |
| Combination 33 | | 1 | 1 | | 1 |
| Combination 34 | | 1 | | 1 | 1 |
| Combination 35 | | | 1 | 1 | 1 |

It is understood that the arrangement in the above mentioned examples can be similarly applied to the situation when more cancer antigens (e.g., about 5, 10, 15, 20, 25, 30, 35, 40, 45, 50, 55, 60, 65, 70, 75, 80, 85, 90, 95, 100 or more) are included in the recombinant vectors. For example, when there are about 5, about 10, about 15, about 20, about 25, about 30, about 35, about 40, about 45, about 50, about 55, about 60, about 65, about 70, about 75, about 80, about 85, about 90, about 95, about 100, or more cancer antigens, they can be either combined in a single concatemer, and inserted into any of the insertion site, or be divided into different groups to form several concatemers, and the several concatemers are inserted into different insertion sites of the present disclosure. In some embodiments, the cancer antigens are divided into 1, 2, 3, 4, or 5 groups, so that they are be included in 1, 2, 3, 4, 5 concatemers, and inserted into the insertion sites of the present disclosure. Within the same concatemers, a same linker or several different linkers can be used to separate the cancer antigens.

In some aspects, the recombinant vectors disclosed herein may comprise one or more deletions of adenoviral capsid genes to accommodate the insertion of concatemers, referred to herein as compensatory deletions. In some aspects, the recombinant vectors disclosed herein comprise one or more compensatory deletions in E1 region, E2 region, E3 region, E4 region, or any combination thereof. In some aspects, one or more of the genes, RID alpha, RID beta and 14.7K genes in the E3 region of the recombinant vectors disclosed herein may be deleted. In some aspects, the E3 gp19K gene of the recombinant vectors disclosed herein comprises one or more amino acid mutations, as compared to the WT E3 gp19K gene. In some cases, the one or more mutation is a mutation that converts the fourth codon of the E3 gp19K gene into a stop codon. In some aspects, the E4 region of the recombinant vectors disclosed herein retains E4 ORF 6/7.

V. Therapeutic Transgenes

A disclosed recombinant vector, e.g., a recombinant oncolytic virus, may further comprise an exogenous nucleotide sequence encoding a therapeutic transgene. A therapeutic transgene may encode a therapeutic nucleic acid, e.g., an antisense RNA or ribozyme RNA, which enhances the anti-cancer activity of the recombinant vectors disclosed herein. The therapeutic transgene may encode a therapeutic peptide or polypeptide, which enhances the anti-cancer activity of the recombinant vectors disclosed herein, such as, for e.g., an oncoprotein, tumor suppressor peptide or polypeptide, enzyme, cytokine, immune modulating peptide or polypeptide, antibody, lytic peptide, vaccine antigen, a peptide or polypeptide which complements genetic defects in somatic cells, or a peptide or polypeptide which catalyzes processes leading to cell death. In some embodiments, a therapeutic transgene may enhance the activity of immune recognition of a cancer antigen in the recombinant vectors disclosed herein.

In some aspects, the recombinant vectors disclosed herein may encode at least one therapeutic nucleic acid and/or at least one therapeutic polypeptide. In some aspects, the recombination vectors disclosed herein may encode about 1 to about 50 therapeutic nucleic acids. For instance, the recombination vectors disclosed herein may encode 1 therapeutic nucleic acid, 2 therapeutic nucleic acids, 3 therapeutic nucleic acids, 4 therapeutic nucleic acids, 5 therapeutic nucleic acids, 6 therapeutic nucleic acids, 7 therapeutic nucleic acids, 8 therapeutic nucleic acids, 9 therapeutic nucleic acids, 10 therapeutic nucleic acids, 15 therapeutic nucleic acids, 20 therapeutic nucleic acids, 25 therapeutic nucleic acids, 30 therapeutic nucleic acids, 35 therapeutic nucleic acids, 40 therapeutic nucleic acids, 45 therapeutic nucleic acids, or 50 therapeutic nucleic acids, including all values that lie therebetween. In some aspects, the recombination vectors disclosed herein may encode about 1 to about 50 therapeutic polypeptides. For instance, the recombination vectors disclosed herein may encode 1 therapeutic polypeptide, 2 therapeutic polypeptides, 3 therapeutic polypeptides, 4 therapeutic polypeptides, 5 therapeutic polypeptides, 6 therapeutic polypeptides, 7 therapeutic polypeptides, 8 therapeutic polypeptides, 9 therapeutic polypeptides, 10 therapeutic polypeptides, 15 therapeutic polypeptides, 20 therapeutic polypeptides, 25 therapeutic polypeptides, 30 therapeutic polypeptides, 35 therapeutic polypeptides, 40 therapeutic polypeptides, 45 therapeutic polypeptides, or 50 therapeutic polypeptides, including all values that lie therebetween.

In certain embodiments, a recombinant vector, e.g., a recombinant oncolytic vector, described herein comprises an exogenous nucleotide sequence encoding a therapeutic polypeptide selected from GM-CSF, CD80, CD137L, IL-23, IL-23A/p19, IL-27, IL-27A/p28, IL-27B/EBI3, ICAM-1, a TGF-β trap, TGF-β, CD19, CD20, IL-1, IL-3, IL-4, IL-5, IL-6, IL-8, IL-9, CD154, CD86, BORIS/CTCFL, FGF, IL-24, MAGE, NY-ESO-1, acetylcholine, interferon-gamma, DKK1/Wnt, p53, thymidine kinase; an anti-PD-1 antibody heavy chain or light chain; an anti-PD-L1 antibody heavy chain or light chain; FLT3L; FLT3 or any combination thereof.

In certain embodiments, the therapeutic polypeptide is IL-24. A nucleotide sequence encoding human IL-24 is depicted in SEQ ID NO: 104, and a nucleotide sequence encoding mouse IL-24 is depicted in SEQ ID NO: 105. In certain aspects, the therapeutic polypeptide is GM-CSF. In some aspects, the therapeutic polypeptides are IL-24 and GM-CSF.

In certain embodiments, the at least one therapeutic transgene is inserted into one insertion site selected from the group consisting of E1b-19K insertion site, E3 insertion site, E4 insertion site, IX-E2 insertion site, and L5-E4 insertion site. In some aspects, at least two therapeutic transgenes are inserted into two or more insertion sites selected from the group consisting of E1b-19K insertion site, E3 insertion site, E4 insertion site, IX-E2 insertion site, and L5-E4 insertion site. In certain embodiments, the recombinant adenovirus selectively expresses the therapeutic transgene in tumor cells.

In certain embodiments, the at least one therapeutic transgene is inserted at the same site as the one or more nucleotide sequences, each encoding one cancer antigen. In some embodiments, the at least one therapeutic transgene is inserted at a different insertion site than the one or more nucleotide sequences, each encoding one cancer antigen.

VI. Pharmaceutical Compositions

For therapeutic use, a recombinant vector, e.g., a recombinant oncolytic virus, disclosed herein is preferably combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

Pharmaceutical compositions containing recombinant viruses can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, intratumoral, intraarterial, intramuscular, intrapleural, intravesicular, intracavitary, peritoneal, oral and rectal administration.

Useful formulations can be prepared by methods known in the pharmaceutical art. For example, see *Remington's Pharmaceutical Sciences,* 18th ed. (Mack Publishing Company, 1990). Formulation components suitable for parenteral administration include a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates; and agents for the adjustment of tonicity such as sodium chloride or dextrose.

For intravenous administration, suitable carriers include physiological saline, bacteriostatic water, Cremophor ELTM (BASF, Parsippany, NJ) or phosphate buffered saline (PBS). The carrier should be stable under the conditions of manufacture and storage, and should be preserved against microorganisms. The carrier can be a solvent or dispersion medium containing, for example, water, ethanol, polyol (for example, glycerol, propylene glycol, and liquid polyethylene glycol), and suitable mixtures thereof.

Pharmaceutical formulations preferably are sterile. Sterilization can be accomplished by any suitable method, e.g., filtration through sterile filtration membranes. Where the composition is lyophilized, filter sterilization can be conducted prior to or following lyophilization and reconstitution.

The term "effective amount" as used herein refers to the amount of an active component (e.g., the amount of a recombinant vector, e.g., a recombinant oncolytic virus) sufficient to effect beneficial or desired results. An effective amount can be administered in one or more administrations, applications or dosages and is not intended to be limited to a particular formulation or administration route.

In certain embodiments, a therapeutically effective amount of active component is in the range of 0.1 mg/kg to 100 mg/kg, e.g., 1 mg/kg to 100 mg/kg, 1 mg/kg to 10 mg/kg. In certain embodiments, a therapeutically effective amount of a recombinant virus e.g., a recombinant oncolytic virus, is in the range of $10^2$ to $10^{15}$ plaque forming units (pfus), e.g., $10^2$ to $10^{10}$, $10^2$ to $10^5$, $10^5$ to $10^{15}$, $10^5$ to $10^{10}$, or $10^{10}$ to $10^{15}$ plaque forming units. The amount administered will depend on variables such as the type and extent of disease or indication to be treated, the overall health of the patient, the in vivo potency of the active component, the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the antibody, and the disease being treated. Exemplary dosing frequencies are once per day, once per week and once every two weeks. A preferred route of administration is parenteral, e.g., intravenous infusion.

VII. Therapeutic Uses

The viruses disclosed herein can be used to treat various medical indications, for example, cancers. As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals (e.g., murines, simians, equines, bovines, porcines, canines, felines, and the like), and more preferably includes humans.

Examples of cancers include solid tumors, soft tissue tumors, hematopoietic tumors and metastatic lesions. Examples of hematopoietic tumors include, leukemia, acute leukemia, acute lymphoblastic leukemia (ALL), B-cell, T-cell or FAB ALL, acute myeloid leukemia (AML), chronic myelocytic leukemia (CML), chronic lymphocytic leukemia (CLL), e.g., transformed CLL, diffuse large B-cell lymphomas (DLBCL), follicular lymphoma, hairy cell leukemia, myelodyplastic syndrome (MDS), a lymphoma, Hodgkin's disease, a malignant lymphoma, non-Hodgkin's lymphoma, Burkitt's lymphoma, multiple myeloma, or Richter's Syndrome (Richter's Transformation). Examples of solid tumors include malignancies, e.g., sarcomas, adenocarcinomas, and carcinomas, of the various organ systems, such as those affecting head and neck (including pharynx), thyroid, lung (small cell or non-small cell lung carcinoma (NSCLC)), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neuroblastoma or glioma), or skin (e.g., melanoma).

In certain embodiments, the cancer is selected from melanoma, squamous cell carcinoma of the skin, basal cell carcinoma, head and neck cancer, breast cancer, anal cancer, cervical cancer, non-small cell lung cancer, mesothelioma, small cell lung cancer, renal cell carcinoma, prostate cancer, gastroesophageal cancer, colorectal cancer, testicular cancer, bladder cancer, ovarian cancer, hepatocellular carcinoma, cholangiocarcinoma, brain cancer, endometrial cancer, neuroendocrine cancer, and pancreatic cancer.

In certain embodiments, the cancer is selected from nasopharyngeal cancer, basal cell carcinoma, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, neuroendocrine, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, brain cancer, oligodendroglioma, neuroblastoma, meningioma, spinal cord tumor, bone cancer, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, colorectal cancer, rectal cancer, esophagus cancer, gall bladder cancer, head cancer, eye cancer, neck cancer, kidney cancer, Wilms' tumor, liver cancer, Kaposi's sarcoma, prostate cancer, lung cancer, testicular cancer, Hodgkin's disease, non-Hodgkin's lymphoma, oral cancer, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

In certain embodiments, a disclosed method or composition is administered to the subject in combination with one or more therapies, e.g., surgery, radiation, chemotherapy, immunotherapy, hormone therapy, phototherapy or virotherapy. In certain embodiments, a disclosed method or composition is administered in combination with a tyrosine kinase inhibitor, e.g., erlotinib. In certain embodiments, a disclosed method or composition is administered in combination with a checkpoint inhibitor, e.g., an anti-CTLA-4 antibody, an anti-PD-1 antibody, or an anti-PD-L1 antibody. Exemplary anti-PD-1 antibodies include, for example, nivolumab (Opdivo®, Bristol-Myers Squibb Co.), pembrolizumab (Keytruda®, Merck Sharp & Dohme Corp.), PDR001 (Novartis Pharmaceuticals), and pidilizumab (CT-011, Cure Tech). Exemplary anti-PD-L1 antibodies include, for example, atezolizumab (Tecentriq®, Genentech), duvalumab (AstraZeneca), MEDI4736, avelumab, and BMS 936559 (Bristol Myers Squibb Co.). In certain embodiments, a disclosed method or composition is administered in combination with a TGF-β trap, or an expression vector, e.g., a recombinant adenovirus, comprising a nucleotide sequence encoding for a TGF-β trap. A TGF-β trap is a fusion protein containing a soluble portion of the extracellular domain of the TGFβ type II receptor or the TGFβ type III receptor. Exemplary TGF-β traps are described in U.S. Provisional Patent Application No. 62/400,338 filed Sep. 27, 2016, and may, e.g., comprise the amino acid sequence of SEQ ID NO: 14 or SEQ ID NO: 15.

The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration.

For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In certain embodiments, a disclosed method or composition is administered in combination with an adjuvant. Exemplary adjuvants include aluminum salts (e.g., aluminium phosphate or aluminium hydroxide), squalene, MF59, virus like particles, tetanus toxoid, Freund's complete adjuvant, Freund's incomplete adjuvant, muramyl dipeptide, Toll-like receptors (TLRs), NOD-like receptors (NLRs), RIG-I-like receptors (RLRs), C-type lectin receptors (CLRs), double-stranded RNA (dsRNA), bacterial lipopolysaccharides (LPS), flagellin, and oligodeoxynucleotides containing specific CpG motifs (CpG ODNs; e.g., ODN 1826 and ODN 2006).

In certain embodiments, a disclosed method or composition is administered in combination with an immunosuppressive drug. Exemplary immunosuppressive drugs include tacrolimus, cyclosporine, mycophenolate mofetil, mycophenolate sodium, azathioprine, and, sirolimus In certain embodiments, a disclosed method or composition is administered in combination with a corticosteroids, e.g., prednisone.

In certain embodiments, a disclosed recombinant vector, e.g., a recombinant oncolytic virus, is administered to one or more organs of a subject. In certain embodiments, a disclosed recombinant vector, e.g., a recombinant oncolytic virus, is administered to the lymphatic system of a subject.

Throughout the description, where viruses, compositions and systems are described as having, including, or comprising specific components, or where processes and methods are described as having, including, or comprising specific steps, it is contemplated that, additionally, there are compositions, devices, and systems of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a virus, a composition, a system, a method, or a process described herein can be combined in a variety of ways without departing from the spirit and scope of the present invention, whether explicit or implicit herein. For example, where reference is made to a particular virus, that virus can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

At various places in the present specification, viruses, compositions, systems, processes and methods, or features thereof, are disclosed in groups or in ranges. It is specifically intended that the description include each and every individual subcombination of the members of such groups and ranges. By way of other examples, an integer in the range of 1 to 20 is specifically intended to individually disclose 1, 2, 3, 4, 5, 6, 7, 8, 9, 10, 11, 12, 13, 14, 15, 16, 17, 18, 19, and 20.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed No language in the specification should be construed as indicating any non-claimed element as essential to the practice of the present invention.

The following examples illustrate various aspects of the invention. The examples should, of course, be understood to be merely illustrative of only certain embodiments of the invention and not to constitute limitations upon the scope of the invention.

EXAMPLES

The following Examples are merely illustrative and are not intended to limit the scope or content of the invention in any way.

Example 1

This Example describes the construction of a recombinant oncolytic adenovirus expressing KRAS. KRAS is a proto-oncogene which is frequently mutated in cancer, including a majority of pancreatic cancers and many colorectal and non-small cell lung cancers. There are no available therapies that directly target activated KRAS, and KRAS mutations are associated with resistance to agents targeting the epidermal growth factor pathway. A common mechanism of KRAS activation is mutation in codon 12 or codon 13, and a common cancer-associated mutation is the glycine to aspartic acid mutation in codon 12 (the G12D mutation).

An adenovirus type 5 virus was constructed that carried the deletion of a nucleotide region located from −304 to −255 upstream of the E1a initiation, which renders E1a expression cancer-selective (as previously described in U.S. Pat. No. 9,073,980). The adenovirus was further modified to carry a SalI site at the start site of the E1b-19k region and an XhoI site 200 base pairs 3' of the SalI site to facilitate insertion of therapeutic transgenes. The resulting virus, is hereafter referred to as TAV. The nucleotide sequence of the modified E1b-19k region is as follows, with the residual bases from the fused SalI and XhoI sites underlined:

(SEQ ID NO: 7)
ATCTTGGTTACATCTGACCTCGTCGAGTCACCAGGCGCTTTTCCAA.

A nucleotide sequence encoding a KRAS peptide including the G12D mutation was cloned in the modified E1b-19k region of TAV. The resulting virus is hereafter referred to as TAV-KRAS-G12D. The nucleotide sequence encoding the KRAS G12D peptide inserted in to the E1b-19k region is as follows, where the KRAS G12D coding region is capitalized, the flanking restriction sites used for cloning are underlined, and the flanking viral sequence including is lowercase:

(SEQ ID NO: 16)
gttacatctgacctcGTCGACATGACTGAATATAAACTTGTGGTAGTTGG
AGCTGATGGCGTAGGCAAGAGTGCCCTCGAGtcaccaggcgcttttc.

Example 2

This Example describes the construction of recombinant oncolytic adenoviruses expressing either a concatemer of multiple cancer antigens or a single cancer antigen identified by genomic sequencing of a patient with cancer.

Genomic sequencing of a cancer patient was performed, which identified multiple mutations that could potentially act as cancer antigens and be recognized by the immune system. To incorporate these cancer antigens into a virus, a series of 38 peptides was generated, each peptide including the cancer-associated point mutation and the eight flanking amino acids 5' or 3' from the point mutation in the mutated protein. These peptides could be processed into a 9-mer peptide to be loaded onto an MHC class I molecule, with the cancer-associated mutation occurring at any position in the 9-mer. Frameshift mutations were incorporated as peptides with eight amino acids N-terminal to the frameshift followed by the mutated amino acids following the frameshift.

A nucleotide sequence was generated that encoded a patient-specific cancer antigen concatemer. The concatemer included the set of 38 peptides described above. Each peptide was separated by an Alanine-Alanine-Tyrosine (AAY; SEQ ID NO: 6) linker to promote proteasomal cleavage between the potential cancer antigen peptides. The concatemer further included a C-terminal ubiquitin, also joined with an AAY linker, in order to promote proteasomal targeting and processing for MHC presentation. A schematic representation of the concatemer is shown in FIG. 1. For simplicity, the schematic in FIG. 1 only depicts 3 cancer antigens/epitopes rather than the full set of 38. The nucleotide sequence of the entire concatemer with the C-terminal ubiquitin, N-terminal start codon, and 3' stop codon is provided in SEQ ID NO: 96. A list of the cancer antigen peptides that were incorporated into the concatemer is shown in FIG. 2.

An adenovirus type 5 with a TAV deletion and a modified E1b-19k region to facilitate insertion of therapeutic transgenes was generated as described in Example 1. The nucleotide sequence encoding the patient-specific cancer antigen concatemer (SEQ ID NO: 96) was inserted into modified E1b-19k region. To accommodate insertion of the large patient-specific cancer antigen concatemer into the viral genome without exceeding the packaging capacity of an adenoviral capsid, compensatory deletions were made in the E3 and E4 regions. In the E3 region, the RID alpha, RID beta, and 14.7K genes positioned after adenoviral death protein were deleted, and the E3 gp19k gene was disrupted by mutating the fourth codon to a stop codon. The E4 region retained E4 ORF6/7. This virus was named PSV1 and the full genomic sequence of the virus is provided in SEQ ID NO: 97. The complete nucleic acid sequence of the concatemer present in PSV1 encoding multiple cancer antigens, including the start methionine, linking AAY residues, ubiquitin, and stop codon (all shown in uppercase) and flanking adenoviral sequence around the E1B-19K insertion site and residual SalI and XhoI site nucleotides (all lowercase) is set forth in SEQ ID NO: 108.

Genomic sequencing of two additional cancer patients was performed. In each patient, sequencing identified mutations in only a single gene, the APC gene. The first patient had a frameshift mutation in the APC gene, and the second patient had a point mutation in the APC gene. Nucleotide sequences were generated that encoded the single APC mutation from each patient and a C-terminal ubiquitin, joined with an AAY linker. The nucleotide sequence encoding the APC mutation from the first patient (with a point mutation in APC) is shown in SEQ ID NO: 98. The virus carrying SEQ ID NO: 98 was named PSV2. The amino acid sequence encoded by SEQ ID NO: 98 is E K I G T R S A Q D P V S E V P A (SEQ ID NO. 111), in which the mutated amino acid "Q" replaces the wild type residue "E" at that position. The complete nucleic acid sequence encoding the cancer antigen present in PSV2 including the start methionine, linking AAY residues, ubiquitin, and stop codon (all shown in uppercase) and flanking adenoviral sequence around the E1B-19K insertion site and residual SalI and XhoI site nucleotides (all lowercase) is set forth in SEQ ID NO: 109.

The nucleotide sequence encoding the APC mutation from the second patient (with a frameshift mutation in APC) is shown in SEQ ID NO: 99. The virus carrying SEQ ID NO: 99 was named PSV3. The amino acid sequence encoded by SEQ ID NO: 99 is T L Q I A E I K D W N (SEQ ID NO: 112) comprising the mutated amino acids "D W N" as compared to the wild type sequence of APC. The complete nucleic acid sequence encoding the cancer antigen present in PSV3 including the start methionine, linking AAY residues, ubiquitin, and stop codon (all shown in uppercase) and flanking adenoviral sequence around the E1B-19K insertion site and residual SalI and XhoI site nucleotides (all lowercase) is set forth in SEQ ID NO: 110.

An adenovirus type 5 with a TAV deletion and a modified E1b-19k region to facilitate insertion of therapeutic transgenes was generated as described in Example 1. Nucleotide sequences that encoded the APC mutations linked to a C-terminal ubiquitin (SEQ ID NO: 98 or SEQ ID NO: 99) were inserted into the modified E1b-19k region. Deletions were made in the E3 and E4 regions. In the E3 region, the RID alpha, RID beta, and 14.7K genes positioned after adenoviral death protein were deleted, and the E3 gp19k gene was disrupted by mutating the fourth codon to a stop codon. The E4 region retained E4 ORF6/7.

PSV1, PSV2, and PSV3 were manufactured and formulated for clinical use. The patient for whom PSV1 was prepared clinically deteriorated and expired without being dosed with the virus. The patient for whom PSV2 was prepared was treated with intratumoral injections of 1E12 viral particles given every 2 weeks. With the first injection of PSV2, circulating adenoviral genomes were measured in the blood with the following results, with persistence of circulating viral DNA suggesting ongoing viral shedding.

| Timepoint | Adenovirus copies |
|---|---|
| Baseline | 0 |
| 3 hours | 11651 |
| 3 days | 951 |
| 9 days | 2686 |

Figure 4:
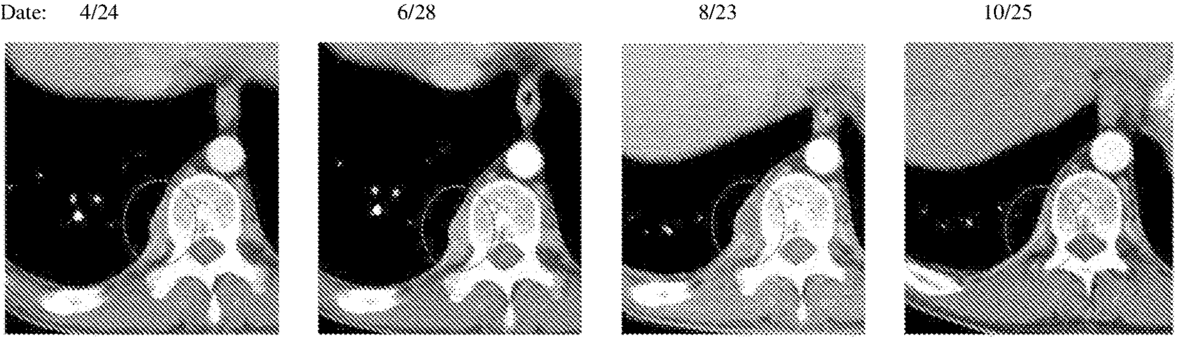
FIG. 4A to FIG. 4D depict an example of a pseudoprogressing paraspinal metastasis which enlarged and developed central radiolucency before regressing. The photos in FIG. 4A to FIG. 4D were taken on different dates.

The patient treated with PSV2 had a mixed response to therapy, including some tumors which showed pseudoprogression—initial enlargement followed by regression—suggestive of an immune mediated response, see FIG. 4.

The patient for whom PSV3 was prepared could not be treated with intratumoral injections of the virus because the cancer's location was not amenable to safely inject, so the patient was dosed subcutaneously. With subcutaneous administration, the cancer-associated antigen can be expressed by infected normal cells and potentially induce an immune response against the antigen, but direct cell killing by the virus is not expected to occur.

Example 3

This Example describes the construction of a recombinant oncolytic adenovirus expressing both IL-24 and GM-CSF.

Additional modifications could potentially enhance the activity of oncolytic viruses expressing cancer antigens. For example, GM-CSF is a cytokine that promotes dendritic cell activity. Viruses can be modified to express GM-CSF, or other immunomodulatory transgenes.

An adenovirus type 5 with a TAV deletion and a modified E1b-19k region to facilitate insertion of therapeutic transgenes was generated as described in Example 1. The gene for interleukin 24 (IL-24) was inserted into the modified E1b-19k region. The nucleotide sequence of the IL-24 gene is as follows:

```
                                         (SEQ ID NO: 104)
ATGAATTTTCAACAGAGGCTGCAAAGCCTGTGGACTTTAGCCAGACCCTT
CTGCCCTCCTTTGCTGGCGACAGCCTCTCAAATGCAGATGGTTGTGCTCC
CTTGCCTGGGTTTTACCCTGCTTCTCTGGAGCCAGGTATCAGGGGCCCAG
GGCCAAGAATTCCACTTTGGGCCCTGCCAAGTGAAGGGGGTTGTTCCCCA
GAAACTGTGGGAAGCCTTCTGGGCTGTGAAAGACACTATGCAAGCTCAGG
ATAACATCACGAGTGCCCGGCTGCTGCAGCAGGAGGTTCTGCAGAACGTC
TCGGATGCTGAGAGCTGTTACCTTGTCCACACCCTGCTGGAGTTCTACTT
GAAAACTGTTTTCAAAAACTACCACAATAGAACAGTTGAAGTCAGGACTC
```

-continued

```
TGAAGTCATTCTCTACTCTGGCCAACAACTTTGTTCTCATCGTGTCACAA

CTGCAACCCAGTCAAGAAAATGAGATGTTTTCCATCAGAGACAGTGCACA

CAGGCGGTTTCTGCTATTCCGGAGAGCATTCAAACAGTTGGACGTAGAAG

CAGCTCTGACCAAAGCCCTTGGGGAAGTGGACATTCTTCTGACCTGGATG

CAGAAATTCTACAAGCTCTGA.
```

The virus was further modified in the E3 region, and the gene for GM-CSF was inserted into the modified E3 region. The nucleotide sequence of the GM-CSF gene (capitalized) with flanking viral nucleotides indicating its insertion site in the viral E3 region (lowercase) is as follows:

```
                                   (SEQ ID NO: 100)
atgttcttttctcttacagtatgattaaatgagacATGTGGCTGCAATCC

CTGCTGCTCTTGGGCACTGTTGCCTGCTCCATCTCTGCACCCGCCCGCTC

GCCCTCCCCCTCCACGCAACCCTGGGAACATGTTAATGCCATCCAAGAAG

CCCGGCGCCTCCTGAACCTGTCCCGGGACACTGCTGCTGAAATGAATGAA

ACCGTTGAAGTTATCTCTGAAATGTTTGACCTCCAAGAACCGACCTGCCT

ACAAACCCGCCTGGAACTCTACAAACAAGGCCTGCGGGGCTCCCTCACCA

AACTCAAAGGCCCCTTGACCATGATGGCCTCCCACTACAAACAACACTGC

CCTCCAACCCCGGAAACTTCCTGCGCAACCCAAATTATCACCTTTGAATC

CTTCAAAGAAAACCTGAAAGACTTTCTGCTTGTTATCCCCTTTGACTGCT

GGGAACCTGTTCAAGAATGAcggtctcaaagatcttattccctttaacta

ataaa.
```

Figure 3:
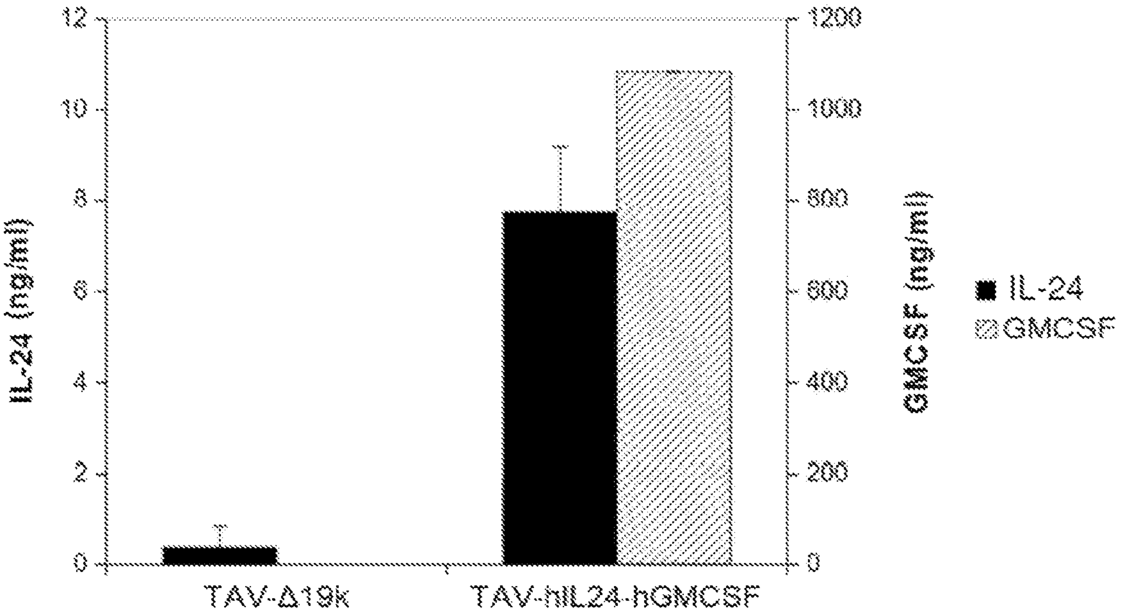
FIG. 3 is a graph that shows ELISA-based quantification of IL-24 and GM-CSF expression in A549 cells infected with control virus (TAV-419k) or IL-24 and GM-CSF expressing virus (TAV-hIL24-hGMCSF).

This resulting virus was called TAV-hIL24-hGMCSF. To test expression of both IL-24 and GM-CSF, A549 cells were infected at 5 MOI with TAV-hIL24-hGMCSF or with a control virus, TAV-Δ19k, which has a deletion in the E1B-19K site and disruption of the E3 site present in the dl309 strain of adenovirus. Four days after infection, conditioned media from the cells was collected and the levels of IL-24 and GM-CSF were measured by ELISA. As shown in FIG. 3, both genes were expressed.

Example 4

This example describes a recombinant oncolytic adenovirus expressing both a mutated p53 protein, incorporating the mouse isoform of p53 with a mutation homologous to the human p53 R175H mutation for use in mouse experiments, and mouse Flt3L to stimulate dendritic cell maturation. The TP53 R175H gene (SEQ ID NO: 114) encoding the mutant mouse p53 was inserted in the L5-E4 site, and the FLT3L gene (SEQ ID NO: 115) encoding Flt3L was inserted in the E1B-19K site. The recombinant oncolytic adenovirus also incorporated the same TAV deletion in the E1A promoter used in PSV1, the same E3 region deletion of RID alpha, RID beta, and 14.7K genes used in PSV1, the same partially deleted E4 region retaining E4 ORF6/7 used in PSV1, and the same mutation in E3 gp19k converted the fourth codon to a stop codon used in PSV1. This recombinant oncolytic adenovirus is named AdFL-Gen-p53.

In another example, a recombinant oncolytic adenovirus was constructed with the same design except with a transgene encoding only the soluble extracellular domain of Flt3L instead of the full-length Flt3L gene. The sequence of the transgene encoding only the soluble extracellular domain of Flt3L is shown in SEQ ID NO: 116. This recombinant oncolytic adenovirus is named AdFL-Sol-p53.

Figure 5:
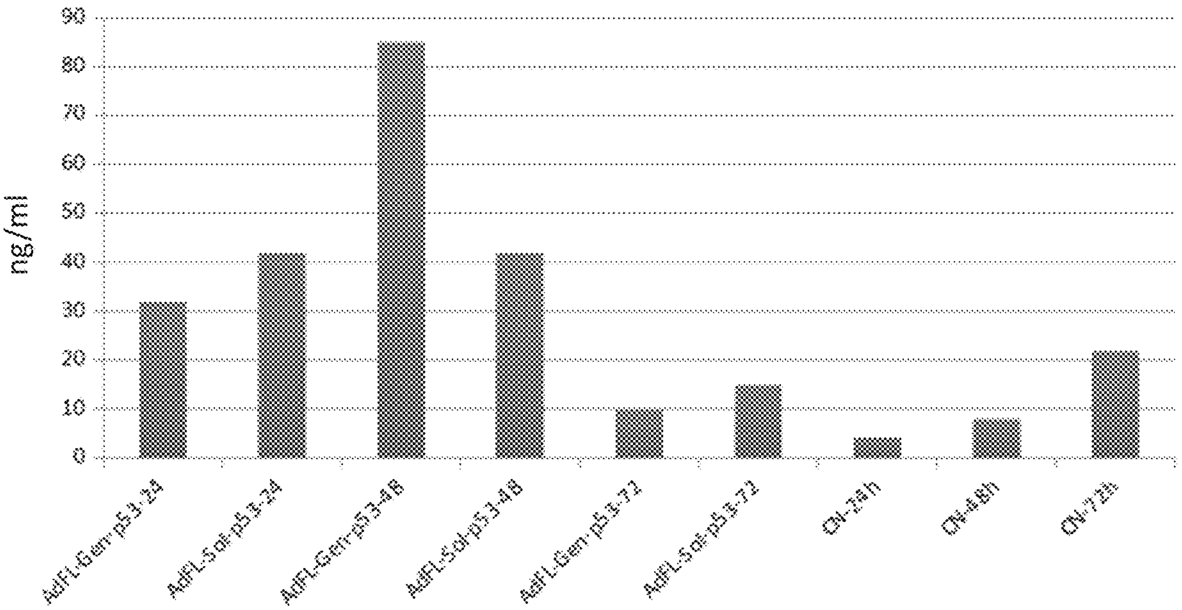
FIG. 5 is a graph showing ELISA-based quantification of mouse p53 expression in A549 cells infected with the virus AdFL-Gen-p53, the virus AdFL-Sol-p53, or kept as non-infected controls (labeled CN). Cells were assayed at 24 hours, 48 hours, or 72 hours after infection as indicated on the x-axis labels.

To test for expression of the mutated mouse p53 gene by these viruses, A549 cells (human cancer cells) were infected with either virus or kept as non-infected controls. 24 hours, 48 hours, and 72 hours after infection, mouse p53 expression was measured with an ELISA. As shown in FIG. 5, higher levels of mouse p53 were detected in the cells infected with either virus at 24 hours and 48 hours after infection than in control non-infected cells.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

What is claimed is:

1. A method for producing a personalized recombinant adenovirus for a subject in need thereof, comprising the steps of:

1) sequencing DNA or RNA in a sample obtained from the subject to identify one or more mutations resulting in one or more cancer antigen specific to the subject, 2) producing one or more transgenes, wherein each of the transgenes comprises one or more mutations identified in step (1), and wherein the one or more mutations are encoded by mutant nucleotide sequences that are separated by a peptide linker, an internal ribosome entry site (IRES), a ribosome skipping sequence, or a combination thereof; and 3) inserting the one or more transgenes in step (2) into the genome of a recombinant adenovirus to produce the personalized recombinant adenovirus, wherein transcription of the transgenes is active in cancer cells and/or hyperproliferative cells, but is attenuated in normal cells.

2. The method of claim 1, wherein the recombinant adenovirus comprises a modified transcription regulatory sequence compared to a corresponding wild type adenovirus, wherein the modified transcription regulatory sequences comprise a modified Ela promoter.

3. The method of claim 1, wherein the one or more transgenes are inserted into one or more insertion sites selected from the group consisting of an Elb-19K insertion site, an E3 insertion site, an E4 insertions site, an IX-E2 insertion site, an L5-E4 insertion site, and combinations thereof.

4. The method of claim 1, wherein each of the mutant nucleotide sequences encodes a peptide having about 5 to about 30 amino acids of the cancer antigens specific to the subject.

5. The method of claim 1, wherein the one or more transgenes comprises at least two mutant nucleotide sequences each encoding one or more cancer antigens specific to the subject.

6. The method of claim 1, wherein the cancer is selected from melanoma, squamous cell carcinoma of the skin, basal cell carcinoma, head and neck cancer, breast cancer, anal cancer, cervical cancer, non-small cell lung cancer, mesothelioma, small cell lung cancer, renal cell carcinoma, prostate cancer, gastroesophageal cancer, colorectal cancer, testicular cancer, bladder cancer, ovarian cancer, hepatocellular carcinoma, cholangiocarcinoma, brain cancer, endometrial cancer, neuroendocrine cancer, merkel cell carcinoma, gastrointestinal stromal tumors, a sarcoma, and pancreatic cancer.

7. The method of claim 1, wherein the recombinant adenovirus further comprises a nucleotide sequence encoding a therapeutic polypeptide, wherein the therapeutic polypeptide enhances immune response against the one or more cancer antigens when expressed in the subject.

8. The method of claim 1, wherein the recombinant adenovirus is a type 5 adenovirus (Ad5) or a type 2 adenovirus (Ad2).

9. The method of claim 2, wherein the modified Ela promoter comprises one or more modifications on one or more binding sites selected from Pea3 and E2F.

10. The method of claim 9, wherein the one or more binding sites are selected from Pea3 I, E2F I, Pea3 II, E2F II, Pea3 III, Pea3 IV, and Pea3 V.

11. The method of claim 3, wherein the Elb-19K insertion site is:

1) located between the start site of Elb-19K and the stop codon of Elb-19K;

2) comprises a deletion of about 200 nucleotides adjacent the start site of Elb-19K;

3) comprises a deletion of 202 or 203 nucleotides adjacent the start site of Elb-19K; or 4) comprises a deletion corresponding to nucleotides 1714-1917 or 1714-1916 of the Ad5 genome (SEQ ID NO: 1).

12. The method of claim 3, wherein the E3 insertion site:

1) is located between the stop codon of pVIII and the start site of Fiber;

2) is located between the stop codon of E3-10.5K and the stop codon of E3-14.7K and the start site of Fiber;

3) comprises a deletion of from about 500 to about 3185, from about 500 to about 3000, from about 500 to about 2500, from about 500 to about 2000, from about 500 to about 1500, from about 500 to about 1000, from about 1000 to about 3185, from about 1000 to about 3000, from about 1000 to about 2500, from about 1000 to about 2000, from about 1000 to about 1500, from about 1500 to about 3185, from about 1500 to about 3000, from about 1500 to about 2000, from about 2000 to about 3185, from about 2000 to about 3000, from about 2000 to about 2500, from about 2500 to about 3185, from about 2500 to about 3000, or about 3000 to about 3185 nucleotides;

4) comprises a deletion of from about 500 to about 1551, from about 500 to about 1500, from about 500 to about 1000, from about 1000 to about 1551, from about 1000 to about 1500, or from about 1500 to about 1551 nucleotides adjacent the stop codon of E3-10.5K;

5) comprises a deletion of about 1,050 nucleotides adjacent the stop codon of E3-10.5K;

6) comprises a deletion of 1,063 or 1,064 nucleotides adjacent the stop codon of E3-10.5K;

7) comprises a deletion corresponding to the Ad5 dl309 E3 deletion;

8) comprises a deletion of the RID alpha, RID beta, and 14.7K genes positioned after adenoviral death protein;

9) comprises a disrupted E3 gp19K gene wherein the fourth codon is mutated to a stop codon;

10) comprises a deletion corresponding to nucleotides 29773-30836 of the Ad5 genome (SEQ ID NO: 1); or 11) is located between CAGTATGA (SEQ ID NO: 8) and TAATAAAAAA (SEQ ID NO: 9).

13. The method of claim 3, wherein the IX-E2 insertion site is located between the stop codon of adenovirus IX gene and the stop codon of adenovirus IVa2 gene.

14. The method of claim 3, wherein the L5-E4 insertion site is located between the stop codon of adenovirus fiber gene and the stop codon of ORF6 or ORF6/7 of adenovirus E4 gene, is inserted either between nucleotides corresponding to 1714 and 1917 of the Ad5 genome (SEQ ID NO: 1), or is inserted between CTGACCTC (SEQ ID NO: 4) and TCACCAGG (SEQ ID NO: 5).

15. The method of claim 5, wherein the one or more transgenes encode a concatemer comprising at least two cancer antigens specific to the subject, wherein each of the cancer antigens is separated by a peptide linker, an internal ribosome entry site (IRES), a ribosome skipping sequence, or a combination thereof.

16. The method of claim 15, wherein the peptide linker promotes proteasomal cleavage between the cancer antigens, optionally wherein the peptide linker consists of SEQ ID NO: 6.

17. The method of claim 15, wherein the concatemer further comprises a C-terminal ubiquitin.

18. The method of claim 15, wherein the IRES is an encephalomyocarditis virus IRES, a foot-and-mouth disease virus IRES, a poliovirus IRES, or a combination thereof.

19. The method of claim 7, wherein the therapeutic polypeptide is selected from GM-CSF, CD80, CD137L, IL-23, IL-23A/p19, IL-27, IL-27A/p28, IL-27B/EB13, ICAM-1, a TGF-beta trap, TGF-beta, CD19, CD20, IL-1, IL-3, IL-4, IL-5, IL-6, IL-8, IL-9, CD154, CD86, BORIS/CTCFL, FGF, IL-24, MAGE, NY-ESO-1, acetylcholine, interferon-gamma, DKKI/Wnt, p53, thymidine kinase; an anti-PD-1 antibody heavy chain or light chain, an anti-PD-LI antibody heavy chain or light chain, FLT3L, FLT3, or any combination thereof.

* * * * *